United States Patent [19]

Goodman et al.

[11] Patent Number: 4,802,486
[45] Date of Patent: Feb. 7, 1989

[54] METHOD AND APPARATUS FOR DETECTING OPTICAL PULSES

[75] Inventors: David E. Goodman, San Francisco; James E. Corenman, Menlo Park, both of Calif.

[73] Assignee: Nellcor Incorporated, Hayward, Calif.

[21] Appl. No.: 742,720

[22] Filed: Jun. 7, 1985

Related U.S. Application Data

[63] Continuation of Ser. No. 718,525, Apr. 1, 1985.

[51] Int. Cl.$^4$ .............................................. A61B 5/02
[52] U.S. Cl. .................................... 128/633; 128/666; 128/687; 128/700
[58] Field of Search ............................... 128/632–633, 128/637, 668, 670, 687–690, 696, 700, 706, 708, 664–667

[56] References Cited

U.S. PATENT DOCUMENTS

| | | | |
|---|---|---|---|
| Re. 27,042 | 1/1971 | Jorgensen et al. | 128/700 |
| 2,827,040 | 3/1958 | Gilford . | |
| 2,933,081 | 4/1960 | Passannante . | |
| 3,318,303 | 5/1967 | Hammacher | 128/687 X |

(List continued on next page.)

FOREIGN PATENT DOCUMENTS

| | | |
|---|---|---|
| 102816 | 3/1984 | European Pat. Off. . |
| 0104771 | 4/1984 | European Pat. Off. . |
| 104772 | 4/1984 | European Pat. Off. . |
| 2089999 | 6/1982 | United Kingdom . |

OTHER PUBLICATIONS

Schotz et al., "The Ear Oximeter as a Circulating Monitor," Anesthesiology, vol. 19, p. 386 (1958).

Cohen et al., "Self-Balancing System for Medical and Physiological Instrumentation," IEEE Trans. Bio-Med. Eng., vol. BME-18, p. 66, (1971).
Goodlin, "Interpartum fetal heart rate responses and plethysmo-graphic pulse," Amer. J. Obstet. Gynec., vol. 110, p. 210 (1971).
Goodlin et al., "Systolic Time Intervals in the Fetus and Neonate," Obstetrics and Gynecology, vol. 34, p. 295 (Feb. 1972).
Goodlin, Care for the Fetus, p. 101 (Masson, 1979).
Huch et al., "Continuous $PO_2$ and Heart Rate Recording in the Human Newborn"; Advances in Experimental Medicine and Biology pp. 737–745 (1975).

Primary Examiner—Edward M. Coren
Assistant Examiner—Angela D. Sykes
Attorney, Agent, or Firm—Robert M. Isackson

[57] ABSTRACT

A method and apparatus for measuring and correlating a patient's heart activity with optical detection of the patient's blood flow. The method and apparatus permit more accurate determination of blood flow characteristics such as oxygen saturation and pulse rate. In a preferred embodiment, the heart activity is detected by monitoring the patient's EKG waveform, and the blood flow is detected by a non-invasive pulse oximeter. The occurrence of the R wave portion of the EKG signal is detected and the time delay by which an arterial pulse follows the R wave is determined to establish a time window in which an arterial is to be expected. The established time window provides the oximeter with a parameter enabling the oximeter to analyze the blood flow only when it is likely to present an arterial blood pulse for waveform analysis. The invention also includes adjusting the polarity of the detected EKG signal to have a preselected uniform upgoing or downgoing polarity.

28 Claims, 15 Drawing Sheets

U.S. PATENT DOCUMENTS

| | | | |
|---|---|---|---|
| 3,412,729 | 11/1968 | Smith, Jr. . | |
| 3,520,295 | 7/1970 | Kelly | 128/708 |
| 3,590,811 | 7/1971 | Harris . | |
| 3,608,545 | 9/1971 | Novack et al. | 128/700 |
| 3,618,592 | 11/1971 | Stewart . | |
| 3,651,806 | 3/1972 | Hirshberg . | |
| 3,658,060 | 4/1972 | Eklof . | |
| 3,704,706 | 12/1972 | Herczfeld et al. . | |
| 3,734,086 | 5/1973 | Phelps, Sr. . | |
| 3,742,938 | 7/1973 | Stern | 128/687 |
| 3,773,033 | 11/1973 | Rodbard et al. . | |
| 3,948,248 | 4/1976 | Zuckerman et al. . | |
| 3,994,284 | 11/1976 | Voelker . | |
| 3,994,285 | 11/1976 | Doll . | |
| 3,998,550 | 12/1976 | Konishi et al. | 356/39 |
| 4,000,461 | 12/1976 | Barber et al. | 324/102 |
| 4,023,563 | 5/1977 | Reynolds et al. . | |
| 4,023,564 | 5/1977 | Valiguette et al. | 128/206 A |
| 4,030,485 | 6/1977 | Warner . | |
| 4,036,211 | 7/1977 | Veth et al. . | |
| 4,053,911 | 10/1977 | Hudspeth et al. | 364/415 |
| 4,063,551 | 12/1977 | Sweeney . | |
| 4,086,915 | 5/1978 | Kofsky | 128/22 |
| 4,154,230 | 5/1979 | Lee | 128/661 |
| 4,181,134 | 1/1980 | Mason et al. | 128/689 |
| 4,216,779 | 8/1980 | Squires et al. | 128/682 |
| 4,266,554 | 5/1981 | Hamaguri | 128/633 |
| 4,325,384 | 4/1982 | Blaser et al. | 128/696 |
| 4,353,998 | 12/1982 | Sawa | 128/633 |
| 4,402,325 | 6/1983 | Sawa | 128/666 |
| 4,406,658 | 9/1983 | Lattin et al. | 128/802 X |
| 4,407,290 | 10/1983 | Wilber | 128/633 |
| 4,422,458 | 12/1983 | Kravath | 128/671 |
| 4,425,921 | 1/1984 | Fujisaki et al. | 128/700 |
| 4,425,922 | 1/1984 | Conti et al. | 128/691 |
| 4,440,176 | 4/1984 | Miodownik | 128/708 |
| 4,446,868 | 5/1984 | Aronson | 128/708 |
| 4,450,838 | 5/1984 | Miodownik | 128/204.23 |
| 4,545,387 | 10/1985 | Balique | 128/666 X |
| 4,573,478 | 3/1986 | Arnold et al. | 128/670 |
| 4,577,639 | 3/1986 | Simon et al. | 128/709 |
| 4,586,513 | 6/1986 | Hamaguri | 128/633 |
| 4,589,420 | 5/1986 | Adams et al. | 128/702 |
| 4,617,937 | 10/1986 | Peel et al. | 128/686 |

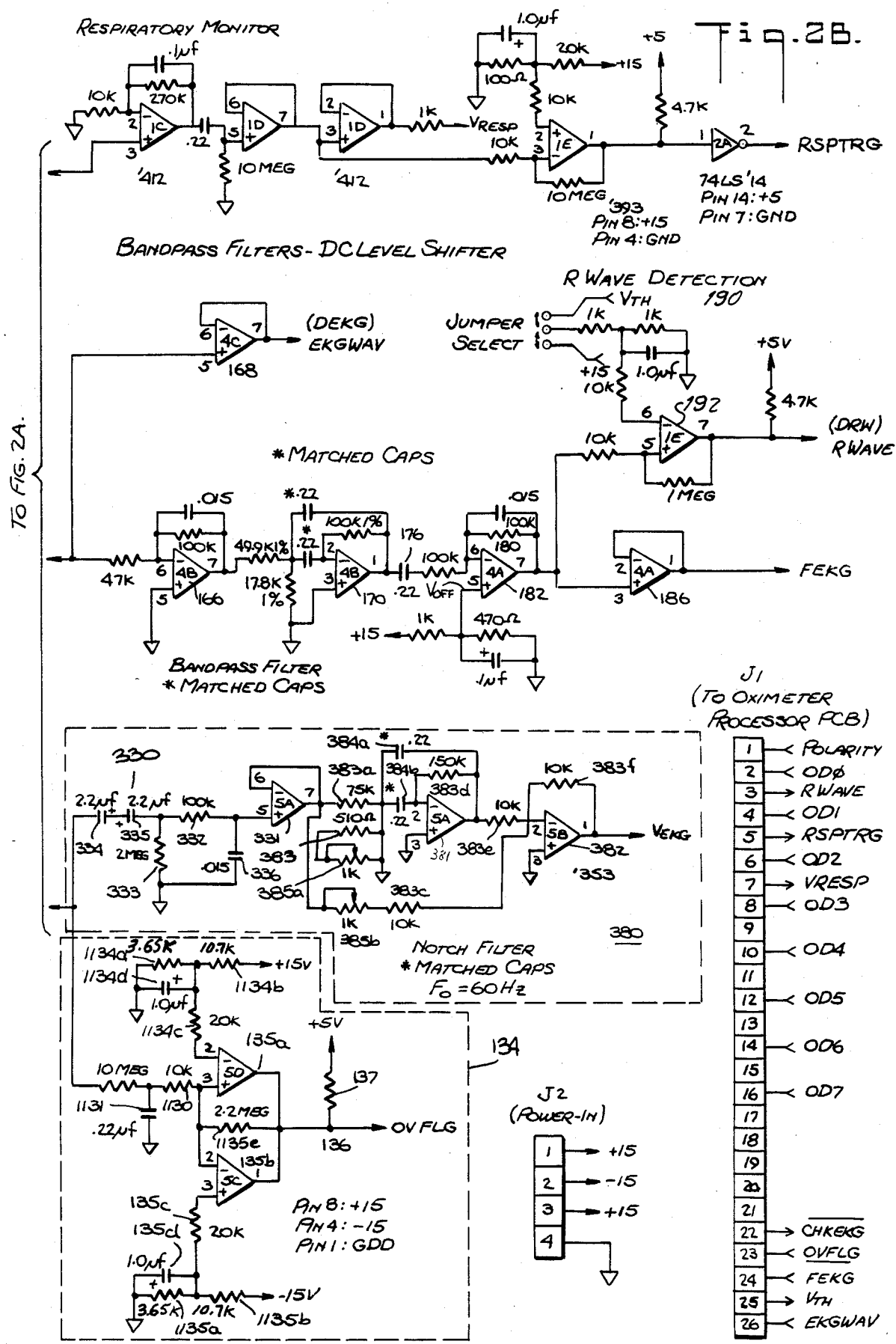

Fig. 3.
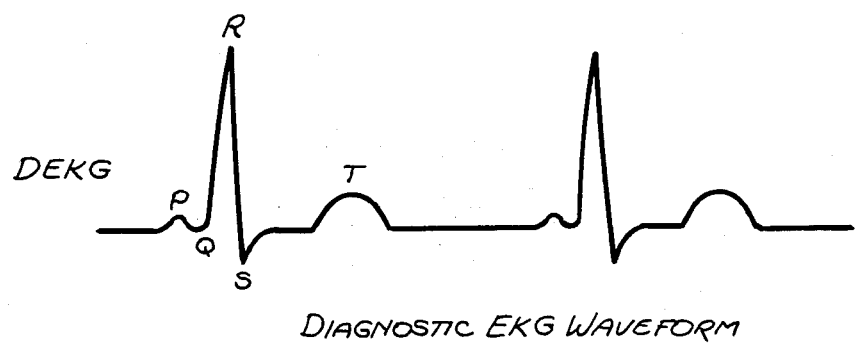
DIAGNOSTIC EKG WAVEFORM
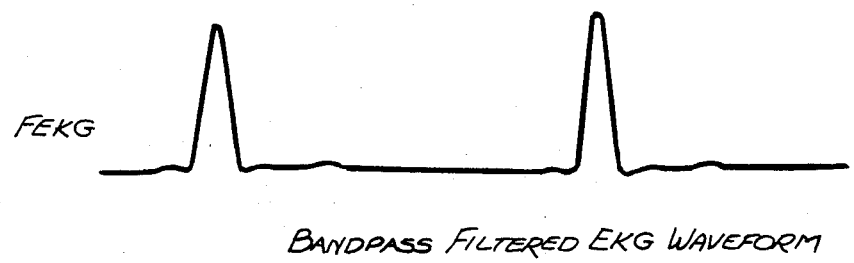
BANDPASS FILTERED EKG WAVEFORM
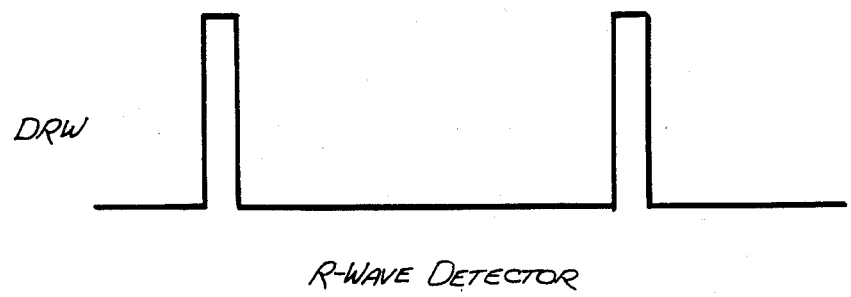
R-WAVE DETECTOR

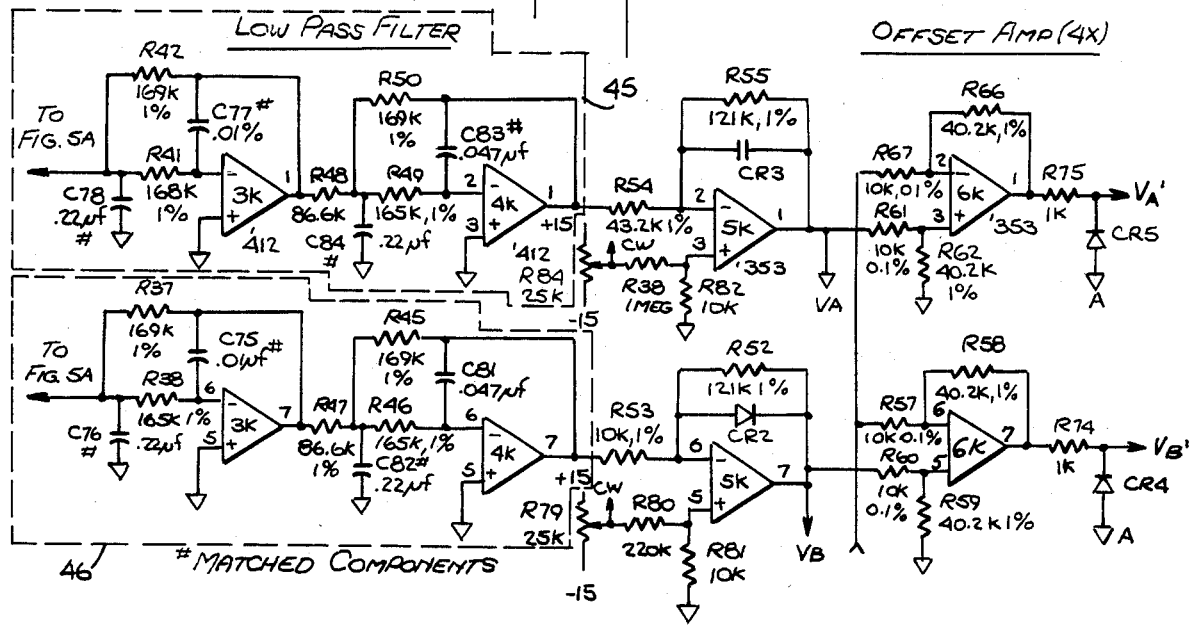
Fig. 5B.
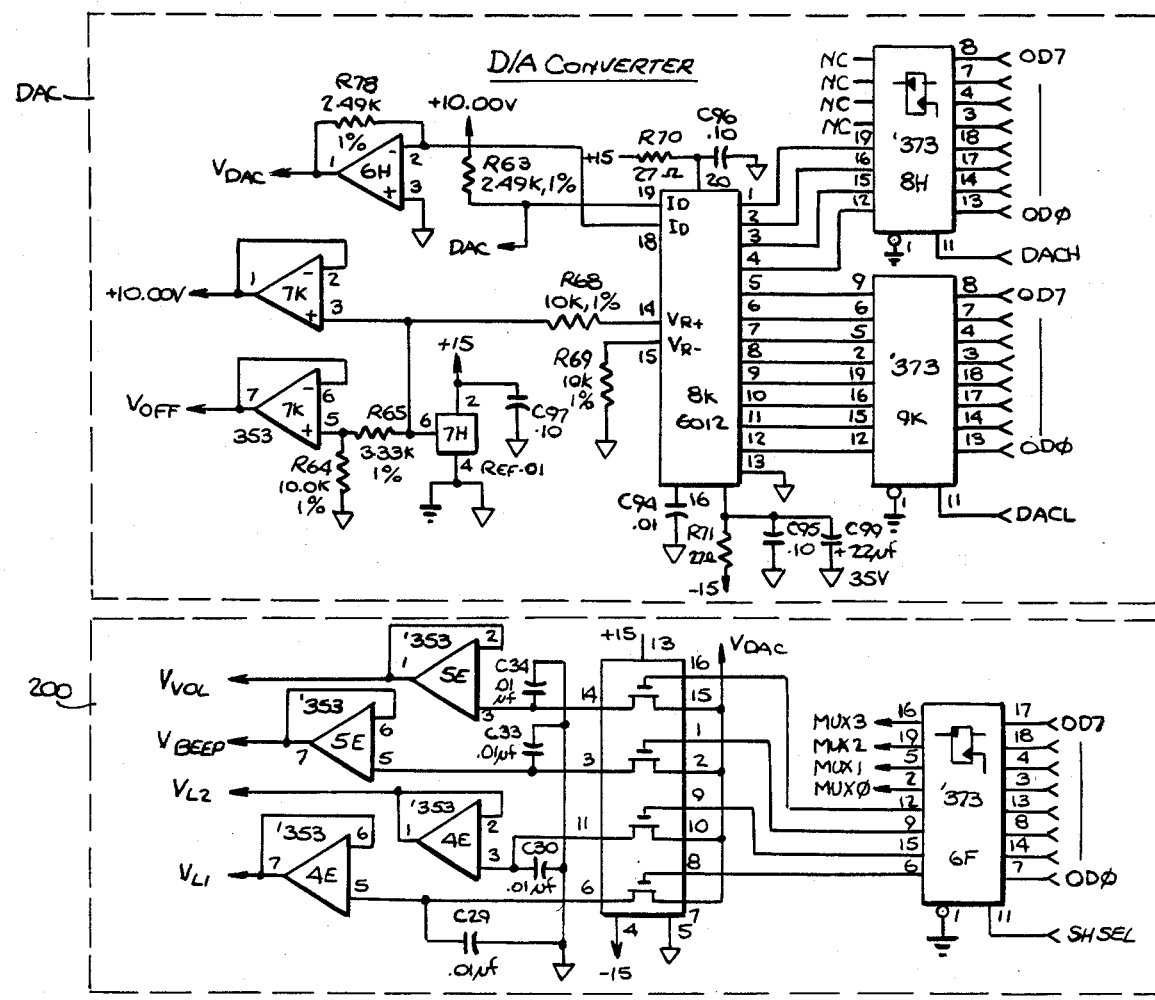

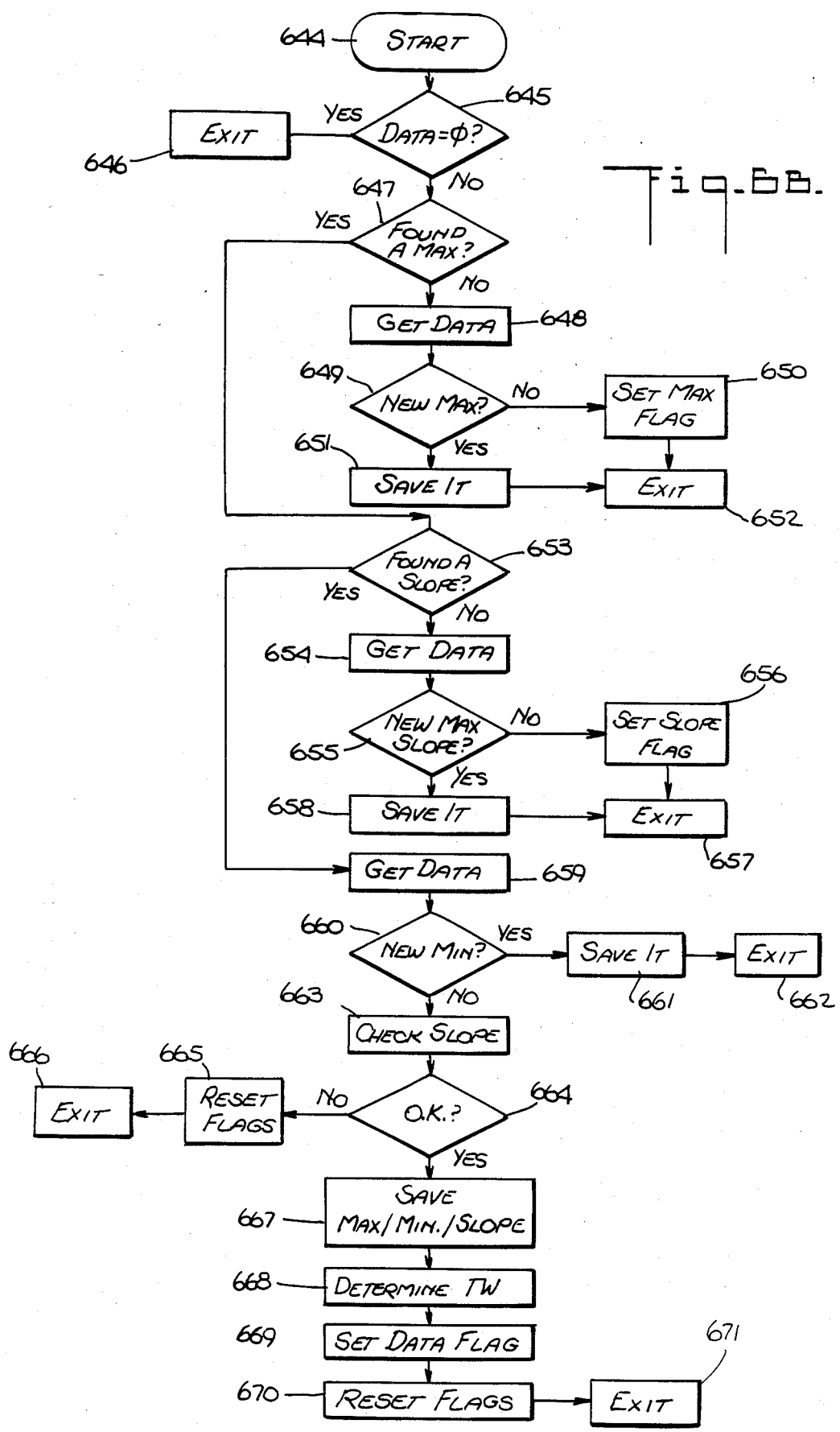

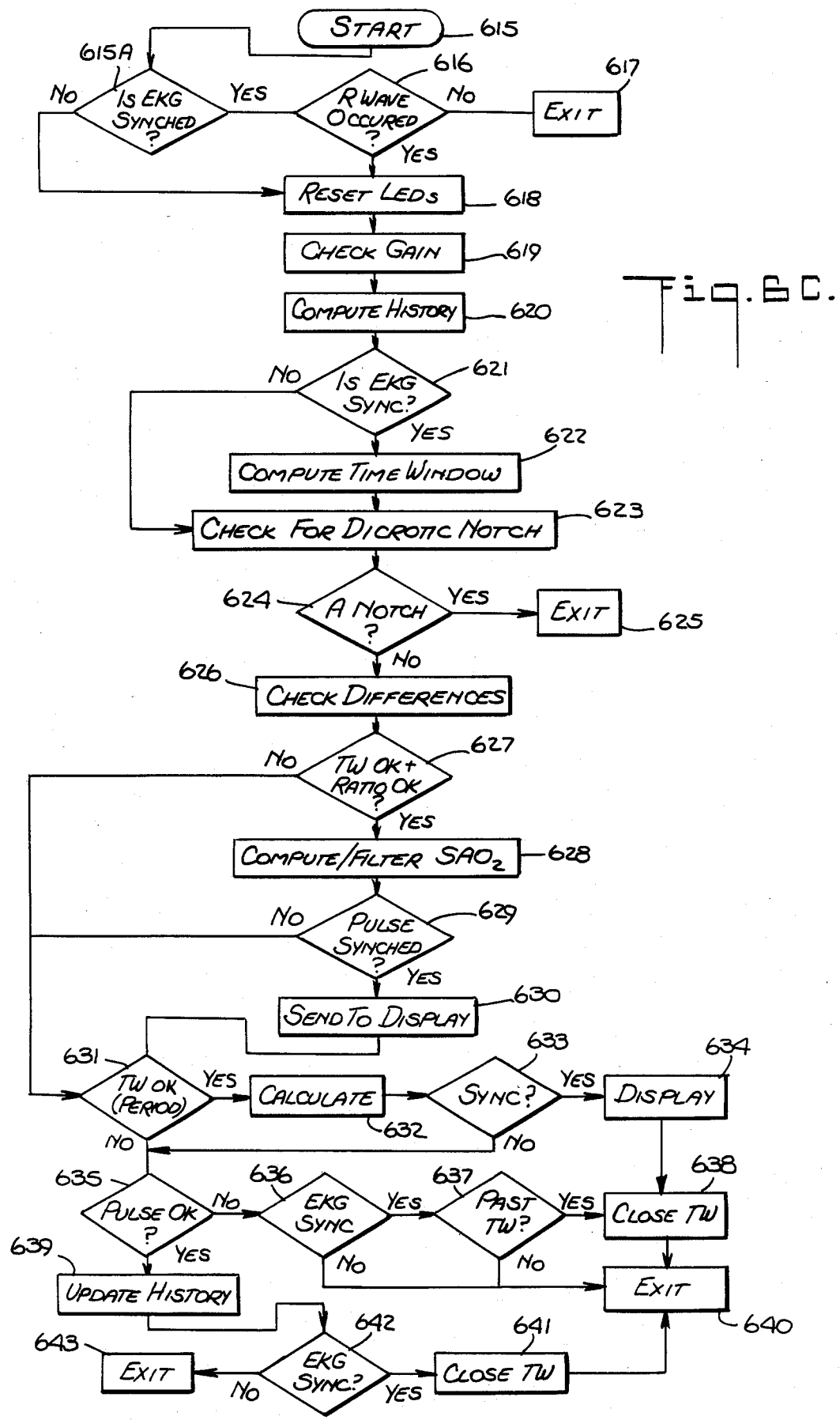

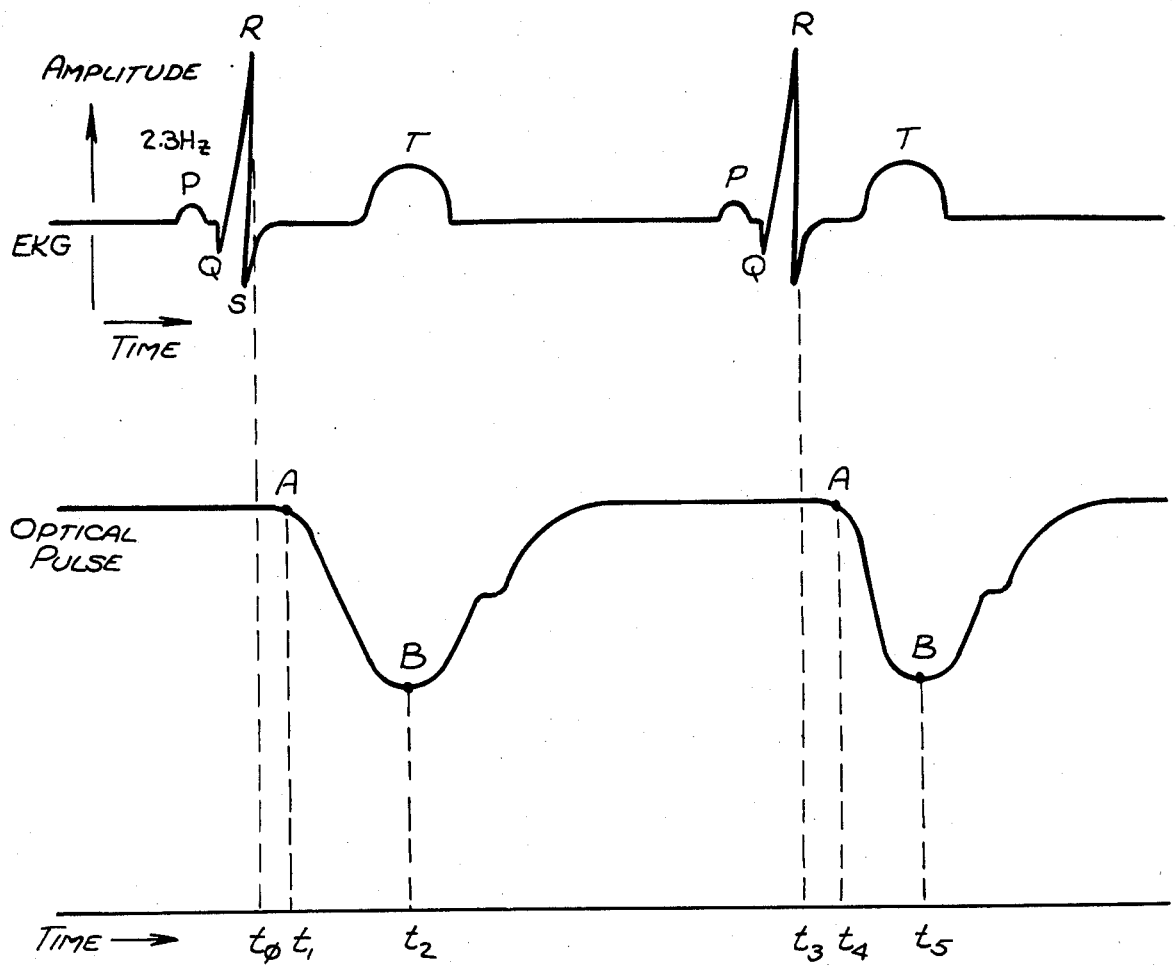

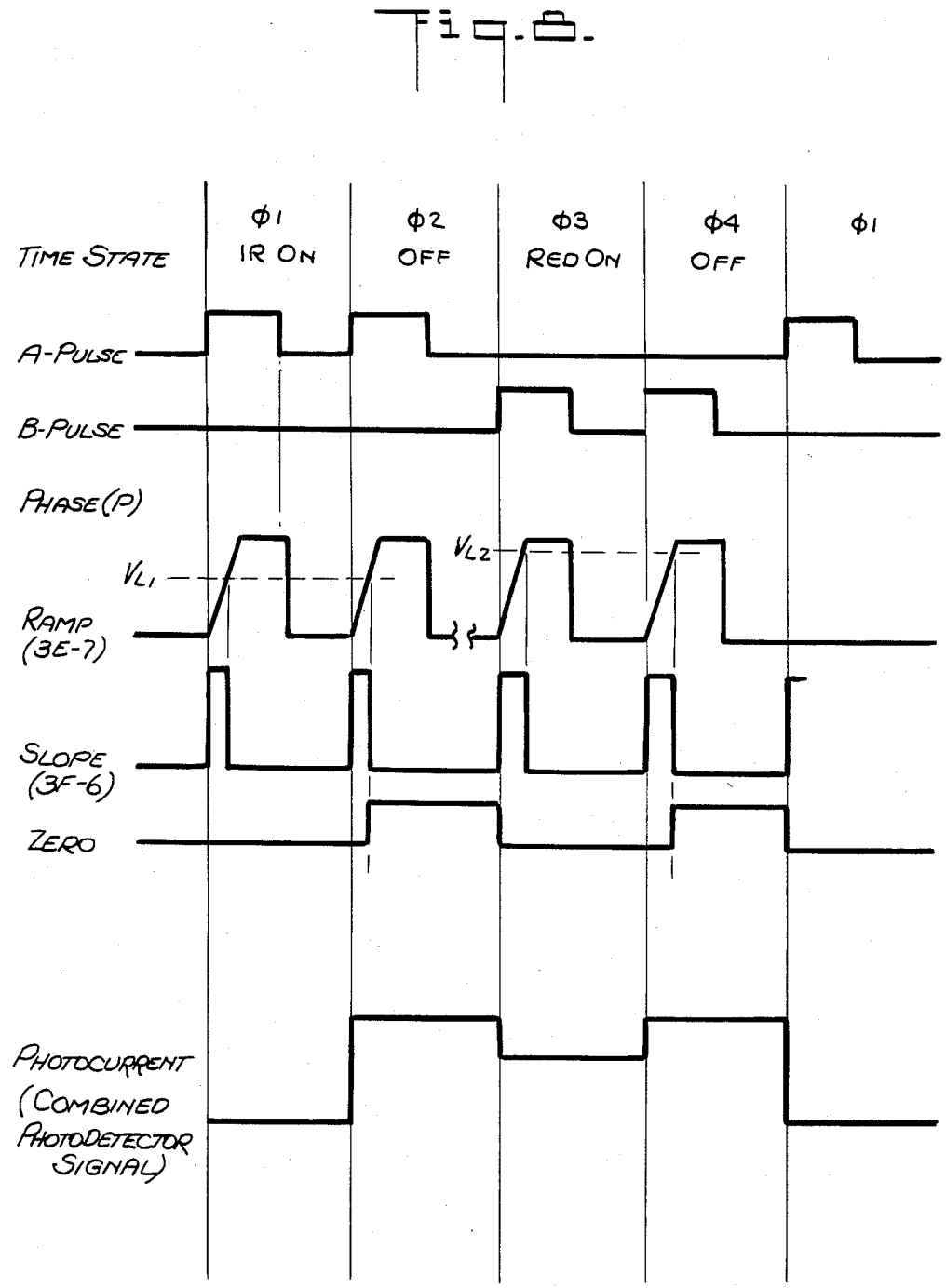

METHOD AND APPARATUS FOR DETECTING OPTICAL PULSES

CROSS REFERENCE TO RELATED APPLICATIONS

This application is a continuation application of co-pending and commonly assigned pending application Ser. No. 718,525 filed Apr. 1, 1985 by David E. Goodman and James E. Corenman entitled IMPROVED METHOD AND APPARATUS FOR DETECTING OPTICAL PULSES.

This invention relates to non-invasive pulse oximetry and specifically to an improved method and apparatus for photoelectric determination of blood constituents. A 123 page computer program is appended as a part of this application.

BACKGROUND OF THE INVENTION

Non-invasive photoelectric pulse oximetry has been previously described in U.S. Pat. No. 4,407,290, U.S. Pat. No. 4,266,554, U.S. Pat. No. 4,086,915, U.S. Pat. No. 3,998,550, U.S. Pat. No. 3,704,706, European patent application Ser. No. 102,816 published Mar. 13, 1984, European patent application No. 104,772 published Apr. 4, 1984, and European patent application No. 104,771 published Apr. 4, 1984. Pulse oximeters are commercially available from Nellcor Incorporated, Hayward, Calif., and are known as, for example, Pulse Oximeter Model N-100.

Pulse oximeters typically measure and display various blood flow characteristics including but not limited to blood oxygen saturation of hemoglobin in arterial blood, volume of individual blood pulsations supplying the flesh, and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption. For example, the Nellcor N-100 Pulse Oximeter measures oxygen saturation of hemoglobin using two light emitting diodes ("LED's"), one having a discrete frequency of about 660 nanometers in the red light range and the other having a discrete frequency of about 925 nanometers in the infrared range. The two LED's are illuminated alternately with a four-state clock so that the incident light will pass through a fingertip and the detected or transmitted light will be detected by a single photodetector. The clock uses a high strobing rate, e.g., two thousand cycles per second, to be easily distinguished from other light sources. The photodetector current changes in response to both red and infrared transmitted light, in sequence, and is then amplified and separated by a two-channel synchronous detector—one channel for processing the red light waveform and the other channel for processing the infrared light waveform. The separated signals are filtered to remove the strobing frequency, electrical noise, and ambient noise and then digitized by an analog to digital converter ("ADC"). As used herein, incident light or transmitted light refers to light generated by the LED or other light source, as distinguished from ambient or environmental light.

The light source intensity may be adjusted to accommodate variations among patients' skin color, flesh thickness, hair, blood, and other variants. The light transmitted is thus modulated by the variants, particularly the arterial blood pulse or pulsatile component, and is referred to as the optical signal. The digital representation of the optical signal is referred to as the digital optical signal. The portion of the digital optical signal that refers to the pulsatile component is labeled the optical pulse.

The digital optical signal is processed by the microprocessor of the Nellcor N-100 Pulse Oximeter in order to identify individual optical pulses and to compute the oxygen saturation from the ratio of maximum and minimum pulse levels as seen by the red wavelength compared to the pulse seen by the infrared wavelength.

Several alternate methods of processing and interpreting optical signal data have been disclosed in the patents and references cited above.

A problem with non-invasive pulse oximeters is that the optically derived pulse rate may be subject to irregular variants that interfere with the detection of the blood flow characteristics including but not limited to motion artifact. Motion artifact is caused by the patient's muscle movement proximate to the oximeter sensor, for example, the patient's finger, ear or other body part to which the oximeter sensor is attached, and may cause spurious pulses that are similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A second problem exists in circumstances where the patient is in poor condition and the pulse strength is very weak. In continuously processing the optical data, it can be difficult to separate the true pulsatile component from artifact pulses and noise because of a low signal to noise ratio. Inability to reliably detect the pulsatile component in the optical signal may result in a lack of the information needed to calculate blood constituents.

It is well known that electrical heart activity occurs simultaneously with the heartbeat and can be monitored externally and characterized by the electrocardiogram ("EKG") waveform. The EKG waveform, as is known to one skilled in the art, comprises a complex waveform having several components that correspond to electrical heart activity. The QRS component relates to ventricular heart contraction. The R wave portion of the QRS component is typically the steepest wave therein, having the largest amplitude and slope, and may be used for indicating the onset of cardiovascular activity. The arterial blood pulse flows mechanically and its appearance in any part of the body typically follows the R wave of the electrical heart activity by a determinable period of time. See, e.g., Goodlin et al., "Systolic Time Intervals in the Fetus and Neonate", *Obstetrics and Gynecology*, Vol. 39, No. 2, February 1972, where it is shown that the scalp pulse of fetuses lag behind the EKG "R" wave by 0.03–0.04 second, and U.S. Pat. No. 3,734,086.

It is therefore an object of this invention to provide an improved method and apparatus for detecting the pulsatile component of the optical signal and measuring the amount of blood constituent and the pulse rate by incorporating the patient's heart activity, preferably detected electrically in the form of an EKG waveform, into the oximeter operation and thereby solve problems caused by motion artifact and low signal to noise ratio, as well as simplify and improve the operation of oximeters.

Another object of this invention is to have the oximeter analyze only those digital optical signals occurring during a period of time when the optical pulses are expected to be found and use information from that portion of the signal to calculate the amount of blood constituent. This increases the likelihood that the oximeter will process only optical waveforms that contain the pulsatile component of arterial blood, and will not process spurious pulses.

Another object of the invention is to provide for using pulse oximeters to monitor patients having irregular heartbeats by using the EKG information, particularly the R wave component, to determine when an arterial pulse is likely to occur and processing the digital optical signal waveform during that time period to make the desired measurement.

A further object of this invention is to cross correlate the pulse rate information determined by the oximeter from the digital optical signal with the heart rate determined from the EKG. The cross correlation function will allow measurement of the time relationship between the EKG and the optical pulse and is particularly advantageous when the optical signal may be weak and in the delivery room where fetal heart rate is an important and commonly monitored vital sign.

A further object of this invention is to provide for redundant measurement of the heart rate from both the optical signal and the EKG to continuously monitor the patient even if one of the signals were to be lost.

A further object of this invention is to provide a polarity compensation circuit for use with EKG detection so that the polarity of the EKG waveform can be made uniform, upgoing or downgoing, without having to adjust the leads.

SUMMARY OF THE INVENTION

This invention increases the accuracy and reliability of pulse oximeters used during surgery, life threatening medical situations, and childbirth, by measuring the patient's heart activity and correlating it with the patient's blood flow to more accurately calculate and measure vital information such as oxygen saturation and pulse rate. In one embodiment the correlation comprises using auto- and cross correlation techniques to enhance periodic information contained in each individual waveform as well as determine the time relationship of one waveform to another. In the preferred embodiment, the method comprises correlating the occurrence of cardiovascular activity with the detection of arterial pulses by measuring an EKG signal, detecting the occurrence of the R wave portion of the EKG signal, determining the time delay by which an optical pulse follows the R wave, and using the determined time delay between an R wave and the following optical blood pulse so as to evaluate arterial blood flow only when it is likely to present a true blood pulse for waveform analysis. The method also includes determining the heart rate of the patient based on the EKG signal, the optical pulse, or both.

In a preferred embodiment, the method and apparatus comprises an improvement in the use of a Model N-100 Pulse Oximeter (herein "N-100 oximeter") manufactured and sold by Nellcor Incorporated, Hayward, Calif. The improved method provides an oximeter with an additional parameter enabling the oximeter to better analyze the digital optical signal waveform of the patient. The apparatus comprises a heart activity detection device, the pulse oximeter functions of a Nellcor N-100 Pulse Oximeter, and a microprocessor system incorporating software and memory for controlling and processing the oximeter and heart activity information. Additional inputs to a multiplexer and a digital status input latch of the oximeter are provided to receive the inputs from the heart activity detection electronics. The improved oximeter processes the detected heart activity waveforms simultaneously with and independent of the optical signals, both waveforms having been converted to digital signals for signal processing by the signal processing components of the N-100 oximeter.

The heart activity parameter may be provided by conventional and nonconventional methods capable of detecting heart activity independent of peripheral arterial pulses, including but not limited to EKG signals, ultrasound, ballistocardiogram, accelerometers, nuclear magnetic resonators, electrical impedance techniques, and the like. The primary requirement of the heart activity parameter and the related circuitry is that it provide an identifiable and detectable signal in response to each heartbeat for use by the signal processing of the oximeter.

In the preferred embodiment, heart activity parameter is detected by electronic heart detection circuitry in the form of an EKG signal which is passed through an instrumentation amplifier electrically isolated from the oximeter, and system electronics to generate a variety of waveforms derived from the EKG signal. The amplifier differentially amplifies the raw EKG data, inverts and returns the common mode signal to the patient to null the patient's common mode voltage, amplifies and AC couples the signal to eliminate any DC (offset) voltage component, filters the signal to eliminate unwanted frequencies such as, for example, frequencies below 0.05 Hz, buffers, and then couples the EKG signal to the system electronics. Coupling may be effected, for example, by amplitude modulation of a carrier signal across a transformer having the appropriate circuitry, or by an optically coupled isolation barrier.

The system electronics demodulates the coupled signal, where necessary, amplifies the signal and passes it to an automatic gain control ("AGC") amplifier to maintain the EKG signal output within a desired range even though the actual EKG signal strength may vary from patient to patient or from lead location to lead location.

In the preferred embodiment, the output of the AGC amplifier is routed through a polarity compensation circuit that changes the polarity of the waveform to have a preselected upgoing or downgoing polarity, without having to switch the leads or manipulate the patient. This is advantageous in critical life threatening situations where an incorrect connection of EKG leads otherwise might not permit proper detection of a heart rate and correlation with an optical pulse, and with fetal patients where it is not desirable to apply and reapply leads.

The resultant signal, referred to as the diagnostic EKG, is an analog representation of the electrical heart activity and can be displayed on an analog device such as a cathode ray tube or a chart recorder. The diagnostic EKG is filtered to select for the R wave of the EKG waveform and AC coupled to remove the DC component. The resulting signal is the filtered EKG signal.

The filtered EKG is processed to detect when an R wave occurs so that a digital pulse may be generated and sent to the oximeter to indicate that an R wave has occurred.

The oximeter functions remain essentially unchanged, except as specified herein. The microprocessor provides a bipolar drive current for the two LED's so that a positive current pulse drives the infrared LED and a negative current pulse drives the red LED. The magnitude of the current is adjusted by the microprocessor to help account for the variants of the patient's tissue. The light emitted by the LED's is detected by a single photodetector, preferably a photodiode, which generates a current proportional to the amount of transmitted light detected. The photocurrent may be amplified by a current to voltage converter. The resulting voltage is processed by the system electronics under the control of the microprocessor, to analyze and detect arterial pulses and to develop a history as to pulse periodicity, pulse shape, and oxygen saturation. The oximeter decides whether or not to accept a detected pulse as corresponding to an arterial pulse by comparing the detected pulse against the pulse history. To be accepted, a detected pulse must meet certain predetermined criteria in accordance with a desired degree of confidence. The blood constituent measurement is then made on the basis of accepted pulses.

According to the improved method and apparatus, the EKG signals from the electronic heart detection circuitry are processed using the analog to digital conversion and digital processing circuitry of the N-100 Pulse Oximeter to determine polarity, rhythmicity, and amplitude of the EKG signals. During this determination, the microprocessor converts the diagnostic EKG, the filtered EKG signal, or both, into digital EKG signals, analyzes the digital EKG signals, determines the amplitude and the polarity of the EKG, and adjusts the AGC amplifier and the polarity compensation circuit accordingly.

In the preferred embodiment the microprocessor operates in an integrated mode in which it develops and compares information from an EKG waveform and the optical pulse signal. The microprocessor first separately measures the time period by which an optical pulse follows an R wave, averages it over several pulses, independently calculates the pulse rate for each waveform, and compares the optical and EKG pulse rates. This insures reliability of both the electrical heart and arterial blood flow waveform analyses.

Predetermined criteria for optical pulse signals may include, for example, the expected size of the pulse, when the pulse is expected to occur, and the expected ratio of the red light to infrared light of the detected optical pulse. The predetermined criteria may be preselected or established by creating a pulse history. The pulse history may comprise a number of most recent pulses, e.g., four, in a pushdown stack memory which may automatically store the data for the last four accepted detected optical pulses.

The improved oximeter uses the measured time delay between an R wave and an optical pulse to determine a time window when, following the occurrence of an R wave, the probability of finding an optical pulse corresponding to a true arterial pulse is high. The time window provides an additional criterion to be used in accepting or rejecting a detected pulse as an optical pulse. Any pulses detected that do not fall within the time window are rejected and not used to calculate the amount of blood constituent. Similarly these rejected pulses normally do not become a part of the pulse history. However, if there have been no acceptable pulses within the time window for approximately 3 pulse periods, pulses within the time window that normally would be rejected will be accepted. This may be accomplished, as discussed below, by changing the predetermined optical pulse criteria.

Adjustments may be made to the microprocessor so that, when the optical signals are of high quality and easily detected a relatively high correlation between a detected pulse and the pulse history can be required before a detected pulse is accepted as an optical pulse. This would provide measurements having a high confidence level. When the optical signals are of low quality, the degree of correlation necessary can be lessened, providing measurements having a lower confidence level. This confidence factor may be adjusted in accordance with the beat to beat variability of the optical signals or the relative strength of the optical pulse signal.

If, even with degraded criteria no acceptable optical pulse is detected within the window for a specified period, e.g., 10 seconds, the microprocessor will revert to the initialization procedure and re-establish a relationship between EKG R waves and acceptable optical pulses.

In its integrated mode, the improved oximeter can calculate the blood constituent amount from the digital optical signal detected only during the determined time window. The time window thus can be used to reduce the processing of any spurious pulses caused by motion artifact or noise so that integrating the EKG information establishes reliable measurement of oxygen saturation.

One advantage to the integrated measurement of heart activity and optical signals is that it indicates that the oximeter is detecting an optical pulse when it is expected to occur. One advantage to using EKG signals is the determinable relationship between an R wave and an arterial pulse, which can confirm the regularity or irregularity of the heart beat, and ensure, for example, that the oxygen saturation measurements are based on the pulsatile component of the blood flow and are accurate.

Another advantage is that if one of the EKG or optical signals were to fail, the oximeter can revert to a non-integrated mode, allowing independent processing of the EKG and optical signals. The non-failing signal would continue to provide certain vital information and, more importantly, indicate that the failure of the signal was not due to the patient's loss of bodily function, e.g., cardiac arrest. Thus, the improved oximeter provides for redundant measuring of the heart rate of the patient, and indicates that one of the EKG or optical signal detection devices is not working properly. In the event that the missing signal is restored, integrated operations would resume as described above.

A further advantage of the improved method and apparatus is that patients who do not have a regularly occurring heartbeat can now be reliably monitored.

The improved oximeter of this invention has improved capability to deal with arrhythmias and can detect and analyze the period of time by which an optical pulse follows an R wave and determine an appropriate time window. Then, on the occurrence of successive R waves, including irregularly occurring R waves, the determined time window is used so that the oximeter digitally processes the digital optical signal detected during the time window, develops an optical pulse history, and calculates the amount of blood constituent present. A patient having an irregular heartbeat also can be monitored, and an amount of blood constituent measured based on the actual blood pulse.

BRIEF DESCRIPTION OF THE DRAWINGS

FIGS. 2a and 2b are a circuit schematic of the EKG detection circuitry and the system electronics of this invention.

FIG. 3 is a graphical representation of the outputs of FIG. 2.

FIGS. 5a and 5b are a detailed schematic of the microprocessor analog multiplexors and digital to analog converter of FIG. 1.

FIGS. 6a, 6b, and 6c are flow charts for the EKG and optical pulse related microprocessor operation of this invention.

FIG. 7 is a graphical representation of the outputs of FIG. 1.

FIG. 8 is a graphical representation of the oximeter timing diagram.

DETAILED DESCRIPTION OF THE INVENTION

Figure 1:
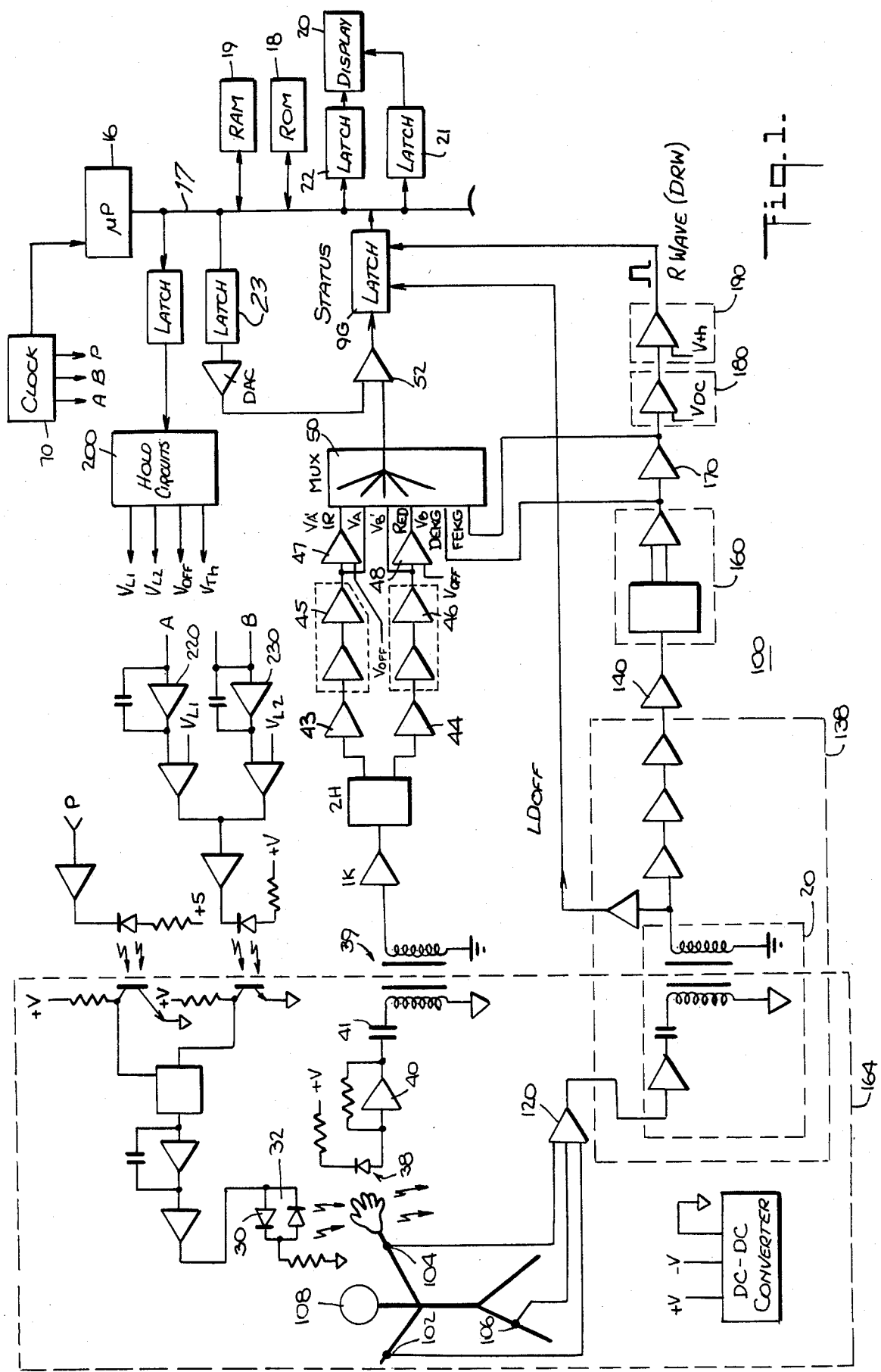
FIG. 1 is a block diagram of the improved method and apparatus of this invention.

As shown in FIG. 1, an embodiment of this invention comprises EKG detection means 100 and pulse oximeter 200. EKG detection means 100 has positive lead 102, negative lead 104, and reference lead 106, each electrically connected to patient 108. Typically, positive lead 102 is connected to the right arm, negative lead 104 is connected to the left arm and reference lead 106 is connected to the right leg. When the patient is a fetus, positive lead 102 is connected to the fetus, negative lead 104 is connected to the material vaginal canal, and reference lead 106 is connected to the maternal right leg. An alternate perinatal oximeter probe combining optical detecting means and EKG detecting leads is described in co-pending and commonly assigned U.S. patent application Ser. No. 644,051, filed Aug. 24, 1984, which disclosure is incorporated herein by reference.

EKG detection means 100 also includes preamplifier 120, coupling circuit 138, automatic gain control ("AGC") amplifier 140, polarity switch 160, bandpass filter 170, DC level shifter 180, and R wave detector 190. In operation, EKG detector means 100 produces three outputs, diagnostic EKG waveform DEKG, filtered EKG waveform FEKG, and detected R wave DRW. These outputs are shown in FIG. 3.

Figure 2A:
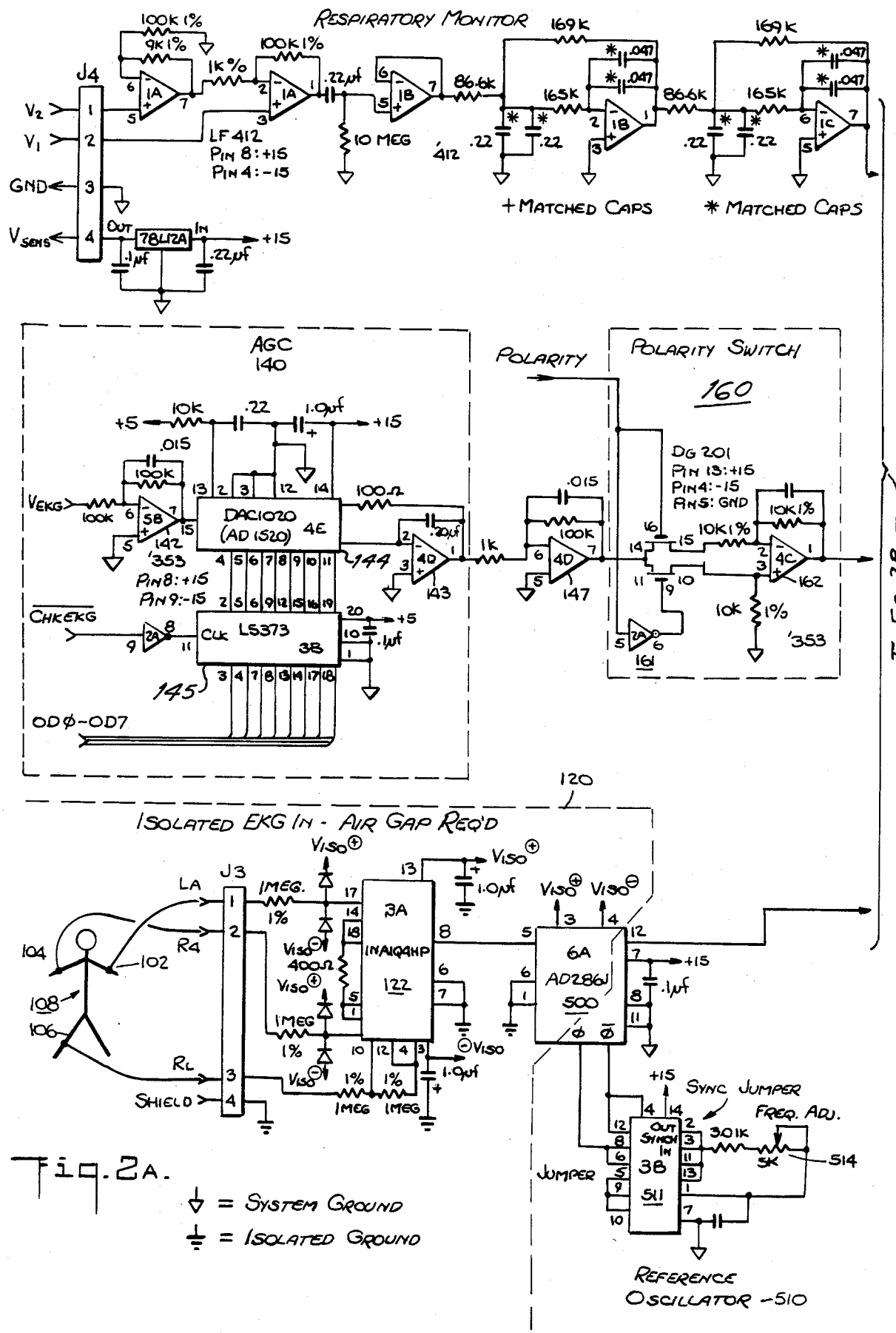

Referring to FIGS. 2a and 2b preamplifier 120 is mounted on the EKG front end printed circuit board 164 ("board 164") which is electrically isolated to protect patient 108 from strong electrical signals used to analyze and process the EKG and the optical signal waveforms. Preamplifier 120 comprises instrumentation amplifier 122, preferably a Burr-Brown INA104HP Very High Accuracy Instrumentation Amplifier, protected against high voltage inputs by diodes 124 and isolation voltages $\pm V_{iso}$. It is designed to have a gain factor of about 100.

The signal generated at negative lead 104 is input to pin 17, the signal generated at positive lead 102 is input to pin 2, common mode signal CMS is returned to the patient by reference lead 106 thus lowering the null common mode voltage of the patient, increasing rejection of common mode signals. The other pins are connected as indicated in FIGS. 2a and 2b, as known to one skilled in the art. For ease of understanding and distinguishing what input or output of the particular solid state element is being discussed, the electronic circuit drawings may be referred to herein as element "A101-16", meaning element A101 at pin 16.

The output of instrumentation amplifier 122 is passed to isolation amplifier 500, preferably model 286J, manufactured by Analog Devices, Inc. Isolation amplifier 500 provides transformer coupling of the EKG signal from isolated preamplifier 120 to the system electronics. Isolation amplifier 500 also provides isolated power for instrumentation amplifier 122. Oscillation circuit 510 consists of hex Schmitt inverter 511, resistor 512, capacitor 513, and variable resistor 514. This circuit provides a 100 kHz signal for proper operation of isolation amplifier 500.

The EKG signal, once coupled to the system electronics, travels to two different circuits. The first circuit is LDOFF detector circuit 134. LDOFF circuit 134 indicates when the EKG leads have become disconnected or inoperative and comprises parallel comparators 135a and 135b arranged in a window comparator configuration so that when the output of isolated preamplifier 120 is within + or −3.8 volts, the voltage at node 136 will be at +5 volts, realized from the pullup resistor 137. Comparator 135a has a resistor-divider network with a filter capacitor connected to the inverting input of comparator 135a consisting of resistors 1134a, b and capacitor 1134d, and is provided with a +15 volt reference voltage. This voltage is divided down to +3.8 volts and is presented to the inverting input across resistor 1134c. Similarly, comparator 135b has resistor-divider network with a filter capacitor connected to the non-inverting input of comparator 135b consisting of resistors 1135a, b and capacitor 1135d and is provided a −15 volt reference voltage. This reference voltage is divided down to −3.8 volts which is presented to the non-inverting input of comparator 135b across resistor 1135c. Comparator 135a has feedback resistor 1135e connected to the non-inverting input from the output to provide hysteresis.

The output from isolated preamplifier 120 is fed to both the inverting input of comparator 135b and the non-inverting input of comparator 135a across filter capacitor 1131 and resistor 1130. The voltage at node 136 will be at +5 volts when the leads 102 and 104 are properly connected to patient 108. If either lead 102 or 104 becomes disconnected or inoperative, the voltage at node 136 will be at 0 volts. This is the digital OVFLG which is presented to status latch 9G-13.

The EKG signal is also fed to the second circuit, a bandpass filter circuit 330 consisting of buffer amplifier 331, resistors 332-333 and capacitors 334-336 designed to selectively filter out frequencies below about 0.05 Hz and frequencies above about 100 Hz. The signal is then passed through notch filter 380 to eliminate selected signal components for example, 60 Hz or 50 Hz, primarily designed to eliminate any interference from noise sources such as from the power line. Notch filter 380 consists of amplifiers 381 and 382, resistors 383a-f, capacitors 384a-b, and variable resistors 385a and b, for tuning the filter to 60 Hz. The output of notch filter 380 is substantially identical in waveform to the output of instrumentation amplifier 122.

The output of notch filter 380, the EKG signal, is input to bandwidth limited inverting amplifier 142, and to AGC amplifier 140 which receives the bandwidth limited signal at pin 15, and an analog input, of digital to analog converter ("DAC") 144, located in the feedback loop of inverting amplifier 143. DAC 144 also receives digital input from latch 145. The digital word fed to DAC 144 is entered into latch 145 by microprocessor 16 of the oximeter. By changing the digital word fed to latch 145 in response to the amplitude of diagnostic EKG signal DEKG, microprocessor 16 can adjust the gain of AGC amplifier 140—DAC 144 is utilized as a variable resistor in the feedback loop.

Amplifier 147 provides a second level of gain to the signal, which is then fed to polarity switch 160. Polarity switch 160, preferably a DG201 Analog Switch, manufactured by Siliconix, is designed to maintain uniform polarity of the EKG signal as it is being processed by appropriately gating the signal to one of either an inverting or noninverting input of amplifier 162. Microprocessor 16 processes the filtered EKG waveform, detects polarity, and generates a voltage signal, for example, +5 volts, which is also inverted by inverter 161 to form a second voltage signal, e.g., 0.0 volts, which together to form a logical word (polarity, $\overline{polarity}$). The voltage values of the logical word causes polarity switch 160 to gate the EKG signal being processed to the appropriate input of amplifier 162 accordingly. The output of amplifier 162 is diagnostic EKG signal DEKG which is buffered by amplifier 168 and sent to the analog to digital converter ("ADC") of the pulse oximeter for conversion by microprocessor 16.

The output of amplifier 162 is amplified by amplifier 166 and also fed to bandpass filter 170, for selectively passing frequencies from about 15 to about 40 Hz having a center frequency of about 20 Hz. The filtered signal is passed through capacitor 176 for eliminating any DC voltage components that may have been introduced during prior amplifications, and is then inputted to DC level-shifter 180. DC level-shifter 180 comprises an offset voltage $V_{off}$, preferably +5 volts, being fed to the noninverting input of amplifier 182 and the filtered signal being fed to the inverting input of amplifier 182. $V_{off}$ is adjusted so that the output of amplifier 182 will be within the detectable range of the ADC of the pulse oximeter. In the preferred mode, the ADC of the pulse oximeter can only detect positive voltages, necessitating DC level-shifter 180. In circumstances where the ADC of the pulse oximeter can detect a bipolar signal having positive negative voltages, a DC level-shifter may not be required.

The output signal of amplifier 182 is filtered EKG signal FEKG, which is buffered by amplifier 186 and sent to the ADC of the pulse oximeter for waveform analysis. Output FEKG is also fed to R wave detector 190 comprising comparator 192, threshold voltage $V_{th}$, preferably +5.5 volts, and digital pulse voltage $V_{CL2}$, preferably a pull up voltage of +5 volts. When the amplitude of filtered EKG signal FEKG rises above the value of threshold voltage $V_{th}$ input to the inverting input of the comparator 192, comparator 192 generates as its output a digital pulse representing a logical 1, having an amplitude equal to $V_{CL2}$, e.g., +5 volts. At all other times, comparator 192 has an output that is a logical 0, e.g., about 0 volts. $V_{th}$ may be adjustable by the operator of the pulse oximeter so that if no R wave pulses are generated, the threshold voltage (and the confidence level) can be reduced until R wave pulses occur. Alternately, $V_{th}$ can be adjusted by the microprocessor if no R wave pulses are detected and the LDOFF signal indicates there should be R wave pulses. The output signal of R wave detector 190 is detected R wave DRW, and each pulse (+5 volts) represents the occurrence of R waves (logical 1's) in the patient's EKG waveform, as shown in FIG. 3.

Figure 4A:
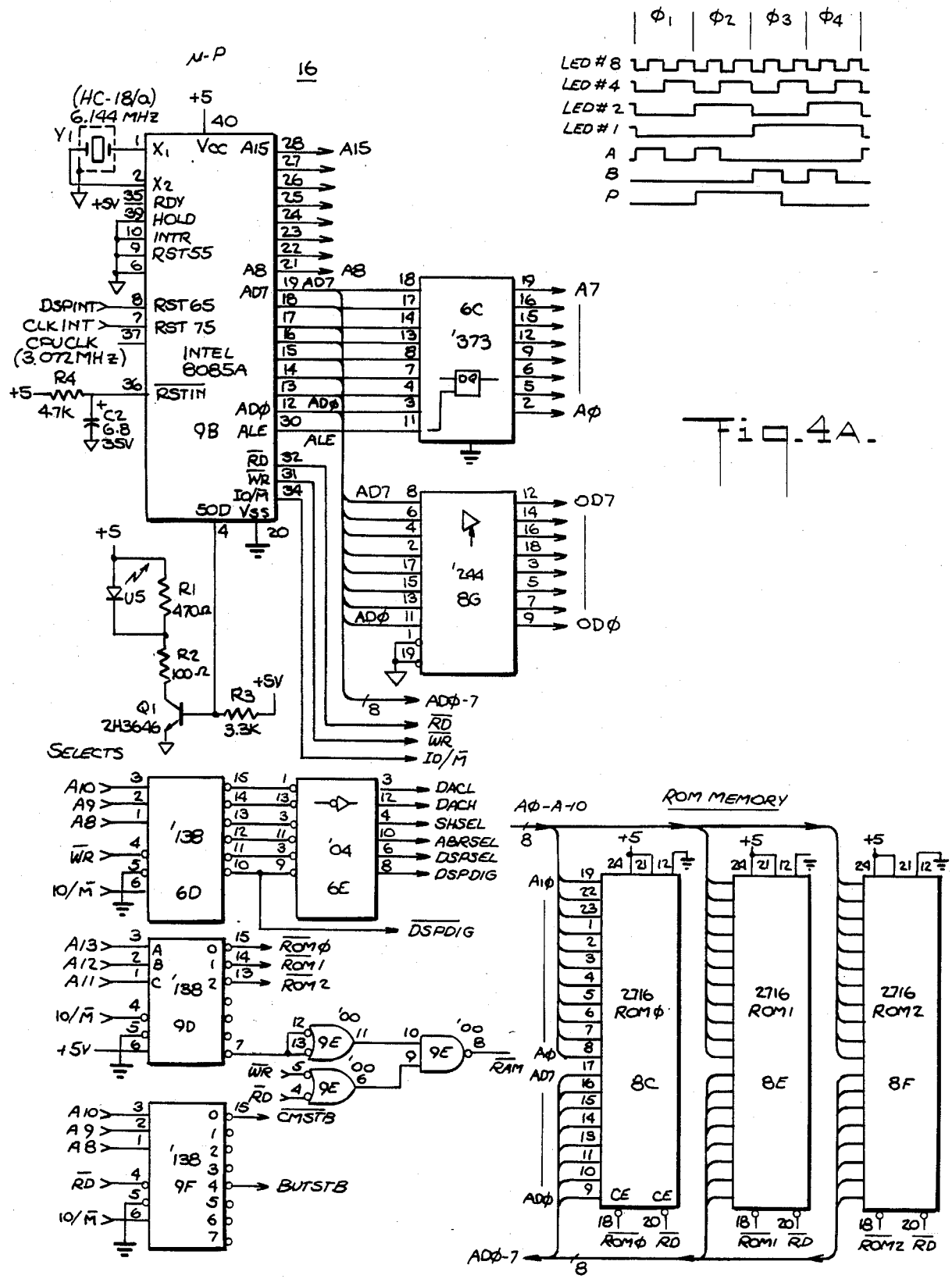
FIGS. 4a and 4b are a detailed circuit schematic of the microprocessor status input of FIG. 1.
Figure 4B:
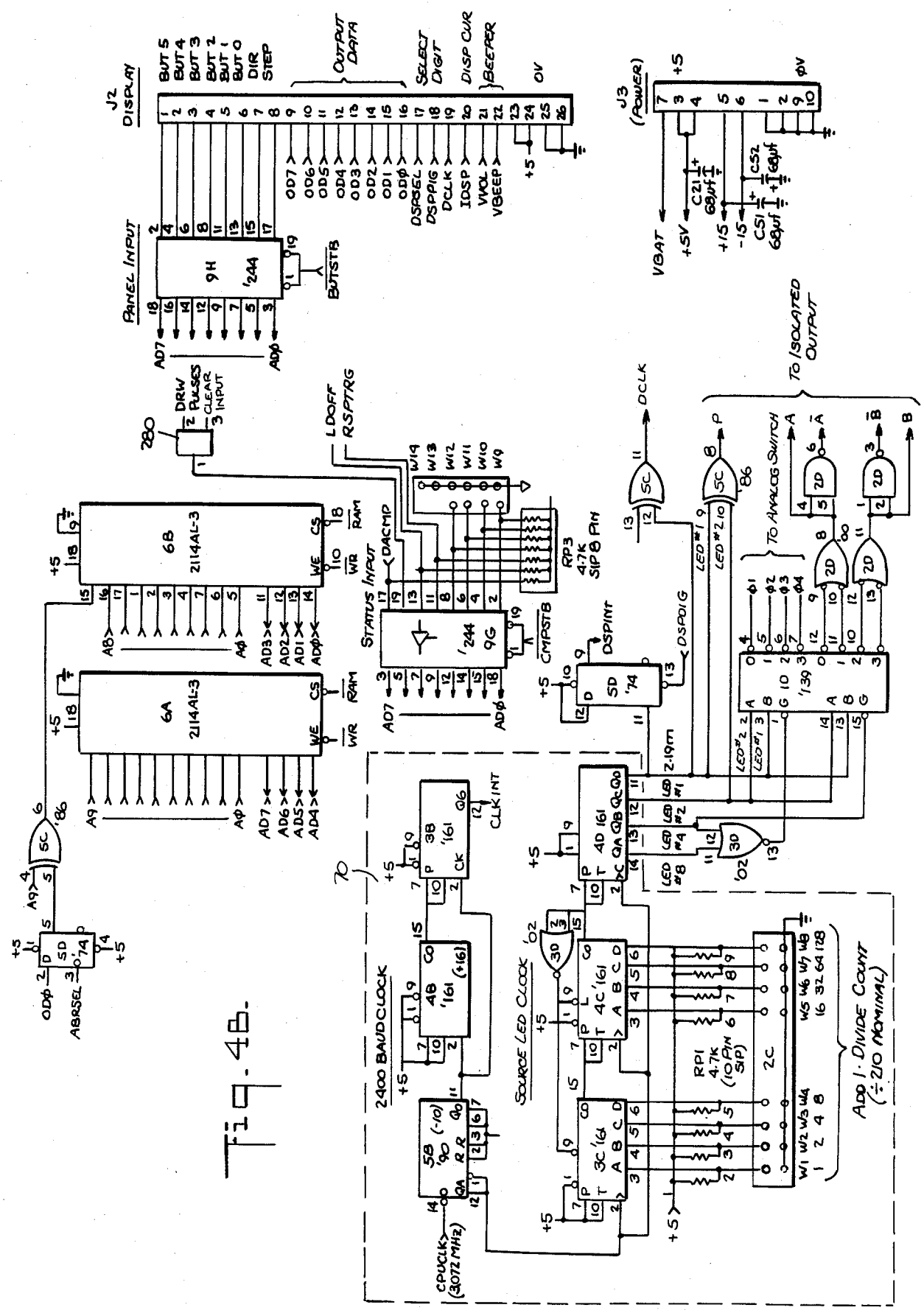

Referring to FIGS. 4a and 4b, detected R wave DRW is then fed to input 280-2 of flipflop 280. Flipflop 280 changes logical conditions from a logical 0 to a logical 1 output at output 280-1 when it detects the rising edge of an R wave pulse as the voltage of signal DRW rises from about 0 to $V_{Cl2}$, and will maintain a logical 1 output until cleared by microprocessor 16 at clear input 280-3. When cleared, flipflop 280 has a logical 0 at output 280-1. The output of flipflop 280 is fed to status input latch 9G-19, where it is stored as a logical 1, representing an R wave flag. In this manner, the presence of an R wave pulse is indicated even though the instantaneous R wave signal DRW voltage has returned to logical 0.

Microprocessor 16 frequently checks the condition of each input of status input latch 9G for information relating to signal processing sequence control. As indicated in FIGS. 6(a-c), the presence of an R wave flag causes microprocessor 16 to (1) reset output 280-1 of flipflop 280 to a logical zero output, thereby clearing the R wave flag at status input latch 9G-19 so that flipflop 280 will return to a logical 1 output when it next detects an R wave pulse, and (2) either initiate non-integrated EKG waveform analysis to determine frequency and regularity of R waves to establish the period of delay between an R wave and an optical pulse (see FIG. 7) or initiate integrated searching for an optical pulse waveform during the established time period to analyze vital signs such as oxygen saturation, pulse flow, and pulse rate.

As shown in FIG. 3, diagnostic EKG waveform DEKG comprises an analog wave train of signals having components labeled P, Q, R, S, and T. The QRS portion is representative of ventricular contraction of the heart, the occurrence of the heartbeat. For normal patients, each heartbeat generates a similar PQRST pattern. Filtered EKG waveform FEKG is also an analog signal but contains substantially only the R portion of the diagnostic waveform as the other components are filtered out. The R portion is more distinctive than the other components having a significantly greater slope and amplitude. The R wave of filtered EKG waveform FEKG corresponds to the R wave portion of diagnostic EKG waveform DEKG, and detected R wave DRW contains a step or digital R pulse waveform that corresponds to the R wave portion of diagnostic EKG waveform DEKG.

The arterial blood pulse detection circuitry is the same as that found in the N-100 Pulse Oximeter manufactured and sold by Nellcor Incorporated, Hayward, Calif.

Referring to FIGS. 1, 4a, 4b, and 8, pulse oximetry occurs as follows. Clock 70 has a duty cycle of four segments $\phi 1$, $\phi 2$, $\phi 3$, $\phi 4$ that are sequential. Clock 70 is connected to microprocessor 16. Segment $\phi 1$ turns on LED 30, segment $\phi 2$ turns off LED 30, segment $\phi 3$ turns on LED 32 and segment $\phi 4$ turns off LED 32. The LED's are strobed in sequence so that only one LED is transmitting at a time. The LED's are turned off to allow the photoelectric detector to return to a quiescent condition to measure ambient environmental light levels. As clock 70 operates through its duty cycle, the light transmitted through the tissue of patient 108 is received by photodetector 38. Clock 70 has three signal outputs A, B and P. Outputs A and B are input to a conventional pulse width modulation circuit to couple the pulse widths from the system electronics to board 164, and to establish the desired LED intensities for the LEDs 30 and 32. The reference intensities are established by microprocessor 16 which generates intensity voltage $V_{L1}$ for infrared LED 30 and intensity voltage $V_{L2}$ for red LED 32. These reference voltages are adjusted as described elsewhere herein, and form a part of the output of hold circuit 200.

Figure 5A:
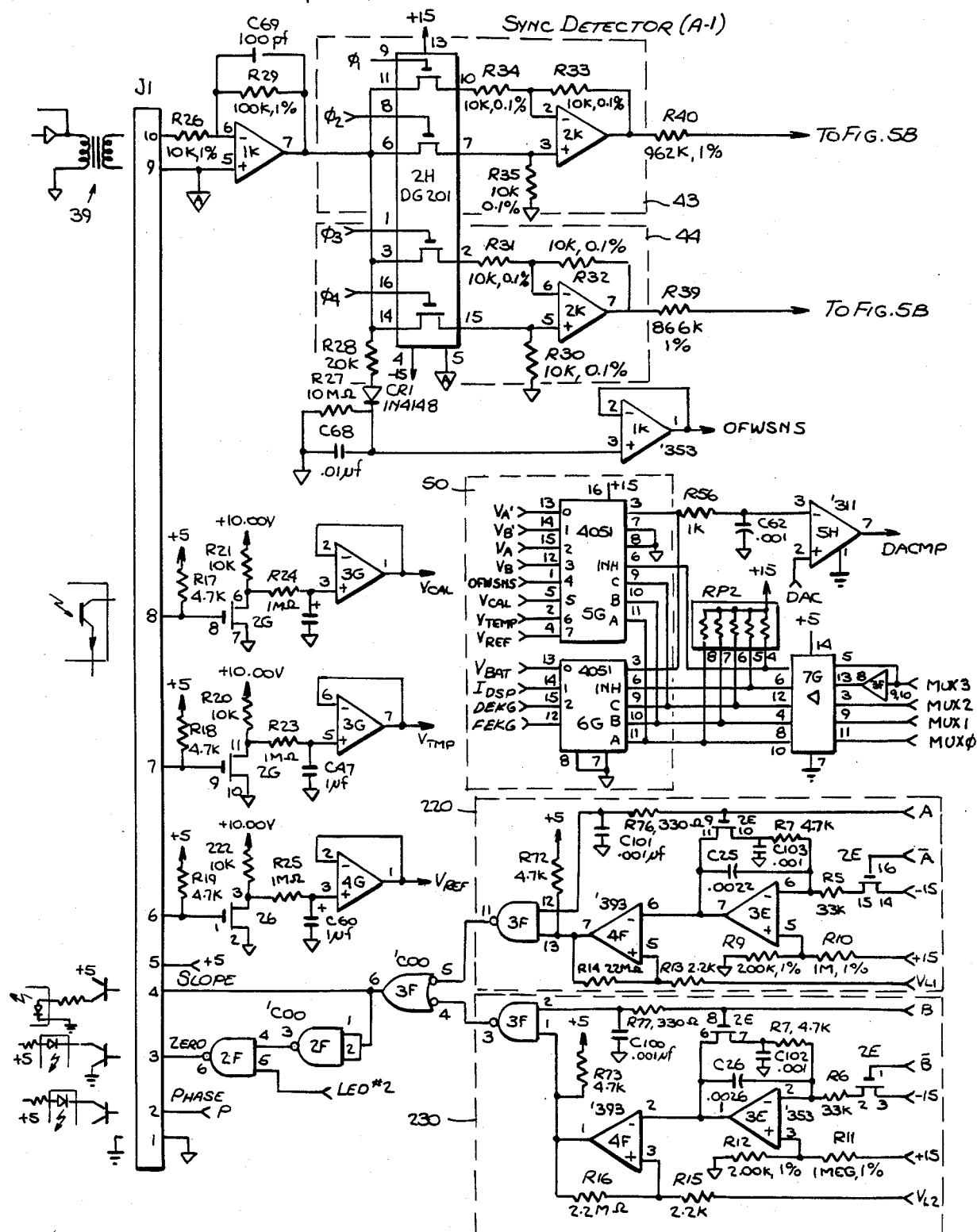

Referring to FIG. 1 and FIGS. 5a and 5b parallel pulse width modulation circuits 220 and 230 are shown. Circuit 220 has as inputs A, $\bar{A}$, −15 volts, +15 volts, and $V_{L1}$. Matching amplifiers 3E are used with the same resistor, gates, and capacitor networks shown as ramping generators to provide the waveform labeled "ramp" in FIG. 8. When A is a logical 1, gate 2E will open circuit, the −15 volt supply, otherwise connected to inverting input 3E-6 and the feedback loop comprising resistors R5 and R7 and capacitors C25 and C103, will be made conductive by the closing of gate 2E-9. This condition will cause the amplifier output to ramp from 0 volts to +15 volts as shown in FIG. 8 labeled ramp. When A is a logical 0, or at about 0 volts, gate 2E-16 is closed and a −15 volt supply is input to amplifier 3E at 3E-6, and feedback loop resistor R7 is open circuited by gate 2E-9 so that output 3E-7 will be and maintained at about 0 volts. During the time A is a logical 1, signal B is a logical 0. Because pulse width modulation circuit 230 works the same as circuit 220, ramping output 3E-1 will be at about 0 volts, except when signal B is a logical high when it will ramp from about 0 to +15 volts.

Outputs 3E-7 and 3E-1 are inputted to comparators 4F-6 and 4F-2, respectively. Intensity voltage inputs $V_{L1}$ and $V_{L2}$ L1 are fed to comparator inputs 4F-5 and 4F-3, respectively, so that when a ramping voltage exists it is compared to its respective intensity voltage. Thus, comparator output 4F-7 will reflect a logical 1 condition, about +5 volts from pull up voltage at resistor R72, for the time period when ramping voltage at 3E-7 is less than intensity voltage $V_{L1}$. When ramping voltage is greater than $V_{L1}$, output 4F-7 will change to a logical 0, creating a pulse having a width responsive to the intensity level. Similarly, comparator output 4F-1 will be a logical 1, about +5 volts, during the time period when ramp voltage 3E-1 is less than intensity voltage $V_{L2}$ from pull up voltage +5 volts across resistor R73. Thus, the outputs of 4F-7 and 4F-1 are pulses having a width representing the desired voltage intensity for $V_{L1}$ and $V_{L2}$, respectively.

The outputs of comparators 4F-7 and 4F-1 are input to NAND gate inputs 3F-13 and 3F-1, respectively. Signal A is input to NAND gate input 3F-12 and signal V is input to NAND gate input 3F-2. The outputs of NAND gates 3F-11 and 3F-3 are input to NAND gate 3F-5 and 3F-4 respectively, where the signals are effectively combined to that output 3F-6 is a digital wave form slope shown in FIG. 8.

Output 3F-6 is also input to both inputs 2F-1 and 2F-2 of NAND gate 2F, and output 2F-3 is input to NAND gate input 2F-4. Signal LED*2 is input to NAND gate input 2F-5, and output 2F-6 is digital waveform zero, shown in FIG. 8.

Figure 9A:
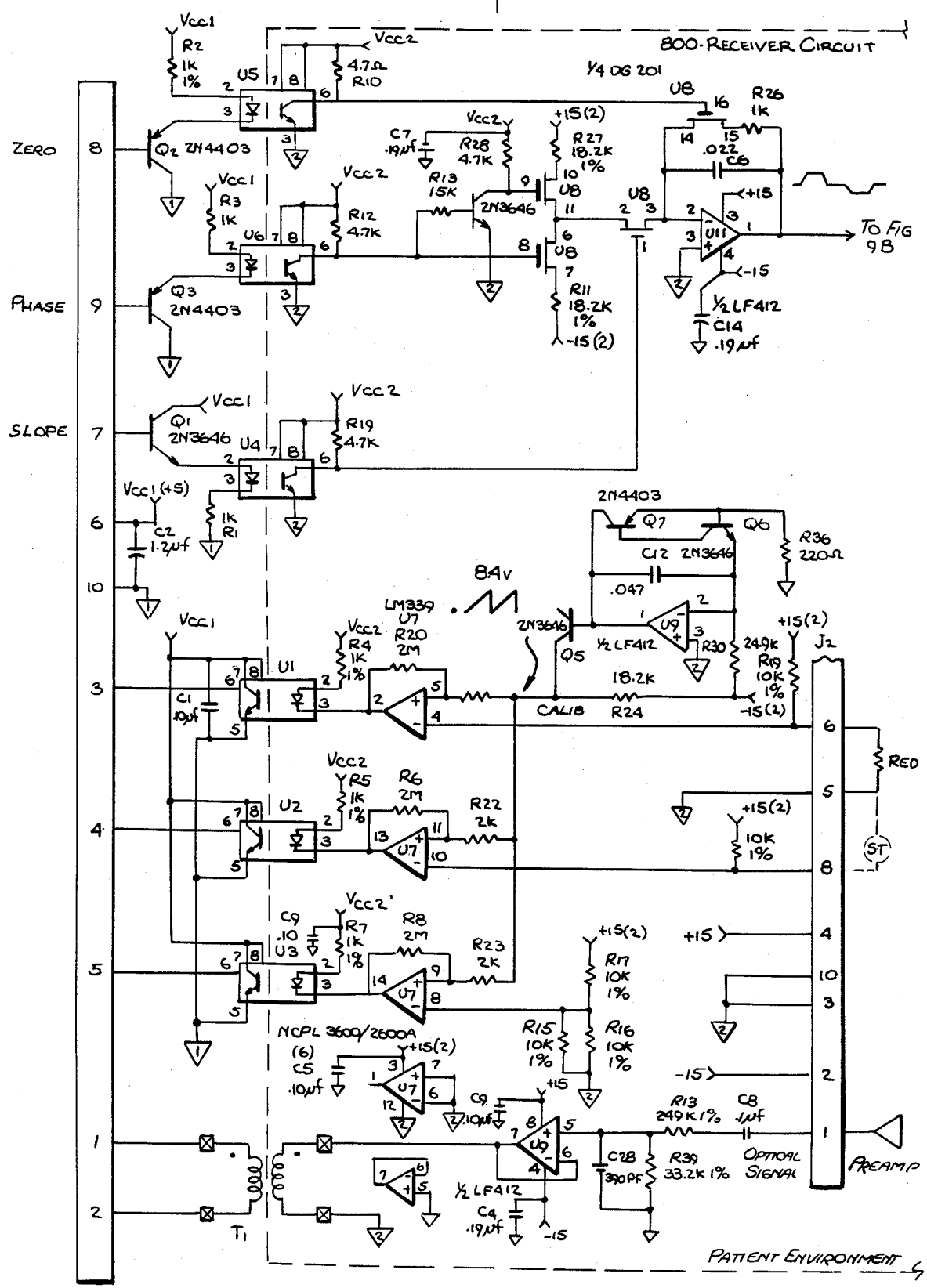
FIGS. 9a and 9b are a detailed circuit schematic of the isolated front end printed circuit board of FIG. 1.
Figure 9B:
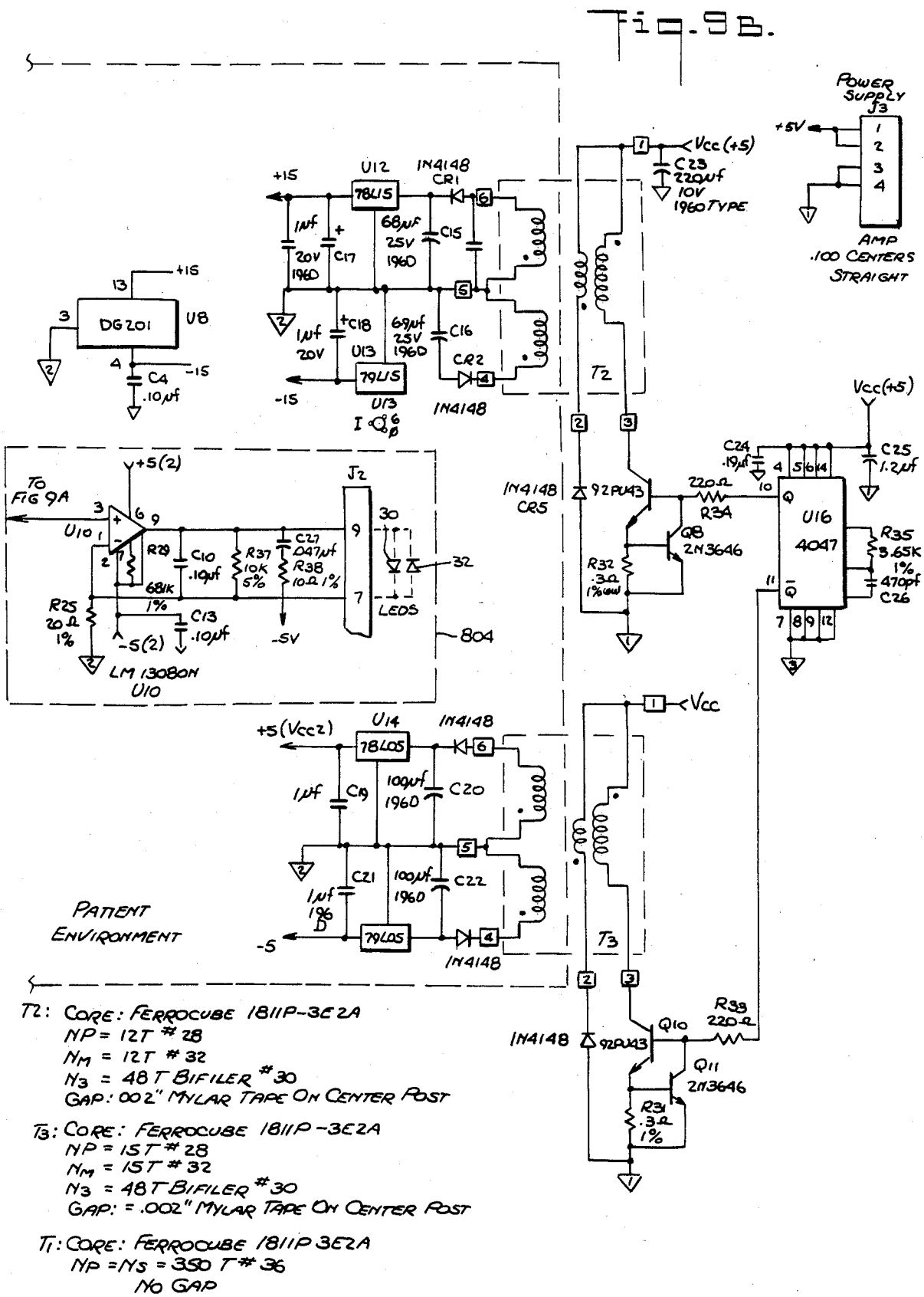

Signals "Slope", "Zero", and "Phase", the latter being generated by clock 70 and shown in FIG. 8, are coupled to board 164 by optical couplers U4, U5, and U6, respectively (shown in FIGS. 9a and 9b). The signals are input to receiver circuit 800 for decoding of the pulse width information contained in signals Slope, Zero, and Phase and for generating voltages to be used for driving infrared LED 30 and red LEd 32 in accordance with the stated duty cycle.

Referring to FIGS. 8, 9a and 9b, signal Zero controls switching gate U8-16 which alters the gain of amplifier U11. Signal Slope controls gate U8-1 which controls whether there is input to integrator amplifier U11 and associated capacitor C6. The magnitude of output U11-1 is dependent upon the width of signal Slope. The greater the width is, the longer gate U8-1 will be closed. This directly relates to how long amplifier U11 and capacitor C6 will integrate the input signal, or the peak value at output U11-1. This in turn relates to a proportional current level in amplifier circuit 804 through the selected LED resulting in the selected intensity of emitted light. Signal Zero acts to turn off the gain of amplifier U11 at selected intervals so that the voltage will decay to about zero and the current in amplifier circuit 804 will decay to about zero, thus turning off whichever LED was on and allowing it to return to its quiescent state. Signal Zero also prevents leakage current from causing a progressive error in integrator amplifier U11 and associated capacitor C6. Signal Phase controls gates U8-8 and U8-9 which selects which voltage supply, +15 volts or −15 volts will be input to gate U8-2 for through-put to integrator amplifier U11 when gate U8-1 is closed by signal Slope.

The signal at amplifier output U11-1 thus provides the waveform (shown in FIG. 8) that controls LEDs 30 and 32. LEDs 30 and 32 are connected in parallel, anode to cathode and cathode to anode at the output ports J2-9 and J2-7 of amplifier circuit 804. Amplifier circuit 804 converts the voltage output U11-1 to the LED drive current using power amplifier U10 and current sensing resistor R25. Therefore, as output U11-1 varies from positive to negative, as converted to current by circuit 804, a positive current at port J2-9 turns on LED 30, LED 32 remaining off and open circuited by the current bias, and a negative current turns on LED 32 and open circuits LED 30. Between the positive and negative currents, the LED drive current has been turned off, turning off LEDs 30 and 32, due to the effect of signal Zero.

The light emitted by LEDs 30 and 32 is passed through tissue of patient 108, preferably through a finger. Alternate preferred tissue locations include the ear lobe, nasal septum, reflected light off the forehead and the like. In situations where reflected light is used, it is preferred to place an optical barrier (not shown) between the emitting LEDs and the detecting photodetector to prevent distortion of the light content transmitted through the tissue.

Referring to FIG. 1, photodetector 38 receives all light transmitted through the tissue of patient 108 so that photodetector 38 receives infrared plus ambient light and noise during clock output $\phi 1$, ambient light and noise during clock output $\phi 2$, red plus ambient light and noise during clock output $\phi 3$ and ambient light and noise during clock output $\phi 4$. This signal ("DLS") is passed through preamplifier 40, which converts the photodetected current into a voltage at a rate of about one volt per microamp, capacitor 41, and is then coupled by transformer 39 from electrically isolated board 164 to the system electronics. After coupling to system electronics, which may itself be electrically isolated, the signal is processed by parallel circuitry for separating the red and infrared signals, in order to adjust for the different gains required to process red and infrared signals. Clock 70 outputs $\phi 1-\phi 4$ control the synchronization detector gates 2H to divide composite signals DLS into infrared light signal IRLS and red light signal RLS and direct signals IRLS and RLS to parallel amplifiers 43 and 44. Parallel synchronous detector gates 2H and parallel amplifiers 43 and 44 also act to invert the pure ambient light and noise signals and, using a slow time constant filter, add them to the adjacent LED light plus ambient light and noise signals to subtract out the ambient light and noise signal components. These filtered signals then pass through parallel low pass filters 45 and 46 to eliminate the switching frequencies and noise. Signal outputs $V_a$ and $V_b$ are sent to the ADC of the oximeter for digitization, and also sent through parallel offset amplifiers 47 and 48 for subtracting out a portion of the DC bias and amplifying the remaining voltage signals. Offset amplifiers 47, 48 increase the resolution of the AC voltage signal component for digital conversion. Outputs $V_{a'}$ and $V_{b'}$ are also sent to the ADC of the oximeter for analog to digital conversion.

Referring to FIGS. 5a and 5b, the system electronics for processing signal DLS is described in more detail. Signal DLS is coupled through transformer 39 on front end printed circuit board 164 and enters the system electronics at pin 10 of connecting strip J1. Signal DLS consists of the time-sequenced response of photodetector 38 to infrared LED 30 and red LED 32 as shown in the timing diagram (see FIG. 8 under the label "Photocurrent"). Signal DLS is amplified by one-half of dual amplifier 1K.

The output of amplifier 1K is connected to four analog switches forming switching element 2H of parallel two-channel synchronous detectors 43 and 44 which separate the pulses of infrared and red light detected by photodetector 38 and eliminate low frequency noise and DC offset voltages. As clock 70 goes through its duty cycle, during state $\phi 1$ first analog switch 2H-10 closes, coupling preamplified signal DLS through detector channel 43 and amplifier 2K-1 having a gain of about $-1$ formed by resistors R33 and R34. During state $\phi 2$, first switch 2H-10 opens and second switch 2H-7 closes so that amplifier 2K-1 has a gain of about $+1$ wherein it acts essentially as a voltage follower with resistors R34 open circuited and resistor R33 forming the feedback loop. During states $\phi 3$ and $\phi 4$ red LED 32 turns on and off and a similar switching occurs for second detector channel 44 and amplifier 2K-7. The output of detector amplifiers 2K-1 and 2K-7 will thus be active with a duty cycle of 50 percent, half of that inverting and half non-inverting. Any DC or low-frequency voltage should be cancelled by the two adjacent pulses of opposite polarity, while photodetector signal DLS, which is present in only one of the two time states, will be amplified with an effective gain of about 0.25.

The outputs of amplifiers 2K-1 and 2K-7, signals IRLS and RLS, respectively, are fed to matched low-pass filters 45 and 46 for passing only frequencies below about 10.0 Hz, having amplifiers 3K-1 and 4K-1, and 3K-7 and 4K-7, for providing a respective gain of about 4 to signals IRLS and RLS. These filters remove the switching component which is about 2 kilohertz and filter out any high frequency noise.

The signal processing means for processing the EKG signals and the optical signals includes a programmed microprocessor such as the Intel 8085 A. The basic functions of the equipment will be described for comprehension, while the improvements forming a part of this invention will be described in detail.

Referring to FIG. 1, the signal processing means comprises microprocessor 16, data bus 17, RAM 19, ROM 18, latch 23, comparator 52, analog multiplexor 50, hold circuits 200, gate 24, latch select 21, latch digit 22, and display 20, each connected to bus 17 and thereby under the control of microprocessor 16. Data bus 17 shunts digital information into and out of microprocessor 16 and each of the components. Latch select 21, latch digit 22, and display 20 all relate to a preferred numerical display of the amount of blood constituent measured, e.g., optical pulse rate and oxygen saturation.

The function of the signal processing means is to convert the analog signals from the optical signal detector and from the EKG detector, independently, to digital signals, for subsequent waveform analysis. The waveform analysis is controlled by microprocessor 16, ROM 18, and RAM 19.

FIGS. 6(a-c) and the 123 page software appendix relate to the software used by the oximeter to control the signal processing of the optical signals and the EKG detection system. The microprocessor of the oximeter evaluates the optical signal to determine the oxygen saturation and pulse rate according to the following method.

A preferred embodiment of this invention incorporates into microprocessor 16 the means for processing the EKG signals and displaying the calculated EKG pulse rate, converting the analog diagnostic EKG signal DEKG and filtered EKG signal FEKG to digital EKG signals using the same analog to digital conversion circuits used for processing the optical signals. Referring to FIGS. 5a and 5b, analog multiplexer 50 is the input to the ADC of the pulse oximeter, and comprises two analog multiplexors 5G and 6G. Optical pulse signals $V_{a'}$, $V_{b'}$, $V_a$, and $V_b$ are connected to pins 13, 14, 15 and 12 of multiplexer 5G. According to the improved apparatus, diagnostic EKG signal DEKG is connected to pin 15 of multiplexer 6G and filtered EKG signal FEKG is connected to pin 12 of multiplexor 6G.

In order to convert any of the analog inputs to digital signals, microprocessor 16 must address the proper channel of one of analog multiplexers 5G and 6G by inputting a three bit word through bus 17 to pins 9, 10, and 11 of both multiplexers 5G, 6G. The microprocessor program is configured to allow for analog to digital conversion of the EKG signals DEKG, FEKG in addition to $V_a$, $V_b$, $V_{1'}$, and $V_{b'}$, and appropriate storage of the digital signals in RAM 19.

Referring to FIGS. 4a, 4b, 5a and 5b, microprocessor 16 converts analog signals to digital signals by selecting which input is to be converted and loading a digital word into latches 8AH and 9K. Latches 8H and 9K store the digital word presented to the inputs of digital to analog converter ("DAC") 8K, which converts the digital word to analog signal DAC. Signal DAC is fed to pin 2 of comparator 5H. The other input to comparator 5H, at pin 3, is the analog signal from multiplexer 50 selected by microprocessor 16 for conversion. When the analog signal provided by DAC 8K exceeds the analog value presented by multiplexer 50, output DACMP of comparator 5H is at logical 1. The digital word which generates the analog voltage from DAC 8K that is less than the analog voltage present at multiplexer 50 will cause output DACMP of comparator 5H to change to logical 0. Output DACMP is inputted to status latch 9G-17 shown in FIG. 4b which is sampled by microprocessor 16 at a rate of about 57 cycles per second. When the microprocessor detects a logical 0, the word stored in latches 8H and 9K of FIG. 6 represents the digital value of the analog signal and is stored by microprocessor 16 into the accessed address of RAM 19 for later processing.

In connection with EKG signal processing, as shown in the software appendix, microprocessor 16 analyzes the stored digital words and calculates an amplitude for the EKG waveform. This amplitude is used to control AGC amplifier 140 by changing the digital word fed to DAC 144 so that outputs DEKG and FEKG will fall within and be compatible with the voltage range limits of the electronic circuitry used to process the signals, without losing any of the significant information contained therein. The start up or non-integrated condition includes independent and continuous signal processing of the optical pulse to calculate and display oxygen saturation and pulse rate, and simultaneously, continuously processing EKG waveforms DEKG, FEKG, and DRW. When certain conditions exist, flags are raised at status input latch 9G and internally within microprocessor 16, indicating what operation is to follow. Referring to FIGS. 4a, 4b, 5a and 5b, microprocessor 16 regularly searches status input latch 9G at a rate of about 57 cycles per second. According to this invention, output DRW is also input to status latch 9G through flipflop 280. Thus when detected R wave DRW is a logical 1, the microprocessor detects the 1 status and based upon that status selects the next operation. That operation can be one of the following events which occur in sequence. At startup conditions, upon detecting an R wave, microprocessor 16 clears output 280-1 of flipflop 280 to logical 0, clearing status input latch at input 9G-19 relating to EKG output DRW. At this first level, microprocessor 16 begins counting time intervals, using clock 70, from the detection of an R wave pulse DRW until the occurrence of the next logical 1 at status input latch 9G. Based upon this time interval, the improved pulse oximeter displays the pulse rate. After averaging several time intervals and establishing a regular EKG pulse rate, microprocessor 16 will change to the second level of processing.

With the detection of an R wave pulse, microprocessor 16 will begin to correlate the period of time by which an optical pulse, as separately determined by microprocessor 16 analyzing the digital optical signal, follows the detected R wave pulse to establish the time window during which the optical pulse is likely to occur. During this second level, the pulse oximeter is still calculating and displaying the time period or pulse rate between detected R wave DRW pulses.

The third level of processing is reached after a time window has been established. On detecting an R wave pulse, microprocessor 16 activates the time window so that only optical signals detected within the time window, following the occurrence of a R wave pulse, will be evaluated for acceptance or rejection for use in calculating and displaying vital measurements such as oxygen saturation, pulse flow, and pulse rate. The evaluation of a detected pulse is made in conjunction with a preselected confidence factor that is associated with the quality of the optical signals. The higher the optical signal quality, the better the correlation between the recorded pulse history and a detected pulse, and the higher the confidence level. The confidence level may be set automatically by the microprocessor, or it may be adjusted by the operator of the improved oximeter. Microprocessor 16 will reject any detected pulses occurring outside a time window. A typical time window for an adult male having a fingertip oximeter probe may be about 50 milliseconds, plus or minus 10 milliseconds, after the occurrence of an R wave.

The oximeter will also reject any additional pulses detected after an optical pulse is detected within the same time window, even though the time window has not expired.

However, if an optical pulse is not found within an opened time window, microprocessor 16 will continue to search for optical pulses using the degraded criteria during the time window period for a limited number of successive detected R wave DRW pulses, e.g., 3, after which it continues to search with degraded criteria. After a specific interval, e.g., 10 seconds, without detection of an optical pulse, microprocessor 16 will revert to independent or non-integrated processing of the optical signal and the EKG signals, returning the pulse oximeter to the start up condition. Therefore, if the oximeter cannot establish or maintain a reliable correlation between the R wave and the optical pulse, the waveforms will be processed independently. Preferably there is a display to indicate that the oximeter is integrating the EKG and optical signal data and so calculating the blood constituent amount. After attaining the third level of processing, losing either the EKG or optical pulse signals will activate an alarm and return the program to the start up condition.

Figure 6A:
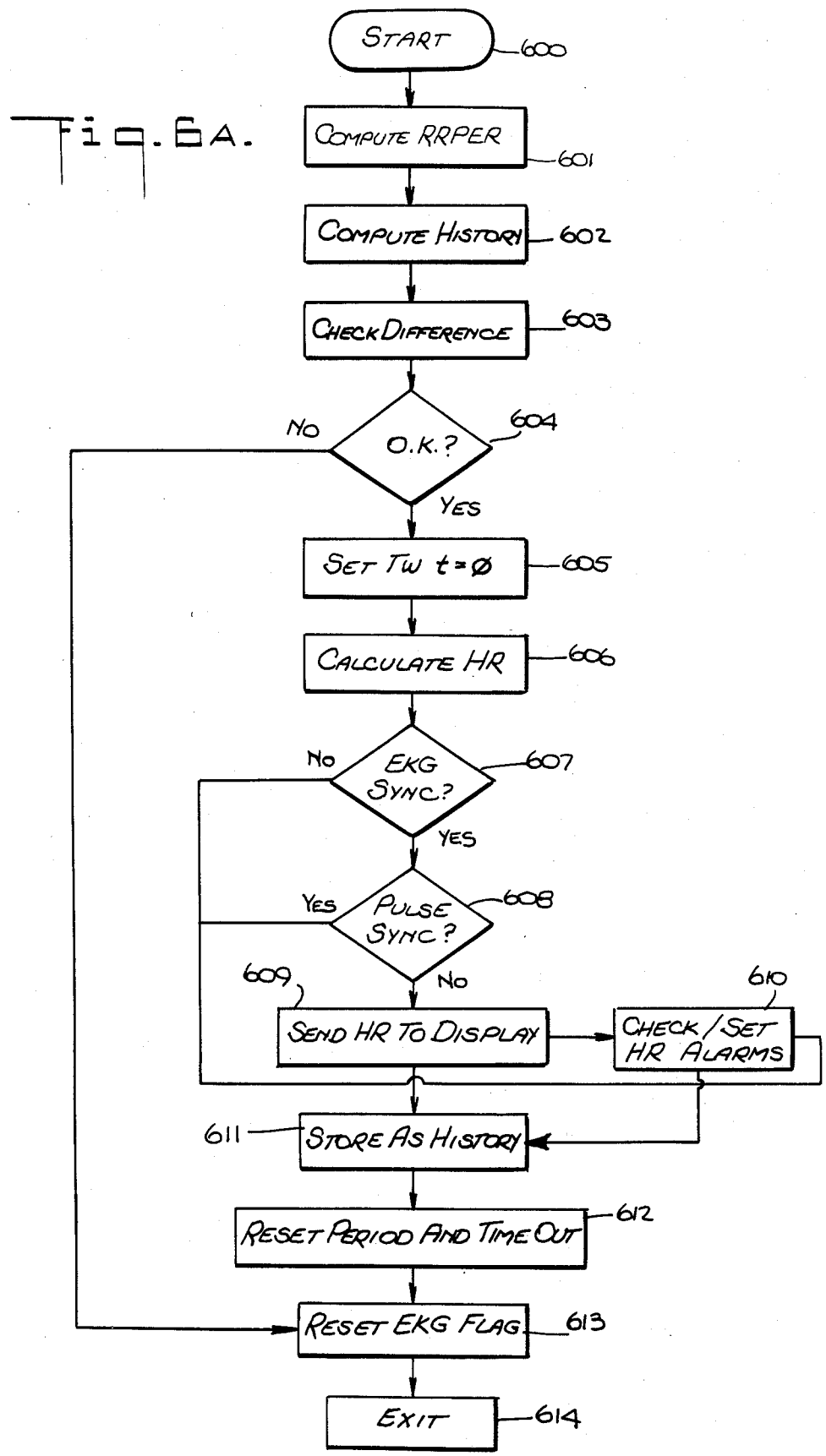

Having described the overall operation, referring to FIGS. 6a, 6b, and 6c the flow chart for the software calculations is shown and described. In FIG. 6a, the R wave determination routine begins at 600 with electrical signals received from the EKG leads and calculating the period RRPER between the last detected R wave and the presented R wave at 601. The average period HISTORY from previous R waves and the present R wave is calculated at 602 and the determined period RRPER from 601 is compared to the average period HISTORY at 603. If RRPER does not correspond to HISTORY at 604, then the routine jumps to 613 where the R wave (or EKG flag) at flip flop 280 is reset and the routine is exited to await another R wave. If RRPER does correspond to HISTORY at 604, then a timer is activated at 605 to measure the interval from the occurrence of the R wave to the occurrence of the optical pulse. At 606, output HR (EKG heart rate) is calculated based on successive R waves. At 607, the system inquires whether a series of R-R periods have been synchronized (EKG synchronization). If not synchronized, then the system checks for alarms by comparing output HR at 609, to a preselected heart rate and generating an alarm if output HR is too low. If the EKG is synchronized but the optical pulse to optical pulse series is not synchronized at 608, then output HR is sent to display at 609 and then checked for alarms at 610.

However, if the optical pulse is synchronized at 608, then the system just checks for alarms at 610. Only if the EKG is synchronized and the optical pulse is not synchronized, and if the R wave looks like a valid R wave by comparison with HISTORY, then HISTORY is updated using the new R wave at 611. After updating HISTORY, the system itself is updated (TIME OUT) to maintain synchronization at 612. If TIME OUT is not updated for a period of five seconds, then EKG synchronization is lost and must begin building a new history.

Referring to FIG. 6b the system routine for processing digital optical pulse information for optical pulses to send to LEVEL 3 (shown in FIG. 6c) is flow charted. The system begins by continuously evaluating the data from the detected digital optical signal at 644. The data is first evaluated for compatability with the signal processing at 645. If the data is over or undervalued electronically, i.e., beyond the voltage range of the circuitry, then the system exits the routine at 646, and the LED intensities are adjusted to correct the electrical values accordingly. When the data is compatible, it is next evaluated for a maximum signal. A relative maximum is determined and saved at 651. The next value is compared to the saved value, and if it is a new maximum it is saved at 651 instead. When the value found is now a new max, then a MAX FLAG is set at 650. Thereafter, the system evaluates the following data received, bypassing the maximum value section 648-652, to find the maximum slope at 653, again by successive comparisons. When the largest slope value is found it is saved at 658 and the SLOPE FLAG is raised at 656. Thereafter the following data is evaluated, bypassing the maximum and slope calculations, to find the minimum value corresponding to the end of the pulse at 659-662. When the smallest minimum is found, it is saved at 661 and the slope value saved at 658 is compared to a pre-established minimum threshold to determine whether it is large enough to be a possible optical pulse at 663. If it is not large enough, then the pulse is rejected at 664, the FLAGs raised at 659 and 656 are reset at 665 and the routine begins processing the next possible pulse at 644. If the slope is large enough then the pulse parameters, maximum, minimum, and slope, are saved in memory at 667 for use by LEVEL 3 processing in evaluating the possible pulse. Then, the time delay from the R wave to the possible pulse is calculated. Therafter, the DATA FLAG is set at 669, indicating to LEVEL 3 that there is a possible pulse to be evaluated, the MAX and SLOPE FLAGs are reset at 670, and the routine begins again to process the following data, looking for new maximum values corresponding to possible pulses.

Referring to FIG. 6c, LEVEL 3 of software for computing the saturation measurements is shown. The system starts by inputting a potential optical pulse at 615 after a DATA FLAG has been raised and inquiring whether there is EKG synchronization i.e., a regular EKG period has been established. If a DATA FLAG has not been raised, then the system exits the routine at 617. If there has not been EKG synchronization, then the microprocessor processes the optical pulse signals independent of the EKG, as would occur in the Nellcor N-100 oximeter without EKG capability, bypassing the inquiry into the presence of an R wave at 616.

If there is EKG synchronization, but no R wave has occurred, then the system exits at 617 and the pulse is not processed. If there is EKG synchronization and a R wave has occured, then the microprocessor processes the pulse as described below. The LED intensity is evaluated to see if adjustment is necessary at 618. The reset system gain, based on the minimum LED intensity required for adequate signal strength, is checked to see if adjustment is required. The optical pulse history is then computed at 620, based on the average historical period, amplitude, and ratio. The system then inquires whether the EKG apparatus is operating properly at 621. If it is, then the average time period between an R wave and the following optical pulse for the most recent four prior pulses is computed to give the TIME WINDOW at 622. Then the pulse waveform is analyzed to see if it is a dicrotic notch rather than a real optical pulse at 623. The downward slope of a dicrotic notch or other artifact can be misinterpreted as an optical pulse, but typically the pulse amplitude is less than half the amplitude of an actual pulse. If the pulse is determined to be a notch or artifact at 624, then the system exits at 625 and the next pulse presented will be processed. If not determined to be a notch, then it is analyzed to determine if it is a pulse at 626.

Assuming the EKG is synchronized, then the system determines if two criteria are met. The first is whether the time delay falls within the above-computed TIME WINDOW. If it does not, then the microprocessor rejects the pulse. The second criteria tested is whether or not the ratio is within acceptable limits. Only if the pulse statisfies both criteria, is the pulse accepted and a saturation calculation made.

If the EKG is not synchronized then the comparison must provide any two of three factors, (1) pulse period, (2) amplitude, and (3) ratio, as favorable for the pulse to pass as an accepted pulse at 627. E.g., pulse and period, period and amplitude, pulse and amplitude, or all three. If the pulse is accepted, then the oxygenation saturation is calculated at 628.

After the system is turned on (POWER UP) or after a TIME OUT alarm (a ten second period with no valid optical pulse found) a series of consistant pulses must be found to generate an optical pulse history before the oxygenation saturation will be sent to the display. Thus, if there is no optical pulse synchronization at 629, there will be no saturation display generated at 630. All optical pulses, those accepted and those not accepted, excluding pulses rejected as artifacts, enter the calculation routine section at 631-643. If the EKG is not synchronized then a pulse to pulse period and either an amplitude or a ratio must exist for the optical heart rate (OHR) calculation to be made at 632. If either the EKG or the optical pulse is synchronized, then the HR calculation made at 632 will be displayed at 634. If there is no synchronization, then the OHR is not displayed. At 635-643, the system is evaluating the status for pulse evaluation, i.e., whether signals should continue to be processed after a TIME WINDOW has been opened. If there was EKG synchronization and a good pulse was found, or the TIME WINDOW period has expired then TIME WINDOW is closed until opened by the detection of the next R wave.

In the preferred embodiment, the blood constituent measured is the oxygen saturation of the blood of a patient. The calculation of the oxygen saturation is made based on the ratio of the pulse seen by the red light compared to the pulse seen by the infrared light in accordance with the following equation:

$$\text{Saturation} = 100\% \times \frac{BR2 - R(BR1)}{R(BO1 - BR1) + BR2 - BO2}$$

wherein
BO1 is the extinction coefficient for oxygenated hemoglobin at light wavelength 1 (Infrared)
BO2 is the extinction coefficient for oxygenated hemoglobin at light wavelength 2 (red)
BR1 is the extinction coefficient for reduced hemoglobin at light wavelength 1
BR2 is the extinction coefficient for reduced hemoglobin at light wavelength 2
light wavelength 1 is infrared light
light wavelength 2 is red light
and R is the ratio of the optical density of wavelength 2 to wavelength 1 and is calculated as:

$$R = \frac{\ln[I_{max2}/I_{min2}]}{\ln[I_{max1}/I_{min1}]}$$

wherein
$I_{max2}$ is the maximum light transmitted at light wavelength 2
$I_{min2}$ is the minimum light transmitted at light wavelength 2 P0 $I_{max1}$ is the maximum light transmitted at light wavelength 1
$I_{min1}$ is the minimum light transmitted at light wavelength 1
The various extinction coefficients are determinable by empirical study and are set forth in the software appendix. For convenience of calculation, the natural lo of the ratios may be calculated by use of the Taylor expansion series for the natural log.

In an alternate embodiment, the microprocessor program can be adapted to utilize the relationship between the detected R wave DRW pulses and optical pulses without the need for first determining a pulse history. In this embodiment, microprocessor 16 searches status input latch 9G, and when detected R wave DRW is a logical 1, analyzes the optical signals that follow a detected R wave DRW pulse, regardless of the frequency of R wave pulses. By comparing the optical signals following a number of R wave pulses, microprocessor 16 correlates the detection of a pulse indicative of an optical pulse to the period of time by which such a detected pulse follows a detected R wave DRW pulse.

Referring to FIGS. 2a and 2b, the EKG front end printed circuit board schematic shows a respiratory monitor portion which may be used in conjunction with the EKG enhanced oximeter. The respiratory monitor is designed for use with a pressure sensitive transducer for detecting respiration or chest wall movement by measurement of pressure change. The sensor may be, for example, pneumatic-type sensor such as a Grasby Dynamics pressure capsule sensor, or a liquid mercury filled tube of silicon-like rubber secured across the patient's chest acting as a variable resistor. For a pneumatic type sensor, however it is designed, the small pressure change generated during respiratory chest movement is transmitted to a pressure transducer, for example, a Sensym model LX0503A bridge pressure transducer, for conversion to a voltage signal. The bridge output signal, or other voltage signal, is connected to differential amplifier 1A having a gain factor preferably over 100 nominally. The output of amplifier 1A is AC coupled to reject frequencies below about 0.07 Hz, and then buffered by amplifier 1B. The signal is then passed to low pass filter stages 1B and 1C which have a nominal cut off frequency of about 5 Hz. The output of the lowpass filters is further amplified and AC coupled to first buffer amplifier 1D. At that point the signal goes to second amplifier 1D for producing respiratory voltage $V_{resp}$, an analog waveform of the chest wall movement. The signal output from first amplifier 1D is also passed to threshhold detector 1E which compares the amplitude of the respiratory waveform to a reference threshhold voltage, which may be fixed, or adjusted by the microprocessor. When the amplitude of the respiratory waveform is greater than the referenced threshhold, the output of the detector is driven to +5 volts. That +5 volts is inverted by invertor 2A to create digital pulse RSPTRG, corresponding to a respiratory breath. RSPTRG is then coupled to the system electronics of the oximeter at status latch 9G-11.

The respiratory activity is useful to monitor because, for example, many infants and small children have breathing problems and during their sleep have lapses in their breath. Monitoring chest wall breathing can check for such lapses or stoppage of breathing. In the preferred embodiment, the microprocessor creates a respiration history and establishes a regular pattern of breathing. Afterwords, if no breath is detected for a period of time, e.g., 15 seconds, then an alarm may be activated. Monitoring respiratory activity in conjunction with EKG enhanced oximetry can determine, when patient's blood flow characteristics drop during sleep, whether the reason for that drop was because of abnormal breathing, cessation of breathing, or some other cause.

```
RESPOXI MICROBENCH 8080/8085 CROSS ASSEMBLER (V2)-436

;NELLCOR OXIMETER, PRODUCTION VERSION (8085)
;
; THIS VERSION OF THE OXIMETER PROGRAM INCORPORATES SUBSTANTIAL REVISIONS
; TO THE PULSE WAVE DECODING ALGORITHMS
;
; THIS VERSION IS ANNOTATED, FOR INCORPORATION INTO THE PRODUCTION      ///
; VERSION, BY THE APPLICATION OF SLASHES AT THE END OF EACH LINE        ///
; THAT IS HERE SOLELY FOR THE INTERFACE.                                ///

;COPYRIGHT (C) 1983, 1984, 1985 NELLCOR INCORPORATED
;
; THIS IS AN ORIGINAL, UNPUBLISHED WORK AND IS PROPRIETARY TO NELLCOR, INC.,
; AND MAY NOT BE DIVULGED OR COPIED IN ANY FORM WHATSOEVER WITHOUT
; EXPRESS PERMISSION FROM NELLCOR, INC.
;
005E            ;         VERSN    EQU      94
                          NAME     RESPOX
```

APPENDIX

```
                ;RECENT EDIT HISTORY:
                ;     30 MAR           DEG      ADD MODE 9, CHG LV3TRG & CONF CHK WITH TW
                ;      4 MAR           DEG      MODIFY DEFAULT EKG GAIN SETTING
                ;     18 FEB           DEG      ADD 'TIME WINDOW', SILENT MODE
                ;     27 JAN           DEG      REDO LED SERVO,ADD GAIN SWITCH, FIX CALCHK
                ;     26 JAN '85       DEG      ADD AVG RATIO, LOG (MAX/MIN) & ANALOG OUTS-5,6
                ;     26 OCT           DEG      ALLOW UNFILTERED DATA TO INTERFACE - MODE 6
                ;     24 OCT           DEG      FIX SOME ALARM INTERFACE BUGS
                ;     23 OCT           DEG      ADD RESPIRATORY MONITOR - MODE 5
                ;      6 OCT           DEG      ADD CONFIDENCE CHECKING TO R-WAVE
                ;      5 OCT           DEG      TRIGGER MUNCH ON R WAVE - IF AVAILABLE
                ;      3 OCT           DEG      FIX SOME ALARM BUGS
                ;      2 OCT           DEG      INTEGRATE ALARMS FOR EKG
                ;      1 OCT           DEG      BEGIN INTEGRATING ECG INFO FOR LEVEL3
                ;     27 SEPT          DEG      ADD ECG R-WAVE DETECT - MANUAL ECG GN CNTRL
                ;      9 AUGUST        DEG      MAKE LED SERVO LINEAR - USE VLED DIRECTLY
                ;     28 JUNE, 1984    DEG      USE 2732A,CHG CHKMCH,CNFLIMS,TWKLED- 4X GAIN
                ;     18 APR           JEC      FIX MUNCH BUG (MAXIDX) - 5.3
                ;     27 FEB           JEC      ADD SYNDLY, FIX MATH BUGS; LEVEL 5.0
                ;     26 FEB           JEC      ADD NEW CALIBRATION
                ;     24 FEB           JEC      DISPLAY D.P. IN MODE 4
                ;      1 SEP '83       EMR      FIRST PROD. VERSION W/INTERFACE. VERSION = 4.0
                ;     11 AUG           JEC      'NEW' LIMITS, FMODE ADDED
                ;     10 AUG '83       JEC      FIX CORRECTION, NEW FILTER, VERSION = 3.4
                ;     13 JULY 83       JEC      ADD BUTTON ESCAPE TO ERRDSP, VERSION = 3.3
                ;     18 MARCH, 1982   JEC      STARTED
                ;
0000                    ASEG
                ; DEFINITIONS...HARDWARE FIRST
                ; OUTPUT REGISTER DEFS...
0000            DACL    EQU     00H             ;DAC VALUE, LOWER 8 BITS
0001            DACH    EQU     01H             ;DITTO, HIGH 4 BITS (0-3)
0002            MUXSEL  EQU     02H             ;INPUT MULTIPLEXER SELECT CODES
000F                            V1PRM   EQU     0FH     ;IR CHANNEL, OFFSET
001F                            V2PRM   EQU     1FH     ;RED CHANNEL, OFFSET
002F                            V1MX    EQU     2FH     ;DITTO, WITHOUT OFFSETS
003F                            V2MX    EQU     3FH
004F                            OFWMX   EQU     4FH     ;FRONT-END OVERFLOW SENSE
005F                            VCALMX  EQU     5FH     ;CALIBRATION RESISTOR
006F                            VTMPMX  EQU     6FH     ;THERMISTOR
007F                            VREFMX  EQU     7FH     ;CALIBRATION REFERENCE
008F                            VBMX    EQU     8FH     ;BATTERY VOLTAGE
009F                            IDSPMX  EQU     9FH     ;DISPLAY CURRENT
00AF                            DEKGMX  EQU     0AFH    ;ECG WAVEFORM
00BF                            FEKGMX  EQU     0BFH    ;BANDPASS FILTERED ECG

000E                            SHLED1  EQU     0EH     ;SAMPLE/HOLD FOR LED1
000D                            SHLED2  EQU     0DH     ;DITTO, LED2
000B                            SHBEEP  EQU     0BH     ;BEEP PITCH
0007                            SHVOL   EQU     07H     ;BEEPER VOLUME
0003            EKGPOL  EQU     03H             ;SELECT EKG POLARITY
0004            DSPSEL  EQU     04H             ;DISPLAY SELECT BITS
0005            DSPDIG  EQU     05H             ;DISPLAY DIGIT (UNCODED, ALSO RESETS INTERRUPT)
0006            CHGEKG  EQU     06H             ;SELECT EKG GAIN FOR AGC AMP
0007            RSTRWV  EQU     07H             ;RESET RWAVE FLIPFLOP

0077                            SEG0    EQU     77H     ;SEGMENT CODE DEFS
0024                            SEG1    EQU     24H
005D                            SEG2    EQU     5DH
006D                            SEG3    EQU     6DH
002E                            SEG4    EQU     2EH
006B                            SEG5    EQU     6BH
007B                            SEG6    EQU     7BH
0025                            SEG7    EQU     25H
007F                            SEG8    EQU     7FH
002F                            SEG9    EQU     2FH
005B                            SEGE    EQU     5BH
0018                            SEGR    EQU     18H
001B                            SEGF    EQU     1BH

0001                            ALICOD  EQU     1       ;ALARM INHIBIT
0008                            SLOCOD  EQU     8       ;SAT LOW ALARM
0010                            SHICOD  EQU     16      ;SAT HIGH ALARM
0002                            RLOCOD  EQU     2       ;RATE LOW ALARM
0004                            RHICOD  EQU     4       ;RATE HIGH ALARM
0020                            SYNCOD  EQU     32      ;NO-SYNC ALARM
0080                            BATCOD  EQU     128     ;BATTERY ALARM
0007                            FD1MSK  EQU     000111B ;BLINK MASKS
0038                            FD2MSK  EQU     111000B

; INPUTS:
0004            BUTREG  EQU     04H             ;BUTTON INPUT REGISTER (BIT 7 = DAC COMP.)
                                                ; BITS 0 = CONTROL DIRECTION, BIT 1 = STROBE
                                                ; BITS 2-6 = BUTTONS
0000            STSREG  EQU     00H             ;STATUS: BIT7 = COMPARATOR, BITS 0-5 = JUMPERS
0001                            DIDJPR  EQU     1       ;ENABLE DIDDLE MODE
0002                            DRTJPR  EQU     2       ;DISABLE ROM TEST JUMPER

; OTHER DEFS...
F8F8            BATLM1  EQU     0F8F8H          ;BLINK LIMIT
FB50            BATLM2  EQU     0FB50H          ;BAT IN USE LIMIT

006E            ALMPCH  EQU     110             ;ALARM PITCH
```

; COMMUNICATION STUFF...

```
        0001            SRCBIT  EQU     1               ;SEARCH BIT MASK                        ///
        0008            BATBIT  EQU     8               ;BATTERY IN USE BIT MASK                ///
        0002            OXIATT  EQU     2               ;OXIMETER ATTACHED BIT MASK             ///
        0004            AUDENB  EQU     4               ;AUDIO ALARM ENABLED BIT MASK           ///
        0004            SATBIT  EQU     4               ;SATURATION ALARM BIT MASK              ///
        0002            LRTBIT  EQU     2               ;LOW RATE ALARM BIT MASK                ///
        0001            HRTBIT  EQU     1               ;HIGH RATE BIT MASK                     ///

0040            MARK    EQU     40H             ;MARK CONDITION (INVERTS AT OPTO-CPLR)  ///
        00C0            SPACE   EQU     0C0H            ;SPACE CONDITION (INVERTS AT OPTO-CPLR) ///
```
;START-UP CODE....
; (FILLED FROM ORG 0 FOR THE SILLY PROM PROGRAMMER)
;
```
        0000                    ORG     0

0000    F3                      DI
0001    31      7400            LXI     SP,STCK         ;LOAD STACK POINTER
0004    C3      0040            JMP     START
```

;COPYRIGHT NOTICE IN ROM...

```
0007    43      4F              DB      'COPYRIGHT 1983 NELLCOR INC.'
0009    50      59
000B    52      49
000D    47      48
000F    54      20
0011    31      39
0013    38      33
0015    20      4E
0017    45      4C
0019    4C      43
001B    4F      52
001D    20      49
001F    4E      43
0021    2E

0012                    REPT    34H-$
                                RST     0
                                ENDR
```

;INTERRUPT VECTORS...
;
;DISPLAY (4*60HZ) = RST6.5, RESET BY 'DSPDIG' OUTPUT
;
```
0034    C3      1913            JMP     DSPINT

0005                    REPT    3CH-$
                                RST     0
                                ENDR
```
;
;CLOCK (2400 BAUD) INTERRUPT = RST7.5, EDGE TRIGGERED.
;
```
003C    C3      18B0            JMP     CLKINT

0001                    REPT    40H-$
                                RST     0
                                ENDR
```
;
;CHECK RAM AND LEAVE CLEARED...
;
```
0040    CD      00B3    START:  CALL    HRESET          ;RESET HARDWARE
0043    CD      00DE            CALL    ROMTST          ;CHECK ROM CHECKSUMS
0046    CD      00FB            CALL    RAMTST          ;CHECK RAM
0049    CD      01A6            CALL    LEDTST          ;CHECK LED'S
004C    CD      022A            CALL    INIT            ;INITIALIZE VARIABLES
004F    CD      0242            CALL    INIDSP          ;INITIALIZE DISPLAY
0052    CD      1BFC            CALL    COMBEG          ;INITIALIZE COMMUNICATIONS              ///
                        ;
0055    3E      19              MVI     A,19H           ;RESET 7.5 LATCH + MASK OFF 5.5
0057    30              SIM                             ;
0058    FB                      EI                      ;GO FOR IT....
```
;IDLE LOOP....CHECK FOR DATA IN BUFFER, PROCESS IF NOT EMPTY
;CHECK FOR UP/DOWN KNOB STROBES, THEN CHECK FOR BUTTON CODES.
;        NOTE- BATCHK HAS BEEN DISABLED, TEMPORARILY
;
```
0059    CD      081A    LOOP:   CALL    RSPLV3          ;CHECK FOR RESPIRATORY ACTIVITY
005C    CD      0F38            CALL    MUNCH           ;GO CRUNCH SOME RAW DATA...
005F    CD      110D            CALL    BLIP            ;RUN THE METER
0062    CD      0266            CALL    LEVEL3          ;COMPUTE...
0065    CD      072B            CALL    LVL3JR          ;CHECK R-WAVE, COMPUTE IF OK
0068    CD      14CE            CALL    BUTTON          ;CHECK FOR BUTTON INPUTS
006B    CD      16FF            CALL    KNOB            ;CHECK CONTROL KNOB INPUT
006E    CD      17A1            CALL    CLOCK           ;CHECK FOR QUARTER-SECOND ACTION
0071    CD      15E7            CALL    RFSHOP          ;REFRESH OPEN PARAMETER
0074    CD      1C11            CALL    COMIDL          ;DO IDLE LOOP COMMUNICATIONS CHECKS     ///
0077    CD      0141            CALL    ROMIDL          ;DO IDLE-TIME DIAGNOSTICS
007A    CD      0176            CALL    RAMIDL
007D    CD      13F9            CALL    BLKOUT          ;CHECK/IMPLEMENT SILENT RUNNING MODE
0080    C3      0059            JMP     LOOP            ;
```

;CHECK SUPPLY VOLTS, LIGHT WARNING IF GOING...
;

```
0083   0E   80         BATCHK: MVI   C,BATCOD       ;LAMP CODE
0085   2A   7158               LHLD  VBAT           ;GET VOLTS
0088   EB                      XCHG
0089   21   F8F8               LXI   H,BATLM1       ;UPPER LIMIT OF BATTERY OP.
008C   19                      DAD   D
008D   DA   00A7               JC    1$             ;IS OK, PLUG IS IN THE WALL.
0090   21   F850               LXI   H,BATLM2
0093   19                      DAD   D
0094   DA   009B               JC    2$             ;IS SORT OF OK, BUT TURN ON THE LIGHT
0097   CD   1484               CALL  BNKLIT         ;BLINK IT, WE'RE RUNNING OUT...
009A   C9                      RET
009B   CD   146C         2$:   CALL  SETLIT
009E   3A   727C               LDA   COSTA                                           ///
00A1   F6   08                 ORI   BATBIT                                          ///
00A3   32   727C               STA   COSTA          ;SET BATTERY IN USE FLAG BIT     ///
00A6   C9                      RET
00A7   CD   1475         1$:   CALL  CLRLIT
00AA   3A   727C               LDA   COSTA          ;CLEAR BATTERY IN USE BIT        ///
00AD   E6   F7                 ANI   NOT BATBIT                                      ///
00AF   32   727C               STA   COSTA                                           ///
00B2   C9                      RET
```

;RESET HARDWARE AND FLASH THE PRETTY LIGHTS...
;

```
00B3   3E   FF         HRESET: MVI   A,0FFH         ;SET ANALOG VALUES TO FULL-SCALE
00B5   D3   00                 OUT   DACL
00B7   D3   01                 OUT   DACH
00B9   AF                      XRA   A
00BA   D3   02                 OUT   MUXSEL         ;SELECT ALL CHANNELS
00BC   11   4000               LXI   D,4000H
00BF   06   00           1$:   MVI   B,0
00C1   78           2$:        MOV   A,B
00C2   04                      INR   B
00C3   FE   09                 CPI   9
00C5   CA   00BF               JZ    1$
00C8   D3   04                 OUT   DSPSEL         ;SELECT DIGIT
00CA   3E   FF                 MVI   A,0FFH
00CC   D3   05                 OUT   DSPDIG         ;LIGHT ALL SEGMENTS
00CE   1D                      DCR   E
00CF   C2   00C1               JNZ   2$
00D2   15                      DCR   D
00D3   C2   00C1               JNZ   2$
00D6   AF                      XRA   A
00D7   D3   00                 OUT   DACL
00D9   D3   01                 OUT   DACH
00DB   D3   05                 OUT   DSPDIG
00DD   C9                      RET
```

;
;ROM CHECK TEST.....ADD UP ALL THE BYTES AND CALL ERROR IF IT ISN'T RIGHT...

```
00DE   21   0000       ROMTST: LXI   H,0
00E1   11   20FF               LXI   D,20FFH        ;2 ROMS - 2732A'S
00E4   AF                      XRA   A
00E5   86           1$:        ADD   M
00E6   23                      INX   H
00E7   1D                      DCR   E
00E8   C2   00E5               JNZ   1$
00EB   15                      DCR   D
00EC   C2   00E5               JNZ   1$
00EF   77                      MOV   M,A            ;STORE SUM IF EMULATING IN RAM
00F0   BE                      CMP   M
00F1   C8                      RZ                   ;IS OK
00F2   3E   02                 MVI   A,2            ;ROM ERROR= ERROR 2
00F4   32   72AE               STA   DIGERR         ;STORE DIAGNOSTIC ERROR            ///
00F7   CD   01F0               CALL  ERRDSP
00FA   C9                      RET
```

;TEST RAM MEMORY ON START-UP...WRITE ALL ZERO'S, ONE'S AND THE ADDRESS IN EACH BYTE
;

```
00FB   E3           RAMTST: XTHL                    ;SAVE RETURN IN D,E
00FC   EB                      XCHG
00FD   21   7000               LXI   H,RAMORG
0100   01   0400               LXI   B,RAMLEN
0103   3E   00           1$:   MVI   A,0
0105   77                      MOV   M,A
0106   BE                      CMP   M              ;TEST FOR ZERO
0107   C2   0133               JNZ   10$
010A   3E   FF                 MVI   A,0FFH
010C   77                      MOV   M,A
010D   BE                      CMP   M              ;AND ALL 1'S
010E   C2   0133               JNZ   10$
0111   7D                      MOV   A,L
0112   84                      ADD   H
0113   77                      MOV   M,A            ;STORE LOW + HIGH ADDRESS
0114   23                      INX   H
0115   0B                      DCX   B
0116   78                      MOV   A,B
0117   B1                      ORA   C
0118   C2   0103               JNZ   1$             ;LOOP UNTIL END OF RAM
011B   21   7000               LXI   H,RAMORG       ;RESET POINTER TO BEGINNING
011E   01   0400               LXI   B,RAMLEN
```

```
0121   7D              2$:     MOV     A,L
0122   84                      ADD     H
0123   BE                      CMP     H                       ;CHECK STORED ADDRESS
0124   C2    0133              JNZ     10$
0127   36    00                MVI     M,0                     ;CLEAR M
0129   23                      INX     H
012A   0B                      DCX     B
012B   78                      MOV     A,B
012C   B1                      ORA     C
012D   C2    0121              JNZ     2$
0130   C3    013E              JMP     11$
0133   3E    01      10$:      MVI     A,1                     ;ERROR CODE
0135   32    72AE              STA     DIGERR                  ;STORE DIAGNOSTIC ERROR
0138   CD    01F0              CALL    ERRDSP
013B   C3    00FB              JMP     RAMTST                  ;NO EXIT
013E   EB              11$:    XCHG
013F   E3                      XTHL
0140   C9                      RET
                       ;IDLE-TIME ROM TEST...
                       ;ADD UP A BYTE AT A TIME, CHECK THE CHECKSUM IF AT THE END.
                       ;
0141   2A    7174    ROMIDL:   LHLD    ROMIDX                  ;GET INDEX TO NEXT BYTE TO BE TESTED
0144   3A    7176              LDA     ROMSUM                  ;PARTIAL SUM
0147   86                      ADD     M
0148   32    7176              STA     ROMSUM
014B   23                      INX     H
014C   7D                      MOV     A,L
014D   FE    FF                CPI     0FFH
014F   C2    0167              JNZ     1$                      ;NOT THE END
0152   7C                      MOV     A,H
0153   FE    1F                CPI     1FH
0155   C2    0167              JNZ     1$
0158   3A    7176              LDA     ROMSUM
015B   77                      MOV     M,A                     ;STORE IF EMULATING
015C   BE                      CMP     M                       ;CHECK THE CHECKSUM
015D   C2    016B              JNZ     10$                     ;NOT OK
0160   AF                      XRA     A
0161   32    7176              STA     ROMSUM                  ;RESET SUM
0164   21    0000              LXI     H,0
0167   22    7174    1$:       SHLD    ROMIDX
016A   C9                      RET
016B   3E    02      10$:      MVI     A,2                     ;ERROR CODE
016D   32    72AE              STA     DIGERR
0170   CD    01F0              CALL    ERRDSP
0173   C3    0000              JMP     0
                       ;
                       ;IDLE-TIME RAM TEST...DISABLE INTERRUPT AND TEST A BYTE...
                       ;
0176   2A    7172    RAMIDL:   LHLD    RAMIDX
0179   F3                      DI
017A   7E                      MOV     A,M                     ;GET CURRENT BYTE CONTENTS
017B   2F                      CMA
017C   77                      MOV     M,A                     ;COMPLIMENT IT AND RESTORE IT
017D   BE                      CMP     M                       ;CHECK IT
017E   C2    019B              JNZ     10$                     ;FAILED
0181   2F                      CMA
0182   77                      MOV     M,A                     ;RESTORE
0183   BE                      CMP     M                       ;CHECK
0184   C2    019B              JNZ     10$
0187   FB                      EI
0188   23                      INX     H
0189   7D                      MOV     A,L                     ;CHECK FOR END OF RAM
018A   B7                      ORA     A
018B   C2    0197              JNZ     1$
018E   7C                      MOV     A,H
018F   FE    74                CPI     HIGH(RAMORG+RAMLEN)
0191   C2    0197              JNZ     1$
0194   21    7000              LXI     H,RAMORG
0197   22    7172    1$:       SHLD    RAMIDX
019A   C9                      RET
019B   3E    01      10$:      MVI     A,1
019D   32    72AE              STA     DIGERR
01A0   CD    01F0              CALL    ERRDSP
01A3   C3    0000              JMP     0
                       ;TEST LED'S ON INITIALIZATION...LIGHT ONE SEGMENT AT A TIME, CHECK CURRENT
                       ; AGAINST HIGH/LOW BOUNDS.
01A6   3E    9F      LEDTST:   MVI     A,IDSPMX                ;SELECT DISPLAY CURRENT FOR MUX
01A8   D3    02                OUT     MUXSEL
01AA   01    0001              LXI     B,01H                   ;B = DIGIT SELECT CODE, C = SEGMENT BIT
01AD   78              1$:     MOV     A,B
01AE   D3    04                OUT     DSPSEL                  ;SELECT DIGIT
01B0   79                      MOV     A,C
01B1   D3    05                OUT     DSPDIG
01B3   AF                      XRA     A
01B4   3C      5$:             INR     A                       ;DELAY FOR COSMETICS AND SETTLING
01B5   C2    01B4              JNZ     5$
01B8   C5                      PUSH    B
01B9   CD    1E5E              CALL    ADCVT                   ;DIGITIZE LED CURRENT
01BC   C1                      POP     B
01BD   21    FFC0              LXI     H,0FFC0H                ;- LOWER LIMIT
```

```
01C0   19                    DAD    D                ;TOO LOW
01C1   D2    01E7            JNC    10$
01C4   21    FF00            LXI    H,0FF00H         ;UPPER LIMIT
01C7   19                    DAD    D
01C8   DA    01E7            JC     10$              ;TOO HIGH (SHORTED)
01CB   79            2$:     MOV    A,C
01CC   07                    RLC                     ;INCREMENT SEGMENT BIT
01CD   4F                    MOV    C,A
01CE   D2    01D8            JNC    3$               ;KEEP TRUCKIN'
01D1   04                    INR    B                ;NEXT DIGIT
01D2   78                    MOV    A,B
01D3   FE    09              CPI    9
01D5   CA    01EF            JZ     11$              ;ALL DONE
01D8   78            3$:     MOV    A,B              ;CHECK FOR UNUSED LAMPS...
01D9   FE    08              CPI    8
01DB   C2    01AD            JNZ    1$               ;NOT LAMPS, LOOP...
01DE   79                    MOV    A,C
01DF   E6    50              ANI    64+16            ;CHECK FOR UNUSED LAMPS...
01E1   C2    01CB            JNZ    2$               ;HIT ONE
01E4   C3    01AD            JMP    1$
01E7   3E    03     10$:     MVI    A,3              ;BAD LAMP = ERROR 3
01E9   32    72AE            STA    DIGERR           ;STORE FOR POSSIBLE SENDING
01EC   CD    01F0            CALL   ERRDSP
01EF   C9            11$:    RET
                     ;ERROR DISPLAY...CALLED WITH ERROR CODE IN AC.

01F0   F3            ERRDSP: DI
01F1   01    7122            LXI    B,DSPFD2
01F4   CD    13A9            CALL   DSPCVT
01F7   21    711C            LXI    H,DSPFD1
01FA   36    18              MVI    M,SEGR
01FC   23                    INX    H
01FD   23                    INX    H
01FE   36    18              MVI    M,SEGR
0200   23                    INX    H
0201   23                    INX    H
0202   36    5B              MVI    M,SEGE
0204   21    711C   1$:      LXI    H,DIGBUF
0207   06    00              MVI    B,0
0209   3E    FF     2$:      MVI    A,0FFH
020B   D3    04              OUT    DSPSEL           ;BLANK DISPLAY WHILE WE CHANGE DIGITS
020D   7E                    MOV    A,M
020E   D3    05              OUT    DSPDIG
0210   78                    MOV    A,B
0211   D3    04              OUT    DSPSEL
0213   0D            3$:     DCR    C
0214   C2    0213            JNZ    3$
0217   23                    INX    H
0218   23                    INX    H
0219   04                    INR    B
021A   78                    MOV    A,B
021B   FE    09              CPI    9
021D   C2    0209            JNZ    2$
0220   DB    04              IN     BUTREG           ;CHECK FOR BUTTON ESCAPE
0222   E6    3C              ANI    3CH
0224   FE    38              CPI    38H
0226   C2    0204            JNZ    1$
0229   C9                    RET
                     ;INITIALIZE PARAMETERS FROM INILST...
                     ;
022A   21    1F33   INIT:    LXI    H,INILST
022D   4E            5$:     MOV    C,M
022E   23                    INX    H
022F   46                    MOV    B,M
0230   23                    INX    H
0231   78                    MOV    A,B
0232   B1                    ORA    C
0233   CA    0241            JZ     6$               ;ZERO ADDRESS TERMINATES
0236   7E            7$:     MOV    A,M
0237   23                    INX    H
0238   B7                    ORA    A                ;ZERO BYTE TERMINATES
0239   CA    022D            JZ     5$
023C   02                    STAX   B
023D   03                    INX    B
023E   C3    0236            JMP    7$               ;LOOP FOR NEXT BYTE
0241   C9            6$:     RET

;INITIALIZE DISPLAY
                     ;
0242   3E    00     INIDSP:  MVI    A,0              ;INITIALIZE EKG FLAG AND POLARITY
0244   D3    07              OUT    RSTRWV
0246   D3    03              OUT    EKGPOL
0248   01    711C            LXI    B,DSPFD1         ;UPPER DISPLAY
024B   AF                    XRA    A
024C   CD    13A9            CALL   DSPCVT           ;A ZERO...
024F   01    7122            LXI    B,DSPFD2
0252   AF                    XRA    A
0253   CD    13A9            CALL   DSPCVT           ;LOWER DISPLAY ALSO
0256   0E    20              MVI    C,SYNCOD         ;SET NO-SYNC LIGHT
0258   CD    1484            CALL   RNKLIT
025B   3A    70F1            LDA    ALIFLG           ;SET ALARM INHIBIT LIGHT IF ALARM INHIBITED
```

```
025E    B7                          ORA     A
025F    C8                          RZ
0260    0E      01                  MVI     C,ALICOD
0262    CD      1484                CALL    FSTLIT
0265    C9                          RET
                            ;LEVEL 3 ROUTINES...
                            ; CALLED ONCE PER ALLEGED PULSE, THESE ROUTINES TRY TO SORT REAL PULSES
                            ; FROM ARTIFACT.
                            ;
0266    CD      0E4E        LEVEL3: CALL    CALCHK          ;CHECK FOR CAL REISTOR
0269    D8                          RC                      ;LEAVE IF NONE
026A    3A      709E                LDA     DATFLG          ;CHECK DATA READY FLAG
026D    B7                          ORA     A
026E    C8                          RZ                      ;NOT SET, BAG IT.
026F    CD      044C                CALL    XFRPLS          ;STORE PULSE PARAMETERS IN CURLST
0272    CD      0E0C                CALL    TWKLED          ;RE-SET THE LED DRIVES
0275    CD      049E                CALL    HSTCMP          ;COMPUTE HISTORY PARAMETERS
0278    CD      061C                CALL    SETLIM          ;SET LIMITS FOR VARIATION AND DIFF
027B    3A      7014                LDA     SYNFLG
027E    B7                          ORA     A
027F    CA      0310                JZ      SYNCOK          ;SYNC'ED
                            ;
                            ;NOT YET SYNC'ED...DECREMENT SYNC COUNTER TO 1 AND WAIT FOR VARIATION TO DROP.
                            ;
0282    3A      703C        1$:     LDA     AMPAVG          ;CHECK FOR MINIMUM AMPLITUDE
0285    FE      08                  CPI     8
0287    DA      02FE                JC      4$              ;TOO SMALL
028A    3A      700A                LDA     LED1            ;SHOULD WE GO TO LO GAIN?
028D    FE      A0                  CPI     160
028F    D2      02BB                JNC     10$             ;>160, DON'T SWITCH GAINS
0292    3A      700D                LDA     LED2            ;DITTO FOR RED
0295    FE      A0                  CPI     160
0297    D2      02BB                JNC     10$
029A    3A      7012                LDA     GNSEL           ;ARE WE IN HI GAIN?
029D    B7                          ORA     A
029E    CA      02BB                JZ      10$             ;NO, DO NOTHING
02A1    3A      700A                LDA     LED1            ;SINCE SWITCHING GAINS, COMPENSATE BY
02A4    C6      40                  ADI     64              ;ADDING 64 TO LED1 AND LED2
02A6    32      700A                STA     LED1
02A9    3A      700D                LDA     LED2
02AC    C6      40                  ADI     64
02AE    32      700D                STA     LED2
02B1    32      7013                STA     LGFLAG
02B4    AF                          XRA     A
02B5    32      7012                STA     GNSEL
02B8    C3      02FE                JMP     4$
02BB    3A      7014        10$:    LDA     SYNFLG          ;LED'S OK, GET SYNC CODE AGAIN
02BE    3D                          DCR     A               ;CHECK FOR FLAG=1
02BF    C2      02FB                JNZ     3$              ;NOT, STORE PULSE AND COUNT
02C2    CD      058A                CALL    VARCHK          ;CHECK FOR EXCESSIVE VARIATION
02C5    D2      02D1                JNC     2$              ;VARIATION IS GOOD, GO FOR IT...
02C8    CD      06B6                CALL    CHKNCH          ;LOOK OUT FOR SMALL PULSES
02CB    DA      0308                JC      5$              ;IS NOTCH, IGNORE IT
02CE    C3      02FE                JMP     4$              ;NOT-A-NOTCH; VARIATION STILL NG, STORE IT
02D1    AF          2$:             XRA     A
02D2    32      7014                STA     SYNFLG          ;SYNC'ED
02D5    32      70F6                STA     ALHDLY          ;NO OBSOLETE DELAYED ALARMS ALLOWED
02D8    0E      20                  MVI     C,SYNCOD
02DA    CD      1475                CALL    CLRLIT
02DD    3E      FF                  MVI     A,255
02DF    32      7005                STA     FSATN           ;TURN FILTERS WAY DOWN
02E2    3A      7104                LDA     SN2DLY          ;CHECK FOR EKG SYNC
02E5    B7                          ORA     A
02E6    CA      02EE                JZ      7$              ;IS SYNCED, DONT CHANGE FILTER FOR HR
02E9    3E      FF                  MVI     A,255           ;NOT SYNCED ,TURN HR FILTER DOWN
02EB    32      7006                STA     FRATN
02EE    3E      05          7$:     MVI     A,5
02F0    32      70B4                STA     SYNDLY
02F3    3E      08                  MVI     A,8
02F5    32      714A                STA     SATTMR
02F8    C3      0310                JMP     SYNCOK          ;GO PROCESS PULSE
02FB    32      7014        3$:     STA     SYNFLG          ;STORE SYNC FLAG
02FE    CD      0668        4$:     CALL    HSTUPD          ;UPDATE HISTORY
0301    AF                          XRA     A
0302    32      70B6                STA     NCHFLG          ;WASN'T A NOTCH, RESET FLAG
0305    32      70B3                STA     PERCTR
0308    3E      03          5$:     MVI     A,3
030A    32      70B5                STA     BPCTR           ;RESET BAD-PULSE COUNTER
030D    C3      03FF                JMP     PLSRET          ;DONE HERE
                            ;
                            ;SYNC'ED...CHECK PULSE AGAINST HISTORY, PROCESS IT IF IT MATCHES.
                            ; IF NOT, DECREMENT BAD PULSE COUNTER AND IGNORE THE FIRST FEW BAD PULSES.
                            ; IF BAD PULSE COUNTER RUNS OUT THEN STORE IT ANYWAY.
                            ;
0310    CD      05D3        SYNCOK: CALL    DIFCHK          ;CHECK DIFFERENCE CODES
0313    FE      02                  CPI     2               ;0 OR 1 IS OK
0315    F2      03CC                JP      PLSERR          ;NO GOOD
0318    CD      06B6                CALL    CHKNCH          ;MAY BE A NOTCH
031B    DA      03CC                JC      PLSERR          ;OH WELL, IT IS...
```

```
031E  3E  03          PLSOK:  MVI   A,3
0320  32  70B5                STA   BPCTR         ;RESET BAD PULSE COUNTER
0323  0E  20                  MVI   C,SYNCOD      ;RESET SYNC LIGHT
0325  CD  1475                CALL  CLRLIT
0328  21  70B4                LXI   H,SYNDLY      ;DID WE JUST START?
032B  35                      DCR   M
032C  F2  0333                JP    2$            ;YES, LEAVE THE FILTER TURNED DOWN
032F  34                      INR   M
0330  CD  0A41                CALL  FILSET        ;SET FILTER COEFICIENTS
0333  3A  7016        2$:     LDA   CURDIF        ;GET DIFF CODES
0336  E6  04                  ANI   4             ;DONT UPDATE SAT IF NOT ZERO
0338  CA  034A                JZ    1$            ;RATIO NO GOOD-
033B  3A  7104        3$:     LDA   SN2DLY        ;IF EKG IS SYNCED - CHECK TIME WINDOW
033E  B7                      ORA   A
033F  C2  037E                JNZ   5$
0342  3A  7016                LDA   CURDIF
0345  E6  08                  ANI   8             ; 8 = TIME WINDOW
0347  C2  037E                JNZ   5$            ; BOTH NOT OK , DON'T COMPUTE SAT
034A  AF          1$:         XRA   A
034B  32  7001                STA   SAT
034E  3A  7141                LDA   IFLG
0351  B7                      ORA   A
0352  CA  036B                JZ    11$
0355  11  FFFF                LXI   D,-(SAT-RAMORG)
0358  2A  713F                LHLD  ICELL
035B  19                      DAD   D
035C  7D                      MOV   A,L
035D  B4                      ORA   H
035E  C2  036B                JNZ   11$
0361  2A  70A9                LHLD  RATRAT
0364  CD  08A0                CALL  XSAT
0367  7C                      MOV   A,H
0368  32  7001                STA   SAT
036B  CD  0947       11$:     CALL  FILRAT        ;FILTER RATIOS
036E  CD  0889                CALL  COMSAT        ;COMPUTE SATURATION
0371  DA  037E                JC    5$
0374  3E  0A                  MVI   A,10
0376  32  714A                STA   SATTMR        ;RESET SAT TIME-OUT COUNTER
0379  3E  08                  MVI   A,8
037B  32  710C                STA   SATCLK        ;RESET SAT ANALOG OUT TIMEOUT
037E  3A  7104       5$:      LDA   SN2DLY        ;IF ECG NOT SYNCED, THEN CHECK HR HERE
0381  B7                      ORA   A
0382  C2  0388                JNZ   8$
0385  C3  0398                JMP   6$
0388  3A  7016       8$:      LDA   CURDIF        ;CHECK PERIOD DIFF
038B  E6  01                  ANI   1
038D  C2  0398                JNZ   6$            ;NO COMPUTE IF NON-ZERO
0390  CD  06E2       10$:     CALL  COMRAT        ;CALC RATE FROM THE PULSE
0393  3E  08                  MVI   A,8           ;RESET HR ANALOG OUT TIMEOUT
0395  32  710B                STA   RATCLK
0398  AF          6$:         XRA   A
0399  32  712E                STA   DSPBKF        ;CLEAR BLANK DISPLAY FLAG
039C  21  714A                LXI   H,SATTMR      ;CHECK SAT TIME-OUT
039F  7E                      MOV   A,M
03A0  3D                      DCR   A
03A1  FA  03A8                JM    7$            ;ALREADY ZERO
03A4  77                      MOV   M,A
03A5  CC  0BB9                CZ    SATTMO        ;ZERO THE SAT
03A8  3A  70B4       7$:      LDA   SYNDLY        ;SEND TO DISPLAY AFTER 2 GOOD BEATS
03AB  FE  03                  CPI   3
03AD  F2  03B9                JP    12$
03B0  CD  0A8F                CALL  DSPSR         ;DISPLAY SAT AND RATE...
03B3  CD  0C37                CALL  ALMCHK        ;AND CHECK ALARMS..
03B6  CD  0404                CALL  SNDMON        ;SEND GOOD NUMBERS TO INTERFACE
03B9  3E  28         12$:     MVI   A,40          ;10 SECONDS WORTH OF TIME-OUT
03BB  32  7149                STA   PLSTMR
03BE  AF                      XRA   A
03BF  32  70B3                STA   PERCTR        ;RESET PERIOD COUNTER ... GOOD PULSES ONLY.
03C2  CD  0668                CALL  HSTUPD        ;UPDATE HISTORY
03C5  AF                      XRA   A
03C6  32  70B6                STA   NCHFLG
03C9  C3  03FF                JMP   PLSRET
                     ;
                     ;BAD PULSE...CHECK BAD PULSE COUNTER FIRST.
                     ;
03CC  AF             PLSERR:  XRA   A             ;RESET TIME WINDOW TIMER
03CD  32  710A                STA   WINFLG
03D0  3A  70B5                LDA   BPCTR
03D3  3D                      DCR   A
03D4  FA  03DD                JM    2$            ;OUT OF COUPONS, STORE IT
03D7  32  70B5                STA   BPCTR         ;STORE COUNT
03DA  C3  03F1                JMP   5$
03DD  CD  0668       2$:      CALL  HSTUPD        ;UPDATE HISTORY
03E0  0E  20                  MVI   C,SYNCOD
03E2  CD  146C                CALL  SETLIT        ;SET SYNC LIGHT (STEADY)
03E5  21  0000                LXI   H,0           ;RESET ANALOG OUTPUTS
03E8  22  7169                SHLD  SATOUT
03EB  22  716B                SHLD  RATOUT
03EE  C3  03FB                JMP   6$            ;RESET PERIOD COUNTER
03F1  21  70B3       5$:      LXI   H,PERCTR
03F4  3A  7028                LDA   PERAVG
```

```
03F7   96              SUB    M
03F8   F2   03FF       JP     PLSRET          ;CURRENT PERIOD LESS THAN HISTORY
03FB   AF          6$: XRA    A
03FC   32   70B3       STA    PERCTR          ;RESET LONG PERIOD COUNTS
03FF   AF       PLSRET: XRA   A               ;RESET DATA FLAG
0400   32   709E       STA    DATFLG
0403   C9              RET

; NOW SEND THE RATE AND SATURATION TO THE INTERFACE BUFFER 0404   3A   7002  SNDMON: LDA  FSAT           ;GET SATURATION
0407   CD   1D3B       CALL   SPLIT           ;SPLIT INTO TWO NIBBLES
040A   7A              MOV    A,D             ;SAT MSB'S
040B   F6   20         ORI    20H             ;MONITOR FUNCTION CODE
040D   CD   1D22       CALL   TOBUFR          ;PUT INTO BUFFER
0410   7B              MOV    A,E             ;SAT LSB'S
0411   CD   1D22       CALL   TOBUFR          ;
0414   3A   7170  DECDON: LDA  FMODE
0417   D6   03         SUI    3
0419   CA   041F       JZ     1$
041C   3A   7004       LDA    FRATE           ;RATE
041F   CD   1D3B  1$:  CALL   SPLIT           ;INTO TWO NIBBLES
0422   7A              MOV    A,D             ;UPPER NIBBLE
0423   CD   1D22       CALL   TOBUFR          ;
0426   3A   7170       LDA    FMODE           ;IF IN MODE 4, SEND DECIMAL PART
0429   FE   04         CPI    4               ;
042B   CA   043D       JZ     SNDDEC          ;
042E   3A   7007       LDA    TSTMOD          ;IN TEST MODE ?
0431   E6   01         ANI    1               ;BIT 0 INDICATES IT
0433   C2   043D       JNZ    SNDDEC          ;YES, DO RATE LSB'S AND SAT DECIMAL
0436   7B              MOV    A,E             ;NO, THEN PUT END OF TRANSMIT ON
0437   F6   70         ORI    70H             ;
0439   CD   1D22       CALL   TOBUFR          ;AND SEND IT
043C   C9              RET                    ;
043D   7B       SNDDEC: MOV   A,E             ;SEND RATE LSB'S FIRST
043E   CD   1D22       CALL   TOBUFR          ;
0441   3A   70BD       LDA    FSATDP          ;THEN GET DECIMAL PART
0444   E6   0F         ANI    0FH             ;STRIP ANY FUNNY STUFF
0446   F6   70         ORI    70H             ;PUT IN END OF TRANSMIT CHARACTER
0448   CD   1D22       CALL   TOBUFR          ;AND PUT IT INTO THE BUFFER
044B   C9              RET                    ;

;LOAD CURRENT DATA LIST FROM MUNCH'S DATA...
; COMPUTE SMALL-A =LOG( MAX1/MIN1), SMALL-B = DITTO AS THEY GO BY...
;
044C   3A   70B3  XFRPLS: LDA  PERCTR         ;GET PERIOD EITHER FROM EKG OR PULSE
044F   32   7026       STA    PERIOD
0452   3A   7104       LDA    SN2DLY          ;TRANSFER TIME WINDOW IF EKG IS USED
0455   B7              ORA    A
0456   C2   045F       JNZ    1$
0459   3A   7109       LDA    WINTMR
045C   32   7062       STA    PLSDLY
045F   2A   709F  1$:  LHLD   MAX1            ;GET MAX1 AS BIG-A
0462   EB              XCHG
0463   2A   70A1       LHLD   MIN1
0466   CD   0505       CALL   LOG             ;COMPUTE LOG (MAX1/MIN1)
0469   22   70AB       SHLD   ARAT
046C   3E   04         MVI    A,4             ;SCALE FOR HISTORY BUFFER
046E   CD   1A71       CALL   SHFTHL
0471   D2   0476       JNC    2$
0474   3E   FF         MVI    A,0FFH
0476   7C       2$:    MOV    A,H
0477   32   703A       STA    CURAMP
047A   2A   70A3       LHLD   MAX2
047D   EB              XCHG
047E   2A   70A5       LHLD   MIN2
0481   CD   0505       CALL   LOG             ;COMPUTE LOG(MAX2/MIN2)
0484   22   70AD       SHLD   BRAT
0487   EB              XCHG
0488   2A   70AB       LHLD   ARAT
048B   3E   02         MVI    A,2
048D   CD   1A71       CALL   SHFTHL          ;B RATIO *2
0490   44              MOV    B,H
0491   4D              MOV    C,L
0492   CD   12F6       CALL   DIV16
0495   EB              XCHG
0496   22   70A9       SHLD   RATRAT
0499   7C              MOV    A,H
049A   32   704E       STA    CURRAT
049D   C9              RET

;COMPUTE HISTORY PARAMETERS...
;COMPUTE MEANS OF HISTORICAL VALUES FOR EACH ROW, THEN COMPUTE VARIATION
; AND CONVERT TO RELATIVE DIFFERENCE CODE (1/16'S).
; THEN COMPARE CURRENT VALUE TO HISTORICAL MEANS AND SET DIFF CODE.

049E   3A   7104  HSTCMP: LDA  SN2DLY         ;COMPUTE TIME WINDOW IF EKG IS SYNCED
04A1   B7              ORA    A
04A2   C2   04AD       JNZ    HSTCP1
04A5   0E   04         MVI    C,4             ;IS SYNCED, ADD TIME WINDOW
04A7   21   7026       LXI    H,HSTBUF
04AA   C3   04B2       JMP    HSTCP2
04AD   0E   03   HSTCP1: MVI  C,3             ;COUNTER
04AF   21   7026       LXI    H,HSTBUF        ;POINT TO BEGINNING OF FIRST ROW
```

```
04B2  C5              HSTCP2: PUSH    B               ;SAVE COUNT
04B3  23                      INX     H               ;POINT TO MEAN
04B4  23                      INX     H
04B5  E5                      PUSH    H               ;SAVE MEAN POINTER
04B6  23                      INX     H               ;POINT TO HISTORY DATA
04B7  23                      INX     H
04B8  CD    053D              CALL    HSTAVG          ;COMPUTE MEAN
04BB  E1                      POP     H
04BC  77                      MOV     M,A             ;STORE IT
04BD  E5                      PUSH    H
04BE  23                      INX     H
04BF  23                      INX     H               ;POINT TO DATA AGAIN
04C0  CD    0567              CALL    HSTVAR          ;COMPUTE VARIATION
04C3  E1                      POP     H
04C4  4E                      MOV     C,M             ;GET MEAN
04C5  CD    04F5              CALL    DIFF            ;COMPUTE DIFF CODE (BETWEEN A & C)
04C8  23                      INX     H
04C9  77                      MOV     M,A             ;STORE IT
04CA  2B                      DCX     H               ;POINT TO MEAN AGAIN
04CB  4E                      MOV     C,M             ;GET IT
04CC  2B                      DCX     H
04CD  2B                      DCX     H               ;POINT TO CURRENT
04CE  79                      MOV     A,C             ;GET MEAN VALUE
04CF  96                      SUB     M               ;MINUS CURRENT = DIFF
04D0  D2    04D6              JNC     2$              ;CHECK FOR NEGATIVE DIFF
04D3  4E                      MOV     C,M             ;CURRENT IS BIGGER, GET IT
04D4  2F                      CMA
04D5  3C                      INR     A
04D6  CD    04F5      2$:     CALL    DIFF            ;COMPUTE DIFF CODE
04D9  23                      INX     H
04DA  77                      MOV     M,A             ;STORE IT
04DB  11    0013              LXI     D,HSTINC-1      ;INCREMENT TO NEXT ROW
04DE  19                      DAD     D
04DF  C1                      POP     B
04E0  0D                      DCR     C               ;COUNTER
04E1  C2    04B2              JNZ     HSTCP2
04E4  C9                      RET
                      ;
                      ; CALL ONLY THE EKG HISTORY ROW FROM LVL3JR
                      ;
04E5  0E    01        HSTEKG: MVI     C,1
04E7  21    7076              LXI     H,EKGHBF        ;EKG HISTORY BUFFER
04EA  C3    04B2              JMP     HSTCP2
                      ;
                      ; CALL ONLY THE RESPIRATORY HISTORY ROW FROM RSPLV3
                      ;
04ED  0E    01        HSTRSP: MVI     C,1
04EF  21    708A              LXI     H,RSPHBF
04F2  C3    04B2              JMP     HSTCP2
                      ;
                      ;COMPUTE DIFF CODE BETWEEN A & C REG'S:
04F5  5F              DIFF:   MOV     E,A
04F6  06    00                MVI     B,0
04F8  16    00                MVI     D,0
04FA  CD    12F6              CALL    DIV16
04FD  7A                      MOV     A,D
04FE  1F                      RAR
04FF  1F                      RAR
0500  1F                      RAR
0501  1F                      RAR
0502  E6    0F                ANI     0FH
0504  C9                      RET
                      ;
                      ;COMPUTE LOG (A/B) (FOR B<A<2*B) BY TAYLOR EXPANSION
                      ;USES 3-TERM EXPANSION:
                      ;     LOG (A/B)= (A/B-1) - (A/B-1)^2/2 + (A/B-1)^3/3
                      ;CALLED WITH A (MAX) IN D,E AND B (MIN) IN H,L
                      ;RETURNS CARRY SET IF A IS NOT BETWEEN B & 2*B
                      ;
0505  E5              LOG:    PUSH    H               ;SAVE B
0506  CD    1348              CALL    NEGHL           ;-B
0509  19                      DAD     D               ;A-B
050A  EB                      XCHG                    ;TO D,E AS NUMERATOR
050B  C1                      POP     B               ;B TO DENOMINATOR
050C  D2    0538              JNC     10$             ;ERROR, A<B
050F  CD    12F6              CALL    DIV16           ;FORM (A-B)/B=A/B-1
0512  DA    0538              JC      10$             ;ERROR, A>2*B
0515  D5                      PUSH    D               ;SAVE TERM 1
0516  42                      MOV     B,D             ;COPY TO B,C
0517  4B                      MOV     C,E
0518  CD    1232              CALL    MPY32           ;(A/B-1)^2
051B  AF                      XRA     A
051C  78                      MOV     A,B             ;DIVIDE RESULT BY 2
051D  1F                      RAR
051E  67                      MOV     H,A
051F  79                      MOV     A,C
0520  1F                      RAR
0521  6F                      MOV     L,A             ;H,L=(A/B-1)^2/2
0522  EB                      XCHG                    ;TERM 2 TO D,E
0523  C1                      POP     B               ;TERM 1 TO B,C
```

```
0524  C5                  PUSH  B                 ;SAVE TERM 2 (W/ + SIGN)
0525  D5                  PUSH  D                 ;(A/B-1)*(A/B-1)^2/2
0526  CD   1232           CALL  MPY32             ;.66667
0529  11   AAAB           LXI   D,43691
052C  CD   1232           CALL  MPY32             ;B,C=(A/B-1)^3/3
052F  E1                  POP   H                 ;2ND TERM
0530  CD   1348           CALL  NEGHL             ;-2ND TERM
0533  09                  DAD   B                 ;SUBTRACT FROM 3RD
0534  D1                  POP   D
0535  19                  DAD   D                 ;ADD 1ST TERM
0536  AF                  XRA   A                 ;CLEAR CARRY
0537  C9                  RET
0538  37           10$:   STC                     ;ERROR RETURN
0539  21   0000           LXI   H,0
053C  C9                  RET
;RETURN MEAN OF ONE ROW OF HISTORY BUFFER...
; CALLED WITH H,L = POINTER TO HISTORY DATA, RETURNS MEAN IN A.
; CHECKS HSTLEN POINTS, IGNORES ZERO'S, RETURNS (IN B) # POINTS SUMMED.
;
053D  06   00      HSTAVG: MVI  B,0               ;DATA COUNT
053F  3A   7017           LDA   HSTLEN            ;HIST LENGTH
0542  B7                  ORA   A
0543  C8                  RZ
0544  4F                  MOV   C,A               ;COUNTER
0545  11   0000           LXI   D,0               ;CLEAR SUM
0548  7E           1$:    MOV   A,M               ;GET NEXT POINT
0549  B7                  ORA   A
054A  CA   0554           JZ    2$                ;SKIP ZERO'S
054D  83                  ADD   E
054E  5F                  MOV   E,A
054F  7A                  MOV   A,D
0550  CE   00             ACI   0
0552  57                  MOV   D,A
0553  04                  INR   B
0554  23           2$:    INX   H                 ;INC POINTER
0555  0D                  DCR   C
0556  C2   0548           JNZ   1$
0559  78                  MOV   A,B
055A  B7                  ORA   A
055B  C8                  RZ                      ;NO DATA, NO DIVIDE
055C  C5                  PUSH  B                 ;SAVE COUNT
055D  CD   12F6           CALL  DIV16
0560  21   0080           LXI   H,80H
0563  19                  DAD   D                 ;ROUND
0564  7C                  MOV   A,H
0565  C1                  POP   B
0566  C9                  RET
;COMPUTE VARIATION OF ONE ROW OF HISTORY...CALLED THE SAME AS HSTMN.
;
0567  3A   7017   HSTVAR: LDA  HSTLEN
056A  B7                  ORA   A
056B  C8                  RZ
056C  4F                  MOV   C,A               ;C=COUNTER, B=DATA BYTES
056D  06   00             MVI   B,0               ;CLEAR MIN (E) & MAX (D)
056F  11   00FF           LXI   D,0FFH
0572  7E           1$:    MOV   A,M               ;GET NEXT DATA BYTE
0573  B7                  ORA   A
0574  CA   0582           JZ    10$               ;ZERO, IGNORE IT
0577  04                  INR   B
0578  BA                  CMP   D                 ;COMPARE WITH MAX
0579  DA   057D           JC    2$                ;NOT HIGHER
057C  57                  MOV   D,A
057D  BB           2$:    CMP   E                 ;COMPARE WITH MIN
057E  D2   0582           JNC   10$
0581  5F                  MOV   E,A
0582  23           10$:   INX   H                 ;INC POINTER
0583  0D                  DCR   C
0584  C2   0572           JNZ   1$
0587  7A                  MOV   A,D               ;MAX
0588  93                  SUB   E                 ;-MIN
0589  C9                  RET
;CHECK VARIATION...
;CHECK EACH ROW OF HISTORY TABLE AGAINST ITS LIMITS,
; THEN CHECK NUMBER OF ROWS OUT OF LIMIT.
; SETS 'CURVAR' WITH FAILURE BITS: 1 = PERIOD, 2 = AMPLITUDE, 4 = RATIO,
;       8 = TIME WINDOW, 16 = EKG , 32 = RESP
;
058A  0E   00      VARCHK: MVI  C,0               ;CLEAR FLAGS
058C  06   01             MVI   B,1               ;FIRST FLAG BIT
058E  21   7018           LXI   H,VARLIM          ;POINT TO VARIATION LIMIT
0591  E5                  PUSH  H
0592  21   7029           LXI   H,PERVAR          ;POINT TO FIRST VARIATION
0595  E3           1$:    XTHL                    ;GET LIMIT POINTER
0596  7E                  MOV   A,M               ;GET LIMIT
0597  23                  INX   H
0598  E3                  XTHL
0599  96                  SUB   M                 ;MINUS VARIATION
059A  D2   05A0           JNC   2$                ;OK
059D  79                  MOV   A,C
059E  B0                  ORA   B
```

```
059F  4F              MOV   C,A           ;COUNT FAILURE
05A0  11    0014   2$: LXI   D,HSTINC
05A3  19              DAD   D             ;BUMP VAR POINTER
05A4  78              MOV   A,B           ;INCREMENT FLAG BIT
05A5  07              RLC
05A6  47              MOV   B,A
05A7  FE    40         CPI   64
05A9  C2    0595       JNZ   1$
05AC  E1              POP   H
05AD  79              MOV   A,C
05AE  32    7015       STA   CURVAR        ;SAVE FLAGS
05B1  F5              PUSH  PSW
05B2  3A    7104       LDA   SN2DLY        ;IF EKG IS SYNCED, LEAVE TIME WINDOW BIT
05B5  B7              ORA   A
05B6  C2    05BF       JNZ   4$            ;IF NOT, MASK IT OFF AND USE PER, AMP, RATIO
05B9  F1              POP   PSW
05BA  E6    0E         ANI   14            ;AMPLITUDE, TIME WINDOW, AND RATIO
05BC  C3    05C2       JMP   7$
05BF  F1         4$:   POP   PSW           ;RESTORE FLAGS
05C0  E6    07         ANI   7             ;LVL3JR CHECKS EKG
05C2  0E    00   7$:   MVI   C,0           ;CLEAR COUNT
05C4  B7         5$:   ORA   A
05C5  1F              RAR                 ;NEXT FLAG TO CARRY
05C6  D2    05CA       JNC   6$            ;NOT SET
05C9  0C              INR   C
05CA  B7         6$:   ORA   A             ;CHECK FOR NO MORE BITS
05CB  C2    05C4       JNZ   5$            ;LOOP (WITH CLEAR CARRY)
05CE  79              MOV   A,C
05CF  B7              ORA   A             ;RETURN COUNT IN AC
05D0  C8              RZ
05D1  37              STC
05D2  C9              RET
                     ;CHECK DIFFERENCE CODES...
                     ;  RETURNS NUMBER OF FAILURES IN A, WITH CARRY SET IF NON-ZERO, AND
                     ;  SETS 'CURDIF' WITH FLAGS FOR FAILURES: 1 = PERIOD, 2 = AMPLITUDE, 4 = RATIO
                     ;    8 = TIME WINDOW, 16 = EKG, 32 = RESP
                     ;
05D3  0E    00   DIFCHK: MVI C,0          ;CLEAR COUNT
05D5  06    01        MVI   B,1           ;FIRST FLAG BIT
05D7  21    701E      LXI   H,DIFLIM      ;POINT TO DIFF LIMIT
05DA  E5              PUSH  H
05DB  21    7027      LXI   H,PERDIF      ;POINT TO FIRST DIFF CODE
05DE  E3         1$:   XTHL                ;GET LIMIT POINTER
05DF  7E              MOV   A,M           ;GET LIMIT
05E0  23              INX   H
05E1  E3              XTHL
05E2  96              SUB   M             ;MINUS DIFF CODE
05E3  D2    05E9       JNC   2$            ;OK
05E6  79              MOV   A,C           ;UPDATE FAILURE CODE
05E7  B0              ORA   B
05E8  4F              MOV   C,A
05E9  11    0014  2$:  LXI   D,HSTINC
05EC  19              DAD   D             ;BUMP DIFF POINTER
05ED  78              MOV   A,B           ;SHIFT FAILURE CODE BIT
05EE  07              RLC
05EF  47              MOV   B,A
05F0  FE    40         CPI   64            ;DONE?
05F2  C2    05DE       JNZ   1$
05F5  E1              POP   H
05F6  79              MOV   A,C
05F7  32    7016       STA   CURDIF
05FA  F5              PUSH  PSW
05FB  3A    7104       LDA   SN2DLY        ; CHECK FOR EKG SYNC
05FE  B7              ORA   A
05FF  C2    0608       JNZ   4$
0602  F1              POP   PSW
0603  E6    0E         ANI   14            ;AMPLITUDE, TIME WINDOW AND RATIO
0605  C3    060B       JMP   7$
0608  F1         4$:   POP   PSW
0609  E6    07         ANI   7             ;MASK OFF EKG BIT SO LEVEL3 DOESN'T USE IT
060B  0E    00   7$:   MVI   C,0
060D  B7         5$:   ORA   A             ;CLC
060E  1F              RAR
060F  D2    0613       JNC   6$
0612  0C              INR   C
0613  B7         6$:   ORA   A
0614  C2    060D       JNZ   5$
0617  79              MOV   A,C
0618  B7              ORA   A
0619  C8              RZ
061A  37              STC
061B  C9              RET
                     ;SET LIMITS FOR VARIATION AND DIFF PER AMPLITUDE
                     ;
061C  3A    7007  SETLIM: LDA TSTMOD     ;DON'T DO THIS IF TEST MODE =128
061F  17              RAL
0620  D8              RC
0621  21    0641      LXI   H,LIMTB0
0624  3A    703C      LDA   AMPAVG
0627  BE         1$:   CMP   M
0628  D2    0632       JNC   5$
```

```
062B  11    0007          LXI   D,7
062E  19                  DAD   D              ;TRY NEXT ENTRY
062F  C3    0627          JMP   1$
0632  23          5$:     INX   H              ;MOVE TO LIMITS
0633  11    7018          LXI   D,VARLIM       ;POINT D,E TO DESTINATION TABLE
0636  0E    0C            MVI   C,12
0638  7E          2$:     MOV   A,M
0639  12                  STAX  D
063A  13                  INX   D
063B  23                  INX   H
063C  0D                  DCR   C
063D  C2    0638          JNZ   2$
0640  C9                  RET

;LIMITS:   AMPL, VAR..., DIFF...
0641  1E    06    LIMTB0: DB     30, 6, 8, 8, 4, 7, 6, 4, 7, 7, 4, 6, 7
0643  08    08
0645  04    07
0647  06    04
0649  07    07
064B  04    06
064D  07
064E  0F    06            DB     15, 6, 10, 10, 4, 7, 6, 4, 8, 8, 4, 6, 7
0650  0A    0A
0652  04    07
0654  06    04
0656  08    08
0658  04    06
065A  07
065B  00    06            DB      0, 6, 12, 10, 5, 7, 6, 5, 10, 10, 5, 6, 7
065D  0C    0A
065F  05    07
0661  06    05
0663  0A    0A
0665  05    06
0667  07
```

RESPOX: MICROBENCH 8080/8085 CROSS ASSEMBLER (V2)-436  30-MAR-85 13:30:07 PAGE 26

```
 1
 2                        ;STORE CURRENT DATA AS HISTORY...
 3                        ;  LOOKS AT HSTLEN FOR BUFFER SIZE
 4                        ;
 5 0668  3A   7104  HSTUPD: LDA   SN2DLY      ;IF EKG SYNCED, ADD TIME WINDOW
 6 066B  B7                  ORA   A
 7 066C  C2   0677          JNZ   HSTUP1
 8 066F  0E   04            MVI   C,4
 9 0671  21   7026          LXI   H,HSTBUF
10 0674  C3   067C          JMP   HSTUP2
11 0677  0E   03    HSTUP1: MVI   C,3         ;ROW COUNTER
12 0679  21   7026          LXI   H,HSTBUF    ;POINTER
13 067C  46         HSTUP2: MOV   B,M         ;GET DATA
14 067D  C5                 PUSH  B
15 067E  11   0004          LXI   D,4         ;MOVE POINTER TO FIRST DATA POINT
16 0681  19                 DAD   D
17 0682  3A   7017          LDA   HSTLEN      ;GET HISTORY LENGTH
18 0685  3D                 DCR   A
19 0686  FA   06A4          JM    11$
20 0689  CA   0699          JZ    10$
21 068C  4F                 MOV   C,A
22 068D  06   00            MVI   B,0
23 068F  09                 DAD   B           ;POINT TO LAST DATA POINT
24 0690  2B         2$:    DCX   H
25 0691  7E                 MOV   A,M
26 0692  23                 INX   H
27 0693  77                 MOV   M,A         ;SHUFFLE DATA
28 0694  2B                 DCX   H           ;BACK UP POINTER
29 0695  0D                 DCR   C           ;CHECK COUNT
30 0696  C2   0690          JNZ   2$
31 0699  C1         10$:   POP   B           ;GET DATA
32 069A  70                 MOV   M,B
33 069B  11   0010          LXI   D,HSTINC-4
34 069E  19                 DAD   D
35 069F  0D                 DCR   C           ;DECREMENT ROW COUNT
36 06A0  C2   067C          JNZ   HSTUP2
37 06A3  C9                 RET
38 06A4  C1         11$:   POP   B
39 06A5  C9                 RET
40                        ;
41                        ;UPDATE HISTORY FOR EKG
42                        ;
43 06A6  0E   01    EKGHUP: MVI   C,1
44 06A8  21   7076          LXI   H,EKGHBF
45 06AB  C3   067C          JMP   HSTUP2
46                        ;
47                        ; UPDATE HISTORY FOR RESPIRATIONS
48                        ;
49 06AE  0E   01    RSPHUP: MVI   C,1
50 06B0  21   708A          LXI   H,RSPHBF
51 06B3  C3   067C          JMP   HSTUP2
```

```
                        ;CHECK FOR A DICROTIC NOTCH....
                        ;IF AMPLITUDE OF CURRENT PULSE < LAST PULSE /2 AND FLAG NOT SET,
                        ; THEN RETURN CARRY SET.
                        ;
 06B6  AF       CHKNCH:  XRA   A                    ;CLEAR CARRY
 06B7  3A  703E          LDA   AMPHST               ;GET MOST RECENT AMPLITUDE
 06BA  1F               RAR                         ;/2
 06BB  6F               MOV   L,A
 06BC  3A  703A          LDA   CURAMP               ;CURRENT
 06BF  BD               CMP   L
 06C0  DA  06D7          JC    1$                   ;IS OK
 06C3  3A  7014          LDA   SYNFLG               ; CHECK IF SYNCED
 06C6  B7               ORA   A
 06C7  C2  06E1          JNZ   2$                   ;IF SYNCED, CHECK FOR PERIOD /2
 06CA  AF               XRA   A
 06CB  3A  702A          LDA   PERHST
 06CE  1F               RAR
 06CF  6F               MOV   L,A
 06D0  3A  7026          LDA   PERIOD
 06D3  BD               CMP   L
 06D4  D2  06E1          JNC   2$                   ; NO NOTCHES HERE
 06D7  21  70B6  1$:    LXI   H,NCHFLG             ;CHECK FOR CONSECUTIVE NOTCHES
 06DA  7E               MOV   A,M
 06DB  B7               ORA   A
 06DC  C2  06E1          JNZ   2$                   ;CAN'T HAVE CONSECUTIVE NOTCHES
 06DF  34               INR   M
 06E0  37               STC
 06E1  C9        2$:    RET

;COMPUTE PULSE RATE...
                        ;
 06E2  3A  7026  COMRAT: LDA   PERIOD              ;CHECK FOR ZERO PERIOD
 06E5  B7       COMRT3:  ORA   A                   ;ENTER HERE FOR EKG HR
 06E6  CA  06F8          JZ    1$
 06E9  47               MOV   B,A
 06EA  0E  00           MVI   C,0                  ;B,C = PERIOD * 256
 06EC  11  0D95          LXI   D,3477              ;60 SECONDS/MIN * 57 SAMPLES/SEC, FUDGED,
 06EF  CD  12F6          CALL  DIV16               ;3600/PERIOD
 06F2  3E  00           MVI   A,0
 06F4  DA  06F8          JC    1$                  ;CHECK FOR OVERFLOW
 06F7  7A               MOV   A,D
 06F8  32  7003  1$:    STA   RATE
 06FB  CD  09CA          CALL  FILPLS              ;FILTER IT
 06FE  3A  7004          LDA   FRATE               ;SCALE 0-1V = 0-250 BPM
 0701  CD  1276          CALL  SCL250
 0704  22  716B          SHLD  RATOUT              ;CALL IT RATOUT
 0707  C9               RET

; ENTER COMRAT WITH EKG R-R PERIOD
                        ;
 0708  3A  7076  COMRT2: LDA   RRPER
 070B  C3  06E5          JMP   COMRT3

;COMPUTE RESPIRATORY RATE FROM RESPIRATORY PERIOD
                        ;
 070E  3A  708A  COMRSP: LDA   RSPPER
 0711  B7               ORA   A
 0712  CA  0724          JZ    1$
 0715  47               MOV   B,A
 0716  0E  00           MVI   C,0
 0718  11  0366          LXI   D,870               ;60 SEC/MIN * 14SAMPLES/SEC - FUDGED
 071B  CD  12F6          CALL  DIV16
 071E  3E  00           MVI   A,0
 0720  DA  0724          JC    1$
 0723  7A               MOV   A,D
 0724  32  7113  1$:    STA   RESP
 0727  CD  0A1A          CALL  FILRSP
 072A  C9               RET

;COMPUTE HEART RATE FROM ECG R WAVE
                        ;THIS ROUTINE FIGURES OUT WHETHER EKG AND OR OXIMETER
                        ;ARE SYNCED. IF EKG ONLY, THEN DO CONFIDENCE CHECKING ON
                        ;PERIOD AND DISPLAY AND ALARM CHECK FOR THE HEART RATE
                        ;IF OXIMETER IS SYNCED, THEN DETERMIN HR BY THE R-WAVE PERIOD
                        ;IF THE CONFIDENCE IS GOOD.
                        ;
                        ;BEGIN CHECKING R-WAVE
 072B  CD  07F9  LVL3JR: CALL  LDSCHK              ;CHECK FOR LEADS OFF
 072E  D8               RC                         ;CARRY SET IF LEADS OFF DETECTED
 072F  3A  7100          LDA   EKGFLG              ;IS THE EKG FLAG SET?
 0732  B7               ORA   A
 0733  C8               RZ                         ;NOT THIS TIME
```

RESPOX: MICROBENCH 8080/8085 CROSS ASSEMBLER (V2)-436  30-MAR-85 13:30:07 PAGE 29

```
 1 0734   3A   70FF            LDA    EKGPER       ;R-WAVE PERIOD COUNT
 2 0737   32   7076            STA    RRPER        ;STORE AS R-R PERIOD
 3 073A   CD   04E5            CALL   HSTEKG       ;COMPUT EKG HISTORY PARAMS
 4 073D   21   7104            LXI    H,SN2DLY     ;5 PULSE DELAY FOR EKG SYNC
 5 0740   7E                   MOV    A,M
 6 0741   3D                   DCR    A
 7 0742   FA   0749            JM     1$
 8 0745   77                   MOV    M,A
 9 0746   C3   07BF            JMP    7$           ;NOT TIMED DOWN - CHECK R-WAVE VARIATION
10 0749   3E   00        1$:   MVI    A,0          ;WE'RE SYNCED
11 074B   32   7106            STA    EKGSNC       ;EKG HAS BEEN USED
12 074E   CD   05D3            CALL   DIFCHK       ;CHECK DIFFERENCE CODES
13 0751   3A   7016            LDA    CURDIF       ;CHECK ONLY THE PERIOD HERE
14 0754   E6   10              ANI    16           ;MASK FOR EKG BIT
15 0756   C2   079B            JNZ    4$           ;FAILED PERIOD, DON'T CALC HR THIS TIME
16 0759   3E   14              MVI    A,20         ;PERIOD IS GOOD, RESET EKG TIMEOUT
17 075B   32   70F8            STA    EKGTMR       ;5 SEC TIMEOUT
18 075E   CD   07E3            CALL   SETTRG       ;SET WINDOW AND FLAG TO TRIGGER MUNCH
19 0761   3E   03              MVI    A,3
20 0763   32   7107            STA    BADEKG       ;BAD EKG TICKET BOOK
21 0766   3A   7014            LDA    SYNFLG       ;CHECK FOR OXIMETER SYNC
22 0769   B7                   ORA    A
23 076A   C2   0777            JNZ    19$          ;NOT
24 076D   3A   70B4            LDA    SYNDLY       ;HAVE 5 PULSES BEEN PROCESSED?
25 0770   B7                   ORA    A
26 0771   CA   0777            JZ     19$          ;YES, DON'T CHANGE FILTER CONSTS
27 0774   C3   077A            JMP    20$          ;NOT YET, SO DON'T DIDDLE FILTER CONSTS FOR IT
28 0777   CD   0A41      19$:  CALL   FILSET       ;SET FILTER CONSTANTS
29 077A   CD   0708      20$:  CALL   COMRT2       ;CALCULATE HR
30 077D   CD   0A8F            CALL   DSPSR        ;SEND TO DISPLAY
31 0780   3A   7014            LDA    SYNFLG       ;CHECK OXIMETER SYNC FOR ALARM CHECKING
32 0783   B7                   ORA    A
33 0784   CA   0795            JZ     5$           ;IS SYNCED, CHECK ALL ALARMS
34 0787   3A   70C9            LDA    ALMFLG       ;NOT SYNCED, MASK OFF HR ALARM ONLY
35 078A   E6   01              ANI    1            ;PRESERVES ALARM DISPLAY FOR OXIMETER NOSYNC
36 078C   32   70C9            STA    ALMFLG
37 078F   CD   0CA0            CALL   ALMCKB       ;RATE AND EKG ALARM CHECKS
38 0792   C3   07A8            JMP    10$          ;GO UPDATE HISTORY
39 0795   CD   0C37      5$:   CALL   ALMCHK       ;FULL ALARM CHECK
40 0798   C3   07A8            JMP    10$
41 079B   3A   7107      4$:   LDA    BADEKG       ;SEE IF WE CAN IGNORE THIS ONE
42 079E   3D                   DCR    A
43 079F   FA   07A8            JM     10$          ;OUT OF TICKETS, STORE IT
44 07A2   32   7107            STA    BADEKG       ;IGNORE THIS ONE
45 07A5   C3   07B7            JMP    12$          ;EXIT HERE
46 07A8   CD   06A6      10$:  CALL   EKGHUP       ;UPDATE HISTORY FOR EKG
47 07AB   AF                   XRA    A            ;RESET TIME WINDOW AND ENABLE
48 07AC   32   7109            STA    WINTMR
49 07AF   32   710A            STA    WINFLG
50 07B2   3E   08              MVI    A,8          ;RESET HR ANALOG OUT TIMEOUT
51 07B4   32   710B            STA    RATCLK
52 07B7   AF              12$: XRA    A
53 07B8   32   7100            STA    EKGFLG       ;RESET EKG FLAG
54 07BB   32   70FF            STA    EKGPER       ;RESET EKG PERIOD
55 07BE   C9                   RET
56 07BF   CD   058A      7$:   CALL   VARCHK       ;NOT QUITE SYNCED, CHECK PRESYNC VARIATION
57 07C2   3A   7015            LDA    CURVAR       ;CHECK PERIOD ONLY
```

RESPOX: MICROBENCH 8080/8085 CROSS ASSEMBLER (V2)-436  30-MAR-85 13:30:07 PAGE 30

```
 1 07C5   E6   10              ANI    16
 2 07C7   CA   07CE            JZ     8$           ;IS OK
 3 07CA   21   7104            LXI    H,SN2DLY     ;NOT OK, BUMP BACK EKG DELAY COUNTER
 4 07CD   34                   INR    M
 5 07CE   3E   14        8$:   MVI    A,20         ;RESET EKG TIMEOUT COUNTER
 6 07D0   32   70F8            STA    EKGTMR
 7 07D3   3E   03              MVI    A,3          ;ONLY USE TICKETS WHEN SYNCED
 8 07D5   32   7107            STA    BADEKG       ;SET HR FILTER LOW AND CALC BASELINE HR
 9 07D8   3E   FF              MVI    A,255
10 07DA   32   7006            STA    FRATN
11 07DD   CD   0708            CALL   COMRT2       ;CALCULATE, BUT DON'T DISPLAY.....YET
12 07E0   C3   07A8            JMP    10$
13
14                             ;
15                             ; RESET MUNCH ON THE R-WAVE.
16                             ;
17 07E3   21   7108      SETTRG: LXI  H,DATTRG     ;SYNCHRONIZE DATBUF TO R-WAVE
18 07E6   7E                   MOV    A,M
19 07E7   E6   FF              ANI    BUFMSK
20 07E9   32   7179            STA    DTOIDX       ;CAUSE MUNCH TO START HERE
21 07EC   21   70CB            LXI    H,MCHMOD     ;INITIALIZE MUNCH PARAMETERS
22 07EF   1E   0B              MVI    E,11
23 07F1   36   00        1$:   MVI    M,0
24 07F3   23                   INX    H
25 07F4   1D                   DCR    E
26 07F5   C2   07F1            JNZ    1$
27 07F8   C9                   RET
28
29                             ;
30                             ;CHECK FOR A LEADS OFF CONDITION
31                             ; THIS IS SENSED BY A WINDOW COMPARATOR (-4V => +4V)
```

```
32                                 ; IF LEADS OFF DETECTED, SET CARRY
33                                 ;
34 07F9  3A  7106   LDSCHK: LDA  EKGSNC
35 07FC  B7                 ORA  A
36 07FD  C0                 RNZ                    ;DON'T CHECK IF EKG IS NOT BEING USED
37 07FE  3A  70CA           LDA  STATUS            ;GET COMPARATOR BIT
38 0801  E6  08             ANI  8
39 0803  CA  080B           JZ   1$                ;LEADS OFF IF LOW
40 0806  AF                 XRA  A                 ;CLEAR FLAG AND CARRY BIT
41 0807  32  710D           STA  LDSFLG
42 080A  C9                 RET
43 080B  3A  710D   1$:     LDA  LDSFLG            ;ONLY DO THIS ONCE PER EVENT
44 080E  B7                 ORA  A
45 080F  C0                 RNZ
46 0810  3E  01             MVI  A,1
47 0812  32  70F8           STA  EKGTMR            ;FORCE A TIMEOUT
48 0815  32  710D           STA  LDSFLG
49 0818  37                 STC
50 0819  C9                 RET
51                                 ;
52                                 ;
53                                 ; COMPUTE RESPIRATORY RATE
54                                 ; CHECK RESPIRATORY PERIOD
55                                 ; THE RESPIRATORY RATE IS DISPLAYED IN MODE 5
56                                 ; THERE IS A 15 SEC APNEA TIMEOUT ONCE THE RESP IS SYNCED
57                                 ;
```

RESPOX; MICROBENCH 8080/8085 CROSS ASSEMBLER (V2)-436   30-MAR-85 13:30:07 PAGE 31

```
 1 081A  3A  7110   RSPLV3: LDA  RSPFLG            ;CHECK FLAG
 2 081D  B7                 ORA  A
 3 081E  C8                 RZ                     ;NO NEW RESP
 4 081F  3A  710E           LDA  RSPCNT            ;TRANSFER COUNT TO PERIOD
 5 0822  32  708A           STA  RSPPER
 6 0825  CD  04ED           CALL HSTRSP            ;COMPUTE RESP HISTORY PARAMS
 7 0828  21  7112           LXI  H,SN3DLY          ;HAVE TWO RESPS BEEN PROCESSED?
 8 082B  7E                 MOV  A,M
 9 082C  3D                 DCR  A
10 082D  FA  0834           JM   1$                ;YES, RESP IS SYNCED
11 0830  77                 MOV  M,A
12 0831  C3  0879           JMP  7$                ;NO, NOT YET
13 0834  AF         1$:     XRA  A
14 0835  32  7111           STA  RSPSNC            ;RESP MONITOR HAS BEEN USED
15 0838  3E  3C             MVI  A,60
16 083A  32  710F           STA  RSPTMR            ;RESET APNEA TIMEOUT
17 083D  3E  80             MVI  A,128
18 083F  32  7115           STA  FRSPN             ;RESP FILTER CONSTANT
19 0842  3A  70C9           LDA  ALMFLG            ;RESET RESP ALARM BIT
20 0845  E6  07             ANI  7
21 0847  32  70C9           STA  ALMFLG
22 084A  3A  7014           LDA  SYNFLG            ;TURN OFF AUDIO ALARM IF OXIM/EKG NOT SYNCED
23 084D  B7                 ORA  A
24 084E  CA  085B           JZ   5$
25 0851  3A  7106           LDA  EKGSNC
26 0854  B7                 ORA  A
27 0855  CA  085B           JZ   5$
28 0858  CD  0D49           CALL ALMCKC            ;NEITHER SYNCED, TURN OFF RESP ALARM
29 085B  3A  7170   5$:     LDA  FMODE             ;CHECK FOR MODE 5
30 085E  FE  05             CPI  5
31 0860  C2  0868           JNZ  11$
32 0863  0E  38             MVI  C,FD2MSK
33 0865  CD  1464           CALL DSPUBK            ;UNBLINK DISPLAY IF MODE 5 IS ACTIVE
34 0868  CD  070E   11$:    CALL COMRSP            ;CALC RESP RATE
35 086B  CD  0A8F           CALL DSPSR            ;SEND TO DISPLAY
36 086E  CD  06AE   4$:     CALL RSPHUP            ;UPDATE HISTORY
37 0871  AF                 XRA  A
38 0872  32  7110           STA  RSPFLG            ;RESET FLAG
39 0875  32  710E           STA  RSPCNT            ;RESET COUNT
40 0878  C9                 RET
41 0879  3E  3C     7$:     MVI  A,60              ;DON'T TIMEOUT UNTIL SYNCED
42 087B  32  710F           STA  RSPTMR
43 087E  3E  FF             MVI  A,255             ;TURN DOWN FILTER COEFFICIENT
44 0880  32  7115           STA  FRSPN
45 0883  CD  070E           CALL COMRSP
46 0886  C3  086E           JMP  4$
47
48                                 ;
49                                 ;
50                                 ;COMPUTE OXYGEN SATURATION
51                                 ;COMPUTE SAT=100*(BR2-R*BR1)/(R*(B01-BR1)+(BR2-B02))
52                                 ;  TYPICAL VALUES ARE R= .4 TO 2.2 (RATRAT=R/4)
53                                 ;                     B01=41.4, BR1=115.2, B02=20.0, BR2=228.6
54                                 ;   SO THE COMPUTATION IS IMPLEMENTED AS
55                                 ;     SAT=200*(BR2/2-2*RATRAT*BR1)/(-4*RATRAT*(BR1-B01)+(BR2-B02))
56                                 ;
57 0889  2A  70AF   COMSAT: LHLD FRATIO
```

RESPOX: MICROBENCH 8080/8085 CROSS ASSEMBLER (V2)-436   30-MAR-85 13:30:07 PAGE 32

```
  1 088C  CD  08A0           CALL   XSAT
  2 088F  D8                 RC
  3 0890  22  70B7           SHLD   SATX
  4 0893  CD  0974           CALL   FILSAT
  5 0896  3A  7002           LDA    FSAT
  6 0899  CD  125F           CALL   SCL100           ;SCALE 0-1V = 0-100% SAO2
  7 089C  22  7169           SHLD   SATOUT
  8 089F  C9                 RET
  9
 10 08A0  22  70B1   XSAT:   SHLD   XRATIO
 11 08A3  3A  7008           LDA    CALOK            ;CHECK CAL FLAG
 12 08A6  B7                 ORA    A
 13 08A7  CA  0928           JZ     20$              ;NO SAT IF NOT SET
 14 08AA  AF                 XRA    A
 15 08AB  32  70B7           STA    SATX             ;RESET FLAG
 16 08AE  2A  70E3           LHLD   B02
 17 08B1  EB                 XCHG
 18 08B2  2A  70E5           LHLD   BR2
 19 08B5  CD  1340           CALL   NEGDE
 20 08B8  19                 DAD    D                ;H.L = BR2-B02
 21 08B9  E5                 PUSH   H                ;SAVE IT
 22 08BA  2A  70DF           LHLD   B01
 23 08BD  EB                 XCHG
 24 08BE  2A  70E1           LHLD   BR1
 25 08C1  CD  1340           CALL   NEGDE
 26 08C4  19                 DAD    D                ;H.L = BR1-B01
 27 08C5  DA  08D0           JC     1$               ;BR1 > B01, OK
 28 08C8  CD  1348           CALL   NEGHL            ;BR1 < B01, FIX IT
 29 08CB  3E  01             MVI    A,1
 30 08CD  32  70B7           STA    SATX             ;FLAG IT
 31 08D0  4D          1$:    MOV    C,L              ;TO B,C
 32 08D1  44                 MOV    B,H
 33 08D2  2A  70B1           LHLD   XRATIO           ;R/4
 34 08D5  EB                 XCHG
 35 08D6  CD  1232           CALL   MPY32            ;B.CDE = (R/4)*(BR1-B01)
 36 08D9  3E  02             MVI    A,2
 37 08DB  CD  092D           CALL   SHBCDE           ;MULTIPLY BY 4
 38 08DE  D1                 POP    D
 39 08DF  DA  0929           JC     11$              ;ERROR IF OVERFLOWED
 40 08E2  60                 MOV    H,B
 41 08E3  69                 MOV    L,C
 42 08E4  3A  70B7           LDA    SATX
 43 08E7  B7                 ORA    A
 44 08E8  C2  08EE           JNZ    2$
 45 08EB  CD  1348           CALL   NEGHL            ;NEGATE IT, H.L = R*(B01-BR1)
 46 08EE  19          2$:    DAD    D                ;H.L = R*(B01-BR1)+(BR2-B02)
 47 08EF  E5                 PUSH   H                ;SAVE DENOMINATOR
 48 08F0  2A  70E1           LHLD   BR1
 49 08F3  EB                 XCHG
 50 08F4  2A  70B1           LHLD   XRATIO
 51 08F7  44                 MOV    B,H
 52 08F8  4D                 MOV    C,L
 53 08F9  CD  1232           CALL   MPY32            ;B.CDE = (R/4)*BR1
 54 08FC  3E  01             MVI    A,1
 55 08FE  CD  092D           CALL   SHBCDE           ;B.CDE = (R*BR1)/2
 56 0901  2A  70E5           LHLD   BR2
 57 0904  3E  FF             MVI    A,-1
```

RESPOX: MICROBENCH 8080/8085 CROSS ASSEMBLER (V2)-436   30-MAR-85 13:30:07 PAGE 33

```
  1 0906  CD  1A71           CALL   SHFTHL
  2 0909  59                 MOV    E,C
  3 090A  50                 MOV    D,B
  4 090B  CD  1340           CALL   NEGDE
  5 090E  19                 DAD    D                ;H.L = BR2/2-(R*BR1)/2
  6 090F  EB                 XCHG
  7 0910  C1                 POP    B
  8 0911  D2  0929           JNC    11$
  9 0914  CD  12F6           CALL   DIV16            ;DO THE DIVIDE
 10 0917  DA  0928           JC     20$              ;OVERFLOW MEANS BAD BOOGIE
 11 091A  01  C800           LXI    B,200*256        ;200.00
 12 091D  CD  1232           CALL   MPY32            ;B.CDE = SAT
 13 0920  60                 MOV    H,B
 14 0921  69                 MOV    L,C
 15 0922  7C                 MOV    A,H
 16 0923  B7                 ORA    A
 17 0924  FA  0928           JM     20$              ;CHECK FOR BAD SAT'S
 18 0927  C9                 RET
 19 0928  37          20$:   STC
 20 0929  21  0000   11$:   LXI    H,0
 21 092C  C9                 RET
 22
 23                          ;SHIFT B,C,D,E LEFT BY (A) BITS
 24
 25 092D  B7          SHBCDE: ORA   A
 26 092E  C8                 RZ
 27 092F  F5                 PUSH   PSW
 28 0930  7B                 MOV    A,E
```

```
29 0931  17                    RAL
30 0932  5F                    MOV   E,A
31 0933  7A                    MOV   A,D
32 0934  17                    RAL
33 0935  57                    MOV   D,A
34 0936  79                    MOV   A,C
35 0937  17                    RAL
36 0938  4F                    MOV   C,A
37 0939  78                    MOV   A,B
38 093A  17                    RAL
39 093B  47                    MOV   B,A
40 093C  DA  0944              JC    2$
41 093F  F1                    POP   PSW
42 0940  3D                    DCR   A
43 0941  C3  092D              JMP   SHBCDE
44 0944  F1          2$:       POP   PSW
45 0945  37                    STC
46 0948  C9                    RET
47
48                  ;
49                  ;FILTER RATIO...
50                  ;COMPUTE FRATIO=RATRAT*(N/256) + FRATIO*(256-N)/256
51                  ;WHERE N IS FSATN, THE SAT FILTER CONSTANT
52                  ;
53 0947  2A  70A9   FILRAT: LHLD  RATRAT    ;GET RATIO B/A
54 094A  3A  7007           LDA   TSTMOD    ;CHECK  TEST FLAGS
55 094D  E6  02             ANI   2         ;NO FILTER BIT
56 094F  C2  0970           JNZ   1$        ;BYPASS THE FILTER
57 0952  3A  7170           LDA   FMODE     ;DITTO FOR MODE 6
```

RESPOX: MICROBENCH 8080/8085 CROSS ASSEMBLER (V2)-436   30-MAR-85 13:30:07 PAGE 34

```
 1 0955  FE  06               CPI   6
 2 0957  CA  0970             JZ    1$
 3 095A  EB                   XCHG              ;RATIO TO D,E
 4 095B  3A  7005             LDA   FSATN
 5 095E  CD  09BA             CALL  FILMPY     ;DO RATRAT*(N/256)
 6 0961  E5                   PUSH  H          ;SAVE THE DATA
 7 0962  2A  70AF             LHLD  FRATIO
 8 0965  EB                   XCHG
 9 0966  3A  7005             LDA   FSATN      ;GET   256-N
10 0969  2F                   CMA
11 096A  3C                   INR   A
12 096B  CD  09BA             CALL  FILMPY     ;DO FRATIO *(256-N)/256
13 096E  D1                   POP   D
14 096F  19                   DAD   D
15 0970  22  70AF    1$:      SHLD  FRATIO
16 0973  C9                   RET
17
18
19
```

RESPOX: MICROBENCH 8080/8085 CROSS ASSEMBLER (V2)-436   30-MAR-85 13:30:07 PAGE 35

```
 1
 2              ;SAT FILTER...
 3              ;COMPUTE FSAT=INT(FSAT/2 + FSATX/2)
 4              ; WHERE  FSATX= SATX*(N/256) + FSATX*(256-N)/256
 5              ; N IS THE FILTER CONSTANT (SET ELSEWHERE) THAT NORMALLY RANGES FROM 1 TO 64
 6              ; FSAT IS THE INTEGER DISPLAYED SAT
 7              ; FSATX IS THE 16-BIT (INT.FCT) ACCUMULATOR
 8              ; SATX IS THE 16-BIT COMPUTED SAT.
 9              ;
10 0974  2A  70B7   FILSAT: LHLD  SATX      ;GET DATA
11 0977  3A  7170           LDA   FMODE     ;CHECK FOR MODE 4 (XX.X)
12 097A  FE  04             CPI   4
13 097C  CA  09A2           JZ    2$        ;IT IS, SKIP ROUNDING
14 097F  3A  70B4           LDA   SYNDLY    ;CHECK FOR START-UP
15 0982  B7                 ORA   A
16 0983  C2  09A2           JNZ   2$        ;IT IS, SKIP THIS STEP
17 0986  3A  7007           LDA   TSTMOD    ;CHECK FOR TEST MODE
18 0989  E6  03             ANI   3         ;NO-FILTER OR XX.X MODE
19 098B  C2  09AE           JNZ   3$        ;SKIP ROUNDING AND 100 CHECK
20 098E  3A  7170           LDA   FMODE     ;DITTO FOR MODE 6
21 0991  FE  06             CPI   6
22 0993  CA  09AE           JZ    3$
23 0996  3A  7002           LDA   FSAT      ;OLD DISPLAYED SAT
24 0999  57                 MOV   D,A
25 099A  1E  00             MVI   E,0
26 099C  19                 DAD   D
27 099D  3E  FF             MVI   A,-1
28 099F  CD  1A71           CALL  SHFTHL    ;DIVIDE BY 2
29 09A2  EB          2$:    XCHG             ;NEW 16-BIT SAT TO D,E
30 09A3  21  9C00           LXI   H,-100*256
31 09A6  19                 DAD   D
32 09A7  EB                 XCHG
33 09A8  D2  09AE           JNC   3$        ;LESS THAN 100, IS OK
```

```
34 09AB  21   6400          LXI   H,100*256      ;100.0
35 09AE  22   70B9    3$:   SHLD  FSATX          ;STORE IT AT LAST
36 09B1  11   0080          LXI   D,80H          ;ROUND SUM
37 09B4  19                 DAD   D
38 09B5  7C                 MOV   A,H
39 09B6  32   7002          STA   FSAT
40 09B9  C9                 RET
41                     ;
42                          ;MULTIPLY (A)/256 BY (D,E) AND LEAVE ROUNDED RESULT IN H,L
43                     ;
44 09BA  4F          FILMPY: MOV  C,A            ;TO B,C AS N/256
45 09BB  06   00            MVI   B,0
46 09BD  CD   1232          CALL  MPY32          ;MULTIPLY INTO BC,DE
47 09C0  21   0080          LXI   H,80H          ;ROUND UP FRACT TO 8 BITS
48 09C3  19                 DAD   D
49 09C4  6C                 MOV   L,H
50 09C5  79                 MOV   A,C
51 09C6  CE   00            ACI   0
52 09C8  67                 MOV   H,A            ;SATX*N/256 IN H,L
53 09C9  C9                 RET
```

```
                             ;FILTER RATE....SAME AS ABOVE
                             ;
 4 09CA  3A   7003   FILPLS: LDA   RATE
 5 09CD  57                  MOV   D,A
 6 09CE  1E   00             MVI   E,0           ;DATA TO D,E
 7 09D0  3A   7170           LDA   FMODE
 8 09D3  FE   06             CPI   6             ;NO FILTERING IF MODE 6
 9 09D5  C2   09DD           JNZ   4$
10 09D8  3E   FF             MVI   A,255
11 09DA  32   7006           STA   FRATN
12 09DD  3A   7006    4$:    LDA   FRATN         ;GET N
13 09E0  CD   09BA           CALL  FILMPY        ;MULTIPLY DATA BY N/256
14 09E3  E5                  PUSH  H             ;SAVE IT
15 09E4  2A   70BE           LHLD  FRATX         ;GET OLD DATA
16 09E7  EB                  XCHG
17 09E8  3A   7006           LDA   FRATN
18 09EB  2F                  CMA
19 09EC  3C                  INR   A
20 09ED  CD   09BA           CALL  FILMPY        ;OLD DATA * (256-N)/256
21 09F0  D1                  POP   D             ;NEW DATA
22 09F1  19                  DAD   D
23 09F2  22   70BE           SHLD  FRATX         ;SAVE NEW OLD DATA
24 09F5  3A   7170           LDA   FMODE
25 09F8  FE   06             CPI   6             ;SKIP NEXT STAGE IF MODE 6
26 09FA  CA   0A11           JZ    1$
27 09FD  3A   70B4           LDA   SYNDLY        ;CHECK OR START-UP
28 0A00  B7                  ORA   A
29 0A01  C2   0A11           JNZ   1$            ;SKIP SECOND STAGE
30 0A04  3A   7004           LDA   FRATE         ;OLD DISPLAY
31 0A07  57                  MOV   D,A
32 0A08  1E   00             MVI   E,0
33 0A0A  19                  DAD   D
34 0A0B  7C                  MOV   A,H
35 0A0C  1F                  RAR
36 0A0D  67                  MOV   H,A
37 0A0E  7D                  MOV   A,L
38 0A0F  1F                  RAR
39 0A10  6F                  MOV   L,A
40 0A11  11   0080    1$:    LXI   D,80H
41 0A14  19                  DAD   D
42 0A15  7C                  MOV   A,H
43 0A16  32   7004           STA   FRATE
44 0A19  C9                  RET
```

```
                             ;
                             ;
                             ; FILTER RESP...SAME AS ABOVE
                             ;
 6 0A1A  3A   7113   FILRSP: LDA   RESP
 7 0A1D  57                  MOV   D,A
 8 0A1E  1E   00             MVI   E,0
 9 0A20  3A   7115           LDA   FRSPN
10 0A23  CD   09BA           CALL  FILMPY
11 0A26  E5                  PUSH  H
12 0A27  2A   7116           LHLD  FRSPX
13 0A2A  EB                  XCHG
14 0A2B  3A   7115           LDA   FRSPN
15 0A2E  2F                  CMA
```

```
16 0A2F   3C                     INR    A
17 0A30   CD    09BA             CALL   FILMPY
18 0A33   D1                     POP    D
19 0A34   19                     DAD    D
20 0A35   22    7116             SHLD   FRSPX
21 0A38   11    0080             LXI    D,80H
22 0A3B   19                     DAD    D
23 0A3C   7C                     MOV    A,H
24 0A3D   32    7114             STA    FRSP
25 0A40   C9                     RET
26                               ;
27                               ;
28                               ;SET FILTER CONSTANTS...
29                               ;
30 0A41   3A    7007    FILSET:  LDA    TSTMOD          ;DON'T RESET FILTERS IF TEST MODE = 128
31 0A44   17                     RAL
32 0A45   D8                     RC
33 0A46   3A    7170             LDA    FMODE
34 0A49   5F                     MOV    E,A
35 0A4A   16    00               MVI    D,0
36 0A4C   21    0A85             LXI    H,FILTBL-1
37 0A4F   19                     DAD    D
38 0A50   4E                     MOV    C,M             ;GET FILTER INDEX
39 0A51   41                     MOV    B,C
40 0A52   3A    7028             LDA    PERAVG          ;CHECK AVERAGE PERIOD
41 0A55   FE    23               CPI    35              ;CHECK FOR RATE > 100
42 0A57   D2    0A5E             JNC    1$              ;LESS
43 0A5A   AF                     XRA    A
44 0A5B   79                     MOV    A,C             ;GREATER THAN 100 BEATS, UP THE FILTER
45 0A5C   1F                     RAR
46 0A5D   4F                     MOV    C,A
47 0A5E   3A    7014    1$:      LDA    SYNFLG          ;IF NOT PULSE SYNCED, SKIP THIS
48 0A61   B7                     ORA    A
49 0A62   C2    0A7D             JNZ    4$
50 0A65   3A    703C             LDA    AMPAVG          ;CHECK AMPLITUDE
51 0A68   FE    1E               CPI    30              ;SMALL PULSE?
52 0A6A   D2    0A75             JNC    2$              ;NO
53 0A6D   AF                     XRA    A               ;CLEAR CARRY
54 0A6E   79                     MOV    A,C
55 0A6F   1F                     RAR
56 0A70   4F                     MOV    C,A
57 0A71   AF                     XRA    A 1 0A72   78                     MOV    A,B
 2 0A73   1F                     RAR
 3 0A74   47                     MOV    B,A
 4 0A75   3A    7005    2$:      LDA    FSATN
 5 0A78   81                     ADD    C
 6 0A79   1F                     RAR
 7 0A7A   32    7005             STA    FSATN
 8 0A7D   3A    7006    4$:      LDA    FRATN
 9 0A80   80                     ADD    B
10 0A81   1F                     RAR
11 0A82   32    7006             STA    FRATN
12 0A85   C9                     RET
13
14 0A86   20            FILTBL:  DB     32              ;MODE 1
15 0A87   80                     DB     128
16 0A88   10                     DB     16
17 0A89   10                     DB     16              ;DECIMAL MODE
18 0A8A   20                     DB     32              ;RESP RATE INSTEAD OF HR
19 0A8B   80                     DB     128             ;UNFILTERED MODE
20 0A8C   20                     DB     32              ;ZERO ON ANALOG OUTPUTS
21 0A8D   20                     DB     32              ;1/2 SCALE ON ANALOG OUTPUT
22 0A8E   20                     DB     32              ;FULL SCALE ON ANALOG OUTS
23

1
 2                               ;DISPLAY RATE AND SATURATION
 3                               ; WITH, OF COURSE, DUE CONCERN FOR ANYTHING ELSE GOING ON...
 4                               ;
 5 0A8F   3A    712F    DSPSR:   LDA    DSPOK           ;IF SET, THEN WE'RE IN SILENT MODE
 6 0A92   B7                     ORA    A
 7 0A93   C0                     RNZ                    ;WE ARE, SO LONG
 8 0A94   3A    713A             LDA    OPNFLG          ;SKIP ALL OF THIS IF A PARAMETER IS OPEN
 9 0A97   B7                     ORA    A
10 0A98   C0                     RNZ
11 0A99   3A    712E             LDA    DSPBKF
12 0A9C   B7                     ORA    A
13 0A9D   C2    0AF4             JNZ    2$              ;BLANK DISPLAY
14 0AA0   11    0100             LXI    D,0100H         ;FIELD 1, XX.X FORMAT
15 0AA3   3A    7170             LDA    FMODE           ;CHECK FOR MODE 4
16 0AA6   FE    04               CPI    4
17 0AA8   CA    0AB5             JZ     1$              ;IT IS, USE XX.X FORMAT
18 0AAB   3A    7007             LDA    TSTMOD          ;CHECK FOR TEST MODE BIT 0
```

```
19 0AAE  E6    01              ANI   1            ;IT IS, USE XX.X
20 0AB0  C2    0AB5            JNZ   1$           ;OTHERWISE INTEGERS
21 0AB3  16    00              MVI   D,0
22 0AB5  2A    70B9    1$:     LHLD  FSATX        ;16-BIT SAT
23 0AB8  44                    MOV   B,H          ;TO B,C
24 0AB9  4D                    MOV   C,L
25 0ABA  CD    1356            CALL  DECDSP
26 0ABD  3A    7170            LDA   FMODE        ;DON'T DISPLAY RATE IN MODE 3
27 0AC0  FE    03              CPI   3
28 0AC2  CA    0B09            JZ    5$
29 0AC5  FE    05              CPI   5            ;DISPLAY RESP IN MODE 5
30 0AC7  C2    0AD0            JNZ   7$
31 0ACA  3A    7114            LDA   FRSP
32 0ACD  C3    0AE5            JMP   6$
33 0AD0  3A    7014    7$:     LDA   SYNFLG       ;SEE IF CALLED BY BUTCLS
34 0AD3  B7                    ORA   A
35 0AD4  CA    0AE2            JZ    10$          ;IF SYNCED, DISPLAY FRATE
36 0AD7  3A    7104            LDA   SN2DLY       ;IF EKG NOT SYNCED AND PULSE NOT SYNCED
37 0ADA  B7                    ORA   A
38 0ADB  CA    0AE2            JZ    10$          ;THEN INSURE THAT 0 IS DISPLAYED
39 0ADE  AF                    XRA   A
40 0ADF  C3    0AE5            JMP   6$
41 0AE2  3A    7004    10$:    LDA   FRATE
42 0AE5  01    7122    6$:     LXI   B,DSPFD2     ;RATE IN LOWER DISPLAY
43 0AE8  CD    13A9            CALL  DSPCVT
44 0AEB  3A    727C            LDA   COSTA        ;SET OXISENSOR ATTACHED BIT
45 0AEE  F6    02              ORI   OXIATT       ;
46 0AF0  32    727C            STA   COSTA        ;
47 0AF3  C9                    RET
48 0AF4  01    711C    2$:     LXI   B,DSPFD1     ;BLANK DISPLAY
49 0AF7  CD    1452            CALL  DSPBLK
50 0AFA  3A    7170    3$:     LDA   FMODE        ;CHECK FOR MODE 3 ONCE MORE FOR EKG ONLY
51 0AFD  FE    03              CPI   3
52 0AFF  CA    0B09            JZ    5$
53 0B02  3A    70F8            LDA   EKGTHR
54 0B05  B7                    ORA   A
55 0B06  C2    0B18            JNZ   4$           ;DON'T BLANK HR UNLESS TIMED OUT ALSO
56 0B09  3A    7170    5$:     LDA   FMODE        ;DONT BLANK DIPLAY IF RESP IS ON
57 0B0C  FE    05              CPI   5
```

RESPOX; MICROBENCH 8080/8085 CROSS ASSEMBLER (V2)-436  30-MAR-85 13:30:07 PAGE 40

```
 1 0B0E  CA    0B22            JZ    8$           ;AND UPDATE THE DISPLAY
 2 0B11  01    7122            LXI   B,DSPFD2
 3 0B14  CD    1452            CALL  DSPBLK
 4 0B17  C9                    RET
 5 0B18  01    7122    4$:     LXI   B,DSPFD2     ;REFRESH HR DISPLAY FOR EKG
 6 0B1B  3A    7004            LDA   FRATE
 7 0B1E  CD    13A9            CALL  DSPCVT
 8 0B21  C9                    RET
 9 0B22  3A    7114    8$:     LDA   FRSP
10 0B25  01    7122            LXI   B,DSPFD2
11 0B28  CD    13A9            CALL  DSPCVT
12 0B2B  C9                    RET
```

RESPOX; MICROBENCH 8080/8085 CROSS ASSEMBLER (V2)-436  30-MAR-85 13:30:07 PAGE 41

```
 1
 2                     ;PULSE TIME-OUT...RAISE AN ALARM, NO PULSE FOUND.
 3                     ;  CALLED BY CLOCK WHEN PLSTMR GOES TO ZERO, DISPLAYS ZERO RATE AND SETS ALARM.
 4
 5 0B2C  3A    7014    PLSTMO: LDA   SYNFLG       ;CHECK FOR NOT SYNC'ED
 6 0B2F  B7                    ORA   A
 7 0B30  C2    0BB3            JNZ   5$
 8 0B33  AF                    XRA   A            ;ZERO RATE AND SAT
 9 0B34  32    7002            STA   FSAT
10 0B37  21    0000            LXI   H,0          ;ZERO SAT OUTPUT
11 0B3A  22    7169            SHLD  SATOUT
12 0B3D  3A    7104            LDA   SN2DLY       ;ZERO RATE IF EKG TIMED OUT TOO
13 0B40  B7                    ORA   A
14 0B41  CA    0B4E            JZ    1$
15 0B44  AF                    XRA   A
16 0B45  32    7004            STA   FRATE
17 0B48  21    0000            LXI   H,0
18 0B4B  22    716B            SHLD  RATOUT
19 0B4E  21    0000    1$:     LXI   H,0
20 0B51  22    70B9            SHLD  FSATX
21 0B54  3A    712F            LDA   DSPOK        ;IF SILENT MODE, FORGET THIS STUFF
22 0B57  B7                    ORA   A
23 0B58  C2    0B7E            JNZ   3$
24 0B5B  CD    0C37            CALL  ALMCHK       ;CALL ALARM CHECKER
25 0B5E  0E    20              MVI   C,SYNCOD     ;NO-SYNC LITE
26 0B60  CD    1484            CALL  BNKLIT
27 0B63  0E    08              MVI   C,SLOCOD     ;CLR RATE,SAT LED
28 0B65  CD    1475            CALL  CLRLIT
29 0B68  0E    10              MVI   C,SHICOD
30 0B6A  CD    1475            CALL  CLRLIT
31 0B6D  3A    70F8            LDA   EKGTHR       ;DON'T RESET RATE ALARMS UNLESS EKG TIMED OUT
32 0B70  B7                    ORA   A
```

```
33 0B71  C2   0B7E          JNZ   3$
34 0B74  0E   04            MVI   C,RHICOD
35 0B76  CD   1475          CALL  CLRLIT
36 0B79  0E   02            MVI   C,RLOCOD
37 0B7B  CD   1475          CALL  CLRLIT
38 0B7E  3E   04      3$:   MVI   A,4            ;RESET SYNC CODE
39 0B80  32   7014          STA   SYNFLG
40 0B83  3E   04            MVI   A,4            ;AND HISTOR LENGTH
41 0B85  32   7017          STA   HSTLEN
42 0B88  3A   700C          LDA   L1ITHR         ;CHECK LED'S FOR SERVO'ING
43 0B8B  47                 MOV   B,A
44 0B8C  3A   700F          LDA   L2ITHR
45 0B8F  B0                 ORA   B
46 0B90  3E   00            MVI   A,0
47 0B92  CA   0B9F          JZ    2$             ;NOT, SHOW ZERO'S
48 0B95  3A   727C          LDA   COSTA          ;CLEAR OXISENSOR ATTACHED BIT   ///
49 0B98  E6   FD            ANI   NOT OXIATT     ;                               ///
50 0B9A  32   727C          STA   COSTA          ;                               ///
51 0B9D  3E   01            MVI   A,1            ;BLANK DISPLAY
52 0B9F  32   712E    2$:   STA   DSPBKF
53 0BA2  CD   0404          CALL  SNDMON         ;AND LET THE INTERFACE KNOW     ///
54 0BA5  CD   0A8F          CALL  DSPSR          ;DISPLAY ZERO'S OR BLANK'S
55 0BA8  3A   70F2          LDA   ALICTR
56 0BAB  B7                 ORA   A              ;CHECK FOR ALARM INHIBITED
57 0BAC  C8                 RZ                   ;IS NOT
```

RESPOX; MICROBENCH 8080/8085 CROSS ASSEMBLER (V2)-436   30-MAR-85  13:30:07 PAGE 42

```
 1 0BAD  3E   01            MVI   A,1
 2 0BAF  32   70F6          STA   ALMDLY         ;SET UP DELAYED ALARM
 3 0BB2  C9                 RET
 4 0BB3  3E   04      5$:   MVI   A,4
 5 0BB5  32   7014          STA   SYNFLG
 6 0BB8  C9                 RET
 7
 8                          ;SAT UPDATE TIME-OUT...SET IT TO ZERO
 9                          ;
10 0BB9  AF          SATTMO: XRA  A
11 0BBA  32   7002          STA   FSAT
12 0BBD  21   0000          LXI   H,0
13 0BC0  22   7169          SHLD  SATOUT
14 0BC3  22   70B9          SHLD  FSATX
15 0BC6  3E   FF            MVI   A,255
16 0BC8  32   7005          STA   FSATN          ;TURN DOWN FILTER FOR QUICK RETURN
17 0BCB  C9                 RET
18                          ;
19                          ;EKG TIMED OUT - ZERO RATE IF NOT SYNCED
20                          ;
21 0BCC  AF          EKGTMO: XRA  A
22 0BCD  32   70FF          STA   EKGPER         ;RESET EKG PERIOD
23 0BD0  32   7100          STA   EKGFLG         ;RESET FLAG
24 0BD3  3A   7106          LDA   EKGSNC         ;CHECK FOR EKG SYNC
25 0BD6  B7                 ORA   A
26 0BD7  C0                 RNZ
27 0BD8  3E   05            MVI   A,5            ;RESET EKG SYNC DELAY
28 0BDA  32   7104          STA   SN2DLY
29 0BDD  3A   7014          LDA   SYNFLG
30 0BE0  B7                 ORA   A
31 0BE1  C8                 RZ
32 0BE2  AF                 XRA   A
33 0BE3  32   7004          STA   FRATE
34 0BE6  21   0000          LXI   H,0
35 0BE9  22   716B          SHLD  RATOUT         ;ZERO RATE ANALOG OUTPUT
36 0BEC  CD   0A8F          CALL  DSPSR
37 0BEF  3A   70C9          LDA   ALMFLG
38 0BF2  E6   01            ANI   1
39 0BF4  32   70C9          STA   ALMFLG
40 0BF7  CD   0CA0          CALL  ALMCKB
41 0BFA  0E   04            MVI   C,RHICOD
42 0BFC  CD   1475          CALL  CLRLIT
43 0BFF  0E   02            MVI   C,RLOCOD
44 0C01  CD   1475          CALL  CLRLIT
45 0C04  3A   70F2          LDA   ALICTR
46 0C07  B7                 ORA   A
47 0C08  C8                 RZ
48 0C09  3E   01            MVI   A,1
49 0C0B  32   70F6          STA   ALMDLY
50 0C0E  C9                 RET
51                          ;
52                          ;RESP TIMED OUT - SET ALARM
53                          ;
54 0C0F  AF          RSPTMO: XRA  A
55 0C10  32   710E          STA   RSPCNT
56 0C13  32   7114          STA   FRSP           ;ZERO COUNT, FLAG, AND RESP
57 0C16  32   7110          STA   RSPFLG
```

RESPOX; MICROBENCH 8080/8085 CROSS ASSEMBLER (V2)-436   30-MAR-85 13:30:07 PAGE 43

```
   1 0C19   3E    02              MVI    A,2
   2 0C1B   32    7112            STA    SN3DLY
   3 0C1E   CD    0A8F            CALL   DSPSR            ;ZERO RESP DISPLAY
   4 0C21   3A    70C9            LDA    ALMFLG
   5 0C24   E6    07              ANI    7                ;PRESERVE OTHER ALARM STATUSES
   6 0C26   32    70C9            STA    ALMFLG
   7 0C29   CD    0D49            CALL   ALHCKC           ;SET RESP ALARM
   8 0C2C   3A    70F2            LDA    ALICTR           ;CHECK FOR DELAYED ALARMS
   9 0C2F   B7                    ORA    A
  10 0C30   C8                    RZ
  11 0C31   3E    01              MVI    A,1
  12 0C33   32    70F6            STA    ALMDLY
  13 0C36   C9                    RET
  14                            ;
```

RESPOX; MICROBENCH 8080/8085 CROSS ASSEMBLER (V2)-436   30-MAR-85 13:30:07 PAGE 44

```
   1                            ;CHECK ALARM VALUES, OUTPUT TO BEEPER...
   2                            ; A NICE LITTLE BEEP FOR A NORMAL PULSE, A LOUD RAUCUS NOISE FOR ALARM
   3                            ;
   4
   5 0C37   AF             ALMCHK: XRA    A                ;CLEAR ALARM FLAG
   6 0C38   32    70C9            STA    ALMFLG
   7 0C3B   3A    712F            LDA    DSPOK            ;NO ALARMS IN SILENT MODE
   8 0C3E   B7                    ORA    A
   9 0C3F   C0                    RNZ
  10                            ;
  11                            ;CHECK LOW SAT, SET LIGHT AND STATUS BIT AND RESET HI SAT ALARM IF SO.
  12                            ;
  13 0C40   21    70C2    13$:    LXI    H,SATLL          ;POINT H,L TO LIMITS
  14 0C43   3A    7002            LDA    FSAT             ;FILTERED SATURATION
  15 0C46   BE                    CMP    M                ;CHECK SAT-LIMIT
  16 0C47   D2    0C5F            JNC    1$               ;NO ALARM
  17 0C4A   0E    08              MVI    C,SLOCOD
  18 0C4C   CD    1484            CALL   BNKLIT           ;TURN ON ALARM LIGHT
  19 0C4F   0E    10              MVI    C,SHICOD         ;TURN OFF HIGH ALARM
  20 0C51   CD    1475            CALL   CLRLIT
  21 0C54   3A    727D            LDA    CPSTA            ;SET ALARM BIT FOR SATURATION      ///
  22 0C57   F6    04              ORI    SATBIT           ;                                  ///
  23 0C59   32    727D            STA    CPSTA            ;                                  ///
  24 0C5C   C3    0C79            JMP    2$
  25                            ;
  26                            ;CHECK HIGH SAT, SET LIGHT AND BIT AND RESET LOW SAT ALARM IF SO.
  27                            ;
  28 0C5F   23             1$:    INX    H
  29 0C60   BE                    CMP    M
  30 0C61   CA    0C89            JZ     3$               ;NO ALARM
  31 0C64   DA    0C89            JC     3$
  32 0C67   0E    10              MVI    C,SHICOD         ;TURN ON LIGHT
  33 0C69   CD    1484            CALL   BNKLIT
  34 0C6C   0E    08              MVI    C,SLOCOD         ;TURN OFF LOW SAT
  35 0C6E   CD    1475            CALL   CLRLIT
  36 0C71   3A    727D            LDA    CPSTA
  37 0C74   E6    FB              ANI    NOT SATBIT
  38 0C76   32    727D            STA    CPSTA
  39                            ;
  40                            ;SAT ALARM (HI OR LOW), BLINK FIELD AND SET ALARM FLAG
  41                            ;
  42 0C79   0E    07      2$:     MVI    C,FD1MSK
  43 0C7B   CD    145D            CALL   DSPBNK           ;BLINK THE DIGITS
  44 0C7E   3A    70C9            LDA    ALMFLG
  45 0C81   F6    01              ORI    1
  46 0C83   32    70C9            STA    ALMFLG           ;SET FLAG FOR BEEPER, ETC.
  47 0C86   C3    0CA0            JMP    4$
  48                            ;
  49                            ;NO SAT ALARM, RESET LIGHTS AND BLINKS.
  50                            ;
  51 0C89   0E    07      3$:     MVI    C,FD1MSK         ;NO ALARM, CLEAR BLINKING
  52 0C8B   CD    1464            CALL   DSPUBK
  53 0C8E   0E    08              MVI    C,SLOCOD         ;CLEAR LIGHT
  54 0C90   CD    1475            CALL   CLRLIT
  55 0C93   0E    10              MVI    C,SHICOD
  56 0C95   CD    1475            CALL   CLRLIT
  57 0C98   3A    727D            LDA    CPSTA            ;CLEAR SATURATION ALARM            ///
```

RESPOX; MICROBENCH 8080/8085 CROSS ASSEMBLER (V2)-436   30-MAR-85 13:30:07 PAGE 45

```
   1 0C9B   E6    FB              ANI    NOT SATBIT       ;                                  ///
   2 0C9D   32    727D            STA    CPSTA            ;                                  ///
   3                            ;
   4                            ;CHECK RATE ALARM, BUT FIRST MAKE SURE IT'S NOT MODE 3.
   5                            ;
   6 0CA0                 4$:
   7 0CA0   3A    712F    ALMCKB: LDA    DSPOK            ;EXIT IF WE'RE IN SILENT MODE
   8 0CA3   B7                    ORA    A
```

```
 9 0CA4  C0                     RNZ
10 0CA5  3A   7170              LDA    FMODE           ;DONT CHECK RATE IN MODE 3
11 0CA8  FE   03                CPI    3
12 0CAA  CA   0D37              JZ     17$
13 0CAD  3A   7106              LDA    EKGSNC          ;CHECK FOR EKG SYNC
14 0CB0  B7                     ORA    A
15 0CB1  C2   0CD0              JNZ    15$
16 0CB4  3A   7104              LDA    SN2DLY          ;IF TIMED OUT ALSO, THEN ALARM CHECK
17 0CB7  B7                     ORA    A
18 0CB8  CA   0CD0              JZ     15$
19 0CBB  0E   80                MVI    C,BATCOD
20 0CBD  CD   1484              CALL   BNKLIT
21 0CC0  0E   38                MVI    C,FD2MSK        ;SET UP ALARM HERE FOR EKG TIMEOUT
22 0CC2  CD   145D              CALL   DSPBNK          ;IF SYNCED, RATE ALARMS WILL ALSO BE CHECKED
23 0CC5  3A   70C9              LDA    ALMFLG
24 0CC8  F6   04                ORI    4               ;4 = LOST EKG SYNC
25 0CCA  32   70C9              STA    ALMFLG
26 0CCD  C3   0CD5              JMP    14$
27 0CD0  0E   80         15$:   MVI    C,BATCOD
28 0CD2  CD   1475              CALL   CLRLIT
29
30                              ;CHECK LOW RATE
31                              ;
32 0CD5  21   70C6       14$:   LXI    H,RATLL         ;POINT TO RATE LIMITS
33 0CD8  3A   7004              LDA    FRATE           ;CHECK RATE
34 0CDB  BE                     CMP    M               ;LOWER LIM
35 0CDC  D2   0CF6              JNC    5$              ;NOT BELOW LOWER LIMIT...
36 0CDF  3A   727D              LDA    CPSTA           ;SET LOW RATE ALARM BIT     ///
37 0CE2  F6   02                ORI    LRTBIT          ;                           ///
38 0CE4  E6   FE                ANI    NOT HRTBIT      ;                           ///
39 0CE6  32   727D              STA    CPSTA           ;                           ///
40 0CE9  0E   02                MVI    C,RLOCOD
41 0CEB  CD   1484              CALL   BNKLIT
42 0CEE  0E   04                MVI    C,RHICOD
43 0CF0  CD   1475              CALL   CLRLIT
44 0CF3  C3   0D12              JMP    6$
45
46                              ;CHECK HIGH RATE
47                              ;
48 0CF6  23          5$:        INX    H
49 0CF7  BE                     CMP    M               ;UPPER LIMIT
50 0CF8  CA   0D2A              JZ     7$              ;OK IF EQUAL
51 0CFB  DA   0D2A              JC     7$              ;OR LESS
52 0CFE  0E   04                MVI    C,RHICOD        ;SET HI RATE ALARM LITE
53 0D00  CD   1484              CALL   BNKLIT
54 0D03  3A   727D              LDA    CPSTA           ;SET HIGH RATE ALARM BIT    ///
55 0D06  F6   01                ORI    HRTBIT          ;                           ///
56 0D08  E6   FD                ANI    NOT LRTBIT      ;CLEAR LOW RATE BIT         ///
57 0D0A  32   727D              STA    CPSTA           ;IN PATIENT STATUS BYTE     ///
```

RESPOX: MICROBENCH 8080/8085 CROSS ASSEMBLER (V2)-436   30-MAR-85 13:30:07 PAGE 46

```
 1 0D0D  0E   02                MVI    C,RLOCOD
 2 0D0F  CD   1475              CALL   CLRLIT
 3
 4                              ;RATE ALARM, BLINK THE FIELD AND SET FLAG
 5                              ;
 6 0D12  3A   7170       6$:    LDA    FMODE           ;DONT BLINK IF IN MODE 5
 7 0D15  FE   05                CPI    5
 8 0D17  CA   0D1F              JZ     19$
 9 0D1A  0E   38                MVI    C,FD2MSK        ;RATE ALARM, BLINK FIELD 2
10 0D1C  CD   145D              CALL   DSPBNK
11 0D1F  3A   70C9       19$:   LDA    ALMFLG          ;SET FLAG BIT
12 0D22  F6   02                ORI    2
13 0D24  32   70C9              STA    ALMFLG
14 0D27  C3   0D49              JMP    8$
15
16                              ;NO RATE ALARM, RESET LIGHTS AND BLINKS
17                              ;
18 0D2A  3A   7170       7$:    LDA    FMODE           ;DON'T CLEAR BLINK IF IN MODE 5
19 0D2D  FE   05                CPI    5
20 0D2F  CA   0D37              JZ     17$
21 0D32  0E   38                MVI    C,FD2MSK        ;NO ALARM, CLEAR BLINK
22 0D34  CD   1464              CALL   DSPUBK
23 0D37  3A   727D       17$:   LDA    CPSTA           ;CLEAR HIGH RATE BIT        ///
24 0D3A  E6   FC                ANI    NOT (HRTBIT OR LRTBIT) ;                   ///
25 0D3C  32   727D              STA    CPSTA           ;AND LOW RATE BIT           ///
26 0D3F  0E   02                MVI    C,RLOCOD
27 0D41  CD   1475              CALL   CLRLIT          ;AND CLEAR LIGHT
28 0D44  0E   04                MVI    C,RHICOD
29 0D46  CD   1475              CALL   CLRLIT
30
31                              ;CHECK FOR AUDIO ALARM...ENTER HERE ALSO FROM CLOCK FOR A DELAYED ALARM...
32                              ;ENTER HERE ALSO IF RESP TIMED OUT
33                              ;
34 0D49              8$:
35 0D49  3A   712F       ALMCKC:LDA    DSPOK
36 0D4C  B7                     ORA    A
37 0D4D  C0                     RNZ
38 0D4E  3A   7111              LDA    RSPSNC          ;SEE IF RESP IS SYNCED
39 0D51  B7                     ORA    A
40 0D52  C2   0D71              JNZ    8$
41 0D55  3A   710F              LDA    RSPTHR
42 0D58  B7                     ORA    A
```

```
43 0D59   C2      0D71            JNZ     8$
44 0D5C   3A      70C9            LDA     ALMFLG
45 0D5F   F6      08              ORI     8                       ;8=RESP ALARM BIT
46 0D61   32      70C9            STA     ALMFLG
47 0D64   3A      7170            LDA     FMODE                   ;BLINK DISPLAY IF IN MODE 5
48 0D67   FE      05              CPI     5
49 0D69   C2      0D71            JNZ     8$
50 0D6C   0E      38              MVI     C,FD2MSK
51 0D6E   CD      145D            CALL    DSPBNK
52 0D71   3A      70C9    8$:     LDA     ALMFLG
53 0D74   E6      01              ANI     1                       ;CHECK FOR A SAT ALARM
54 0D76   CA      0D7E            JZ      ALMCK2
55 0D79   0E      07              MVI     C,FD1MSK                ;IF SO, SET FIELD 1 BLINKING
56 0D7B   CD      145D            CALL    DSPBNK
57 0D7E   3A      70C9    ALMCK2: LDA     ALMFLG
```

RESPOX; MICROBENCH 8080/8085 CROSS ASSEMBLER (V2)-436   30-MAR-85 13:30:07 PAGE 47

```
 1 0D81   B7                      ORA     A
 2 0D82   CA      0DC4            JZ      10$                     ;NO ALARMS...
 3 0D85   3A      70F1            LDA     ALIFLG                  ;CHECK FOR ALARM INHIBIT
 4 0D88   B7                      ORA     A
 5 0D89   C2      0DC4            JNZ     11$                     ;NOT ZERO, STILL INHIBITED...
 6 0D8C   3A      7014            LDA     SYNFLG                  ;MAKE SURE WE ALARM ONLY ONCE PER PULSE
 7 0D8F   B7                      ORA     A
 8 0D90   C2      0DB5            JNZ     9$                      ;NOT PULSE SYNCED, SEE IF EKG SYNCED
 9 0D93   3A      7100            LDA     EKGFLG
10 0D96   B7                      ORA     A                       ;IF SET THEN ENABLE ALARM
11 0D97   C2      0D9F            JNZ     16$                     ;IF NOT TIMED OUT, THEN WE ALREADY SET ALA
12 0D9A   3A      70F8            LDA     EKGTMR
13 0D9D   B7                      ORA     A
14 0D9E   C0                      RNZ
15 0D9F   3A      70EF    16$:    LDA     ALMVOL                  ;GET VOLUME CODE
16 0DA2   5F                      MOV     E,A
17 0DA3   0E      6E              MVI     C,ALMPCH                ;GET ALARM PITCH
18 0DA5   06      FE              MVI     B,254
19 0DA7   3A      7170            LDA     FMODE
20 0DAA   FE      03              CPI     3                       ;CHECK FOR MODE 3 AGAIN
21 0DAC   C2      0DB1            JNZ     18$                     ;NOT
22 0DAF   06      FF              MVI     B,255                   ;STEADY ALARM
23 0DB1   CD      148E    18$:    CALL    BEEP
24 0DB4   C9                      RET
25 0DB5   3A      7100    9$:     LDA     EKGFLG
26 0DB8   B7                      ORA     A
27 0DB9   C2      0D9F            JNZ     16$                     ;NOT PULSE SYNCED, BUT EKG IS
28 0DBC   3A      70F8            LDA     EKGTMR
29 0DBF   B7                      ORA     A                       ;IF TIMED OUT, THEN CALLED BY EKGTMO
30 0DC0   CA      0D9F            JZ      16$
31 0DC3   C9                      RET
32                                ;
33                                ;NO ALARM.....MAKE A BEEP
34                                ;
35 0DC4                   10$:
36 0DC4   1E      00      11$:    MVI     E,0
37 0DC6   01      0000            LXI     B,0                     ;TO SHUT UP ALARM IF NO BEEP
38 0DC9   3A      70F7            LDA     ALCFLG                  ;GET ALARM-CHECKING FLAG
39 0DCC   B7                      ORA     A
40 0DCD   C2      0E08            JNZ     19$                     ;NO BEEP IF SET
41 0DD0   3A      7170            LDA     FMODE                   ;NO BEEP IN MODE 3
42 0DD3   FE      03              CPI     3
43 0DD5   CA      0E08            JZ      19$
44 0DD8   3A      7014            LDA     SYNFLG                  ;NO BEEP IF NOT SYNC'ED
45 0DDB   B7                      ORA     A
46 0DDC   C2      0DF9            JNZ     12$
47 0DDF   3A      7100            LDA     EKGFLG                  ;IF EKGFLG SET, THEN BEEP
48 0DE2   B7                      ORA     A
49 0DE3   C2      0DEB            JNZ     20$
50 0DE6   3A      7104            LDA     SN2DLY                  ; IF EKG NOT TIMED OUT - MUST HAVE BEEPED
51 0DE9   B7                      ORA     A
52 0DEA   C8                      RZ
53 0DEB   3A      70EC    20$:    LDA     BEEVOL
54 0DEE   5F                      MOV     E,A
55 0DEF   3A      7002            LDA     FSAT                    ;COMPUTE PITCH FROM SAT
56 0DF2   4F                      MOV     C,A
57 0DF3   06      05              MVI     B,5
```

RESPOX; MICROBENCH 8080/8085 CROSS ASSEMBLER (V2)-436   30-MAR-85 13:30:07 PAGE 48

```
 1 0DF5   CD      148E            CALL    BEEP
 2 0DF8   C9                      RET
 3 0DF9   3A      7100    12$:    LDA     EKGFLG                  ;NOT SYNCED, BUT CHECK FOR EKG
 4 0DFC   B7                      ORA     A
 5 0DFD   CA      0E08            JZ      19$                     ;BEEP, BUT FUDGE A TONE
 6 0E00   3A      70EC            LDA     BEEVOL
 7 0E03   5F                      MOV     E,A
 8 0E04   0E      64              MVI     C,100
 9 0E06   06      05              MVI     B,5
10 0E08   CD      148E    19$:    CALL    BEEP
11 0E0B   C9                      RET
12
13
```

RESPOX: MICROBENCH 8080/8085 CROSS ASSEMBLER (V2)-436   30-MAR-85 13:30:07 PAGE 49

```
  1                                    ;TWEAK LED LEVELS....
  2                                    ; IF MAX1 > 87% THEN LED1 = LED1 - DELTL1, AND IF
  3                                    ;    MIN1 < 12% THEN LED1 = LED1 + DELTL1, REPEAT FOR LED2
  4                                    ;
  5
  6  0E0C  3A   7011    TWKLED: LDA   INHLED       ;CHECK INHIBIT FLAG
  7  0E0F  B7                   ORA   A
  8  0E10  C0                   RNZ                ;SET
  9  0E11  3A   7007            LDA   TSTMOD
 10  0E14  E6   08               ANI   8
 11  0E16  C0                   RNZ
 12  0E17  21   700A            LXI   H,LED1
 13  0E1A  3A   70A0            LDA   MAX1+1       ;GET HI 4 BITS OF MAX
 14  0E1D  FE   F8               CPI   0F8H        ;>7/8 FS?
 15  0E1F  DA   0E26            JC    2$           ;NO, IS OK
 16  0E22  35                   DCR   M            ;YES, DECREMENT LED BRIGHTNESS
 17  0E23  C3   0E2F            JMP   3$
 18  0E26  3A   70A2    2$:     LDA   MIN1+1       ;GET HI BYTE OF MIN
 19  0E29  FE   C8               CPI   0C8H        ;LESS THAN 1/8?
 20  0E2B  D2   0E32            JNC   5$           ;NO, IS OK...
 21  0E2E  34                   INR   M            ;INCREMENT LED
 22  0E2F  CD   1DF6    3$:     CALL  LD1SET
 23  0E32  21   700D    5$:     LXI   H,LED2
 24  0E35  3A   70A4            LDA   MAX2+1
 25  0E38  FE   F8               CPI   0F8H
 26  0E3A  DA   0E41            JC    6$
 27  0E3D  35                   DCR   M
 28  0E3E  C3   0E4A            JMP   7$
 29  0E41  3A   70A6    6$:     LDA   MIN2+1
 30  0E44  FE   C8               CPI   0C8H
 31  0E46  D2   0E4D            JNC   10$
 32  0E49  34                   INR   M
 33  0E4A  CD   1E05    7$:     CALL  LD2SET
 34  0E4D  C9           10$:    RET
```

RESPOX: MICROBENCH 8080/8085 CROSS ASSEMBLER (V2)-436   30-MAR-85 13:30:07 PAGE 50

```
  1                                    ;CHECK CALIBRATION...LOOK AT RESISTOR VOLTAGE, SET COUNT-DOWN FLAG IF NO RESISTOR.
  2                                    ; IF RESISTOR IS THERE, CHECK FLAG, DECREMENT IF NON-ZERO. IF IT GOES ZERO,
  3                                    ; DIVIDE REISTOR BY REFERNCE AND USE AS INDEX INTO CAL TABLE.
  4
  5
  6  0E4E  2A   7152    CALCHK: LHLD  VCAL         ;GET CAL RESISTOR
  7  0E51  EB                   XCHG               ;INTO D,E (FOR LATER DIVIDE)
  8  0E52  21   FFE0            LXI   H,-32        ;THESHHOLD
  9  0E55  19                   DAD   D
 10  0E56  DA   0E67            JC    2$           ;NEAR-ZERO MEANS NO RESISTOR
 11  0E59  3E   FF      1$:     MVI   A,255        ;SET COUNT-DOWN FLAG
 12  0E5B  32   70E7            STA   CALFLG
 13  0E5E  AF                   XRA   A
 14  0E5F  32   7009            STA   CALIDX
 15  0E62  32   7008            STA   CALOK
 16  0E65  37                   STC
 17  0E66  C9                   RET
 18  0E67  3A   70E7    2$:     LDA   CALFLG       ;CHECK FLAG
 19  0E6A  3D                   DCR   A
 20  0E6B  32   70E7            STA   CALFLG
 21  0E6E  CA   0E73            JZ    5$           ;JUST BECAME ZERO, GO COMPUTE CAL
 22  0E71  B7                   ORA   A            ;CLEAR CARRY
 23  0E72  C9                   RET
 24
 25                             ; COMPUTE RESISTANCE FROM DAC VALUES FOR RESISTOR AND REFERENCE.
 26                             ;
 27  0E73  2A   7156    5$:     LHLD  VREF
 28  0E76  3E   00               MVI   A,0         ;SUBTRACT REF FROM FULL SCALE (4096)
 29  0E78  95                   SUB   L
 30  0E79  4F                   MOV   C,A
 31  0E7A  3E   10               MVI   A,10H
 32  0E7C  9C                   SBB   H
 33  0E7D  47                   MOV   B,A
 34  0E7E  11   018D            LXI   D,256+141    ;10-VREF IN B,C
 35  0E81  CD   1232            CALL  MPY32        ;1.54 IN D,E
 36  0E84  41                   MOV   B,C          ;1.54(10-VREF) IN BCD,E
 37  0E85  4A                   MOV   C,D
 38  0E86  2A   7152            LHLD  VCAL         ;
 39  0E89  3E   00               MVI   A,0
 40  0E8B  95                   SUB   L
 41  0E8C  5F                   MOV   E,A
 42  0E8D  3E   10               MVI   A,10H
 43  0E8F  9C                   SBB   H             ;10V - VCAL IN D,E
 44  0E90  57                   MOV   D,A
 45  0E91  CD   12F6            CALL  DIV16        ;DIVIDE BY REFERENCE TO MAKE RESISTANCE COU
 46  0E94  21   FF6A            LXI   H,-150       ;ADD OFFSET TO CORRECT CIRCUIT ERROR
 47  0E97  19                   DAD   D
 48  0E98  DA   0E9E            JC    4$
 49  0E9B  21   0000            LXI   H,0
 50  0E9E  EB           4$:     XCHG               ;RESISTOR NOW IN D,E
```

```
51
52                              ;CHECK FOR STABILITY, SET FLAG IF SO.
53                              ;
54 0E9F  2A    70E8      LHLD   CALRES          ;GET OLD VALUE
55 0EA2  CD    1348      CALL   NEGHL
56 0EA5  19              DAD    D               ;COMPUTE DIFF
57 0EA6  DA    0EAC      JC     6$
```

RESPOX: MICROBENCH 8080/8085 CROSS ASSEMBLER (V2)-436   30-MAR-85 13:30:07 PAGE 51

```
 1 0EA9  CD    1348          CALL   NEGHL           ;NEGATIVE DIFF
 2 0EAC  01    FA24   6$:    LXI    B,-1500         ;STABILITY THRESHHOLD + 3 INDICES
 3 0EAF  09                  DAD    B
 4 0EB0  3E    00            MVI    A,0
 5 0EB2  DA    0EB6          JC     7$
 6 0EB5  3C                  INR    A               ;NOT STABLE
 7 0EB6  32    7008   7$:    STA    CALOK           ;STABLE, SET OK FLAG
 8 0EB9  EB                  XCHG                   ;SET OK FLAG
 9 0EBA  22    70E8          SHLD   CALRES          ;SAVE FOR REFERENCE
10                           ;
11                           ; CONVERT RESISTANCE CODE TO INDEX BY LOOKING IT UP IN CALTBL.
12                           ;
13 0EBD  3A    7007          LDA    TSTMOD
14 0EC0  E6    04            ANI    4
15 0EC2  C2    0EE7          JNZ    9$
16 0EC5  AF                  XRA    A
17 0EC6  95                  SUB    L               ;NEGATE RESISTANCE CODE
18 0EC7  4F                  MOV    C,A             ;AND MOVE TO B,C
19 0EC8  3E    00            MVI    A,0
20 0ECA  9C                  SBB    H
21 0ECB  47                  MOV    B,A
22 0ECC  21    1EA5          LXI    H,CALTBL        ;POINT TO TABLE
23 0ECF  5E           8$:    MOV    E,M
24 0ED0  23                  INX    H
25 0ED1  56                  MOV    D,M
26 0ED2  23                  INX    H               ;GET TABLE FRACTION
27 0ED3  7A                  MOV    A,D
28 0ED4  B3                  ORA    E               ;CHECK FOR ZERO
29 0ED5  CA    0F36          JZ     20$             ;ERROR, FOUND THE END.
30 0ED8  EB                  XCHG                   ;MOVE TABLE FRACT TO H,L
31 0ED9  09                  DAD    B               ;- RESISTOR
32 0EDA  EB                  XCHG
33 0EDB  D2    0ECF          JNC    8$
34 0EDE  11    E159          LXI    D,-(CALTBL+2)   ;NOT FOUND
35 0EE1  19                  DAD    D
36 0EE2  7D                  MOV    A,L             ;SUBTRACT TABLE BASE ADDRESS
37 0EE3  0F                  RRC
38 0EE4  32    7009          STA    CALIDX          ;SAVE INDEX
39 0EE7                9$:
40                           ;
41                           ;CONVERT CALIBRATION INDEX INTO INDICES FOR RED AND IR BETA'S...
42                           ; IR INDEX IS INTEGER PART OF CALIDX DIVIDED BY 21 (THE NUMBER OF RED STEPS),
43                           ; AND THE RED INDEX IS CALIDX MOD 21, SUBTRACTED FROM 20 (IE INVERTED) IF IR INDEX IS ODD...
44                           ; (SO THAT AN ERROR OF 1 IN CALIDX IS JUST AN ERROR OF 1, NOT 20.)
45                           ;
46 0EE7  3A    7009          LDA    CALIDX
47 0EEA  01    0000          LXI    B,0
48 0EED  3D                  DCR    A               ;DECREMENT INDEX, CHECK FOR ZERO
49 0EEE  FA    0EFE          JM     14$             ;IS ZERO, USE BETA ZERO CODE ZERO.
50 0EF1  4F                  MOV    C,A             ;SAVE CALIDX
51 0EF2  C6    40            ADI    64              ;OFFSET CODE
52 0EF4  32    7009          STA    CALIDX
53 0EF7  3E    14            MVI    A,20
54 0EF9  91                  SUB    C
55 0EFA  4F                  MOV    C,A
56 0EFB  06    01     13$:   MVI    B,1
57 0EFD  0C                  INR    C
```

RESPOX: MICROBENCH 8080/8085 CROSS ASSEMBLER (V2)-436   30-MAR-85 13:30:07 PAGE 52

```
 1                           ;
 2                           ;LOOK UP CONSTANTS FOR SAT CALCULATION...B,C = IR & RED INDICES, RESP.
 3                           ;
 4 0EFE  C5           14$:   PUSH   B
 5 0EFF  79                  MOV    A,C
 6 0F00  07                  RLC
 7 0F01  07                  RLC                    ;INDEX * 4
 8 0F02  4F                  MOV    C,A
 9 0F03  06    00            MVI    B,0
10 0F05  21    1EDB          LXI    H,BBTBL
11 0F08  09                  DAD    B               ;POINTER TO RED BETAS
12 0F09  5E                  MOV    E,M
13 0F0A  23                  INX    H
14 0F0B  56                  MOV    D,M
15 0F0C  23                  INX    H
16 0F0D  EB                  XCHG
17 0F0E  22    70E3          SHLD   B02
18 0F11  EB                  XCHG
19 0F12  5E                  MOV    E,M
20 0F13  23                  INX    H
```

```
 21 0F14    56              MOV    D,M
 22 0F15    EB              XCHG
 23 0F16    22   70E5       SHLD   BR2
 24 0F19    C1              POP    B
 25 0F1A    78              MOV    A,B
 26 0F1B    07              RLC
 27 0F1C    07              RLC
 28 0F1D    4F              MOV    C,A
 29 0F1E    06   00         MVI    B,0
 30 0F20    21   1ED3       LXI    H,BATBL
 31 0F23    09              DAD    B
 32 0F24    5E              MOV    E,M
 33 0F25    23              INX    H
 34 0F26    56              MOV    D,M
 35 0F27    23              INX    H
 36 0F28    EB              XCHG
 37 0F29    22   70DF       SHLD   B01
 38 0F2C    EB              XCHG
 39 0F2D    5E              MOV    E,M
 40 0F2E    23              INX    H
 41 0F2F    56              MOV    D,M
 42 0F30    EB              XCHG
 43 0F31    22   70E1       SHLD   BR1
 44 0F34    AF              XRA    A
 45 0F35    C9              RET
 46 0F36    37        20$:  STC
 47 0F37    C9              RET
```

```
  1          ;DATA PROCESSING ROUTINES...
  2          ; MONITOR CH. 1 INPUT, LOOKING FOR BASELINE (MAXIMA), SLOPES AND MINIMA.
  3          ; IF A LIKELY PULSE IS FOUND GET THE CORRESPONDING CH. 2 VALUES AND CALL THE
  4          ; LEVEL 3 CHECKING AND COMPUTATION ROUTINES...
  5          ;
  6          ;THE OPERATING MODE IS DEFINED BY MCHMOD; MODE 0 IS THE INITIAL MODE, LOOKING
  7          ;FOR A SIGNAL MAXIMUM; MODE 1 IS LOOKING FOR A MAX SLOPE; AND MODE 2 IS LOOKING
  8          ;FOR A MINIMUM.
  9          ;
 10
 11 0F38  21  7178   MUNCH: LXI  H,DATIDX    ;POINT TO DATA (IN) INDEX
 12 0F3B  7E                MOV  A,M         ;GET IT (POINTS TO NEXT FREE BYTE)
 13 0F3C  23                INX  H           ;POINT TO BUFFER INDEX (DTOIDX)
 14 0F3D  BE                CMP  M           ;SAME??
 15 0F3E  C8                RZ               ;YES, WE'RE CAUGHT UP.
 16 0F3F  5E         3$:    MOV  E,M         ;GET IT
 17 0F40  16  00            MVI  D,0
 18 0F42  23                INX  H           ;ADJUST POINTER TO BUFFER ORIGIN
 19 0F43  19                DAD  D           ;POINT INTO BUFFER
 20 0F44  4E                MOV  C,M         ;GET DATA WORD INTO B,C
 21 0F45  23                INX  H
 22 0F46  46                MOV  B,M
 23 0F47  23                INX  H           ;(LEAVE POINTER AT CH.2 WORD)
 24 0F48  78                MOV  A,B
 25 0F49  B1                ORA  C
 26 0F4A  CA  10D4          JZ   MCHER9      ;ZERO DATA MEANS ERROR 9
 27
 28                 ;CHECK FOR MODE 0 (LOOKING FOR MAX)
 29
 30 0F4D  3A  70CB          LDA  MCHMOD      ;GET MODE
 31 0F50  B7                ORA  A
 32 0F51  C2  0FB3          JNZ  MCH1        ;NOT MODE ZERO, GO CHECK FOR 1
 33
 34                 ;LOOK FOR MAX....IF DATA>MAX THEN STORE DATA AS MAX;
 35                 ;IF DATA < (MAX-NOISE) THEN GO TO MODE 1
 36
 37 0F54  2A  70CC          LHLD PLSMX1      ;GET MAX
 38 0F57  CD  10D9          CALL BCGTHL      ;DATA > MAX?
 39 0F5A  DA  0F6B          JC   1$          ;NO, NOT A NEW MAX
 40 0F5D  69                MOV  L,C
 41 0F5E  60                MOV  H,B
 42 0F5F  22  70CC          SHLD PLSMX1      ;STORE DATA AS NEW MAX
 43 0F62  3A  7179          LDA  DTOIDX
 44 0F65  32  70D6          STA  MAXIDX      ;SAVE POINTER
 45 0F68  C3  10BD          JMP  MCHRET
 46 0F6B  3A  70D8   1$:    LDA  NOISE       ;GET NOISE, NEGATE IT
 47 0F6E  2F                CMA
 48 0F6F  3C                INR  A
 49 0F70  5F                MOV  E,A         ;TO D,E
 50 0F71  16  FF            MVI  D,0FFH
 51 0F73  19                DAD  D           ;MAX-NOISE
 52 0F74  CD  10D9          CALL BCGTHL      ;DATA > (MAX-NOISE)?
 53 0F77  D2  10BD          JNC  MCHRET      ;YES, NOT READY FOR MODE 1 YET
 54 0F7A  21  70CB          LXI  H,MCHMOD    ;INCREMENT THE MODE
 55 0F7D  34                INR  M
 56 0F7E  3A  70D6          LDA  MAXIDX      ;NOW INTEGRATE 2 POINTS BACKWARDS
 57 0F81  47                MOV  B,A
```

```
 1 0F82  3E   02           MVI    A,2
 2 0F84  11   0000         LXI    D,0
 3 0F87  CD   10E0         CALL   ISUM
 4 0F8A  DA   10D4         JC     MCHER9
 5 0F8D  EB                XCHG
 6 0F8E  3E   01           MVI    A,1
 7 0F90  CD   1A71         CALL   SHFTHL        ;SCALE UP TO DATA*4
 8 0F93  22   70CC         SHLD   PLSMX1
 9 0F96  3A   70D6         LDA    MAXIDX
10 0F99  C6   02           ADI    2
11 0F9B  47                MOV    B,A
12 0F9C  3E   02           MVI    A,2
13 0F9E  11   0000         LXI    D,0
14 0FA1  CD   10E0         CALL   ISUM
15 0FA4  DA   10D4         JC     MCHER9
16 0FA7  EB                XCHG
17 0FA8  3E   01           MVI    A,1
18 0FAA  CD   1A71         CALL   SHFTHL
19 0FAD  22   70D2         SHLD   PLSMX2
20 0FB0  C3   10BD         JMP    MCHRET
```

```
                         ;CHECK FOR MODE 1 (LOOKING FOR SLOPE)
                         ;
 4 0FB3  3D          MCH1: DCR    A
 5 0FB4  C2   1014         JNZ    MCH2           ;NOT 1, CHECK FOR 2...
                         ;
                         ;FIND MAX SLOPE, INTEGRATING BACKWARDS 2*SPLEN POINTS
                         ;
 9 0FB7  11   0000         LXI    D,0            ;CLEAR SUM ACCUMULATOR (C,D,E)
10 0FBA  0E   00           MVI    C,0
11 0FBC  3A   7179         LDA    DTOIDX         ;CURRENT DATA INDEX, CHANNEL A
12 0FBF  47                MOV    B,A
13 0FC0  3A   70D7         LDA    SPLEN          ;SPAN
14 0FC3  CD   10E0         CALL   ISUM           ;SUM LAST (SPLEN) POINTS
15 0FC6  DA   10D4         JC     MCHER9         ;ERROR IF A ZERO ENCOUNTERED
16 0FC9  CD   134E         CALL   NEGCDE         ;NEGATE SUM
17 0FCC  3A   70D7         LDA    SPLEN          ;RESET COUNT (POINTER KEEPS GOING BACKWARDS)
18 0FCF  CD   10E0         CALL   ISUM           ;SUM SECOND HALF
19 0FD2  DA   10D4         JC     MCHER9         ;ERROR IF A ZERO ENCOUNTERED
20 0FD5  79                MOV    A,C            ;CHECK FOR OVERFLOW
21 0FD6  B7                ORA    A
22 0FD7  F2   0FE0         JP     4$             ;NEG?
23 0FDA  0E   00           MVI    C,0            ;YES, ZERO SLOPE
24 0FDC  11   0000         LXI    D,0
25 0FDF  AF                XRA    A
26 0FE0  CA   0FE6   6$:   JZ     7$             ;OVERFLOW?
27 0FE3  11   FFFF         LXI    D,0FFFFH       ;SET TO MAX
28 0FE6  2A   70D0   7$:   LHLD   PLSSLP         ;GET OLD MAX SLOPE
29 0FE9  42                MOV    B,D            ;TO B,C
30 0FEA  4B                MOV    C,E
31 0FEB  CD   10D9         CALL   BCGTHL         ;NEW SLOPE > OLD SLOPE?
32 0FEE  DA   0FF8         JC     15$            ;NOPE, MUST BE OVER THE TOP...
33 0FF1  EB          8$:   XCHG
34 0FF2  22   70D0         SHLD   PLSSLP         ;STORE NEW MAX
35 0FF5  C3   10BD         JMP    MCHRET
36 0FF8  21   70CB   15$:  LXI    H,MCHMOD
37 0FFB  34                INR    M
38 0FFC  3A   70D7         LDA    SPLEN          ;OVER THE TOP, GO TO MODE 2
39 0FFF  57                MOV    D,A            ;BACK UP POINTER TO MID-SLOPE
40 1000  07                RLC
41 1001  07                RLC
42 1002  5F                MOV    E,A
43 1003  21   7179         LXI    H,DTOIDX
44 1006  7E                MOV    A,M
45 1007  93                SUB    E
46 1008  E6   FF           ANI    BUFMSK
47 100A  77                MOV    M,A
48 100B  21   70B3         LXI    H,PERCTR       ;FUDGE COUNTER FOR THE BACK-UP
49 100E  7E                MOV    A,M
50 100F  92                SUB    D
51 1010  77                MOV    M,A
52 1011  C3   10BD         JMP    MCHRET
```

```
                         ;IF MODE 2 LOOK FOR MIN...
                         ;
 4 1014  3D          MCH2: DCR    A
 5 1015  C2   10BD         JNZ    MCHRET
                         ;
                         ;IF DATA > MIN THEN SET MODE=3
                         ;IF DATA < MIN THEN STORE AS NEW MIN
                         ;
10 1018  2A   70CE         LHLD   PLSMN1         ;GET OLD MIN
11 101B  7D                MOV    A,L            ;CHECK FOR ZERO
12 101C  B4                ORA    H
```

```
13 101D  CA  1026           JZ      1$              ;IT IS, STORE DATA
14 1020  CD  10D9           CALL    BCGTHL          ;DATA LARGER?
15 1023  D2  102E           JNC     MCH3            ;YES, PAST MIN.
16 1026  60         1$:     MOV     H,B             ;STORE NEW MIN
17 1027  69                 MOV     L,C
18 1028  22  70CE           SHLD    PLSMN1
19 102B  C3  10BD           JMP     MCHRET
20                  ;
21 102E  3A  7179   MCH3:   LDA     DTOIDX
22 1031  47                 MOV     B,A
23 1032  3E  02             MVI     A,2
24 1034  11  0000           LXI     D,0
25 1037  CD  10E0           CALL    ISUM            ;SUM LAST 2 POINTS AS MIN
26 103A  DA  10D4           JC      MCHER9
27 103D  EB                 XCHG
28 103E  3E  01             MVI     A,1
29 1040  CD  1A71           CALL    SHFTHL
30 1043  22  70CE           SHLD    PLSMN1
31 1046  3A  7179           LDA     DTOIDX
32 1049  C6  02             ADI     2
33 104B  47                 MOV     B,A
34 104C  3E  02             MVI     A,2
35 104E  11  0000           LXI     D,0
36 1051  CD  10E0           CALL    ISUM
37 1054  DA  10D4           JC      MCHER9
38 1057  EB                 XCHG
39 1058  3E  01             MVI     A,1
40 105A  CD  1A71           CALL    SHFTHL
41 105D  22  70D4           SHLD    PLSMN2
```

RESPOX; MICROBENCH 8080/8085 CROSS ASSEMBLER (V2)-436  30-MAR-85 13:30:07 PAGE 57

```
                            ;DATA IS READY FOR COMPUTE ROUTINES...STORE MIN/MAX AND INDEX, SET FLAG
                            ;
 4 1060  2A  70D0           LHLD    PLSSLP          ;GET INTEGRATED SLOPE
 5 1063  EB                 XCHG
 6 1064  2A  70D9           LHLD    PLSTHD          ;GET THRESHHOLD
 7 1067  AF                 XRA     A               ;NEGATE THRESHHOLD
 8 1068  95                 SUB     L
 9 1069  6F                 MOV     L,A
10 106A  3E  00             MVI     A,0
11 106C  9C                 SBB     H
12 106D  67                 MOV     H,A
13 106E  3E  01             MVI     A,1             ;ERROR CODE
14 1070  19                 DAD     D               ;SLOPE - THRESHHOLD
15 1071  D2  10AE           JNC     MCHERR          ;TOO SMALL
16 1074  21  709E           LXI     H,DATFLG        ;CHECK FOR FLAG ALREADY SET...
17 1077  7E                 MOV     A,M
18 1078  B7                 ORA     A
19 1079  3E  0A             MVI     A,10            ;ERROR 10 IF SO
20 107B  C2  10AE           JNZ     MCHERR          ;ALREADY SET, SKIP THIS...ERROR 10...
21 107E  34                 INR     M               ;SET FLAG
22 107F  2A  70CC           LHLD    PLSMX1
23 1082  22  709F           SHLD    MAX1            ;STORE DATA
24 1085  2A  70CE           LHLD    PLSMN1
25 1088  22  70A1           SHLD    MIN1
26 108B  2A  70D0           LHLD    PLSSLP
27 108E  22  70A7           SHLD    MXSLOP
28 1091  2A  70D2           LHLD    PLSMX2
29 1094  22  70A3           SHLD    MAX2
30 1097  2A  70D4           LHLD    PLSMN2
31 109A  22  70A5           SHLD    MIN2
32 109D  2A  709F           LHLD    MAX1            ;STORE MAX FOR BLIP...
33 10A0  3E  FE             MVI     A,-2
34 10A2  CD  1A71           CALL    SHFTHL
35 10A5  22  70DC           SHLD    OLDMAX
36 10A8  3E  01             MVI     A,1             ;STOP TIME WINDOW TIMER
37 10AA  32  710A           STA     WINFLG
38 10AD  AF         4$:     XRA     A               ;NO ERROR, CODE = 0
```

RESPOX; MICROBENCH 8080/8085 CROSS ASSEMBLER (V2)-436  30-MAR-85 13:30:07 PAGE 58

```
                            ;ERROR...STORE ERROR CODE, RESET PARAMETERS AND START OVER...SIGH...
                            ;
 4 10AE  32  70DB   MCHERR: STA     ERRCOD
 5 10B1  21  70CB           LXI     H,MCHMOD        ;POINT TO PARAMETERS, SET COUNTER AND CLEAR
 6 10B4  1E  0B             MVI     E,11
 7 10B6  36  00     1$:     MVI     M,0
 8 10B8  23                 INX     H
 9 10B9  1D                 DCR     E
10 10BA  C2  10B6           JNZ     1$
11 10BD  3A  70B3   MCHRET: LDA     PERCTR          ;INCREMENT LEVEL 3'S PERIOD COUNTER
12 10C0  3C                 INR     A
13 10C1  CA  10C7           JZ      1$
14 10C4  32  70B3           STA     PERCTR
15 10C7  21  7179   1$:     LXI     H,DTOIDX        ;INCREMENT INDEX
16 10CA  7E                 MOV     A,M
17 10CB  C6  04             ADI     4
```

```
18 10CD  E6    FF           ANI    BUFMSK
19 10CF  77                 MOV    H,A
20 10D0  CD    110D         CALL   BLIP       ;OUTPUT TO METER
21 10D3  C9                 RET
22 10D4  3E    09    MCHER9: MVI   A,9
23 10D6  C3    10AE         JMP    MCHERR
24
25          ;
26          ;COMPARE BC, TO H,L AND RETURN CARRY IF BC NOT GREATER
27          ;
28 10D9  78    BCGTHL: MOV  A,B
29 10DA  BC                 CMP    H
30 10DB  D8                 RC
31 10DC  C0                 RNZ
32 10DD  79                 MOV    A,C
33 10DE  BD                 CMP    L
34 10DF  C9                 RET
```

RESPOX: MICROBENCH 8080/8085 CROSS ASSEMBLER (V2)-436  30-MAR-85 13:30:07 PAGE 59

```
          ;SUM (A) POINTS BACKWARDS FROM INDEX IN B, RETURN (24 BITS) IN C,D,E
          ;RETURN CARRY SET IF A ZERO IS ENCOUNTERED (INDICATING OVERFLOW OR LED'S CH/
          ;
 5 10E0           ISUM:
 6 10E0   F5      1$:   PUSH   PSW             ;SAVE COUNT
 7 10E1   21  717A       LXI    H,DATBUF       ;GENERATE POINTER
 8 10E4   7D               MOV    A,L
 9 10E5   80               ADD    B
10 10E6   6F               MOV    L,A            ;BASE ADDRESS + INDEX
11 10E7   7C               MOV    A,H
12 10E8   CE  00           ACI    0
13 10EA   67               MOV    H,A
14 10EB   7E               MOV    A,H
15 10EC   23               INX    H
16 10ED   B6               ORA    M
17 10EE   CA  110A         JZ     10$            ;CHECK FOR ZERO DATA
18 10F1   2B               DCX    H
19 10F2   7B               MOV    A,E            ;ADD DATA TO SUM
20 10F3   86               ADD    M
21 10F4   5F               MOV    E,A
22 10F5   23               INX    H
23 10F6   7A               MOV    A,D
24 10F7   8E               ADC    M
25 10F8   57               MOV    D,A
26 10F9   79               MOV    A,C
27 10FA   CE  00           ACI    0
28 10FC   4F               MOV    C,A
29 10FD   78               MOV    A,B
30 10FE   D6  04           SUI    4              ;DECREMENT INDEX
31 1100   E6  FF           ANI    BUFMSK
32 1102   47               MOV    B,A
33 1103   F1               POP    PSW            ;GET COUNT BACK
34 1104   B7               ORA    A              ;CLEAR CARRY
35 1105   3D               DCR    A
36 1106   C2  10E0         JNZ    1$             ;LOOP
37 1109   C9               RET
38 110A   F1      10$:     POP    PSW
39 110B   37               STC
40 110C   C9               RET
```

RESPOX: MICROBENCH 8080/8085 CROSS ASSEMBLER (V2)-436  30-MAR-85 13:30:07 PAGE 60

```
          ;COMPUTE OUTPUT FOR ANALOG 'METER' DISPLAY...
          ;  COMPARE DATA (IN B,C) MINUS 'OLDMAX' WITH LIST
          ;  OF THRESHOLDS (BLPTHI) FOR EACH LIGHT.
          ;  TABLE IS TWO BYTES PER LIGHT (8 TOTAL). IF DATA > N'TH ENTRY THEN
          ;  LIGHT N'TH LED. (REMEMBER THAT THE DATA GOES DOWN FROM MAX, DISPLAYED AS A
          ;  RISING BLIP).
          ;
 9 110D   3A  70DE   BLIP:  LDA    BLPIDX        ;GET DATA
10 1110   5F               MOV    E,A
11 1111   16  00           MVI    D,0
12 1113   3A  7178         LDA    DATIDX
13 1116   BB               CMP    E
14 1117   C8               RZ
15 1118   21  717A         LXI    H,DATBUF
16 111B   19               DAD    D
17 111C   4E               MOV    C,M
18 111D   23               INX    H
19 111E   46               MOV    B,M
20 111F   C5               PUSH   B             ;SAVE DATA FOR BARGRAPH      ///
21 1120   60               MOV    H,B
22 1121   69               MOV    L,C           ;TO H,L
23 1122   3E  04           MVI    A,4
24 1124   CD  1A71         CALL   SHFTHL        ;MOVE 8 BITS TO H
25 1127   7C               MOV    A,H
26 1128   CD  1D3B         CALL   SPLIT         ;MAKE INTO TWO NIBBLES (HUH ?)
27 112B   7A               MOV    A,D
28 112C   F6  10           ORI    10H           ;PUT IN IDENTIFIER           ///
29 112E   EA  1133         JPE    STIK1                                     ///
30 1131   F6  80           ORI    80H           ;SET PARITY IF NEEDED       ///
```

```
31 1133  32   7281  STIK1: STA   PLS1           ;STORE FIRST GUY              ///
32 1136  7B               MOV   A,E             ;GET LOWER NIBBLE             ///
33 1137  F6   70           ORI   70H             ;PUT IN END OF MESSAGE IDENTIFIER ///
34 1139  EA   113E         JPE   STIK2           ;                             ///
35 113C  F6   80           ORI   80H             ;MAKE SURE PARITY IS OK       ///
36 113E  32   7282  STIK2: STA   PLS2            ;STORE SECOND GUY             ///
37 1141  3E   02           MVI   A,2             ;                             ///
38 1143  32   72A8         STA   CPLSFL          ;SET FLAG TO SEND THEM        ///
39 1146  C1               POP   B                ;RESTORE DATA WORD            ///
40
41                   ;CHECK FOR LED DRIVE-LEVEL DISPLAY (IF NOT YET SYNC'ED)
42                   ;OTHERWISE COMPUTE BAR-GRAPH FROM PULSE AMPLITUDE
43
44 1147  3A   7014         LDA   SYNFLG
45 114A  FE   03           CPI   3
46 114C  F2   11D0         JP    BLIP2           ;NO SYNC, SHOW LED DRIVE'S
47 114F  3A   713A         LDA   OPNFLG          ;CHECK FOR MODE DISPLAY
48 1152  B7               ORA   A
49 1153  CA   1162         JZ    1$              ;NOPE
50 1156  11   8E90         LXI   D,-FMODE
51 1159  2A   7138         LHLD  OPHPRM
52 115C  19               DAD   D
53 115D  7C               MOV   A,H
54 115E  B5               ORA   L
55 115F  CA   11D0         JZ    BLIP2
56
57                   ;COMPUTE PULSE AMPLITUDE DISPLAY
```

RESPOX: MICROBENCH 8080/8085 CROSS ASSEMBLER (V2)-436  30-MAR-85 13:30:07 PAGE 61

```
 2 1162  78           1$: MOV   A,B
 3 1163  B1               ORA   C
 4 1164  CA   119B         JZ    11$             ;ZERO DATA, NO BLIP
 5 1167  2A   70DC         LHLD  OLDMAX          ;GET LAST MAX VALUE
 6 116A  AF               XRA   A
 7 116B  95               SUB   L               ;NEGATE IT
 8 116C  6F               MOV   L,A
 9 116D  3E   00           MVI   A,0
10 116F  9C               SBB   H
11 1170  67               MOV   H,A
12 1171  09               DAD   B
13 1172  3E   00           MVI   A,0             ;DATA - MAX = DELTA (NEGATIVE SINCE DATA < MAX)
14 1174  DA   119B         JC    11$             ;DATA IS GREATER, NO DISPLAY
15 1177  44           2$: MOV   B,H             ;DELTA TO B,C
16 1178  4D               MOV   C,L
17 1179  11   11B0         LXI   D,BLPTHT        ;TABLE POINTER IN D,E
18 117C  21   0000         LXI   H,0             ;START WITH NO LIGHTS
19 117F  E5               PUSH  H
20 1180  EB           5$: XCHG
21 1181  5E               MOV   E,M             ;GET TABLE ENTRY
22 1182  23               INX   H
23 1183  56               MOV   D,M
24 1184  23               INX   H
25 1185  EB               XCHG
26 1186  09               DAD   B               ;TABLE - DELTA
27 1187  DA   1197         JC    10$             ;TABLE LARGER, ALL DONE
28 118A  37               STC                   ;SET CARRY (THIS MAY BE REDUNDANT??)
29 118B  E3               XTHL                  ;GET LIGHTS FROM TOP OF STACK
30 118C  7D               MOV   A,L
31 118D  17               RAL                   ;SHIFT IN ANOTHER
32 118E  6F               MOV   L,A
33 118F  7C               MOV   A,H
34 1190  17               RAL
35 1191  67               MOV   H,A
36 1192  E3               XTHL                  ;PUT THEM BACK
37 1193  B7               ORA   A               ;CHECK FOR ALL-FULL
38 1194  F2   1180         JP    5$              ;IS NOT, KEEP GOING
39 1197  E1          10$: POP   H               ;GET LIGHTS
40 1198  C3   119E         JMP   12$
41 119B  21   0001  11$: LXI   H,1             ;NO LIGHTS
42 119E  7D          12$: MOV   A,L
43 119F  32   7128         STA   DSPMTL          ;STORE THEM FOR DISPLAY
44 11A2  7C               MOV   A,H
45 11A3  32   712A         STA   DSPMTH
46 11A6  21   70DE         LXI   H,BLPIDX
47 11A9  7E               MOV   A,M
48 11AA  C6   04           ADI   4
49 11AC  E6   FF           ANI   BUFMSK
50 11AE  77               MOV   M,A
51 11AF  C9               RET

;THRESHOLD TABLE...LOG SCALE BASED ON 1.302, 16 STEPS FROM .10% TO 4%
                   ;
55 11B0  0000         BLPTHT: DW   0
56 11B2  0010                 DW   16           ;0.10%
57 11B4  0015                 DW   21
```

```
 1 11B6    001C              DW      28
 2 11B8    0024              DW      36
 3 11BA    002F              DW      47
 4 11BC    003D              DW      61
 5 11BE    0050              DW      80
 6 11C0    006A              DW      106
 7 11C2    0089              DW      137
 8 11C4    00B0              DW      176
 9 11C6    00E5              DW      229
10 11C8    0129              DW      297
11 11CA    0183              DW      387
12 11CC    01F7              DW      503
13 11CE    028F              DW      655     ;4.00%
14
15
16                           ;DISPLAY LED DRIVE LEVEL GRAPHICALLY
17
18 11D0   21   0001   BLIP2:  LXI     H,1
19 11D3   11   0000           LXI     D,0
20 11D6   3A   7008           LDA     CALOK
21 11D9   B7                  ORA     A
22 11DA   CA   11EA           JZ      1$
23 11DD   3A   700A           LDA     LED1
24 11E0   CD   11F5           CALL    XBLIP2
25 11E3   EB                  XCHG
26 11E4   3A   700D           LDA     LED2
27 11E7   CD   11F5           CALL    XBLIP2
28 11EA   7C           1$:    MOV     A,H
29 11EB   B2                  ORA     D
30 11EC   32   712A           STA     DSPMTH
31 11EF   7D                  MOV     A,L
32 11F0   B3                  ORA     E
33 11F1   32   7128           STA     DSPMTL
34 11F4   C9                  RET
35
36 11F5   21   0001   XBLIP2: LXI     H,1
37 11F8   D6   40             SUI     64
38 11FA   D8                  RC
39 11FB   4F           1$:    MOV     C,A
40 11FC   7D                  MOV     A,L
41 11FD   17                  RAL
42 11FE   6F                  MOV     L,A
43 11FF   7C                  MOV     A,H
44 1200   17                  RAL
45 1201   67                  MOV     H,A
46 1202   79                  MOV     A,C
47 1203   D6   0D             SUI     13
48 1205   D2   11FB           JNC     1$
49 1208   C9                  RET
```

```
 1                            ;ARITHMETIC UTILITIES.....
 2                            ;
 3                            ;INTEGER MULTILY ROUTINE:
 4                            ; MULTIPLY B+C BY D+E, PRODUCT RETURNED IN D+E. (MULTIPLIER LOST)
 5                            ; EACH REGISTER PAIR IS TREATED AS AN UNSIGNED INTEGER, ALTHOUGH D.P.'S CAN BE ASSUMED.
 6                            ; A CARRY IS RETURNED IF THE PRODUCT OVERFLOWS..
 7                            ; H,L SAVED
 8                            ;
 9
10 1209   C5           MPY16: PUSH    B
11 120A   E5                  PUSH    H
12 120B   21   0000           LXI     H,0             ;PARTIAL PRODUCT
13
14                            ; SHIFT MULTIPLIER RIGHT ONE BIT, ADD MULTIPLICAND TO PRODUCT IF LOW
15                            ; M'ER BIT WAS SET. QUIT WHEN THERE ARE NO MORE MULT'ER BITS.
16                            ;
17 120E   B7           1$:    ORA     A               ;CLEAR CARRY
18 120F   7A                  MOV     A,D             ;SHIFT MULTIPLIER DOWN
19 1210   1F                  RAR
20 1211   57                  MOV     D,A
21 1212   7B                  MOV     A,E
22 1213   1F                  RAR
23 1214   5F                  MOV     E,A
24 1215   D2   121C           JNC     2$              ;LOW BIT WAS NOT SET
25 1218   09                  DAD     B               ;ADD MULT'AND TO PRODUCT
26 1219   DA   122E           JC      11$             ;OVERFLOW ERROR
27 121C   7B           2$:    MOV     A,E             ;CHECK FOR NO MORE MULTIPLIER BITS
28 121D   B2                  ORA     D
29 121E   CA   122E           JZ      10$             ;DONE IF SO (CARRY CLEAR)
30
31                            ;SHIFT MULTIPLICAND UP ONE BIT...WATCH FOR OVERFLOW
32                            ;
33 1221   B7                  ORA     A               ;CLC
34 1222   79                  MOV     A,C
35 1223   17                  RAL
36 1224   4F                  MOV     C,A
37 1225   78                  MOV     A,B
38 1226   17                  RAL
```

```
39 1227  47              MOV   B,A
40 1228  DA   122E       JC    11$        ;SHIFTED A BIT OUT...ERROR
41 122B  C3   120E       JMP   1$         ;DO IT AGAIN
42 122E           11$:                    ;OVERFLOW ERROR...CARRY ALREADY SET
43 122E  EB      10$:    XCHG             ;MOVE PRODUCT TO D,E
44 122F  E1              POP   H
45 1230  C1              POP   B          ;RESTORE MULT'AND
46 1231  C9              RET
```

```
                ;32-BIT MULTIPLY...
                ;AS ABOVE, EXCEPT MULTIPLIES B,C BY D,E TO FORM A 32-BIT PRODUCT IN B,C,D,E.
                ;
 5 1232  21   0000  MPY32: LXI   H,0       ;CLEAR HI PARTIAL PRODUCT
 6 1235  E5              PUSH  H           ;AND LOW PARTIAL
 7 1236  3E   10         MVI   A,16        ;COUNTER (ALWAYS MULTIPLY ALL 16 BITS)
 8 1238  32   70C0  1$:  STA   XMPY        ;SAVE COUNTER
 9 123B  B7              ORA   A           ;CLEAR CARRY
10 123C  7A              MOV   A,D         ;SHIFT MULTIPLIER DOWN
11 123D  1F              RAR
12 123E  57              MOV   D,A
13 123F  7B              MOV   A,E
14 1240  1F              RAR
15 1241  5F              MOV   E,A
16 1242  D2   1246       JNC   2$          ;NEXT BIT ZERO, NO ADD
17 1245  09              DAD   B           ;ADD MULTIPLICAND TO PRODUCT
18 1246  7C       2$:    MOV   A,H         ;SHIFT PRODUCT DOWN (INCLUDING CARRY)
19 1247  1F              RAR
20 1248  67              MOV   H,A
21 1249  7D              MOV   A,L
22 124A  1F              RAR
23 124B  6F              MOV   L,A
24 124C  E3              XTHL              ;ALL 32 BITS
25 124D  7C              MOV   A,H
26 124E  1F              RAR
27 124F  67              MOV   H,A
28 1250  7D              MOV   A,L
29 1251  1F              RAR
30 1252  6F              MOV   L,A
31 1253  E3              XTHL
32 1254  3A   70C0       LDA   XMPY
33 1257  3D              DCR   A
34 1258  C2   1238       JNZ   1$          ;LOOP 16 BITS WORTH
35 125B  44              MOV   B,H         ;HIGH PRODUCT
36 125C  4D              MOV   C,L
37 125D  D1              POP   D           ;LOW HALF
38 125E  C9              RET
```

```
                ; ENTER WITH VALUE TO BE SCALED IN REGISTER A
                ; OUTPUT WILL BE IN HL REGISTER PAIR
 6 125F  D5         SCL100: PUSH  D
 7 1260  C5                 PUSH  B
 8 1261  F5                 PUSH  PSW
10 1262  11   0FFF          LXI   D,4095
11 1265  CD   12E4          CALL  MULT
12 1268  5F                 MOV   E,A
13 1269  16   00            MVI   D,0
14 126B  01   03E8          LXI   B,1000     ;0-100 % SA02 = 0-1V
15 126E  CD   12C3          CALL  DIVRND
16 1271  EB                 XCHG
17 1272  F1                 POP   PSW
18 1273  C1                 POP   B
19 1274  D1                 POP   D
20 1275  C9                 RET 22 1276  D5         SCL250: PUSH  D
23 1277  C5                 PUSH  B
24 1278  F5                 PUSH  PSW
25 1279  11   0FFF          LXI   D,4095
26 127C  CD   12E4          CALL  MULT
27 127F  5F                 MOV   E,A
28 1280  16   00            MVI   D,0
29 1282  01   09C4          LXI   B,2500     ;0-250 BPM = 0-1V
30 1285  CD   12C3          CALL  DIVRND
31 1288  EB                 XCHG
32 1289  F1                 POP   PSW
33 128A  C1                 POP   B
34 128B  D1                 POP   D
35 128C  C9                 RET

;       MULTIPLICATION AND DIVISION
```

```
39
40                              ; 'DIV' IS A 32 BY 16 BIT DIVISION ROUTINE
41                              ; INPUT DIVIDEND IN DEHL AND DIVISOR IN BC
42                              ; OUTPUT QUOTIENT IN DE, REMAINDER IN HL, AND DIVISOR IN BC.
43
44                              ; 'DMULT' IS A 16 BY 16 BIT MULTIPLICATION ROUTINE.
45                              ; INPUT MULTIPLICAND IN DE AND MULTIPLIER IN BC.
46                              ; OUTPUT PRODUCT IN DEHL.
47
48                              ; MULT IS AN 8 BY 16 BIT MULTIPLICATION
49                              ; INPUT MULTIPLICAND IN DE AND MULTIPLIER IN A
50                              ; OUTPUT PRODUCT IN AHL
51
52  128D   EB              DIV:    XCHG                    ;SWAP HI AND LO WORDS
53  128E   3E      11              MVI     A,17            ;INITIALIZE LOOP COUNTER
54  1290   F5                      PUSH    PSW
55  1291   AF                      XRA     A               ;SAVE ON STACK AND CLEAR A AND CARRY
56
57  1292   F5              DLOOP:  PUSH    PSW
```

```
 1  1293   7D                      MOV     A,L             ;SAVE CARRY BYTE ON STACK
 2  1294   91                      SUB     C               ;HL-BC 16 BIT SUBTRACT
 3  1295   6F                      MOV     L,A
 4  1296   7C                      MOV     A,H
 5  1297   98                      SBB     B
 6  1298   67                      MOV     H,A
 7  1299   E3                      XTHL                    ;RESTORE CARRY BYTE
 8  129A   7C                      MOV     A,H
 9  129B   DE      00              SBI     0               ;COMPLETE SUBTRACTION
10  129D   E1                      POP     H               ;RESTORE REMAINDER TO HL
11
12  129E   D2      12A2            JNC     TEST            ;IF BORROW OCCURRED
13  12A1   09                      DAD     B               ;ADD DIVISOR BACK, HL+BC
14
15  12A2   3F              TEST:   CMC                     ;COMPLEMENT BORROW BIT
16  12A3   7B                      MOV     A,E             ;32 BIT LEFT SHIFT W/CARRY
17  12A4   17                      RAL
18  12A5   5F                      MOV     E,A
19  12A6   7A                      MOV     A,D
20  12A7   17                      RAL
21  12A8   57                      MOV     D,A
22  12A9   E3                      XTHL                    ;GET LOOP COUNTER OFF STACK
23  12AA   25                      DCR     H               ;DECREMENT IT
24  12AB   E3                      XTHL                    ;PUT IT BACK
25  12AC   CA      12B9            JZ      EXIT            ;AND EXIT WHEN DONE
26  12AF   7D                      MOV     A,L
27  12B0   17                      RAL
28  12B1   6F                      MOV     L,A
29  12B2   7C                      MOV     A,H
30  12B3   17                      RAL
31  12B4   67                      MOV     H,A
32  12B5   9F                      SBB     A               ;A=CARRY FROM SHIFT
33  12B6   C3      1292            JMP     DLOOP           ;AND GO ON AROUND AGAIN
34  12B9   F1              EXIT:   POP     PSW             ;RESTORE STACK
35  12BA   C9                      RET
36
37  12BB   29              RNDOFF: DAD     H               ;IF REM > .5 * DIVISOR
38  12BC   CD      1348            CALL    NEGHL           ;HL=-2*REM
39  12BF   09                      DAD     B               ;>DIVISOR ?
40  12C0   D8                      RC                      ;NO, THEN QUOTIENT IS OK
41  12C1   13                      INX     D               ;YES, THEN BUMP QUOTIENT
42  12C2   C9                      RET
43
44  12C3   CD      128D    DIVRND: CALL    DIV             ;FOR DOING WITH ROUNDING
45  12C6   CD      12BB            CALL    RNDOFF          ;MUST CALL IN SEQUENCE
46  12C9   C9                      RET
47
48
49  12CA   79              DMULT:  MOV     A,C             ;MULTIPLIER LO BYTE IN A
50  12CB   C5                      PUSH    B               ;SAVE MULTIPLIER
51  12CC   CD      12E4            CALL    MULT            ;AHL=MPCD*LO(MPLR)
52  12CF   E3                      XTHL                    ;SWAP MPLR AND PP1 LO BYTES
53  12D0   F5                      PUSH    PSW             ;SAVE PP1 HI BYTE
54  12D1   7C                      MOV     A,H             ;MPLR HI BYTE IN A
55  12D2   CD      12E4            CALL    MULT            ;AHL=MPCD * HI(MPLR)
56  12D5   58                      MOV     E,B             ;E=B=0
57  12D6   C1                      POP     B               ;PP1 HI BYTE IN B
```

```
 1  12D7   55                      MOV     D,L
 2  12D8   4C                      MOV     C,H             ;PF2 LO BYTES IN C,D
 3  12D9   E1                      POP     H               ;PP1 LO BYTES IN HL
 4  12DA   19                      DAD     D               ;HL=LO(PF2) + PP1 LO BYTES
 5  12DB   57                      MOV     D,A             ;PF2 HI BYTE IN D
 6  12DC   78                      MOV     A,B             ;ADD PP1 HI BYTE + CARRY
 7  12DD   89                      ADC     C               ;TO PF2 MID BYTE
 8  12DE   5F                      MOV     E,A             ;RESULT TO E
 9  12DF   7A                      MOV     A,D             ;PF2 HI BYTE IN A
```

```
10 12E0  CE  00              ACI   0       ;ADD CARRY FROM MID BYTE
11 12E2  57                  MOV   D,A     ;RESULT NOW IN DEHL.
12 12E3  C9                  RET
13
14 12E4  21  0000    MULT:   LXI   H,0     ;INITIALIZE PARTIAL PRODUCT
15 12E7  06  08              MVI   B,8     ;INITIALIZE LOOP COUNTER
16
17 12E9  29       MLOOP:     DAD   H       ;SHIFT PP LEFT ONE
18 12EA  17                  RAL           ;SHIFT MPLR LEFT ONE
19 12EB  D2  12F1            JNC   DEC     ;IF MSB OF MPLR=1,
20 12EE  19                  DAD   D       ;ADD MPCD TO PP
21 12EF  CE  00              ACI   0       ;INCLUDING CARRY TO A
22 12F1  05       DEC:       DCR   B       ;LAST BIT DONE ?
23 12F2  C2  12E9            JNZ   MLOOP   ;NO, KEEP GOING
24 12F5  C9                  RET
25
26
27
28
```

RESPOX: MICROBENCH 8080/8085 CROSS ASSEMBLER (V2)-436   30-MAR-85 13:30:07 PAGE 68

```
1
2
3                    ;16-BIT DIVIDE ROUTINE....
4                    ; DIVIDE 16-BIT INTEGER IN D,E BY ANOTHER IN B,C, FORMING A 16-BIT FRACTION
5                    ; STORED INTO D,E....ON THE CONDITION THAT D,E < B,C, RETURN CARRY OTHERWISE.
6                    ; H,L SAVED.
7
8 12F6  E5           DIV16:  PUSH  H
9 12F7  AF                   XRA   A       ;FIRST DIVIDE DIVISOR BY 2
10 12F8 78                   MOV   A,B     ; (ON THE ASSUMPTION THAT IT IS BIGGER)
11 12F9 1F                   RAR
12 12FA 47                   MOV   B,A
13 12FB 79                   MOV   A,C
14 12FC 1F                   RAR
15 12FD 4F                   MOV   C,A
16 12FE AF                   XRA   A       ;NOW MAKE THE DIVISOR NEGATIVE
17 12FF 91                   SUB   C
18 1300 4F                   MOV   C,A
19 1301 3E 00                MVI   A,0
20 1303 98                   SBB   B
21 1304 47                   MOV   B,A
22 1305 EB                   XCHG          ;DIVIDEND TO H,L
23 1306 11 0001              LXI   D,1     ;CLEAR PARTIAL PRODUCT, SET CHASE (17TH) BIT
24 1309 E5           1$:     PUSH  H       ;SAVE DIVIDEND IN CASE SUBTRACT FAILS
25 130A 09                   DAD   B       ;SUBTRACT DIVISOR FROM D'END
26 130B DA 1312              JC    2$      ;OK, WAS LESS
27 130E E1                   POP   H       ;WAS TOO BIG, RESTORE DIVIDEND
28 130F C3 1314              JMP   3$
29 1312 33           2$:     INX   SP      ;DUMP UNUSED DIVIDEND
30 1313 33                   INX   SP
31 1314 7B           3$:     MOV   A,E     ;SHIFT NEW BIT INTO QUOTIENT
32 1315 17                   RAL
33 1316 5F                   MOV   E,A
34 1317 7A                   MOV   A,D
35 1318 17                   RAL
36 1319 57                   MOV   D,A
37 131A DA 132B              JC    10$     ;CHASE BIT POPPED OUT
38 131D 7D                   MOV   A,L     ;SHIFT REMAINING DIVIDEND UP...SHOULD NOT OVERFLOW IF DE < BC
39 131E 17                   RAL
40 131F 6F                   MOV   L,A
41 1320 7C                   MOV   A,H
42 1321 17                   RAL
43 1322 67                   MOV   H,A
44 1323 D2 1309              JNC   1$      ;NO OVERFLOW
45 1326 11 FFFF              LXI   D,0FFFFH ;OVERFLOW VALUE
46 1329 E1                   POP   H
47 132A C9                   RET           ;RETURN CARRY SET
48 132B B7           10$:    ORA   A       ;CLEAR CARRY
49 132C E1                   POP   H
50 132D C9                   RET
```

RESPOX: MICROBENCH 8080/8085 CROSS ASSEMBLER (V2)-436   30-MAR-85 13:30:07 PAGE 69

```
1
2                    ;INTEGER ROUTINE...CONVERT D,E FROM INT.FRACT TO INT.000
3                    ;
4 132E EB            INTDE:  XCHG
5 132F CD 1334               CALL  INTHL
6 1332 EB                    XCHG
7 1333 C9                    RET
8
9                    ;SAME FOR H,L
10                   ;
11 1334 D5           INTHL:  PUSH  D
12 1335 11 0080              LXI   D,80H
13 1338 19                   DAD   D
14 1339 D1                   POP   D
15 133A 2E 00                MVI   L,0
16 133C D0                   RNC
```

```
17 133D  26   FF              MVI   H,0FFH
18 133F  C9                   RET
19
20                       ;NEGATE D,E
21                       ;
22 1340  AF              NEGDE: XRA   A
23 1341  93                   SUB   E
24 1342  5F                   MOV   E,A
25 1343  3E   00              MVI   A,0
26 1345  9A                   SBB   D
27 1346  57                   MOV   D,A
28 1347  C9                   RET
29
30                       ;NEGATE H,L
31                       ;
32 1348  EB              NEGHL: XCHG
33 1349  CD   1340             CALL  NEGDE
34 134C  EB                   XCHG                ;ANOTHER TOUGHIE
35 134D  C9                   RET
36
37                       ;NEGATE C,D AND E TOGETHER
38                       ;
39 134E  CD   1340       NEGCDE: CALL NEGDE
40 1351  3E   00              MVI   A,0
41 1353  99                   SBB   C
42 1354  4F                   MOV   C,A
43 1355  C9                   RET
44
```

SPOX; MICROBENCH 8080/8085 CROSS ASSEMBLER (V2)-436  30-MAR-85 13:30:07 PAGE 70

```
 1
 2                       ;DISPLAY SERVICE ROUTINES....
 3                       ;
 4                       ;DISPLAY B,C AS "XXX" (ROUNDED) IF D = 0, OR
 5                       ;           AS "XX.X" IF D = 1 AND B,C < 99.9
 6                       ; E = FIELD CODE (0 = DSPFD1, 1 = DSPFD2)
 7                       ;CALLS XDSPCVT FOR INTEGER PART WITH B,C = DISPLAY POINTER, A=DATA AND
 8                       ; H,L = DECIMAL TABLE POINTER SET APPROPRIATLY.
 9
10 1356  21   9C01       DECDSP: LXI  H,-25599       ;-99.9
11 1359  09                   DAD   B              ;CHECK FOR OVERFLOW
12 135A  D2   135F             JNC   1$             ;OK
13 135D  16   00               MVI   D,0            ;NO DECIMAL FRACTION
14 135F  7A              1$:   MOV   A,D            ;CHECK FOR FRACTION
15 1360  B7                   ORA   A
16 1361  C2   136B             JNZ   2$             ;YUP
17 1364  21   0080             LXI   H,80H          ;ROUND TO INTEGER
18 1367  09                   DAD   B
19 1368  44                   MOV   B,H
20 1369  0E   00               MVI   C,0
21 136B  21   7120       2$:   LXI   H,DSPFD1+4     ;SET FIELD POINTER
22 136E  7B                   MOV   A,E
23 136F  B3                   ORA   E
24 1370  CA   1376             JZ    3$
25 1373  21   7126             LXI   H,DSPFD2+4
26 1376  59              3$:   MOV   E,C            ;SAVE FRACTIONAL DATA
27 1377  D5                   PUSH  D              ;ALONG WITH FLAG
28 1378  E5                   PUSH  H              ;SAVE DISPLAY POINTER
29 1379  21   13F6             LXI   H,DECTBL       ;DECIMAL CONVERT TABLE
30 137C  7A                   MOV   A,D
31 137D  B7                   ORA   A
32 137E  CA   1382             JZ    4$             ;DOING FRACTION, START WITH 10'S DIGIT
33 1381  23                   INX   H              ;GET INTEGER DATA TO A
34 1382  78              4$:   MOV   A,B            ;DISPLAY POINTER TO B,C
35 1383  C1                   POP   B              ;CONVERT INTEGER
36 1384  CD   13B4             CALL  XDSPCV
37 1387  D1                   POP   D              ;D = FRACTION FLAG, E = FRACTION
38 1388  7A                   MOV   A,D
39 1389  B7                   ORA   A
40 138A  CA   13A8             JZ    10$            ;NO FRACTION
41 138D  21   13EB             LXI   H,SEGTBL       ;POINT TO SEGMENT TABLE
42 1390  7B                   MOV   A,E            ;GET DATA
43 1391  1E   FF               MVI   E,-1
44 1393  23              5$:   INX   H              ;BUMP DIGIT POINTER
45 1394  1C                   INR   E
46 1395  D6   1A               SUI   26             ;0.1, ABOUT
47 1397  D2   1393             JNC   5$
48 139A  7E                   MOV   A,M            ;SEGMENT CODE
49 139B  02                   STAX  B              ;TO DISPLAY BUFFER
50 139C  21   0002             LXI   H,2
51 139F  09                   DAD   B              ;BACK UP TO PREVIOUS DIGIT
52 13A0  7E                   MOV   A,M
53 13A1  F6   80               ORI   80H            ;SET D.P.
54 13A3  77                   MOV   M,A
55 13A4  7B                   MOV   A,E
56 13A5  32   70BD             STA   FSATDP         ;SAVE DECIMAL FRACTION DIGIT
57 13A8  C9              10$:  RET
```

```
RESPOX; MICROBENCH 8080/8085 CROSS ASSEMBLER (V2)-436  30-MAR-85 13:30:07 PAGE 71

; CONVERT A INTO DECIMAL 7-SEGMENT CHARACTERS AND STORE IN DISPLAY BUFFER.
                        ; CALLED WITH B,C = DISPLAY BUFFER POINTER ('DSPFD1' OR 'DSPFD2').
                        ; USES E = L.Z. FLAG, B,C = DISPLAY POINTER, C = DIGIT COUNTER, D = REMAINDER
                        ;
  6 13A9  21     0004   DSPCVT: LXI   H,4
  7 13AC  09            DAD   B
  8 13AD  E5            PUSH  H                    ;MOVE POINTER TO M.S.DIGIT
  9 13AE  21     13F6   LXI   H,DECTBL             ;SAVE IT FOR THE DURATION
 10 13B1  C3     13B5   JMP   DSPCV2               ;SET POINTER TO DECIMAL FACTOR TABLE
 11 13B4  C5     XDSPCV: PUSH B
 12 13B5  1E  00 DSPCV2: MVI  E,0                  ;SAVE DISPLAY POINTER
 13 13B7  57            MOV   D,A                  ;RESET LEADING ZERO FLAG
 14 13B8  7A     1$:    MOV   A,D
 15 13B9  01  0000      LXI   B,0                  ;LOOP FOR NEXT DIGIT - GET REMAINING NUMBER
 16 13BC  96     3$:    SUB   M                    ;CLEAR DIGIT COUNTER
 17 13BD  DA  13C4      JC    4$                   ;SUBTRACT FACTOR
 18 13C0  0C            INR   C                    ;DIDN'T FIT
 19 13C1  C3  13BC      JMP   3$                   ;BUMP DIGIT
 20 13C4  86     4$:    ADD   M                    ;UNTIL IT UNDERFLOWS
 21 13C5  57            MOV   D,A                  ;RESTORE LAST SUBTRACTION
 22 13C6  79            MOV   A,C                  ;SAVE REMAINDER
 23 13C7  B3            ORA   E                    ;DIGIT COUNT
 24 13C8  CA  13CD      JZ    6$                   ;CHECK FOR ZERO DIGIT AND LEADING ZERO FLAG=0
 25 13CB  1C            INR   E                    ;IS, OUTPUT A ZERO (= BLANK)
 26 13CC  0C     5$:    INR   C                    ;NOT ZERO, SET FLAG FOR TRAILING ZEROS
 27 13CD  E3     6$:    XTHL                       ;OFFSET DIGIT CODE BY 1 (LOOP HERE FOR LAST DIGIT)
 28 13CE  E5            PUSH  H                    ;TRADE FACTOR POINTER FOR BUFFER POINTER
 29 13CF  21  13EB      LXI   H,SEGTBL             ;SAVE BUFFER POINTER
 30 13D2  09            DAD   B                    ;POINTER TO 7-SEG CODE TABLE
 31 13D3  7E            MOV   A,M                  ;PLUS DIGIT COUNTER (OH, YOU CLEVER DEVIL!)
 32 13D4  E1            POP   H                    ;GET CODE
 33 13D5  77            MOV   M,A                  ;RESTORE FACTOR POINTER
 34 13D6  2B            DCX   H                    ;STORE DIGIT CODE
 35 13D7  2B            DCX   H                    ;BUMP IT
 36 13D8  E3            XTHL                       ;TWICE
 37 13D9  AF            XRA   A                    ;RESTORE FACTOR POINTER
 38 13DA  BE            CMP   M
 39 13DB  CA  13E9      JZ    10$                  ;CHECK FOR ZERO FACTOR
 40 13DE  23            INX   H                    ;IT WAS, MUST BE THE LAST TIME THROUGH
 41 13DF  BE            CMP   M                    ;POINT TO NEXT FACTOR
 42 13E0  C2  13B8      JNZ   1$                   ;IS THAT ZERO?
 43 13E3  06  00        MVI   B,0                  ;NO, LOOP NORMALLY
 44 13E5  4A            MOV   C,D                  ;SHORT-CIRCUIT THE LAST LOOP
 45 13E6  C3  13CC      JMP   5$                   ;REMAINDER BECOMES DIGIT
 46 13E9  C1     10$:   POP   B
 47 13EA  C9            RET                        ;DUMP BUFFER POINTER
                        ;
                        ;TABLE OF 7-SEGMENT CODES, STARTING WITH A BLANK FOR LEADING ZEROS (MORE CLEVERNESS!!!)
                        ;
 51 13EB  00  77 SEGTBL: DB   0, SEG0, SEG1, SEG2, SEG3, SEG4, SEG5, SEG6, SEG7, SEG8, SEG9
    13ED  24  5D
    13EF  6D  2E
    13F1  6B  7B
    13F3  25  7F
    13F5  2F

RESPOX; MICROBENCH 8080/8085 CROSS ASSEMBLER (V2)-436  30-MAR-85 13:30:07 PAGE 72

1 13F6  64  0A  DECTBL: DB  100, 10, 0   ;IT SURE IS A BIG ROUTINE FOR A TWO-ENTRY TABLE!!!!
    13F8  00

;
                        ; CHECK IF SWITCH IS SET FOR SILENT RUNNING. IF SO, DISABLE ALL
                        ; ALARMS AND DISPLAYS, EXCEPT FOR BLIP. ALSO DISABLE BUTTONS AND
                        ; KNOB. OUTPUT SAT AND RATE UNFILTERED
                        ;
  9 13F9  DB  00  BLKOUT: IN    STSREG          ;GET STATUS
 10 13FB  E6  06         ANI   6               ;MASK FOR SWITCH SETTING
 11 13FD  CA  1419       JZ    3$              ;SILENT RUNNING
 12 1400  3A  712F       LDA   DSPOK
 13 1403  B7             ORA   A               ;IF ZERO, WE'VE ALREADY DONE THIS STUFF
 14 1404  C8             RZ
 15 1405  AF             XRA   A               ;NOT ZERO, RESTORE FMODE AND CLEAR FLAG
 16 1406  32  712F       STA   DSPOK
 17 1409  3A  7130       LDA   MODESV          ;GET PRIOR FMODE
 18 140C  32  7170       STA   FMODE           ;RESTORE IT
 19 140F  21  70F4       LXI   H,ALIPER
 20 1412  CD  16C7       CALL  ALICHK          ;CHECK FOR DELAYED ALARMS THAT WERE QUASHED
 21 1415  CD  0ABF       CALL  DSPSR           ;RESTORE DISPLAY
 22 1418  C9             RET
 23 1419  3A  712F  3$:  LDA   DSPOK           ;FORGET ALL THIS IF WE ALREADY DID IT
 24 141C  B7             ORA   A
 25 141D  C2  1451       JNZ   7$
 26 1420  3E  01         MVI   A,1             ;BLANK ALL THE ALARM, STATUS LIGHTS
 27 1422  4F       4$:   MOV   C,A
 28 1423  F5             PUSH  PSW
```

```
29 1424   CD    1475           CALL   CLRLIT
30 1427   F1                   POP    PSW
31 1428   17                   RAL
32 1429   D2    1422           JNC    4$
33 142C   01    711C    5$:    LXI    B,DSPFD1        ;BLANK THE DISPLAYS
34 142F   CD    1452           CALL   DSPBLK
35 1432   01    7122           LXI    B,DSPFD2
36 1435   CD    1452           CALL   DSPBLK
37 1438   01    0000           LXI    B,0             ;SHUT THE BEEPER UP
38 143B   1E    00             MVI    E,0
39 143D   CD    148E           CALL   BEEP
40 1440   21    7170           LXI    H,FMODE         ;SAVE OLD FMODE
41 1443   7E                   MOV    A,M
42 1444   32    7130           STA    MODESV
43 1447   3E    06             MVI    A,6             ;UNFILTER SAT AND RATE
44 1449   32    7170           STA    FMODE           ;DISABLE FURTHER DISPLAY STUFF
45 144C   3E    01             MVI    A,1
46 144E   32    712F           STA    DSPOK
47 1451   C9            7$:    RET
```

RESPOX: MICROBENCH 8080/8085 CROSS ASSEMBLER (V2)-436    30-MAR-85 13:30:07 PAGE 73

```
                        ;BLANK A DISPLAY FIELD...
                        ; CALLED WITH B,C = POINTER TO FIELD
                        ;
 5 1452   1E    03     DSPBLK: MVI    E,3
 6 1454   AF            1$:    XRA    A               ;STORE A ZERO
 7 1455   02                   STAX   B
 8 1456   03                   INX    B
 9 1457   03                   INX    B
10 1458   1D                   DCR    E
11 1459   C2    1454           JNZ    1$
12 145C   C9                   RET

;BLINK A DISPLAY FIELD...CALLED WITH C = FIELD MASK
                        ;
16 145D   21    7118   DSPBNK: LXI    H,DIGBNK
17 1460   79                   MOV    A,C
18 1461   B6                   ORA    M
19 1462   77                   MOV    M,A
20 1463   C9                   RET

;UN-BLINK A FIELD...CALLED WITH C = MASK
                        ;
24 1464   21    7118   DSPUBK: LXI    H,DIGBNK
25 1467   79                   MOV    A,C
26 1468   2F                   CMA
27 1469   A6                   ANA    M
28 146A   77                   MOV    M,A
29 146B   C9                   RET

;SET/CLEAR ANNUNCIATOR LIGHTS...REG C = LITE BIT
                        ;
33 146C   21    712C   SETLIT: LXI    H,DSPLMP        ;FIRST LED BYTE
34 146F   7E                   MOV    A,M
35 1470   B1                   ORA    C
36 1471   77                   MOV    M,A
37 1472   C3    147C           JMP    CLRLT2          ;CLEAR BLINK BITS

;CLEAR LIGHT AND BLINK BITS...
                        ;
41 1475   21    712C   CLRLIT: LXI    H,DSPLMP
42 1478   79                   MOV    A,C
43 1479   2F                   CMA
44 147A   A6                   ANA    M
45 147B   77                   MOV    M,A
46 147C   79    CLRLT2: MOV    A,C
47 147D   2F                   CMA
48 147E   21    7119           LXI    H,INDBNK
49 1481   A6                   ANA    M               ;CLEAR IT
50 1482   77                   MOV    M,A
51 1483   C9                   RET

;SET LITE BLINKING ONCE PER SECOND...
                        ;
                       FSTLIT:                        ;DISABLED FOR NOW
55 1484                BNKLIT: CALL   SETLIT          ;TURN IT ON...
56 1484   CD    146C           CALL   SETLIT
57 1487   21    7119           LXI    H,INDBNK        ;POINT TO BLINK FLAGS
```

RESPOX: MICROBENCH 8080/8085 CROSS ASSEMBLER (V2)-436    30-MAR-85 13:30:07 PAGE 74

```
1 148A   79                    MOV    A,C
2 148B   B6                    ORA    M               ;SET BLINK BIT
3 148C   77                    MOV    M,A
4 148D   C9                    RET
```

```
RESPOX: MICROBENCH 8080/8085 CROSS ASSEMBLER (V2)-436   30-MAR-85 13:30:07 PAGE 75

1          ;MAKE A BEEP....CALLED WITH B = DURATION (1/60'S SEC, MINUS FOR CONTINUOUS) AND
  2          ;  C = PITCH (0 TO 100 LOW TO HIGH), E = VOLUME...
  3          ;  (FOR NEGATIVE DURATION, SET NO TONE FOR THAT DURATION AND THEN START TONE CONTINUOUSLY)
  4          ;
  5
  6  148E  78            BEEP:   MOV    A,B
  7  148F  B7                    ORA    A              ;CHECK FOR MINUS DURATION
  8  1490  F2    1495            JP     1$
  9  1493  2F                    CMA                   ;MAKE IT PLUS
 10  1494  3C                    INR    A
 11  1495  32    70EA    1$:     STA    BEECNT         ;BEEP COUNTER
 12  1498  16    08              MVI    D,08H          ;CHASE BIT TO SHIFT VOLUME UP 5 BITS
 13  149A  AF                    XRA    A
 14  149B  7B            2$:     MOV    A,E
 15  149C  17                    RAL
 16  149D  5F                    MOV    E,A
 17  149E  7A                    MOV    A,D
 18  149F  17                    RAL
 19  14A0  57                    MOV    D,A
 20  14A1  D2    149B            JNC    2$
 21  14A4  21    0190            LXI    H,400          ;1 VOLT OFFSET
 22  14A7  19                    DAD    D
 23  14A8  11    0000            LXI    D,0            ;POST-BEEP VOLTAGE (= OFF)
 24  14AB  78                    MOV    A,B            ;GET DURATION AGAIN
 25  14AC  B7                    ORA    A
 26  14AD  F2    14B1            JP     4$             ;PLUS, BEEP FIRST THEN QUIET
 27  14B0  EB                    XCHG                  ;VICE-VERSA FOR MINUS
 28  14B1  22    7165    4$:     SHLD   VVOL           ;VOLUME VOLTAGE
 29  14B4  EB                    XCHG
 30  14B5  22    7167            SHLD   VVOLSV         ;SAVE THE POST-BEEP VOLTAGE
 31  14B8  1E    04              MVI    E,4
 32  14BA  AF                    XRA    A
 33  14BB  47                    MOV    B,A
 34  14BC  79            3$:     MOV    A,C            ;SHIFT PITCH CODE UP SIMILARY
 35  14BD  17                    RAL
 36  14BE  4F                    MOV    C,A
 37  14BF  78                    MOV    A,B
 38  14C0  17                    RAL
 39  14C1  47                    MOV    B,A
 40  14C2  1D                    DCR    E
 41  14C3  C2    14BC            JNZ    3$
 42  14C6  21    04B0            LXI    H,1200
 43  14C9  09                    DAD    D
 44  14CA  22    7163            SHLD   VBEEP          ;STORE PITCH VOLTAGE (2-9V)
 45  14CD  C9                    RET

RESPOX: MICROBENCH 8080/8085 CROSS ASSEMBLER (V2)-436   30-MAR-85 13:30:07 PAGE 76

1          ;BUTTON SERVICE ROUTINE....
  2          ;  WHEN A BUTTON (OR COMBINATION) IS PRESSED IT GETS LOOKED UP IN THE FIRST HALF
  3          ;  OF THE BUTTON TABLE, BUTTBL, WHICH SPECIFIES THAT A PARAMETER IS TO BE
  4          ;  'OPENED' OR A DISPATCH JUMP TAKEN (VIA A 'CALL'). AN OPEN PARAMETER
  5          ;  IS DISPLAYED AND CAN BE INCREMENTED OR DECREMENTED BY SUBSEQUENCE KNOB STROBES.
  6          ;  THE PARAMETER REMAINS OPEN AS LONG AS THE BUTTON IS HELD, AND, OPTIONALLY FOR
  7          ;  A TWO-SECOND PERIOD FOLLOWING RELEASE.
  8          ;
  9
 10  14CE  3A    712F    BUTTON: LDA    DSPOK          ;IF SILENT MODE, NO BUTTON
 11  14D1  B7                    ORA    A
 12  14D2  C0                    RNZ
 13  14D3  21    7135            LXI    H,BUTFLG       ;POINT TO BUTTON FLAG
 14  14D6  7E                    MOV    A,M
 15  14D7  3D                    DCR    A              ;DECREMENT IT
 16  14D8  F8                    RM                    ;WAS ZERO
 17  14D9  77                    MOV    M,A            ;UPDATE COUNT
 18  14DA  2B                    DCX    H              ;POINT TO NEW BUTTON CODE
 19  14DB  7E                    MOV    A,M            ;CHECK BUTTON-UP'S FIRST ... GET NEW CODE
 20  14DC  32    7137            STA    NEWBUT         ;SAVE IT TO AVOID A RACE
 21  14DF  5F                    MOV    E,A            ;SAVE IN 'E' FOR 3$
 22  14E0  2F                    CMA                   ;1 = BUTTON UP
 23  14E1  57                    MOV    D,A
 24  14E2  3A    7136            LDA    OLDBUT         ;1 = BUTTON USED TO BE DOWN
 25  14E5  A2                    ANA    D              ;1 = UP NOW, WAS DOWN..
 26  14E6  CA    14F5            JZ     2$             ;NONE...GO CHECK NEW BUTTON-DOWNS
 27  14E9  0E    30              MVI    C,30H          ;BIT MASK FOR BUTTON FLAGS
 28  14EB  3A    7136            LDA    OLDBUT         ;USE OLD BUTTON CODE
 29  14EE  C3    1501            JMP    3$
 30  14F1  3A    7137    1$:     LDA    NEWBUT         ;GET NEW BUTTON CODE
 31  14F4  5F                    MOV    E,A
 32  14F5  0E    C0      2$:     MVI    C,0C0H         ;MASK BITS FOR BUTTON-DOWN
 33  14F7  3A    7136            LDA    OLDBUT         ;GET OLD ONE
 34  14FA  2F                    CMA                   ;1 = BIT NOT PREVIOUSLY SET
 35  14FB  A3                    ANA    E              ;COMPARE W/NEW BUTTON CODE
 36  14FC  7B                    MOV    A,E            ;UPDATE OLD CODE
 37  14FD  32    7136            STA    OLDBUT
 38  1500  C8                    RZ                    ;NO NEW BUTTON-DOWN, RETURN
 39  1501  5F            3$:     MOV    E,A            ;BUTTON CODE
```

```
40 1502  16    00            MVI   D,0
41 1504  21    175A          LXI   H,BUTTBL    ;GENERATE POINTER TO BUTTON TABLE
42 1507  19                  DAD   D
43 1508  7E                  MOV   A,M         ;GET CODE (INDEX INTO PRMTBL)
44 1509  B7                  ORA   A
45 150A  CA    14F1          JZ    1$          ;IGNORE THIS ONE
46 150D  17                  RAL               ;*3 BYTES/ENTRY
47 150E  86                  ADD   M
48 150F  5F                  MOV   E,A
49 1510  21    177A          LXI   H,PRMTBL
50 1513  19                  DAD   D           ;POINT INTO PARAM. TABLE
51 1514  E5                  PUSH  H
52 1515  79                  MOV   A,C         ;SAVE MASK
53 1516  23                  INX   H           ;GET ADDRESS
54 1517  5E                  MOV   E,M
55 1518  23                  INX   H
56 1519  56                  MOV   D,M
57 151A  23                  INX   H           ;GET LIMITS
```

RESPOX: MICROBENCH 8080/8085 CROSS ASSEMBLER (V2)-436  30-MAR-85 13:30:07 PAGE 77

```
 1 151B  EB                  XCHG              ;POINTER TO H,L TO GET LIMITS
 2 151C  2B                  DCX   H
 3 151D  4E                  MOV   C,M         ;GET LOWER LIMIT (PRECEEDING BYTE)
 4 151E  23                  INX   H
 5 151F  23                  INX   H
 6 1520  46                  MOV   B,M         ;GET UPPER LIMIT (FOLLOWING BYTE)
 7 1521  2B                  DCX   H
 8 1522  EB                  XCHG
 9 1523  E1                  POP   H           ;POINT BACK TO FLAGS
10 1524  A6                  ANA   M           ;GET FLAGS, MASKED BY A
11 1525  07                  RLC
12 1526  DA    1538          JC    7$          ;BIT 7 = DISPATCH
13 1529  07                  RLC
14 152A  DA    1540          JC    6$          ;BIT 6
15 152D  07                  RLC
16 152E  DA    1545          JC    5$
17 1531  07                  RLC
18 1532  DA    154C          JC    4$
19 1535  C3    14F1          JMP   1$          ;NOTHING TO DO...
20 1538  EB           7$:    XCHG              ;DISPATCH ADDR TO H,L
21 1539  1A                  LDAX  D           ;GET FLAGS IN A
22 153A  11    153F          LXI   D,10$       ;RETURN ADDR
23 153D  D5                  PUSH  D           ;ONTO STACK
24 153E  E9                  PCHL              ;CALL...
25 153F  C9           10$:   RET
26 1540  7E           6$:    MOV   A,M         ;GET FLAGS
27 1541  CD    1552          CALL  BUTOPN      ;OPEN A PARAM...
28 1544  C9                  RET
29 1545  7E           5$:    MOV   A,M         ;GET FLAGS
30 1546  CD    15B7          CALL  BUTCLS      ;REGULAR CLOSE
31 1549  C3    14F1          JMP   1$          ;CHECK FOR OPEN
32 154C  CD    15E0   4$:    CALL  BUTCTO      ;CLOSE AFTER TIME-OUT
33 154F  C3    14F1          JMP   1$
```

RESPOX: MICROBENCH 8080/8085 CROSS ASSEMBLER (V2)-436  30-MAR-85 13:30:07 PAGE 78

```
 1
 2                           ;OPEN AND CLOSE ROUTINES....
 3                           ; A = FLAGS, B = UPPER LIMIT, C = LOWER LIMIT, D,E = PARAMETER ADDRESS
 4
 5 1552  21    7138   BUTOPN: LXI  H,OPNPRM
 6 1555  73                  MOV   M,E         ;STORE POINTER TO OPEN PARAMETER
 7 1556  23                  INX   H
 8 1557  72                  MOV   M,D
 9 1558  23                  INX   H
10 1559  23                  INX   H
11 155A  71                  MOV   M,C         ;LOWER LIMIT
12 155B  23                  INX   H
13 155C  70                  MOV   M,B         ;UPPER LIMIT
14 155D  23                  INX   H
15 155E  36    00            MVI   M,0         ;RESET TIMER
16 1560  1F                  RAR               ;CHECK ALARM INHIBIT FLAG
17 1561  D2    158C          JNC   3$          ;NOT SET
18 1564  F5                  PUSH  PSW
19 1565  21    70F1          LXI   H,ALIFLG    ;POINT TO FLAG
20 1568  7E                  MOV   A,M
21 1569  B7                  ORA   A           ;SET ALREADY?
22 156A  C2    1581          JNZ   1$          ;YES, RESET IT (TURN OFF INHIBIT)
23 156D  34                  INR   M           ;NO, SET IT
24 156E  01    0000          LXI   B,0
25 1571  1E    00            MVI   E,0
26 1573  CD    148E          CALL  BEEP        ;SHUT UP BEEPER
27 1576  3A    727C          LDA   COSTA       ;CLEAR AUDIO ENABLED BIT    ///
28 1579  E6    FB            ANI   NOT AUDENB  ;                           ///
29 157B  32    727C          STA   COSTA       ;                           ///
30 157E  C3    158B          JMP   2$
31 1581  36    00     1$:    MVI   M,0         ;CLEAR TIMER
32 1583  3A    727C          LDA   COSTA       ;SET AUDIO ALARM ENABLED BIT ///
```

```
33 1586   F6   04              ORI    AUDENB
34 1588   32   727C            STA    COSTA
35 158B   F1              2$:  POP    PSW
36 158C   1F              3$:  RAR
37 158D   D2   15A2            JNC    5$              ;CHECK SOUND-ALARM BIT
38                                                    ;NOPE
39                        ;SOUND ALARM (TO SET VOLUME, ETC.)
40                        ;
41 1590   F5              PUSH   PSW
42 1591   0E   6E              MVI    C,ALMPCH
43 1593   06   FF              MVI    B,255
44 1595   3A   70EF            LDA    ALMVOL
45 1598   5F              MOV    E,A
46 1599   CD   148E            CALL   BEEP
47 159C   3E   01              MVI    A,1
48 159E   32   70F7            STA    ALCFLG          ;SET ALARM-CHECKING FLAG
49 15A1   F1              POP    PSW
50 15A2   1F              5$:  RAR                    ;CHECK DISPLAY BIT
51 15A3   DA   15B6            JC     7$              ;SET, INHIBIT DISPLAY
```

RESPOX: MICROBENCH 8080/8085 CROSS ASSEMBLER (V2)-436   30-MAR-85 13:30:07 PAGE 79

```
                          ;DISPLAY PARAMETER...
                          ;
 4 15A6   1F                   RAR
 5 15A7   3E   01              MVI    A,1             ;SET FIELD BIT TO CARRY
 6 15A9   32   713A            STA    OPNFLG          ;SET OPEN FLAG
 7 15AC   D2   15B0            JNC    6$              ;CHECK ALTERNATE (LOWER) FIELD BIT
 8 15AF   3C                   INR    A
 9 15B0   32   7142       6$:  STA    PRMFLD          ;SAVE FLAG (1=FIELD1, 2=FIELD2)
10 15B3   CD   161E            CALL   DSPOPN          ;DISPLAY OPEN PARAM
11 15B6   C9              7$:  RET
12
13                        ;CLOSE OPEN PARAMETER...
14                        ;
15 15B7   E6   02         BUTCLS: ANI  2              ;CHECK BEEPER FLAG
16 15B9   CA   15C3            JZ     2$              ;NOT SET
17 15BC   06   00              MVI    B,0             ;RESET BEEPER
18 15BE   1E   00              MVI    E,0
19 15C0   CD   148E            CALL   BEEP
20 15C3   AF              2$:  XRA    A
21 15C4   32   713A            STA    OPNFLG
22 15C7   32   713D            STA    OPNTMR          ;RESET OPEN PARAMETER FLAG AND TIMER
23 15CA   32   7141            STA    IFLG            ;RESET INDIRECT FLAG
24 15CD   32   70F7            STA    ALCFLG          ;AND ALARM-CHECKING FLAG
25 15D0   21   70EC            LXI    H,BEEVOL        ;SET UP VOLUME FOR DEFAULT CHANGES
26 15D3   22   7138            SHLD   OPNPRM
27 15D6   21   6400            LXI    H,6400H         ;LIMITS
28 15D9   22   713B            SHLD   OPNLL
29 15DC   CD   0A8F            CALL   DSPSR           ;RESTORE DISPLAY
30 15DF   C9                   RET
31
32                        ;SET TIMER TO CLOSE IN 3 SECONDS...IF NO ACTIVITY...
33                        ;
34 15E0   3A   713E       BUTCTO: LDA  OPNDLY         ;NOMINAL DELAY
35 15E3   32   713D            STA    OPNTMR
36 15E6   C9                   RET
37
38                        ;RE-DISPLAY OPEN PARAMETER, CALLED BY MONITOR TO KEEP DISPLAY UP TO DATE.
39                        ;
40 15E7   3A   712F       RFSHOP: LDA  DSPOK          ;DON'T DO THIS IF IN SILENT MODE
41 15EA   B7                   ORA    A
42 15EB   C0                   RNZ
43 15EC   CD   161E            CALL   DSPOPN          ;DISPLAY OPEN PARAM'S...
44 15EF   3A   70F7            LDA    ALCFLG          ;CHECK FOR ALARM-CHECKING
45 15F2   B7                   ORA    A
46 15F3   C8                   RZ                     ;NOPE
47 15F4   0E   6E              MVI    C,ALMPCH        ;RE-START ALARM
48 15F6   06   64              MVI    B,100           ;AN ARBITRARY POSITIVE COUNT
49 15F8   3A   70EF            LDA    ALMVOL
50 15FB   5F                   MOV    E,A
51 15FC   CD   148E            CALL   BEEP
52 15FF   C9                   RET
```

RESPOX: MICROBENCH 8080/8085 CROSS ASSEMBLER (V2)-436   30-MAR-85 13:30:07 PAGE 80

```
                          ;SPECIAL ROUTINE (CALLED VIA DISPATCH) TO OPEN A CELL INDIRECTLY...
                          ;  ASSUMES 'ICELL' HAS BEEN SET, AND SHOWS IT IN THE LOWER FIELD
                          ;  AND OPENS RAMORG+(ICELL).
                          ;
 6 1600   DB   00         INDRCT: IN   STSREG
 7 1602   E6   01              ANI    DIDJPR
 8 1604   C0                   RNZ                    ;CHECK FOR JUMPER FIRST...
 9 1605   3E   02              MVI    A,2             ;SET IFLG = 2 FOR CHANGING CONTENTS
10 1607   32   7141            STA    IFLG
11 160A   C3   1612            JMP    ILOOK2          ;OPEN CELL, DISPLAY CONTENTS
12
13                        ;DISPATCH ROUTINE TO OPEN INDIRECT ADDRESS, AND CAUSE CONTENTS TO BE DISPLAYED.
14                        ;
15 160D   3E   01         ILOOK: MVI   A,1            ;SET INDIRECT FLAG =1 (CHANGING ADDRESS)
```

```
16 160F    32   7141            STA    IFLG
17 1612    11   713F   ILOOK2:  LXI    D,ICELL
18 1615    01   FF00            LXI    B,0FF00H        ;NO LIMITS
19 1618    3E   00              MVI    A,0
20 161A    CD   1552            CALL   BUTOPN          ;OPEN AND DISPLAY ADDRESS & CONTENTS
21 161D    C9                   RET
22                       ;
23                       ;OPEN CELL DISPLAY....DISPLAY (OPNPRM) IN FIELD 1 (TOP), AND IF IFLG NONZERO TH!
24                       ; DISPLAY ((OPNPRM)) ON LOWER DISPLAY.
25                       ;
26 161E    3A   713A   DSPOPN:  LDA    OPNFLG
27 1621    B7                   ORA    A
28 1622    CA   1679            JZ     4$              ;IF NOT OPEN, REBLINK DISPLAYS, IF APPROPRIATE
29 1625    0E   3F              MVI    C,FD1MSK+FD2MSK
30 1627    CD   1464            CALL   DSPUBK          ;TURN OFF BLINKING
31 162A    01   711C            LXI    B,DSPFD1
32 162D    3A   7142            LDA    PRMFLD
33 1630    3D                   DCR    A               ;CHECK FOR FIELD 1/2
34 1631    CA   1637            JZ     1$
35 1634    01   7122            LXI    B,DSPFD2
36 1637    2A   7138    1$:     LHLD   OPNPRM
37 163A    C5                   PUSH   B
38 163B    CD   16C7            CALL   ALICHK          ;CHECK FOR ALARM PERIOD OPEN
39 163E    C1                   POP    B
40 163F    DA   164D            JC     5$              ;IS NOT (PERIOD RETURNED IN A)
41 1642    FE   79              CPI    121             ;CHECK FOR >120
42 1644    C2   164D            JNZ    5$
43 1647    CD   16BB            CALL   OFFDSP
44 164A    C3   1668            JMP    2$
45 164D    7E           5$:     MOV    A,M
46 164E    E5                   PUSH   H
47 164F    CD   13A9            CALL   DSPCVT          ;DISPLAY AS FIELD 1
48 1652    E1                   POP    H
49 1653    3A   7141            LDA    IFLG
50 1656    B7                   ORA    A
51 1657    CA   1668            JZ     2$              ;NOT INDIRECT
52 165A    11   7000            LXI    D,RAMORG        ;LOOK UP (RAMORG+(OPNPRM))
53 165D    5E                   MOV    E,M             ;CONTENTS OF OPEN PARAM (NOMINALLY CONTENTS OF
54 165E    1A                   LDAX   D               ;GET IT
55 165F    01   7122            LXI    B,DSPFD2
56 1662    CD   13A9            CALL   DSPCVT
57 1665    C3   1678            JMP    10$

RESPOX: MICROBENCH 8080/8085 CROSS ASSEMBLER (V2)-436   30-MAR-85 13:30:07 PAGE 81

1 1668    01   7122    2$:     LXI    B,DSPFD2
 2 166B    3A   7142            LDA    PRMFLD
 3 166E    3D                   DCR    A
 4 166F    CA   1675            JZ     3$
 5 1672    01   711C            LXI    B,DSPFD1
 6 1675    CD   1452    3$:     CALL   DSPBLK
 7 1678    C9           10$:    RET
 8 1679    3A   70C9    4$:     LDA    ALMFLG          ;SEE IF ALARM BITS ARE SET
 9 167C    B7                   ORA    A
10 167D    C8                   RZ
11 167E    1F                   RAR                    ;TEST SAT ALARM BIT
12 167F    D2   1689            JNC    6$
13 1682    F5                   PUSH   PSW             ;SAVE THE FLAG
14 1683    0E   07              MVI    C,FD1MSK        ;REBLINK IT
15 1685    CD   145D            CALL   DSPBNK
16 1688    F1                   POP    PSW
17 1689    1F           6$:     RAR                    ;TEST HR BIT
18 168A    D2   16A7            JNC    8$              ;REBLANK HR DISPLAY IF IN MODE 3
19 168D    3A   7170            LDA    FMODE
20 1690    FE   05              CPI    5
21 1692    CA   16A7            JZ     8$              ;DON'T BLINK/BLANK IF IN MODE 5
22 1695    FE   03              CPI    3
23 1697    C2   16A1            JNZ    7$
24 169A    01   7122            LXI    B,DSPFD2        ;BLANK IT
25 169D    CD   1452            CALL   DSPBLK
26 16A0    C9                   RET
27 16A1    0E   38      7$:     MVI    C,FD2MSK
28 16A3    CD   145D            CALL   DSPBNK
29 16A6    C9                   RET
30 16A7    3A   70C9    8$:     LDA    ALMFLG          ;GET IT BACK
31 16AA    1F                   RAR
32 16AB    1F                   RAR                    ;AND GET THE RESP ALARM BIT
33 16AC    1F                   RAR
34 16AD    1F                   RAR                    ;TEST FOR RESP ALARM BIT
35 16AE    D0                   RNC
36 16AF    3A   7170            LDA    FMODE
37 16B2    FE   05              CPI    5
38 16B4    C0                   RNZ                    ;ONLY REBLINK IF MODE 5
39 16B5    0E   38              MVI    C,FD2MSK
40 16B7    CD   145D            CALL   DSPBNK
41 16BA    C9                   RET
42                       ;
43                       ;DISPLAY "OFF" IN THE FIELD POINTED TO BY H,L
44                       ;
45 16BB    3E   1B      OFFDSP: MVI    A,SEGF
```

```
46 16BD  02              STAX  D
47 16BE  03              INX   B
48 16BF  03              INX   B
49 16C0  02              STAX  B
50 16C1  03              INX   B
51 16C2  03              INX   B
52 16C3  3E  77          MVI   A,SEGO
53 16C5  02              STAX  B
54 16C6  C9              RET
55
56                       ;
57                       ;CHECK ALARM INHIBIT ACTION...TRY TO KEEP LIGHTS UP WITH KNOB...
```

RESPOX; MICROBENCH 8080/8085 CROSS ASSEMBLER (V2)-436  30-MAR-85 13:30:07 PAGE 82

```
 1 16C7  EB              ALICHK: XCHG                  ;MOVE OPNPRM TO D,E
 2 16C8  21  8F0C                LXI   H,-ALIPER
 3 16CB  19                      DAD   D
 4 16CC  EB                      XCHG
 5 16CD  7A                      MOV   A,D
 6 16CE  B3                      ORA   E
 7 16CF  37                      STC
 8 16D0  C0                      RNZ                   ;NOT LOOKING AT PERIOD
 9 16D1  E5                      PUSH  H               ;SAVE POINTER
10 16D2  0E  01                  MVI   C,ALICOD        ;TO SET LIGHT
11 16D4  3A  70F1                LDA   ALIFLG          ;CHECK FOR ALARM OFF
12 16D7  B7                      ORA   A
13 16D8  CA  16F4                JZ    10$             ;NOT OFF, PERIOD DOESN'T MATTER
14 16DB  7E                      MOV   A,M             ;GET PERIOD
15 16DC  FE  79                  CPI   121
16 16DE  CA  16EE                JZ    5$              ;PERIOD IS 121, PERMANENTLY OFF.
17 16E1  32  70F2                STA   ALICTR          ;SET TIMER TO PERIOD
18 16E4  AF                      XRA   A
19 16E5  32  70F6                STA   ALMDLY          ;CLEAR ANY PENDING DELAYED ALARMS
20 16E8  CD  146C                CALL  SETLIT          ;TURN LIGHT ON STEADILY
21 16EB  C3  16FB                JMP   12$
22 16EE  CD  1484        5$:     CALL  BNKLIT          ;OFF FOREVER, BLINK THE LIGHT
23 16F1  C3  16F7                JMP   11$
24 16F4  CD  1475        10$:    CALL  CLRLIT          ;NOT OFF, TURN OFF THE LIGHT
25 16F7  AF              11$:    XRA   A
26 16F8  32  70F2                STA   ALICTR          ;CLEAR TIMER
27 16FB  E1              12$:    POP   H
28 16FC  7E                      MOV   A,M             ;GET PERIOD AGAIN
29 16FD  B7                      ORA   A               ;CLEAR CARRY
30 16FE  C9                      RET
```

RESPOX; MICROBENCH 8080/8085 CROSS ASSEMBLER (V2)-436  30-MAR-85 13:30:07 PAGE 83

```
 1
 2                       ; CHECK FOR KNOB ACTION....
 3                       ;
 4 16FF  3A  712F        KNOB:   LDA   DSPOK           ;NO KNOB IN SILENT MODE
 5 1702  B7                      ORA   A
 6 1703  C0                      RNZ
 7 1704  11  7132                LXI   D,KNBCTR        ;POINT TO KNOB COUNT
 8 1707  1A                      LDAX  D               ;GET IT
 9 1708  B7                      ORA   A               ;CHECK FOR ZERO
10 1709  C8                      RZ
11 170A  F5                      PUSH  PSW
12 170B  2A  7138                LHLD  OPNPRM          ;POINT TO PARAM
13 170E  3A  7141                LDA   IFLG
14 1711  FE  02                  CPI   2               ;CHECK FOR INDIRECT DIDDLE-CONTENTS MODE
15 1713  C2  171B                JNZ   1$              ;IS NOT
16 1716  7E                      MOV   A,M             ;GET CONTENTS
17 1717  21  7000                LXI   H,RAMORG
18 171A  6F                      MOV   L,A
19 171B  F1              1$:     POP   PSW
20 171C  B7                      ORA   A
21 171D  FA  1739                JM    3$              ;DOWN COUNT
22 1720  3D                      DCR   A               ;DECREMENT COUNT
23 1721  12                      STAX  D
24 1722  3A  713C                LDA   OPNUL           ;GET UPPER LIMIT
25 1725  BE                      CMP   M
26 1726  CA  1736                JZ    2$              ;AT LIMIT
27 1729  34                      INR   M
28 172A  BE                      CMP   M               ;MAKE SURE THE ALARM IS DISABLED IF WE
29 172B  C2  1736                JNZ   2$              ;HAVE JUST SET ALM DELAY TO OFF
30 172E  FE  79                  CPI   121             ;CHANGING ALM?
31 1730  C2  1736                JNZ   2$
32 1733  32  70F1                STA   ALIFLG          ;LIGHT THE LED AND DISABLE ALM
33 1736  C3  1743        2$:     JMP   5$              ;GO DISPLAY
34 1739  3C              3$:     INR   A               ;DECREMENT COUNT
35 173A  12                      STAX  D
36 173B  3A  713B                LDA   OPNLL           ;LOWER LIMIT
37 173E  BE                      CMP   M
38 173F  CA  1743                JZ    4$              ;AT LIMIT
39 1742  35                      DCR   M               ;DECREMENT PARAM
40 1743                  4$:
41 1743  3A  713A        5$:     LDA   OPNFLG          ;EXIT HERE IF WE ARE TWEAKING VOLUME BY DEFAULT
42 1746  B7                      ORA   A
```

```
43 1747   CA    1759         JZ    6$
44 174A   CD    161E         CALL  DSPOPN       ;RE-DISPLAY PARAMETER
45 174B   21    713D         LXI   H,OPNTMR     ;RESET TIMER IF RUNNING
46 1750   7E                 MOV   A,M
47 1751   B7                 ORA   A
48 1752   CA    1759         JZ    6$
49 1755   3A    713E         LDA   OPNDLY
50 1758   77                 MOV   M,A
51 1759              6$:
52 1759   C9         10$:    RET
```

RESPOX: MICROBENCH 8080/8085 CROSS ASSEMBLER (V2)-436  30-MAR-85 13:30:07 PAGE 84

```
                        ;BUTTON TABLES...
                        ; THE FIRST IS A TRANSLATION TABLE FROM HARDWARE BUTTON CODES (0-31)
                        ; TO TOKENS THAT INDEX THE PARAMETER TABLE...
                        ; THE PARAMETER TABLE IS 5 BYTES PER ACTIVE BUTTON CODE:
                        ;   BYTE 0 = FLAGS....  BIT 7 = DISPATCH CALL ON BUTTON DOWN
                        ;                       BIT 6 = OPEN PARAM ON BUTTON DOWN
                        ;                       BIT 5 = CLOSE PARAM ON BUTTON UP (NO TIME-OUT)
                        ;                       BIT 4 = CLOSE PARAM AFTER TIME-OUT
                        ;                       BIT 3 = ALTERNATE FIELD DISPLAY (FIELD 2)
                        ;                       BIT 2 = INHIBIT PARAMETER DISPLAY
                        ;                       BIT 1 = SOUND ALARM
                        ;                       BIT 0 = INHIBIT ALARM
                        ;   BYTE 1,2 = PARAMETER/DISPATCH ADDRESS
                        ;     LOWER/UPPER LIMITS ARE THE BYTES PRECEEDING AND FOLLOWING A PARAMTER BYTE
17 175A   00     BUTTBL: DB    0       ;0
18 175B   04             DB    4       ;1   BOTTOM BUTTON
19 175C   03             DB    3       ;2
20 175D   0A             DB    10      ;3
21 175E   02             DB    2       ;4
22 175F   08             DB    8       ;5
23 1760   09             DB    9       ;6
24 1761   00             DB    0       ;7
25 1762   01             DB    1       ;8
26 1763   07             DB    7       ;9
27 1764   0B             DB    11      ;10
28 1765   00             DB    0       ;11
29 1766   06             DB    6       ;12
30 1767   00             DB    0       ;13
31 1768   00             DB    0       ;14
32 1769   00             DB    0       ;15
33 176A   05             DB    5       ;16
34 176B   00             DB    0       ;17
35 176C   00             DB    0       ;18
36 176D   00             DB    0       ;19
37 176E   00             DB    0       ;20
38 176F   00             DB    0       ;21
39 1770   00             DB    0       ;22
40 1771   00             DB    0       ;23
41 1772   00             DB    0       ;24
42 1773   00             DB    0       ;25
43 1774   00             DB    0       ;26
44 1775   00             DB    0       ;27
45 1776   00             DB    0       ;28
46 1777   00             DB    0       ;29
47 1778   00             DB    0       ;30
48 1779   00             DB    0       ;31
50 177A   00 00   PRMTBL: DB    0,0,0                ;ZERO UNUSED
   177C   00
52 177D   50             DB    50H              ;1 = SAT LIMIT
53 177E   70C2           DW    SATLL
55 1780   58             DB    58H              ;2 = RATE UPPER LIMIT
56 1781   70C7           DW    RATUL
```

RESPOX: MICROBENCH 8080/8085 CROSS ASSEMBLER (V2)-436  30-MAR-85 13:30:07 PAGE 85

```
 2 1783   58             DB    58H              ;3 = RATE LOWER LIMIT
 3 1784   70C6           DW    RATLL
 5 1786   61             DB    61H              ;4 = INHIBIT ALARM
 6 1787   70F4           DW    ALIPER
 8 1789   50             DB    50H              ;5 = SAT UPPER LIMIT
 9 178A   70C3           DW    SATUL
11 178C   60             DB    60H              ;6 = SET EKG POLARITY - LOSAT/HIRATE BUTS
12 178D   70FA           DW    POLEKG
14 178F   A0             DB    0A0H             ;7 = INDIRECT DIDDLE-ADDRESS DISPATCH
15 1790   160D           DW    ILOOK
17 1792   A0             DB    0A0H             ;8 = INDIRECT DIDDLE-CONTENTS DISPATCH
18 1793   1600           DW    INDRCT
```

```
 19
 20 1795   60                      DB    60H              ;9 = FILTER MODE
 21 1796   7170                    DW    FMODE
 22
 23 1798   60                      DB    60H              ;10 = ALARM INHIBIT PERIOD
 24 1799   70F4                    DW    ALIPER
 25
 26 179B   60                      DB    60H              ;11 = DIDDLE EKG GAIN - LOSAT/LORATE BUTS
 27 179C   70FD                    DW    GNEKG
 28
 29 179E   00                      DB    0
 30 179F   0000                    DW    0
 31
```

RESPOX: MICROBENCH 8080/8085 CROSS ASSEMBLER (V2)-436   30-MAR-85 13:30:07 PAGE 86

```
  2                       ;CLOCK SERVICE ROUTINE.....CALLED EVERY QUARTER-SECOND BY MONITOR.
  3                       ;MAINTAIN TIME REGISTERS, MARK MINUTES ON VEXT'S.
  4                       ;
  5 17A1  21   7145  CLOCK: LXI   H,QSCFLG      ;POINT TO QUARTER-SECOND FLAG
  6 17A4  7E              MOV   A,M
  7 17A5  3D              DCR   A             ;DECREMENT SAME
  8 17A6  F8              RM                  ;WAS ALREADY ZERO, RETURN
  9 17A7  77              MOV   M,A
 10 17A8  2B              DCX   H             ;POINT TO COUNTER (MSCTR)
 11 17A9  3E   8E         MVI   A,142         ;FUDGE FOR 6MHZ CRYSTAL ******
 12 17AB  86              ADD   M
 13 17AC  77              MOV   M,A
 14 17AD  23              INX   H
 15 17AE  D2   17B2       JNC   1$            ;OVERFLOWED THE COUNTER?
 16 17B1  34              INR   M             ;YES, SET ANOTHER COUNT
 17 17B2  23       1$:    INX   H             ;POINT TO QUARTER-SEC COUNTER
 18 17B3  34              INR   M             ;BUMP IT, CHECK FOR END OF MINUTE
 19 17B4  7E              MOV   A,M
 20 17B5  FE   F0         CPI   240
 21 17B7  C2   17C8       JNZ   5$            ;NOT YET
 22 17BA  36   00         MVI   M,0
 23 17BC  23              INX   H
 24 17BD  34              INR   M             ;BUMP MINUTES AND CHECK FOR AN HOUR
 25 17BE  7E              MOV   A,M
 26 17BF  FE   3C         CPI   60
 27 17C1  C2   17C8       JNZ   5$
 28 17C4  36   00         MVI   M,0
 29 17C6  23              INX   H
 30 17C7  34              INR   M             ;BUMP HOURS
 31 17C8  21   713D  5$:  LXI   H,OPNTMR      ;POINT TO TIMER FOR BUTTON CODE
 32 17CB  7E              MOV   A,M
 33 17CC  3D              DCR   A             ;A SPECULATIVE DECREMENT
 34 17CD  FA   17D7       JM    14$           ;WAS ZERO, FORGET IT
 35 17D0  77              MOV   M,A           ;NOT ZERO, STORE DECREMENTED VALUE
 36 17D1  C2   17D7       JNZ   14$           ;NOT YET ZERO
 37 17D4  CD   15B7       CALL  BUTCLS        ;TIMED OUT, CLOSE THE BUT...(A = 0)
 38 17D7  21   7149  14$: LXI   H,PLSTMR      ;CHECK PULSE TIME-OUT
 39 17DA  7E              MOV   A,M
 40 17DB  3D              DCR   A
 41 17DC  FA   17E6       JM    17$           ;NO SET, IGNORE
 42 17DF  77              MOV   M,A
 43 17E0  C2   17E6       JNZ   17$
 44 17E3  CD   0B2C       CALL  PLSTMO
 45 17E6  21   70F8  17$: LXI   H,EKGTMR      ;DECREMENT EKG TIMEOUT COUNTER
 46 17E9  7E              MOV   A,M
 47 17EA  3D              DCR   A
 48 17EB  FA   17F5       JM    3$
 49 17EE  77              MOV   M,A
 50 17EF  C2   17F5       JNZ   3$
 51 17F2  CD   0BCC       CALL  EKGTMO        ;EKG TIMED OUT - CLEAR RATE AND SET ALARM
 52 17F5  21   710F  3$:  LXI   H,RSPTMR      ;DECREMENT RESP TIMEOUT COUNTER
 53 17F8  7E              MOV   A,M
 54 17F9  3D              DCR   A
 55 17FA  FA   1804       JM    19$
 56 17FD  77              MOV   M,A
 57 17FE  C2   1804       JNZ   19$
```

RESPOX: MICROBENCH 8080/8085 CROSS ASSEMBLER (V2)-436   30-MAR-85 13:30:07 PAGE 87

```
  1 1801  CD   0C0F       CALL  RSPTMO
  2 1804  21   710B  19$: LXI   H,RATCLK      ;TIME DOWN RATE CLOCK
  3 1807  7E              MOV   A,M
  4 1808  3D              DCR   A
  5 1809  FA   1816       JM    4$            ;TIMED OUT, ZERO RATE OUTPUT
  6 180C  77              MOV   M,A
  7 180D  C2   1816       JNZ   4$
  8 1810  21   0000       LXI   H,0
  9 1813  22   716B       SHLD  RATOUT
 10 1816  21   710C  4$:  LXI   H,SATCLK      ;DITTO FOR SAT CLOCK
 11 1819  7E              MOV   A,M
 12 181A  3D              DCR   A
 13 181B  FA   1828       JM    6$
 14 181E  77              MOV   M,A
```

```
15 181F   C2   1828         JNZ    6$
16 1822   21   0000         LXI    H,0
17 1825   22   7169         SHLD   SATOUT
18 1828   3A   7105   6$:   LDA    HRRFSH      ;RESET EKG GAIN EVERY SEC WHEN EKTMR IS 0
19 182B   3C                INR    A
20 182C   FE   05           CPI    5
21 182E   CA   1834         JZ     20$
22 1831   32   7105         STA    HRRFSH
23 1834   3A   7146   20$:  LDA    QSCCTR
24 1837   E6   01           ANI    1
25 1839   CC   1881         CZ     BNKON       ;Q-SEC = 0 OR 2...LITES ON.
26
27                          ;CHECK ALARM INHIBIT TIME-OUT, SOUND DELAYED TIME-OUT ALARM IF SET...
28                          ;
29 183C   3A   7146         LDA    QSCCTR
30 183F   2F                CMA
31 1840   E6   03           ANI    3
32 1842   CC   188F         CZ     BNKOFF      ;Q-SEC = 3, SLOW BLINKERS
33 1845   3A   7146         LDA    QSCCTR      ;CHECK FOR 1-SECOND
34 1848   E6   03           ANI    3
35 184A   C2   1880         JNZ    18$         ;IS NOT
36 184D   3A   70F2         LDA    ALICTR      ;CHECK ALARM-INHIBIT TIME-OUT
37 1850   B7                ORA    A
38 1851   CA   1880         JZ     18$         ;NOT SET
39 1854   3D                DCR    A
40 1855   32   70F2         STA    ALICTR
41 1858   C2   1880         JNZ    18$
42 185B   32   70F1         STA    ALIFLG      ;CLEAR INHIBIT FLAG
43 185E   0E   01           MVI    C,ALICOD
44 1860   CD   1475         CALL   CLRLIT      ;CLEAR LIGHT
45 1863   3A   727C         LDA    COSTA
46 1866   F6   04           ORI    AUDENB
47 1868   32   727C         STA    COSTA
48 186B   3A   70F6         LDA    ALMDLY      ;CHECK FOR DELAYED ALARM
49 186E   B7                ORA    A
50 186F   CA   1880         JZ     18$         ;NOT SET
51 1872   AF                XRA    A
52 1873   32   70F6         STA    ALMDLY
53 1876   3A   7014         LDA    SYNFLG      ;CHECK FOR SYNC
54 1879   B7                ORA    A
55 187A   CA   1880         JZ     18$         ;IT IS
56 187D   CD   0D7E         CALL   ALMCK2      ;DELAYED TIME-OUT ALARM IF NOT RE-SYNCED
57 1880   C9           18$: RET
```

```
                            ;SET BLINKING DIGITS AND LIGHTS TO "ON" STATE
                            ;
 4 1881   21   711C  BNKON: LXI    H,DIGBUF
 5 1884   0E   09           MVI    C,9
 6 1886   23          1$:   INX    H
 7 1887   36   FF           MVI    M,0FFH
 8 1889   23                INX    H
 9 188A   0D                DCR    C
10 188B   C2   1886         JNZ    1$
11 188E   C9                RET
12
13                          ;SET BLINKING DIGITS TO "OFF" STATE IF THEIR BLINK BIT IS SET...
14                          ;
15 188F   3A   7118  BNKOFF: LDA   DIGBNK
16 1892   5F                MOV    E,A
17 1893   0E   06           MVI    C,6
18 1895   21   711C         LXI    H,DIGBUF
19 1898   23          1$:   INX    H
20 1899   7B                MOV    A,E
21 189A   1F                RAR
22 189B   5F                MOV    E,A         ;CHECK DIGIT BIT...
23 189C   D2   18A1         JNC    3$
24 189F   AF                XRA    A
25 18A0   77                MOV    M,A
26 18A1   23          3$:   INX    H
27 18A2   0D                DCR    C
28 18A3   C2   1898         JNZ    1$
29 18A6   3A   7119         LDA    INDBNK      ;CLEAR INDICATOR BITS
30 18A9   2F                CMA
31 18AA   21   712D         LXI    H,DSPLMP+1
32 18AD   A6                ANA    M
33 18AE   77                MOV    M,A
34 18AF   C9                RET
```

```
                            ;INTERRUPT HANDLERS...
                            ;
                            ;CLOCK INTERRUPT.....
                            ;THIS IS A SERIAL OUTPUT ROUTINE WITH 6 STATES. DEPENDING ON THE
                            ; ADDRESS OF THE SUBROUTINE STORED AT 'SNDMOD' IT WILL PERFORM ONE OF
```

```
                ; THE FOLLOWING TASKS.
                ;   1.  NULMOD  DOES NOTHING BUT RESTORE THE HL REGISTER PAIR
                ;   2.  STARTS  SETS THE SOD LINE TO SPACE FOR CHARACTER START
                ;   3.  SPINR   SETS THE SOD LINE ACCORDING TO CURRENT BIT AND ROTATES
                ;   4.  STOPBG  SETS THE SOD LINE TO MARK FOR STOP BIT STARTING
                ;   5.  ENDSND  SETS THE SOD LINE TO MARK CONDITION FOR TERMINATION
                ;   6.  WATMOD  FORCES A MINIMUM TIME BETWEEN CHARACTERS SO RECEIVING
                ;               UART CAN BE READY FOR THE NEXT CHARACTER
                ;               RESETS SNDMOD BACK TO NULMOD
                ;
18B0  E5              CLKINT: PUSH    H               ;SAVE THE POOR GUY
18B1  2A  72AA                LHLD    SNDMOD          ;GET ADDRESS OF ROUTINE CURRENTLY ACTIV
18B4  E9                      PCHL                    ;AND GO DO IT

18B5  E1              NULMOD: POP     H               ;RESTORE HL PAIR
18B6  FB                      EI
18B7  C9                      RET                     ;AND WE'RE DONE

18B8  21  18D9        STARTS: LXI     H,SPINR         ;SET MODE TO SPINR FOR NEXT PASS
18BB  22  72AA                SHLD    SNDMOD
18BE  F5                      PUSH    PSW
18BF  3E  C0                  MVI     A,SPACE         ;SET SOD LINE TO SPACE CONDITION
18C1  30                      SIM                     ;SEND IT
18C2  3E  08                  MVI     A,8             ;INITIALIZE NUMBER OF BITS
18C4  32  72AC                STA     BITCNT
18C7  F1                      POP     PSW             ;RESTORE REGGIES
18C8  E1                      POP     H
18C9  FB                      EI
18CA  C9                      RET

18CB  21  18FC        STOPBG: LXI     H,ENDSND
18CE  22  72AA                SHLD    SNDMOD          ;SET MODE TO NULL AT END OF TRANSMISSIO
18D1  F5                      PUSH    PSW
18D2  3E  40                  MVI     A,MARK          ;SET SOD TO MARKING
18D4  30                      SIM
18D5  F1                      POP     PSW             ;RESTORE
18D6  E1                      POP     H
18D7  FB                      EI
18D8  C9                      RET

18D9  F5              SPINR:  PUSH    PSW             ;SAVE HIM
18DA  3A  72A9                LDA     CHAR            ;GET THIS DIZZY CHARACTER
18DD  0F                      RRC                     ;POSITION BIT AT MSB AND ROTATE FOR NEX
18DE  32  72A9                STA     CHAR
18E1  2F                      CMA                     ;INVERT FOR OPTO-COUPLER
18E2  F6  40                  ORI     40H             ;SET SOD ENABLE BIT
18E4  E6  C0                  ANI     0C0H            ;STRIP MASK SET STUFF
18E6  30                      SIM                     ;AND DO IT
18E7  21  72AC                LXI     H,BITCNT
18EA  35                      DCR     M               ;DECREMENT BIT COUNT
18EB  CA  18F2                JZ      MODCHG          ;IF DONE, THEN CHANGE MODE TO STOP BIT
```

RESPOX: MICROBENCH 8080/8085 CROSS ASSEMBLER (V2)-436    30-MAR-85 13:30:07 PAGE 91

```
18EE  F1                      POP     PSW             ;IF NOT, THEN RESTORE REGISTERS
18EF  E1                      POP     H
18F0  FB                      EI
18F1  C9                      RET                     ;AND WE'RE DONE

18F2  21  18CB        MODCHG: LXI     H,STOPBG
18F5  22  72AA                SHLD    SNDMOD          ;SET MODE TO STOP BIT BEGINNING
18F8  F1                      POP     PSW             ;RESTORE REGISTERS
18F9  E1                      POP     H
18FA  FB                      EI
18FB  C9                      RET

18FC  F5              ENDSND: PUSH    PSW             ;SAVE THAT HAPPY ACCUMULATOR
18FD  3E  40                  MVI     A,MARK          ;SET SOD TO MARK CONDITION
18FF  30                      SIM
1900  21  190A                LXI     H,WATMOD        ;JUST WAIT A BIT 'TIL NEXT
1903  22  72AA                SHLD    SNDMOD          ;AND SET TO DO NOTHING NEXT TIME 'ROUND
1906  F1                      POP     PSW             ;RESTORE REGGIES
1907  E1                      POP     H
1908  FB                      EI
1909  C9                      RET 190A  21  18B5        WATMOD: LXI     H,NULMOD        ;SET TO NULL MODE
190D  22  72AA                SHLD    SNDMOD
1910  E1                      POP     H
1911  FB                      EI                      ;JUST WAIT HERE A BIT
1912  C9                      RET
```

```
RESPOX: MICROBENCH 8080/8085 CROSS ASSEMBLER (V2)-436   30-MAR-85 13:30:07 PAGE 92

1
  2                              ;
  3                              ;DISPLAY INTERRUPT...OUTPUT DISPLAY SELECT BIT AND DIGIT, OUTPUT
  4                              ; SAMPLE/HOLD VALUE AND SELECT, AND CHECK FOR BUTTON/CONTROL INPUT.
  5                              ; EVERY FOURTH INTERRUPT DO A/D CONVERSION FOR INPUT CHANNELS, ADJUSTING
  6                              ; OFFSET IF REQUIRED...
  7                              ;
  8 1913  F5                     DSPINT: PUSH  PSW
  9 1914  C5                             PUSH  B
 10 1915  D5                             PUSH  D
 11 1916  E5                             PUSH  H         ;SAVE REGISTERS
 12 1917  2A  7144                       LHLD  MSCTR     ;BUMP CLOCK
 13 191A  23                             INX   H
 14 191B  22  7144                       SHLD  MSCTR
 15 191E  3E  0F                         MVI   A,0FH
 16 1920  D3  04                         OUT   DSPSEL    ;DE-SELECT TO BLANK DISPLAY
 17 1922  21  711B                       LXI   H,DIGIDX  ;POINT TO DIGIT COUNTER
 18 1925  7E                             MOV   A,M
 19 1926  3C                             INR   A         ;INCREMENT IT
 20 1927  FE  09                         CPI   9
 21 1929  C2  192D                       JNZ   1$
 22 192C  AF                             XRA   A         ;RESET IT IF IT REACHED MAX
 23 192D  77                     1$:     MOV   M,A
 24 192E  07                             RLC
 25 192F  5F                             MOV   E,A
 26 1930  16  00                         MVI   D,0       ;D,E = DIGIT INDEX *2
 27 1932  23                             INX   H         ;POINT TO FIRST BYTE
 28 1933  19                             DAD   D         ;POINT TO NEXT DIGIT
 29 1934  7E                             MOV   A,M       ;GET DIGIT
 30 1935  23                             INX   H
 31 1936  A6                             ANA   M         ;MASK WITH MASK BYTE
 32 1937  D3  05                         OUT   DSPDIG    ;OUTPUT, RESETTING INTERRUPT
 33 1939  7B                             MOV   A,E       ;GET INDEX AGAIN
 34 193A  0F                             RRC
 35 193B  D3  04                         OUT   DSPSEL
 36 193D  3A  7012                       LDA   GNSEL     ;LOAD GNMSK WITH CORRECT VALUE
 37 1940  B7                             ORA   A
 38 1941  CA  1946                       JZ    4$        ;LO GAIN=0
 39 1944  3E  80                         MVI   A,128     ;HI GAIN=128
 40 1946  32  72AF             4$:       STA   GNMSK
 41 1949  3E  0A                         MVI   A,0AH
 42 194B  30                             SIM             ;TURN OFF INT 6.5 (OURS)
 43 194C  FB                             EI              ;ALLOW CLOCK INTERRUPTS HERE

RESPOX: MICROBENCH 8080/8085 CROSS ASSEMBLER (V2)-436   30-MAR-85 13:30:07 PAGE 93

1
  2                              ;CHECK BUTTON INPUT REGISTER, STORE IF DIFFERENT...
  3                              ;
  4 194D  21  7132                       LXI   H,KNBCTR  ;POINT TO KNOB UP/DOWN COUNT
  5 1950  DB  04                         IN    BUTREG    ;GET BUTTON/KNOB DATA
  6 1952  4F                             MOV   C,A
  7 1953  E6  03                         ANI   3         ;ISOLATE KNOB BITS
  8 1955  1F                             RAR             ;STEP BIT TO CARRY, DIR TO BIT0
  9 1956  D2  1965                       JNC   3$
 10 1959  07                             RLC             ;DIR TO BIT 1
 11 195A  3D                             DCR   A         ;MAKE A 1 OR -1
 12 195B  2B                             DCX   H         ;POINT TO OUR FLAG
 13 195C  BE                             CMP   M         ;SET SAME AS OUR UP/DOWN CODE?
 14 195D  C2  1961                       JNZ   2$        ;NO, DO IT
 15 1960  AF                             XRA   A         ;CLEAR UP/DOWN CODE (TO SKIP ALTERNATE STEPS)
 16 1961  77                     2$:     MOV   M,A       ;STORE CODE OR ZERO
 17 1962  23                             INX   H
 18 1963  86                             ADD   M
 19 1964  77                             MOV   M,A       ;ADD TO KNOB COUNT
 20 1965  23                     3$:     INX   H         ;POINT TO BUTTON FILTER
 21 1966  79                             MOV   A,C
 22 1967  A6                             ANA   M         ;MASK DATA WITH LAST INPUT (REQUIRING CONSECUTIVE 1'S)
 23 1968  71                             MOV   M,C       ;STORE NEW DATA
 24 1969  23                             INX   H         ;POINT TO BUTCOD
 25 196A  0F                             RRC
 26 196B  0F                             RRC
 27 196C  2F                             CMA             ;BUTTON DOWN = ZERO, MAKE IT ONE.
 28 196D  E6  1F                         ANI   1FH       ;MASK BUTTON CODE
 29 196F  BE                             CMP   M         ;SAME??
 30 1970  CA  1976                       JZ    5$        ;YES
 31 1973  77                             MOV   M,A       ;STORE NEW ONE (HOPE OLD ONE PROCESSED)
 32 1974  23                             INX   H
 33 1975  34                             INR   M         ;FLAG IT
 34 1976                         5$:

RESPOX: MICROBENCH 8080/8085 CROSS ASSEMBLER (V2)-436   30-MAR-85 13:30:07 PAGE 94
```

```
                ;DIGITIZE PRIMARY DATA VALUES EVERY 8TH PASS (57HZ, ABOUT)
                ;
1976  21  7177  ADCHK:  LXI   H,DATCLK
1979  34                INR   M
197A  7E                MOV   A,M
197B  E6  07            ANI   7
197D  C2  19F8          JNZ   ADCHK2      ;NOT TIME YET
1980  3E  0F            MVI   A,V1PRM     ;CHANNEL 1 MUX CODE
1982  D3  02            OUT   MUXSEL      ;PRE-SELECT IT
1984  23                INX   H
1985  7E                MOV   A,M         ;GET BUFFER INDEX
1986  4F                MOV   C,A
1987  C6  04            ADI   4           ;4 BYTES PER SAMPLE
1989  E6  FF            ANI   BUFMSK      ;MASK TO WRAP AT BUFFER END
198B  77                MOV   M,A
198C  06  00            MVI   B,0
198E  23                INX   H           ;FIRST BUFFER BYTE
198F  23                INX   H
1990  09                DAD   B           ;PLUS INDEX
1991  E5                PUSH  H           ;SAVE H,L
1992  CD  1AA6          CALL  CHKEKG      ;CHECK FOR VALID R WAVE
1995  CD  1AF6          CALL  CHKWIN      ;BUMP TIME WINDOW TIMER
1998  E1                POP   H
1999  CD  1E5E          CALL  ADCVT       ;GET DATA INTO D,E
199C  3E  1F            MVI   A,V2PRM     ;PRE-SELECT MUX FOR CH.2
199E  D3  02            OUT   MUXSEL
19A0  E5                PUSH  H
19A1  CD  1D4B          CALL  CKLED1      ;RE-SET LED CURRENT BASED ON DAC DATA
19A4  21  3000          LXI   H,3000H
19A7  19                DAD   D           ;ADD DATA TO OFFSET
19A8  EB                XCHG
19A9  E1                POP   H
19AA  3A  700C          LDA   L1ITMR      ;CHECK LED INHIBIT TIMER
19AD  B7                ORA   A
19AE  CA  19B4          JZ    1$          ;NOT CHANGING, STORE DATA
19B1  11  0000          LXI   D,0         ;ZERO OUR HARD WORK
19B4  73            1$: MOV   M,E         ;STORE LOW BYTE
19B5  23                INX   H
19B6  72                MOV   M,D         ;STORE DATA + OFFSET
19B7  23                INX   H
19B8  CD  1E5E          CALL  ADCVT
19BB  E5                PUSH  H
19BC  CD  1D9F          CALL  CKLED2
19BF  21  3000          LXI   H,3000H
19C2  19                DAD   D
19C3  EB                XCHG
19C4  E1                POP   H
19C5  3A  700F          LDA   L2ITMR
19C8  B7                ORA   A
19C9  CA  19CF          JZ    2$
19CC  11  0000          LXI   D,0
19CF  73            2$: MOV   M,E
19D0  23                INX   H
19D1  72                MOV   M,D
```

RESPOX: MICROBENCH 8080/8085 CROSS ASSEMBLER (V2)-436  30-MAR-85 13:30:07 PAGE 95

```
                ;CHECK THE BEEP COUNTER (57HZ RATE)...
                ;
19D2  21  70EA          LXI   H,BEECNT    ;GET BEEPER COUNTER
19D5  7E                MOV   A,M
19D6  3D                DCR   A
19D7  FA  19E4          JM    3$          ;WAS ZERO, BORING
19DA  77                MOV   M,A         ;UPDATE, CHECK FOR NOW ZERO
19DB  C2  19E4          JNZ   3$
19DE  2A  7167          LHLD  VVOLSV
19E1  22  7165          SHLD  VVOL        ;RESET VOLUME VOLTAGE
19E4  3A  700C      3$: LDA   L1ITMR      ;DECREMENT LED TIMERS
19E7  3D                DCR   A
19E8  FA  19EE          JM    4$
19EB  32  700C          STA   L1ITMR
19EE  3A  700F      4$: LDA   L2ITMR
19F1  3D                DCR   A
19F2  FA  19F8          JM    5$
19F5  32  700F          STA   L2ITMR
19F8                5$:
                ;
                ;DO A/D CONVERSION ON SECONDARY MUX INPUTS EVERY SO OFTEN...
                ;
19F8  3A  7177  ADCHK2: LDA   DATCLK
19FB  3C                INR   A
19FC  E6  07            ANI   7
19FE  C2  1A1F          JNZ   DSPRET      ;DON'T CHECK AT THE SAME TIME AS D/A...
1A01  21  714B          LXI   H,ADIDX
1A04  7E                MOV   A,M         ;GET INDEX
1A05  07                RLC
1A06  5F                MOV   E,A
1A07  16  00            MVI   D,0
```

```
33 1A09    07                    RLC
34 1A0A    07                    RLC
35 1A0B    07                    RLC
36 1A0C    C6  2F                ADI   V1MX
37 1A0E    D3  02                OUT   MUXSEL
38 1A10    7E                    MOV   A,M           ;INCREMENT INDEX
39 1A11    3C                    INR   A
40 1A12    E6  07                ANI   7
41 1A14    77                    MOV   M,A
42 1A15    21  714C              LXI   H,V1          ;FIRST PARAMATER IN BUFFER
43 1A18    19                    DAD   D             ;PLUS INDEX
44 1A19    CD  1E5E              CALL  ADCVT
45 1A1C    73                    MOV   M,E
46 1A1D    23                    INX   H
47 1A1E    72                    MOV   M,D           ;STORE DATA
```

RESPOX: MICROBENCH 8080/8085 CROSS ASSEMBLER (V2)-436  30-MAR-85 13:30:07 PAGE 96

```
 1
 2                              ;RETURN...OUTPUT TO NEXT SAMPLE/HOLD
 3                              ;
 4 1A1F    CD  1B23      DSPRET: CALL  SETEKG        ;CHECK GAIN,POLARITY SETTING
 5 1A22    3A  7177              LDA   DATCLK        ;EVERY 32ND PASS, UPDATE RESP COUNTER
 6 1A25    3C                    INR   A
 7 1A26    E6  1F                ANI   31
 8 1A28    C2  1A2E              JNZ   3$
 9 1A2B    CD  1A98              CALL  RSPCTR
10 1A2E    3E  0F        3$:     MVI   A,0FH
11 1A30    D3  02                OUT   MUXSEL        ;TURN OFF GATES
12 1A32    2A  715D              LHLD  SHPTR         ;GET POINTER AND INDEX
13 1A35    3A  715C              LDA   SHIDX
14 1A38    B7                    ORA   A
15 1A39    C2  1A44              JNZ   1$
16 1A3C    CD  1B66              CALL  SNDOUT        ;OUTPUT SAO2/HR VOLTAGES
17 1A3F    3E  01                MVI   A,1           ;RESET IF INDEX IS ZERO
18 1A41    21  715F              LXI   H,SHBUF
19 1A44    4F            1$:     MOV   C,A           ;SAVE INDEX
20 1A45    5E                    MOV   E,M
21 1A46    23                    INX   H
22 1A47    56                    MOV   D,M           ;GET VALUE
23 1A48    23                    INX   H
24 1A49    22  715D              SHLD  SHPTR
25 1A4C    3A  72AF              LDA   GNMSK         ;ADD GAIN SELECT TO DACH
26 1A4F    B2                    ORA   D
27 1A50    F6  70                ORI   070H          ;MASK OFF MIDDLE 3 BITS (FOR ANALOG OUTPUTS)
28 1A52    D3  01                OUT   DACH
29 1A54    7B                    MOV   A,E
30 1A55    D3  00                OUT   DACL
31 1A57    79                    MOV   A,C
32 1A58    2F                    CMA
33 1A59    E6  0F                ANI   0FH
34 1A5B    D3  02                OUT   MUXSEL
35 1A5D    79                    MOV   A,C
36 1A5E    17                    RAL
37 1A5F    E6  0F                ANI   0FH
38 1A61    32  715C              STA   SHIDX
39 1A64    CD  1CC3              CALL  COM240        ;CALL 240 HZ. COMMUNICATIONS ROUTINE    ///
40 1A67    F3                    DI                  ;RE-ENABLE OUR INTERRUPT
41 1A68    3E  08                MVI   A,08H
42 1A6A    30                    SIM                 ;******** 8085 ********
43 1A6B    E1                    POP   H
44 1A6C    D1                    POP   D
45 1A6D    C1                    POP   B
46 1A6E    F1                    POP   PSW
47 1A6F    FB                    EI
48 1A70    C9                    RET
49                              ;
50                              ;SHIFT H,L RIGHT OR LEFT (A) PLACES (RIGHT FOR NEGATIVE)
51                              ;
52 1A71    B7            SHFTHL: ORA   A
53 1A72    C8                    RZ
54 1A73    C5                    PUSH  B
55 1A74    4F                    MOV   C,A
56 1A75    FA  1A85              JM    2$
57 1A78    AF            1$:     XRA   A             ;NO CARRY AROUND
```

RESPOX: MICROBENCH 8080/8085 CROSS ASSEMBLER (V2)-436  30-MAR-85 13:30:07 PAGE 97

```
 1 1A79    7D                    MOV   A,L
 2 1A7A    17                    RAL
 3 1A7B    6F                    MOV   L,A
 4 1A7C    7C                    MOV   A,H
 5 1A7D    17                    RAL
 6 1A7E    67                    MOV   H,A
 7 1A7F    0D                    DCR   C
 8 1A80    C2  1A78              JNZ   1$
 9 1A83    C1                    POP   B
10 1A84    C9                    RET
```

```
 11 1A85  AF              2$:   XRA   A
 12 1A86  7C                    MOV   A,H
 13 1A87  1F                    RAR
 14 1A88  67                    MOV   H,A
 15 1A89  7D                    MOV   A,L
 16 1A8A  1F                    RAR
 17 1A8B  6F                    MOV   L,A
 18 1A8C  0C                    INR   C
 19 1A8D  C2    1A85            JNZ   2$
 20 1A90  C1                    POP   B
 21 1A91  C9                    RET
 22
 23                       ;SAME EXCEPT SHIFTS D,E INSTEAD OF H,L
 24                       ;
 25 1A92  EB              SHFTDE: XCHG
 26 1A93  CD    1A71              CALL  SHFTHL
 27 1A96  EB                      XCHG
 28 1A97  C9                      RET
 29
 30                       ; COUNTER FOR RESP PERIOD - APPROX 14HZ
 31                       ;
 32 1A98  3A    7110      RSPCTR: LDA   RSPFLG
 33 1A9B  B7                      ORA   A
 34 1A9C  C0                      RNZ                 ;INSURE WE'RE NOT AHEAD OF OURSELVES
 35 1A9D  3A    710E              LDA   RSPCNT
 36 1AA0  3C                      INR   A
 37 1AA1  C8                      RZ
 38 1AA2  32    710E              STA   RSPCNT
 39 1AA5  C9                      RET
 40
 41                       ;
 42                       ;CHECK FOR A VALID R-WAVE AND RESP WAVE. SET FLAG IF SO.
 43                       ;RETURN IF EKG SETTINGS HAVE BEEN CHANGED RECENTLY
 44                       ;
 45 1AA6  3A    7100      CHKEKG: LDA   EKGFLG        ;EXIT IF WE'RE AHEAD OF LEVEL3
 46 1AA9  B7                      ORA   A
 47 1AAA  C0                      RNZ
 48 1AAB  3A    70FF              LDA   EKGPER        ;EKG PERIOD COUNTER
 49 1AAE  3C                      INR   A
 50 1AAF  CA    1AB5              JZ    1$
 51 1AB2  32    70FF              STA   EKGPER
 52 1AB5  3A    7103      1$:     LDA   DLYEKG        ;DELAY FOR CHANGING PARAMETERS
 53 1AB8  3D                      DCR   A
 54 1AB9  FA    1AC2              JM    2$            ;IS ZERO, DATA IS VALID
 55 1ABC  32    7103              STA   DLYEKG
 56 1ABF  C3    1AE7              JMP   4$            ;NOT VALID, RESET R WAVE FLAG AND EXIT
 57 1AC2  DB    00        2$:     IN    STSREG        ;GET FLAG
```

RESPOX: MICROBENCH 8080/8085 CROSS ASSEMBLER (V2)-436  30-MAR-85 13:30:07 PAGE 98.

```
  1 1AC4  32    70CA              STA   STATUS
  2 1AC7  E6    30                ANI   30H           ;MASK FOR EKG + RESP
  3 1AC9  CA    1AEB              JZ    7$
  4 1ACC  CD    1B04              CALL  CHKRSP        ;SEE IF RESP BIT IS SET
  5 1ACF  E6    20                ANI   20H           ;CHECK EKG BIT
  6 1AD1  CA    1AE7              JZ    4$
  7 1AD4  3A    70FF              LDA   EKGPER        ;CHECK IF HR >285 - REJECT
  8 1AD7  FE    0C                CPI   12
  9 1AD9  DA    1AEC              JC    8$
 10 1ADC  21    7100              LXI   H,EKGFLG      ;VALID R WAVE
 11 1ADF  36    01                MVI   M,1
 12 1AE1  3A    7178              LDA   DATIDX
 13 1AE4  32    7108              STA   DATTRG        ;STORE DATBUF POINTER WHEN R-WAVE OCCURRED
 14 1AE7  3E    00        4$:     MVI   A,0           ;RESET THE HARDWARE FLAG
 15 1AE9  D3    07                OUT   RSTRWV
 16 1AEB  C9              7$:     RET
 17 1AEC  AF              8$:     XRA   A             ;ZERO PARAMS DUE TO REJECTED R WAVE
 18 1AED  32    7100              STA   EKGFLG
 19 1AF0  32    70FF              STA   EKGPER
 20 1AF3  D3    07                OUT   RSTRWV
 21 1AF5  C9                      RET
 22
 23                       ;
 24                       ;TIME DELAY BETWEEN R-WAVE AND OPTICAL PULSE
 25                       ;
 26 1AF6  3A    710A      CHKWIN: LDA   WINFLG        ;DON'T DO THIS IF FLAG IS SET
 27 1AF9  B7                      ORA   A
 28 1AFA  C0                      RNZ
 29 1AFB  3A    7109              LDA   WINTHR
 30 1AFE  3C                      INR   A
 31 1AFF  C8                      RZ
 32 1B00  32    7109              STA   WINTHR
 33 1B03  C9                      RET
 34
 35                       ;
 36                       ; CHECK FOR THE RESP BIT - SET FLAG IF SO
 37 1B04  F5              CHKRSP: PUSH  PSW           ;SAVE FOR EKG
 38 1B05  E6    10                ANI   10H           ;MASK FOR RESP
 39 1B07  CA    1B21              JZ    1$            ;RESP NOT SET
 40 1B0A  3A    710E              LDA   RSPCNT
 41 1B0D  FE    07                CPI   7             ;NO RESP >120
```

```
42 1B0F   DA    1B1A              JC     2$
43 1B12   21    7110              LXI    H,RSPFLG
44 1B15   36    01                MVI    M,1
45 1B17   C3    1B21              JMP    1$              ;SET FLAG
46 1B1A   AF              2$:     XRA    A
47 1B1B   32    7110              STA    RSPFLG
48 1B1E   32    710E              STA    RSPCNT          ;RESET PARAMS
49 1B21   F1              1$:     POP    PSW
50 1B22   C9                      RET
51                                ;
52                                ;CHECK TO SEE IF EKG PARAMETERS HAVE BEEN CHANGED.
53                                ;SET A DELAY IF PARAMETERS ARE TO BE CHANGED
54                                ;
55 1B23   CD    1B4D    SETEKG:   CALL   CKRFSH
56 1B26   21    70FA              LXI    H,POLEKG
57 1B29   7E                      MOV    A,H
```

RESPOX: MICROBENCH 8080/8085 CROSS ASSEMBLER (V2)-436   30-MAR-85 13:30:07 PAGE 99

```
 1 1B2A   21    7101              LXI    H,POLSAV        ;COMPARE NEW WITH OLD
 2 1B2D   BE                      CMP    M
 3 1B2E   CA    1B39              JZ     4$              ;SAME - NO CHANGE
 4 1B31   77                      MOV    M,A
 5 1B32   D3    03                OUT    EKGPOL          ;SEND OUT NEW POLARITY DATA
 6 1B34   3E    06                MVI    A,6
 7 1B36   32    7103              STA    DLYEKG          ;SET DELAY
 8 1B39   21    70FD    4$:       LXI    H,GNEKG
 9 1B3C   7E                      MOV    A,H
10 1B3D   21    7102              LXI    H,GAINSV
11 1B40   BE                      CMP    M
12 1B41   CA    1B4C              JZ     6$              ;DITTO FOR GAIN CHANGES
13 1B44   77                      MOV    M,A
14 1B45   D3    06                OUT    CHGEKG          ;SEND IT OUT
15 1B47   3E    06                MVI    A,6
16 1B49   32    7103              STA    DLYEKG
17 1B4C   C9              6$:     RET
18                                ;
19                                ;CHECK REFRESH TO EKG - TEMPORARY UNTIL SOFWARE AGC IS IMPLEMENTED
20                                ;
21 1B4D   21    7105    CKRFSH:   LXI    H,HRRFSH
22 1B50   3A    70F8              LDA    EKGTHR
23 1B53   FE    00                CPI    0
24 1B55   CA    1B59              JZ     1$
25 1B58   C9                      RET
26 1B59   7E              1$:     MOV    A,M
27 1B5A   FE    04                CPI    4
28 1B5C   C2    1B65              JNZ    2$
29 1B5F   36    00                MVI    M,0
30 1B61   21    7102              LXI    H,GAINSV
31 1B64   35                      DCR    M
32 1B65   C9              2$:     RET
33                                ;
34                                ;
35                                ;SEND OUT HR/SAO2 TO SAMPLE/HOLDS EVERY 4TH PASS
36                                ;
37 1B66   3A    7170    SNDOUT:   LDA    FMODE           ;IF MODE 7, THEN OUTPUT 0V
38 1B69   FE    07                CPI    7
39 1B6B   C2    1B7A              JNZ    2$
40 1B6E   21    0000              LXI    H,0
41 1B71   22    7169              SHLD   SATOUT
42 1B74   22    716B              SHLD   RATOUT
43 1B77   C3    1B99              JMP    1$
44 1B7A   FE    08      2$:       CPI    8               ;MODE 8, 1/2 SCALE OUTPUTS
45 1B7C   C2    1B8B              JNZ    3$
46 1B7F   21    00CD              LXI    H,205
47 1B82   22    7169              SHLD   SATOUT
48 1B85   22    716B              SHLD   RATOUT
49 1B88   C3    1B99              JMP    1$
50 1B8B   FE    09      3$:       CPI    9               ;MODE 9 , OUTPUT FULL SCALE
51 1B8D   C2    1B99              JNZ    1$
52 1B90   21    019A              LXI    H,410           ;1VOLT
53 1B93   22    7169              SHLD   SATOUT
54 1B96   22    716B              SHLD   RATOUT
55 1B99   21    7169    1$:       LXI    H,SATOUT
56 1B9C   5E                      MOV    E,M
57 1B9D   23                      INX    H
```

RESPOX: MICROBENCH 8080/8085 CROSS ASSEMBLER (V2)-436   30-MAR-85 13:30:07 PAGE 100

```
 1 1B9E   56                      MOV    D,M
 2 1B9F   3A    72AF              LDA    GNMSK           ;ADD IN GAIN MASK
 3 1BA2   B2                      ORA    D
 4 1BA3   F6    70                ORI    070H            ;MASK OFF GATE, FOR NOW
 5 1BA5   F5                      PUSH   PSW             ;SAVE IT
 6 1BA6   D3    01                OUT    DACH            ;OUTPUT SAT VOLTAGE
 7 1BA8   7B                      MOV    A,E
 8 1BA9   D3    00                OUT    DACL
 9 1BAB   00                      NOP                    ;ALLOW FOR A LITTLE SETTLING
10 1BAC   00                      NOP
11 1BAD   00                      NOP
12 1BAE   F1                      POP    PSW
```

```
13 1BAF  E6  BF      ANI   0BFH       ;NOW SELECT GATE
14 1BB1  D3  01      OUT   DACH
15 1BB3  00          NOP              ;LET THE CAPS CHARGE A BIT
16 1BB4  00          NOP
17 1BB5  00          NOP
18 1BB6  00          NOP
19 1BB7  F6  70      ORI   070H       ;OK, TURN 'EM OFF
20 1BB9  D3  01      OUT   DACH
21 1BBB  23          INX   H          ;SAME FOR RATE OUT
22 1BBC  5E          MOV   E,M
23 1BBD  23          INX   H
24 1BBE  56          MOV   D,M
25 1BBF  3A  72AF    LDA   GNMSK
26 1BC2  B2          ORA   D
27 1BC3  F6  70      ORI   070H
28 1BC5  F5          PUSH  PSW
29 1BC6  D3  01      OUT   DACH
30 1BC8  7B          MOV   A,E
31 1BC9  D3  00      OUT   DACL
32 1BCB  00          NOP
33 1BCC  00          NOP
34 1BCD  00          NOP
35 1BCE  F1          POP   PSW
36 1BCF  E6  DF      ANI   0DFH
37 1BD1  D3  01      OUT   DACH
38 1BD3  00          NOP
39 1BD4  00          NOP
40 1BD5  00          NOP
41 1BD6  00          NOP
42 1BD7  F6  70      ORI   070H
43 1BD9  D3  01      OUT   DACH
44 1BDB  23          INX   H          ;OUTPUT THRESHOLD FOR R-WAVE COMPARATOR
45 1BDC  5E          MOV   E,M
46 1BDD  23          INX   H
47 1BDE  56          MOV   D,M
48 1BDF  3A  72AF    LDA   GNMSK
49 1BE2  B2          ORA   D
50 1BE3  F6  70      ORI   070H
51 1BE5  F5          PUSH  PSW
52 1BE6  D3  01      OUT   DACH
53 1BE8  7B          MOV   A,E
54 1BE9  D3  00      OUT   DACL
55 1BEB  00          NOP
56 1BEC  00          NOP
57 1BED  00          NOP
```

RESPOX; MICROBENCH 8080/8085 CROSS ASSEMBLER (V2)-436  30-MAR-85 13:30:07 PAGE 101

```
 1 1BEE  F1          POP   PSW
 2 1BEF  E6  EF      ANI   0EFH
 3 1BF1  D3  01      OUT   DACH
 4 1BF3  00          NOP
 5 1BF4  00          NOP
 6 1BF5  00          NOP
 7 1BF6  00          NOP
 8 1BF7  F6  70      ORI   070H
 9 1BF9  D3  01      OUT   DACH
10 1BFB  C9          RET
```

RESPOX; MICROBENCH 8080/8085 CROSS ASSEMBLER (V2)-436  30-MAR-85 13:30:07 PAGE 102

```
                    ;COMMUNICATIONS ROUTINES FOR SERIAL OUTPUT.                        ///
                    ;  COMBEG        CALLED AT POWER-UP FOR POINTER AND IMAGE INITIALIZATION ///
                    ;  COMIDL        CALLED FROM IDLE FOR STATUS/LIMIT/MINUTE CHANGE CHECK   ///
                    ;  COM240        CALLED 240 HZ FOR MOVING FROM BUFFER TO OUTPUT   ///
                    ;
                    ; UTILITY ROUTINES FOR COMMUNICATIONS
                    ;  SPLIT         SPLITS A BYTE INTO TWO NIBBLES IN D AND E        ///
                    ;  TOBUFR        PUTS A CHARACTER INTO THE BUFFER AND UPDATES POINTER ///
                    ;  BMPBUF        BUFFER POINTER INCREMENT WITH WRAP-AROUND        ///

12 1BFC  21  7287    COMBEG: LXI  H,COMBUF                                            ///
13 1BFF  22  7283            SHLD LSTOUT        ;INITIALIZE LAST SENT POINTER         ///
14 1C02  22  7285            SHLD BUFPTR        ;AND BUFFER POINTER
15 1C05  21  1B85            LXI  H,NULMOD
16 1C08  22  72AA            SHLD SNDMOD        ;SET OUTPUT ROUTINE TO DO NOTHING
17 1C0B  3E  05              MVI  A,5           ;INITIALIZE OXIMETER STATUS IMAGE
18 1C0D  32  727C            STA  COSTA         ;
19 1C10  C9              RET
20 1C11  3A  7014    COMIDL: LDA  SYNFLG        ;
21 1C14  A7              ANA  A                 ;
22 1C15  3A  727C            LDA  COSTA        ;
23 1C18  4F              MOV  C,A               ;IF SYNC'D
24 1C19  3E  01              MVI  A,SRCBIT      ;CLEAR SEARCH BIT
25 1C1B  CA  1C23            JZ   STKSER        ;IF NOT, THEN SET IT
26 1C1E  2F              CMA                    ;                                      ///
```

```
27 1C1F  A1                        ANA    C                                          ///
28 1C20  C3   1C24         JMP     STKSR2                                            ///
29 1C23  B1        STKSER: ORA     C                                                 ///
30 1C24  32   727C STKSR2: STA     COSTA      ;STORE THE NEW VALUE                   ///
31
32 1C27  21   72AD         LXI     H,OMINS    ;HAS MINUTES COUNTER CHANGED ?         ///
33 1C2A  3A   7147         LDA     MINCTR                                            ///
34 1C2D  BE                CMP     M                                                 ///
35 1C2E  77                MOV     M,A        ;UPDATE ANYWAY                         ///
36 1C2F  C2   1C65         JNZ     UPDALL     ;YES, UPDATE AND SEND LIMITS AND STATUS ///
37 1C32  21   727A         LXI     H,OCOSTA                                          ///
38 1C35  3A   727C         LDA     COSTA                                             ///
39 1C38  AE                XRA     M          ;HAS OXIMETER STATUS CHANGED ?         ///
40 1C39  4F                MOV     C,A                                               ///
41 1C3A  21   727B         LXI     H,OCPSTA                                          ///
42 1C3D  3A   727D         LDA     CPSTA      ;OR ALARM STATUS CHANGED ?             ///
43 1C40  AE                XRA     M                                                 ///
44 1C41  B1                ORA     C                                                 ///
45 1C42  C4   1C6C         CNZ     UPDSTA     ;YES, THEN GO DO STATUS OUTPUT         ///
46
47 1C45  3A   713A  LMCK:  LDA     OPNFLG     ;ARE LIMITS IN FLUX ?                  ///
48 1C48  A7                ANA     A                                                 ///
49 1C49  C0                RNZ                ;YES, THEN GO AWAY                     ///
50 1C4A  21   727E         LXI     H,OSATLL   ;NO, THEN CHECK OLD AGAINST NEW        ///
51 1C4D  3A   70C2         LDA     SATLL                                             ///
52 1C50  BE                CMP     M                                                 ///
53 1C51  C2   1C83         JNZ     UPDLIM     ;IF CHANGED, SEND THEM                 ///
54 1C54  23                INX     H                                                 ///
55 1C55  3A   70C6         LDA     RATLL                                             ///
56 1C58  BE                CMP     M                                                 ///
57 1C59  C2   1C83         JNZ     UPDLIM                                            ///
```

RESPOX; MICROBENCH 8080/8085 CROSS ASSEMBLER (V2)-436  30-MAR-85 13:30:07 PAGE 103

```
 1 1C5C  23                INX     H                                                 ///
 2 1C5D  3A   70C7         LDA     RATUL                                             ///
 3 1C60  BE                CMP     M                                                 ///
 4 1C61  C2   1C83         JNZ     UPDLIM                                            ///
 5 1C64  C9                RET                ;IF NO DIFFERENT, THEN GO AWAY         ///
 6
 7 1C65  CD   1C6C UPDALL: CALL    UPDSTA     ;UPDATE STATUS                         ///
 8 1C68  CD   1C83         CALL    UPDLIM     ;AND LIMITS                            ///
 9 1C6B  C9                RET                                                       ///
10
11 1C6C  2A   727C UPDSTA: LHLD    COSTA      ;GET OXIMETER AND ALARM STATUS         ///
12 1C6F  22   727A         SHLD    OCOSTA     ;UPDATE "OLD" IMAGES                   ///
13 1C72  3A   727C         LDA     COSTA      ;GET OXIMETER STATUS                   ///
14 1C75  F6   30           ORI     30H        ;TAG ON THE IDENTIFIER BITS            ///
15 1C77  CD   1D22         CALL    TOBUFR     ;AND PUT IT INTO BUFFER                ///
16 1C7A  3A   727D         LDA     CPSTA      ;GET ALARM STATUS                      ///
17 1C7D  F6   70           ORI     70H        ;TAG ON END OF MESSAGE                 ///
18 1C7F  CD   1D22         CALL    TOBUFR     ;PUT INTO BUFFER                       ///
19 1C82  C9                RET                                                       ///
20
21 1C83  21   727E UPDLIM: LXI     H,OSATLL   ;FIRST UPDATE OLD LIMITS               ///
22 1C86  3A   70C2         LDA     SATLL                                             ///
23 1C89  77                MOV     M,A                                               ///
24 1C8A  23                INX     H                                                 ///
25 1C8B  3A   70C6         LDA     RATLL      ;AND RATE LOWER                        ///
26 1C8E  77                MOV     M,A                                               ///
27 1C8F  23                INX     H                                                 ///
28 1C90  3A   70C7         LDA     RATUL                                             ///
29 1C93  77                MOV     M,A                                               ///
30 1C94  3A   70C2         LDA     SATLL      ;SATURATION LOWER LIMIT                ///
31 1C97  CD   1D3B         CALL    SPLIT      ;INTO NIBBLES                          ///
32 1C9A  7A                MOV     A,D        ;UPPER NIBBLE                          ///
33 1C9B  F6   40           ORI     40H        ;SAT LIMIT IDENTIFIER                  ///
34 1C9D  CD   1D22         CALL    TOBUFR     ;PUT IT INTO BUFFER                    ///
35 1CA0  7B                MOV     A,E        ;AND LOWER NIBBLE                      ///
36 1CA1  CD   1D22         CALL    TOBUFR                                            ///
37 1CA4  3A   70C6         LDA     RATLL      ;RATE LOWER LIMIT                      ///
38 1CA7  CD   1D3B         CALL    SPLIT      ;INTO TWO NIBBLES                      ///
39 1CAA  7A                MOV     A,D        ;MSB'S                                 ///
40 1CAB  CD   1D22         CALL    TOBUFR                                            ///
41 1CAE  7B                MOV     A,E        ;LSB'S                                 ///
42 1CAF  CD   1D22         CALL    TOBUFR                                            ///
43 1CB2  3A   70C7         LDA     RATUL      ;RATE UPPER LIMIT                      ///
44 1CB5  CD   1D3B         CALL    SPLIT      ;INTO NIBBLES                          ///
45 1CB8  7A                MOV     A,D        ;MSB'S                                 ///
46 1CB9  CD   1D22         CALL    TOBUFR                                            ///
47 1CBC  7B                MOV     A,E        ;LSB'S                                 ///
48 1CBD  F6   70           ORI     70H        ;END OF MESSAGE IDENTIFIER             ///
49 1CBF  CD   1D22         CALL    TOBUFR                                            ///
50 1CC2  C9                RET                                                       ///
51
52 1CC3  11   E74A COM240: LXI     D,-(NULMOD+1) ;SEE IF CHARACTER IN PROGRESS       ///
53 1CC6  2A   72AA         LHLD    SNDMOD                                            ///
54 1CC9  19                DAD     D          ;IF SNDMOD > NULMOD THEN BUG OFF       ///
55 1CCA  D8                RC                                                        ///
56
57 1CCB  3A   72A8         LDA     CFLSFL     ;IS PULSE SAMPLE GOING OUT ?           ///
```

```
 1 1CCE  FE    01              CPI   1
 2 1CD0  C2    1CDE            JNZ   RDYCHK      ;NO, THEN GO SEE IF ONE IS READY TO        ///
 3 1CD3  3A    7282            LDA   PLS2        ;YES, THEN GET THE SECOND HALF OF IT       ///
 4 1CD6  CD    1D12            CALL  SENDIT      ;AND SEND IT IMMEDIATELY                   ///
 5 1CD9  AF                    XRA   A           ;AND CLEAR THE PULSE IN PROGRESS FLAG      ///
 6 1CDA  32    72A8            STA   CPLSFL      ;                                          ///
 7 1CDD  C9                    RET                                                          ///
 8
 9 1CDE  FE    02      RDYCHK: CPI   2           ;SAMPLE READY ?                            ///
10 1CE0  C2    1CEE            JNZ   BUFCHK      ;NO, THEN GO CHECK THE BUFFER              ///
11 1CE3  3D                    DCR   A           ;YES, THEN SET PULSE GOING FLAG            ///
12 1CE4  32    72A8            STA   CPLSFL      ;                                          ///
13 1CE7  3A    7281            LDA   PLS1        ;GET TOP HALF OF MESSAGE                   ///
14 1CEA  CD    1D12            CALL  SENDIT      ;SEND IT OUT                               ///
15 1CED  C9                    RET               ;                                          ///
16
17 1CEE  2A    7283    BUFCHK: LHLD  LSTOUT      ;HAS LAST IN BEEN SENT ?                   ///
18 1CF1  7D                    MOV   A,L         ;I.E. LSTOUT=BUFPTR ?                      ///
19 1CF2  2F                    CMA               ;                                          ///
20 1CF3  6F                    MOV   L,A                                                    ///
21 1CF4  7C                    MOV   A,H                                                    ///
22 1CF5  2F                    CMA                                                          ///
23 1CF6  67                    MOV   H,A                                                    ///
24 1CF7  23                    INX   H           ;TWO'S COMPLEMENT                          ///
25 1CF8  EB                    XCHG              ;                                          ///
26 1CF9  2A    7285            LHLD  BUFPTR      ;GET BUFFER POINTER                        ///
27 1CFC  19                    DAD   D           ;POINTER=LAST ?                            ///
28 1CFD  7C                    MOV   A,H         ;                                          ///
29 1CFE  B5                    ORA   L                                                      ///
30 1CFF  C8                    RZ                ;YES, THEN WE'RE CAUGHT UP, GO AWAY !      ///
31
32 1D00  2A    7283            LHLD  LSTOUT      ;NO, THEN GET CHARACTER TO GO              ///
33 1D03  7E                    MOV   A,M         ;GET CHARACTER                             ///
34 1D04  CD    1D12            CALL  SENDIT      ;PUT IT OUT                                ///
35 1D07  2A    7283            LHLD  LSTOUT      ;                                          ///
36 1D0A  CD    1D2D            CALL  BMPBUF      ;BUMP THE POINTER                          ///
37 1D0D  22    7283            SHLD  LSTOUT      ;FOR NEXT GO AROUND                        ///
38 1D10  7E                    MOV   A,M         ;GET CHARACTER                             ///
39 1D11  C9                    RET                                                          ///
40
41 1D12  A7            SENDIT: ANA   A           ;MAKE SURE PARITY BIT IS OK                ///
42 1D13  EA    1D18            JPE   STKCHR      ;                                          ///
43 1D16  F6    80              ORI   80H         ;NO, THEN SET IT                           ///
44 1D18  32    72A9    STKCHR: STA   CHAR.       ;SET IT INTO THE CANNON                    ///
45 1D1B  21    18B8            LXI   H,STARTS    ;AND LIGHT THE FUSE TO SEND THE SERIAL     ///
46 1D1E  22    72AA            SHLD  SNDMOD      ;                                          ///
47 1D21  C9                    RET                                                          ///
48
49 1D22  2A    7285    TOBUFR: LHLD  BUFPTR      ;GET BUFFER POINTER                        ///
50 1D25  77                    MOV   M,A         ;STORE CHARACTER                           ///
51 1D26  CD    1D2D            CALL  BMPBUF      ;BUMP HL WITH WRAP-AROUND                  ///
52 1D29  22    7285            SHLD  BUFPTR      ;AND UPDATE BUFFER POINTER                 ///
53 1D2C  C9                    RET                                                          ///
54
55 1D2D  23            BMPBUF: INX   H           ;BUMP HL PAIR                              ///
56 1D2E  E5                    PUSH  H           ;SAVE HL                                   ///
57 1D2F  D5                    PUSH  D           ;SAVE FROM CALCULATION                     ///
```

```
 1 1D30  11    8D59            LXI   D,-BUFTOP   ;SEE IF OVER THE TOP                       ///
 2 1D33  19                    DAD   D           ;                                          ///
 3 1D34  D1                    POP   D           ;RESTORE REGGIES                           ///
 4 1D35  E1                    POP   H           ;                                          ///
 5 1D36  D0                    RNC               ;IF NOT, THEN HL IS OK AS IS               ///
 6 1D37  21    7287            LXI   H,COMBUF    ;NO, THEN WRAP-AROUND                      ///
 7 1D3A  C9                    RET                                                          ///
 8
 9 1D3B  F5            SPLIT:  PUSH  PSW         ;SAVE IT                                   ///
10 1D3C  E6    0F              ANI   0FH         ;STRIP OFF MSB'S                           ///
11 1D3E  5F                    MOV   E,A         ;STICK LSB'S INTO E                        ///
12 1D3F  F1                    POP   PSW         ;RETRIEVE IT                               ///
13 1D40  0F                    RRC                                                          ///
14 1D41  0F                    RRC                                                          ///
15 1D42  0F                    RRC                                                          ///
16 1D43  0F                    RRC                                                          ///
17 1D44  E6    0F              ANI   0FH         ;GET MSB'S AND STRIP LSB'S                 ///
18 1D46  57                    MOV   D,A         ;AND PUT MSB'S INTO D                      ///
19 1D47  C9                    RET                                                          ///
20
21
```

```
                    ;CHECK LED LEVELS, CALLED BY A/D CONVERSION ROUTINE
                    ; WITH DATA IN D,E...
                    ; DECREASE LED LEVEL IS DATA IS OVERFLOWED, AND INCREASE IT IF UNDERFLOWED.
                    ;
 6 1D48  3A   7011  CKLED1: LDA  INHLED      ;CHECK INHIBIT FLAG
 7 1D4B  FE   02            CPI  2
 8 1D4D  F0                 RP
 9 1D4E  3A   7007          LDA  TSTMOD      ;SET, NO CHECK
10 1D51  E6   08            ANI  8
11 1D53  C0                 RNZ
12 1D54  21   700C          LXI  H,L1ITMR    ;LED LEVEL CODE
13 1D57  7E                 MOV  A,M         ;GET TIMER
14 1D58  B7                 ORA  A
15 1D59  2B                 DCX  H
16 1D5A  2B                 DCX  H
17 1D5B  C0                 RNZ              ;STILL TIMING FROM LAST TIME, NO CHECK
18 1D5C  7B                 MOV  A,E
19 1D5D  B2                 ORA  D           ;CHECK DATA FOR ZERO
20 1D5E  C2   1D81          JNZ  2$
21 1D61  34                 INR  M           ;INCREMENT
22 1D62  7E                 MOV  A,M         ;FETCH IT
23 1D63  B7                 ORA  A
24 1D64  C2   1D6C          JNZ  5$          ;WRAP AROUND TO 64
25 1D67  32   7013          STA  LGFLAG      ;OVERFLOWED, SO ALLOW EITHER GAIN
26 1D6A  36   40            MVI  M,64
27 1D6C  3A   7013  5$:     LDA  LGFLAG      ;IF LGFLAG<>64, STAY IN LOW GAIN
28 1D6F  B7                 ORA  A
29 1D70  C2   1D9B          JNZ  3$
30 1D73  7E                 MOV  A,M
31 1D74  FE   E0            CPI  224         ;COMPARE LED1 TO 224
32 1D76  DA   1D9B          JC   3$          ;STILL OK, NO GAIN CHANGE
33 1D79  3E   01            MVI  A,1         ;RAISE GAIN
34 1D7B  32   7012          STA  GNSEL
35 1D7E  C3   1D9B          JMP  3$
36 1D81  7A          2$:    MOV  A,D
37 1D82  F6   F0            ORI  0F0H
38 1D84  A3                 ANA  E           ;CHECK FOR ALL 1'S
39 1D85  3C                 INR  A
40 1D86  C2   1D9E          JNZ  4$
41 1D89  35                 DCR  M
42 1D8A  7E                 MOV  A,M         ;FETCH LED CODE
43 1D8B  FE   40            CPI  64          ;WRAP AROUND FROM 64 TO 255
44 1D8D  D2   1D92          JNC  6$
45 1D90  36   FF            MVI  M,255
46 1D92  FE   60     6$:    CPI  96          ;96 IS LOWER LIMIT
47 1D94  D2   1D9B          JNC  3$          ;STILL FINE
48 1D97  AF                 XRA  A           ;CUT GAIN
49 1D98  32   7012          STA  GNSEL
50 1D9B  CD   1DF6   3$:    CALL LD1SET
51 1D9E  C9          4$:    RET
52 1D9F  3A   7011  CKLED2: LDA  INHLED
53 1DA2  FE   02            CPI  2
54 1DA4  F0                 RP
55 1DA5  3A   7007          LDA  TSTMOD
56 1DA8  E6   08            ANI  8
57 1DAA  C0                 RNZ
```

RESPOX: MICROBENCH 8080/8085 CROSS ASSEMBLER (V2)-436   30-MAR-85 13:30:07 PAGE 107

```
 1 1DAB  21   700F          LXI  H,L2ITMR
 2 1DAE  7E                 MOV  A,M
 3 1DAF  B7                 ORA  A
 4 1DB0  2B                 DCX  H
 5 1DB1  2B                 DCX  H
 6 1DB2  C0                 RNZ
 7 1DB3  7A                 MOV  A,D
 8 1DB4  B3                 ORA  E
 9 1DB5  C2   1DD8          JNZ  2$
10 1DB8  34                 INR  M
11 1DB9  7E                 MOV  A,M
12 1DBA  B7                 ORA  A
13 1DBB  C2   1DC3          JNZ  5$
14 1DBE  32   7013          STA  LGFLAG
15 1DC1  36   40            MVI  M,64
16 1DC3  3A   7013   5$:    LDA  LGFLAG
17 1DC6  B7                 ORA  A
18 1DC7  C2   1DF2          JNZ  3$
19 1DCA  7E                 MOV  A,M
20 1DCB  FE   E0            CPI  224
21 1DCD  DA   1DF2          JC   3$
22 1DD0  3E   01            MVI  A,1
23 1DD2  32   7012          STA  GNSEL
24 1DD5  C3   1DF2          JMP  3$
25 1DD8  7A          2$:    MOV  A,D
26 1DD9  F6   F0            ORI  0F0H
27 1DDB  A3                 ANA  E
28 1DDC  3C                 INR  A
29 1DDD  C2   1DF5          JNZ  4$
30 1DE0  35                 DCR  M
31 1DE1  7E                 MOV  A,M
32 1DE2  FE   40            CPI  64
```

```
33 1DE4  D2  1DE9           JNC   6$
34 1DE7  36  FF              MVI   M,255
35 1DE9  FE  60        6$:   CPI   96
36 1DEB  D2  1DF2           JNC   3$
37 1DEE  AF                   XRA   A
38 1DEF  32  7012            STA   GNSEL
39 1DF2  CD  1E05      3$:   CALL  LD2SET
40 1DF5  C9              4$:   RET
```

RESPOX: MICROBENCH 8080/8085 CROSS ASSEMBLER (V2)-436   30-MAR-85 13:30:07 PAGE 108

```
                ;COMPUTE VOLTAGE FROM LED CODE AND OUTPUT...
                ;  CALLED WHENEVER LED CODE CHANGES, DOES A QUASI-LOG CONVERSION TO VOLTS.
                ;
 5 1DF6  21  700A  LD1SET:  LXI   H,LED1      ;POINT TO LED CODE
 6 1DF9  7E                  MOV   A,M         ;GET IT
 7 1DFA  23                  INX   H
 8 1DFB  BE                  CMP   M           ;COMPARE TO LAST CODE
 9 1DFC  C8                  RZ                ;SAME, RETURN
10 1DFD  77                  MOV   M,A
11 1DFE  CD  1E14            CALL  LDXSET      ;NOT THE SAME, UPDATE
12 1E01  22  715F            SHLD  VLED1
13 1E04  C9                  RET
14
15 1E05  21  700D  LD2SET:  LXI   H,LED2
16 1E08  7E                  MOV   A,M
17 1E09  23                  INX   H
18 1E0A  BE                  CMP   M           ;COMPARE TO LAST CODE
19 1E0B  C8                  RZ                ;SAME, RETURN
20 1E0C  77                  MOV   M,A
21 1E0D  CD  1E14            CALL  LDXSET
22 1E10  22  7161            SHLD  VLED2
23 1E13  C9                  RET
24
25 1E14  D5        LDXSET:  PUSH  D
26 1E15  4E                  MOV   C,M         ;GET LED CODE
27 1E16  23                  INX   H
28 1E17  3A  7010            LDA   INHPER
29 1E1A  77                  MOV   M,A         ;SET INHIBIT PERIOD
30 1E1B  3A  7014            LDA   SYNFLG      ;CHECK FOR SYNC
31 1E1E  B7                  ORA   A
32 1E1F  CA  1E24            JZ    3$          ;GO FAST IF NOT
33 1E22  36  01              MVI   M,1
34 1E24  21  1E3F  3$:      LXI   H,LEDTBL-3  ;CONVERSION TABLE
35 1E27  23        1$:      INX   H
36 1E28  23                  INX   H
37 1E29  23                  INX   H           ;MOVE TO 1ST TABLE ENTRY
38 1E2A  79                  MOV   A,C         ;GET CODE
39 1E2B  96                  SUB   M           ;-FACTOR
40 1E2C  23                  INX   H           ;POINT TO INCREMENT
41 1E2D  DA  1E27            JC    1$          ;CODE LESS THAN FACTOR, KEEP LOOKING
42 1E30  4E                  MOV   C,M         ;GET INCREMENT
43 1E31  06  00              MVI   B,0
44 1E33  23                  INX   H
45 1E34  5E                  MOV   E,M
46 1E35  23                  INX   H
47 1E36  56                  MOV   D,M
48 1E37  EB                  XCHG
49 1E38  3D        2$:      DCR   A
50 1E39  FA  1E40            JM    10$
51 1E3C  09                  DAD   B
52 1E3D  C3  1E38            JMP   2$
53 1E40  D1        10$:     POP   D
54 1E41  C9                  RET
                ;TABLE OF LED CODE VALUES, INCREMENTS AND BASE VOLTAGES
                ;IF LED CODE>TABLE CODE, THEN MULT. DIFF BY INCREMENT AND ADD TO BASE
```

RESPOX: MICROBENCH 8080/8085 CROSS ASSEMBLER (V2)-436   30-MAR-85 13:30:07 PAGE 109

```
 2 1E42  E0  40     LEDTBL:  DB    224,64
 3 1E44  0800                DW    2048
 4 1E46  C0  20              DB    192,32
 5 1E48  0400                DW    1024
 6 1E4A  A0  10              DB    160,16
 7 1E4C  0200                DW    512
 8 1E4E  80  08              DB    128,8
 9 1E50  0100                DW    256
10 1E52  60  04              DB    96,4
11 1E54  0080                DW    128
12 1E56  40  02              DB    64,2
13 1E58  0040                DW    64
14 1E5A  00  01              DB    0,1
15 1E5C  0000                DW    0
```

```
                        ;A/D CONVERSION ROUTINE....
                        ; CALLED WITH MUX SELECTED, RETURNS DATA IN D,E
                        ; H,L PRESERVED
                        ;
1E5E  AF        ADCVT:  XRA     A
1E5F  D3  00            OUT     DACL            ;CLEAR LOW BYTE
1E61  57              MOV     D,A
1E62  3A  72AF          LDA     GNMSK
1E65  5F              MOV     E,A             ;GET GAIN SEL INTO E AND ADD TO DACH
1E66  06  08            MVI     B,08H           ;MSB
1E68  16  00            MVI     D,0
1E6A  78              MOV     A,B             ;GET NEXT BIT TO BE CHECKED
1E6B  B2        1$:     ORA     D
1E6C  B3              ORA     E
1E6D  F6  70            ORI     070H            ;MASK OFF ANAOLOG OUTPUT
1E6F  D3  01            OUT     DACH            ;TRY IT
1E71  4F              MOV     C,A             ;HIGH BYTE W/NEW BIT (D = HIGH BYTE W/O)
1E72  00              NOP                     ;SETTLING TIME
1E73  00              NOP
1E74  00              NOP
1E75  DB  00            IN      STSREG
1E77  17              RAL                     ;COMP. FLAG TO CARRY
1E78  DA  1E7C          JC      2$              ;ONE MEANS DAC IS LOWER
1E7B  51              MOV     D,C
1E7C  78        2$:     MOV     A,B
1E7D  0F              RRC
1E7E  47              MOV     B,A             ;SHIFT BIT RIGHT ONE PLACE, CHECK FOR FALLING OFF BOTTOM
1E7F  D2  1E6B          JNC     1$
                        ;
                        ;NOW DO SAME THING FOR LOW BYTE...LEAVE HIGH BYTE SET
                        ;
1E82  7A              MOV     A,D
1E83  B3              ORA     E
1E84  F6  70            ORI     070H
1E86  D3  01            OUT     DACH            ;LAST HI BYTE VALUE
1E88  E6  0F            ANI     0FH             ;STRIP OFF GAIN STUFF FROM DAC DATA
1E8A  57              MOV     D,A
1E8B  0E  80            MVI     C,80H
1E8D  1E  00            MVI     E,0
1E8F  79              MOV     A,C             ;NEW BIT
1E90  B3        3$:     ORA     E               ;PLUS LOW BYTE SO FAR...
1E91  D3  00            OUT     DACL
1E93  47              MOV     B,A             ;SAVE LOW BYTE W/ NEW BIT
1E94  00              NOP
1E95  00              NOP
1E96  00              NOP
1E97  DB  00            IN      STSREG          ;GET COMP. FLAG
1E99  17              RAL
1E9A  DA  1E9E          JC      4$
1E9D  58              MOV     E,B             ;UPDATE LOW BYTE
1E9E  79        4$:     MOV     A,C             ;NEW BIT
1E9F  0F              RRC
1EA0  4F              MOV     C,A
1EA1  D2  1E90          JNC     3$
1EA4  C9              RET
```

```
                        ;CALIBRATION TABLES....
                        ; FIRST A TABLE OF RESISTOR CODES AND BETA INDICES, TO MAP RESISTANCE INTO AN INDEX
                        ;   INDEX = 65536*1.5*R/(10+R), R IN K-OHMS
                        ;
1EA5  3232      CALTBL: DW      12850           ;1500 OHMS

1EA7  91B6              DW      37302           ;64
1EA9  93E9              DW      37865
1EAB  9611              DW      38417
1EAD  9842              DW      38978
1EAF  9A79              DW      39545
1EB1  9CB7              DW      40119
1EB3  9EFA              DW      40698
1EB5  A133              DW      41267
1EB7  A370              DW      41840
1EB9  A5B2              DW      42418
1EBB  A7F7              DW      42999
1EBD  AA40              DW      43584
1EBF  AC7D              DW      44157
1EC1  AEBC              DW      44732
1EC3  B10C              DW      45324
1EC5  B35D              DW      45917
1EC7  B5AF              DW      46511
1EC9  B800              DW      47104
1ECB  BA44              DW      47684
1ECD  BC88              DW      48264
1ECF  BED7              DW      48855

1ED1  0000              DW      0
```

```
RESPOX: MICROBENCH 8080/8085 CROSS ASSEMBLER (V2)-436   30-MAR-85 13:30:07 PAGE 112

1
  2                              ;TABLE OF IR BETA CONSTANTS...
  3                              ;
  4  1ED3   3C66  2833   BATBL:  DW    15462,  10291    ;NOMINAL ( 302,201 )
  5  1ED7   2966  7333           DW    10598,  29491
  6
  7                              ;RED BETA CONSTANTS...
  8                              ;
  9  1EDB   1933  BD9A   BBTBL:  DW    6451,   48538    ;0 = NOMINAL ( 126,948 )
 10  1EDF   129A  BC0D           DW    4762,   48141    ;1 = 670NM
 11  1EE3   129A  C05C           DW    4762,   49244
 12  1EE7   12CD  C4AB           DW    4813,   50347
 13  1EEB   12CD  C8FA           DW    4813,   51450
 14  1EEF   1300  CCC7           DW    4864,   52423
 15  1EF3   1300  D116           DW    4864,   53526
 16  1EF7   1333  D4A2           DW    4915,   54434
 17  1EFB   1333  D7EE           DW    4915,   55278
 18  1EFF   1366  DAF8           DW    4966,   56056
 19  1F03   1366  DDC2           DW    4966,   56770
 20  1F07   139A  E04B           DW    5018,   57419
 21  1F0B   13CD  E293           DW    5069,   58003
 22  1F0F   1400  E4B8           DW    5120,   58552
 23  1F13   1433  E660           DW    5171,   58976
 24  1F17   1466  E7E5           DW    5222,   59365
 25  1F1B   149A  E929           DW    5274,   59689
 26  1F1F   14CD  E9EC           DW    5325,   59884
 27  1F23   1500  EAAF           DW    5376,   60079
 28  1F27   1533  EB30           DW    5427,   60208
 29  1F2B   1566  EBF3           DW    5478,   60403
 30  1F2F   15CD  ECF7           DW    5581,   60663   ;21 = 650NM
 31
```

```
RESPOX: MICROBENCH 8080/8085 CROSS ASSEMBLER (V2)-436   30-MAR-85 13:30:07 PAGE 113

1
  2                              ;DATA SPACE.....
  3                              ;
  4                              ;FIRST, THE INITIALIATION LIST....ADDRESS FOLLOWED BY A BYTE OF DATA, ZERO TERMINATES...
  5                              ;
  6  1F33   7000           INILST: DW    VERCOD
  7  1F35   5E                    DB    VERSN
  8  1F36   00                    DB    0
  9
 10  1F37   70C1                  DW    SATLLL
 11  1F39   32                    DB    50
 12  1F3A   55                    DB    85            ;SATLL
 13  1F3B   64                    DB    100
 14  1F3C   64                    DB    100
 15  1F3D   28                    DB    40
 16  1F3E   37                    DB    55            ;RATLL
 17  1F3F   8C                    DB    140           ;RATUL
 18  1F40   FA                    DB    250
 19  1F41   00                    DB    0
 20
 21  1F42   716F                  DW    FMODLL
 22  1F44   01                    DB    1             ;FMODE LIMIT
 23  1F45   01                    DB    1
 24  1F46   09                    DB    9
 25  1F47   00                    DB    0
 26
 27  1F48   7014                  DW    SYNFLG
 28  1F4A   04                    DB    4             ;SYNC INHIBIT COUNT
 29  1F4B   00                    DB    0
 30
 31  1F4C   7017                  DW    HSTLEN
 32  1F4E   04    00              DB    4,0
 33
 34  1F50   7018                  DW    VARLIM        ;VARIATION AND DIFF LIMITS
 35  1F52   06                    DB    6             ;RATE VAR
 36  1F53   06                    DB    6             ;AMPLITUDE
 37  1F54   03                    DB    3             ;RATIO
 38  1F55   03                    DB    3             ;TIME WINDOW
 39  1F56   06                    DB    6             ;EKG
 40  1F57   06                    DB    6             ;RESP
 41  1F58   04                    DB    4
 42  1F59   04                    DB    4
 43  1F5A   02                    DB    2
 44  1F5B   02                    DB    2
 45  1F5C   04                    DB    4
 46  1F5D   06                    DB    6
 47  1F5E   00                    DB    0
 48
 49  1F5F   70D7                  DW    SPLEN         ;SLOPE SPAN
 50  1F61   03                    DB    3
 51  1F62   14                    DB    20            ;NOISE GATE
 52  1F63   20                    DB    32            ;SLOPE THRESHHOLD
 53  1F64   00                    DB    0
 54
```

```
55 1F65  70EC        DW    BEEVOL
56 1F67  14          DB    20              ;BEEVOL
57 1F68  64          DB    100
```

RESPOX; MICROBENCH 8080/8085 CROSS ASSEMBLER (V2)-436   30-MAR-85 13:30:07 PAGE 114

```
 1 1F69  00          DB    0
 2
 3 1F6A  70FA        DW    POLEKG          ;EKG POLARITY
 4 1F6C  01          DB    1
 5 1F6D  00          DB    0
 6 1F6E  70FB        DW    POLEKG+1
 7 1F70  01          DB    1
 8 1F71  00          DB    0
 9
10 1F72  70F3        DW    ALILL
11 1F74  1E    3C    DB    30, 60, 121, 0
   1F76  79    00
12
13 1F78  713E        DW    OPNDLY
14 1F7A  08          DB    8
15 1F7B  00          DB    0
16
17 1F7C  7138        DW    OPNPRM
18 1F7E  70EC        DW    BEEVOL
19 1F80  00          DB    0
20
21 1F81  713C        DW    OPNUL
22 1F83  64          DB    100
23 1F84  00          DB    0
24
25 1F85  7010        DW    INHPER
26 1F87  06          DB    6
27 1F88  00          DB    0
28
29 1F89  7173        DW    RAMIDX+1
30 1F8B  70          DB    HIGH(RAMORG)
31 1F8C  00          DB    0
32
33 1F8D  70EF        DW    ALMVOL
34 1F8F  28          DB    40
35 1F90  00          DB    0
36
37 1F91  70FD        DW    GNEKG           ;EKG GAIN
38 1F93  03          DB    3
39 1F94  FF          DB    255
40 1F95  00          DB    0
41
42 1F96  7106        DW    EKGSNC          ;EKG SYNC FLAG- RESET ONCE
43 1F98  01          DB    1               ;IF RESET, THEN EKG WAS USED AT SOME POINT
44 1F99  00          DB    0
45
46 1F9A  7111        DW    RSPSNC          ;SYNC FOR RESP - SAME AS EKG
47 1F9C  01          DB    1
48 1F9D  00          DB    0
49
50 1F9E  7104        DW    SN2DLY          ;EKG SYNC DELAY
51 1FA0  05          DB    5
52 1FA1  00          DB    0
53
54 1FA2  7112        DW    SN3DLY          ;RESP SYNC DELAY
55 1FA4  02          DB    2
56 1FA5  00          DB    0
```

RESPOX; MICROBENCH 8080/8085 CROSS ASSEMBLER (V2)-436   30-MAR-85 13:30:07 PAGE 115

```
 1
 2 1FA6  700A        DW    LED1            ;START LED CODES AT 64
 3 1FA8  40          DB    64
 4 1FA9  00          DB    0
 5
 6 1FAA  700D        DW    LED2
 7 1FAC  40          DB    64
 8 1FAD  00          DB    0
 9
10 1FAE  716D        DW    VTH             ;R-WAVE COMPARATOR VOLTAGE = 5.25V
11 1FB0  67          DB    103             ;= 2151 = 5.25V
12 1FB1  08          DB    8
13 1FB2  00          DB    0
14
15 1FB3  0000        DW    0               ;PATCH SPACE
16 1FB5  00          DB    0
17 1FB6  0000        DW    0
18 1FB8  00          DB    0
19 1FB9  0000        DW    0               ;TERMINATOR
20
21
22              ;FILL ROM WITH ZERO'S...
23
24       0045       REPT   2000H-$
25                  DB     0
26                  ENDR
```

RESPOX: MICROBENCH 8080/8085 CROSS ASSEMBLER (V2)-436   30-MAR-85 13:30:07 PAGE 116

```
  1
  2        7000                    RAMORG  EQU     7000H     ;ORIGIN...
  3        0400                    RAMLEN  EQU     0400H     ;AND LENGTH
  4
  5        7000                    ORG     RAMORG
  6
  7                        ;VERSION CODE...FIRST BYTE
  8
  9 7000   00              VERCOD: DB      0
 10
 11                        ;FILTERED DATA AND PARAMETERS
 12
 13 7001   00              SAT:    DB      0         ;SATURATION
 14 7002   00              FSAT:   DB      0         ;FILTERED SAT.
 15 7003   00              RATE:   DB      0         ;PULSE RATE
 16 7004   00              FRATE:  DB      0         ;FILTERED RATE
 17
 18 7005   00              FSATN:  DB      0         ;'N' COUNT FOR SAT FILTER
 19 7006   00              FRATN:  DB      0         ;SAME FOR RATE
 20
 21 7007   00              TSTMOD: DB      0  ;TEST FLAGS: 1=XX.X, 2=NO FILTER, 4=NO CAL, 8=NO LED SET
 22
 23 7008   00              CALOK:  DB      0         ;1 = CALIBRATION STABLE
 24 7009   00              CALIDX: DB      0         ;CALIBRATION INDEX
 25
 26                        ;LED LEVELS
 27
 28 700A   00              LED1:   DB      0         ;LED CODE
 29 700B   00              LED1SV: DB      0         ;OLD LED CODE
 30 700C   00              L1ITHR: DB      0         ;LED CURRENT-CHANGING INHIBIT FLAG
 31 700D   00              LED2:   DB      0
 32 700E   00              LED2SV: DB      0
 33 700F   00              L2ITHR: DB      0
 34 7010   00              INHPER: DB      0         ;INHIBIT PERIOD (A CONSTANT)
 35 7011   00              INHLED: DB      0         ;SET NON-ZERO TO INHIBIT LED TWEAKING
 36 7012   00              GNSEL:  DB      0         ;GAIN SELECT
 37 7013   00              LGFLAG: DB      0         ;HI GAIN INHIBIT FLAG
 38
 39                        ;SOME LEVEL3 STUFF:
 40
 41 7014   00              SYNFLG: DB      0         ;COUNTED DOWN TO ZERO FOR PULSE SYNC (BY LEVEL3)
 42 7015   00              CURVAR: DB      0         ;CURRENT VARIATION FLAGS
 43 7016   00              CURDIF: DB      0         ;DIFFERENCE FLAGS
 44 7017   00              HSTLEN: DB      0         ;CURRENT HISTORY LENGTH
 45 7018   00       00     VARLIM: DB      0,0,0,0,0,0    ;VARIATION LIMITS
    701A   00       00
    701C   00       00
 46 701E   00       00     DIFLIM: DB      0,0,0,0,0,0    ;DIFFERENCE LIMITS
    7020   00       00
    7022   00       00
 47 7024   00       00             DB      0,0       ;FILL....
 48
 49                        ;HISTORY BUFFERS.....
 50
 51 7026                   HSTBUF:
 52        0014                    HSTINC  EQU     20
 53        000F                    HSTMAX  EQU     HSTINC-5
```

RESPOX: MICROBENCH 8080/8085 CROSS ASSEMBLER (V2)-436   30-MAR-85 13:30:07 PAGE 117

```
  1 7026   00              PERIOD: DB      0
  2 7027   00              PERDIF: DB      0
  3 7028   00              PERAVG: DB      0
  4 7029   00              PERVAR: DB      0
  5 702A                   PERHST: BLKB    HSTMAX+1
  6
  7 703A   00              CURAMP: DB      0
  8 703B   00              AMPDIF: DB      0
  9 703C   00              AMPAVG: DB      0
 10 703D   00              AMPVAR: DB      0
 11 703E                   AMPHST: BLKB    HSTMAX+1
 12
 13 704E   00              CURRAT: DB      0
 14 704F   00              RATDIF: DB      0
 15 7050   00              RATAVG: DB      0
 16 7051   00              RATVAR: DB      0
 17 7052                   RATHST: BLKB    HSTMAX+1
 18
 19 7062   00              PLSDLY: DB      0
 20 7063   00              DLYDIF: DB      0
 21 7064   00              DLYAVG: DB      0
 22 7065   00              DLYVAR: DB      0
 23 7066                   DLYHST: BLKB    HSTMAX+1
```

```
24
25 7076                    EKGHBF:
26 7076      00            RRPER:  DB      0
27 7077      00            RRDIF:  DB      0
28 7078      00            RRAVG:  DB      0
29 7079      00            RRVAR:  DB      0
30 707A                    RRHST:  BLKB    HSTMAX+1
31
32 708A                    RSPHBF:
33 708A      00            RSPPER: DB      0
34 708B      00            RSPDIF: DB      0
35 708C      00            RSPAVG: DB      0
36 708D      00            RSPVAR: DB      0
37 708E                    RSPHST: BLKB    HSTMAX+1
38
39                         ;DATA PARAMETERS...
40
41 709E      00            DATFLG: DB      0       ;DATA-READY FLAG (SET BY MUNCH)
42 709F      0000          MAX1:   DW      0       ;WAVEFORM MAX - CH.1 (IR)
43 70A1      0000          MIN1:   DW      0
44 70A3      0000          MAX2:   DW      0
45 70A5      0000          MIN2:   DW      0
46 70A7      0000          MXSLOP: DW      0       ;MAX SLOPE, CH.1
47
48 70A9      0000          RATRAT: DW      0
49 70AB      0000          ARAT:   DW      0
50 70AD      0000          BRAT:   DW      0
51 70AF      0000          FRATIO: DW      0
52 70B1      0000          XRATIO: DW      0
53
54 70B3      00            PERCTR: DB      0       ;PERIOD COUNTER, INCREMENTED BY MUNCH, RESET BY LEVEL3
55
56 70B4      00            SYNDLY: DB      0       ;DELAY FOR FILTERING
57 70B5      00            BPCTR:  DB      0       ;BAD PULSE COUNTER
```

RESPOX: MICROBENCH 8080/8085 CROSS ASSEMBLER (V2)-436   30-MAR-85 13:30:07 PAGE 118

```
 1 70B6      00            NCHFLG: DB      0       ;NOTCH COUNTER
 2
 3 70B7      0000          SATX:   DW      0
 4 70B9      0000          FSATX:  DW      0
 5 70BB      0000          FSATAC: DW      0
 6 70BD      00            FSATDP: DB      0
 7 70BE      0000          FRATX:  DW      0
 8 70C0      00            XMPY:   DB      0
 9
10
11 70C1      00            SATLLL: DB      0       ;SAT LOWER LIMIT LIMIT
12 70C2      00            SATLL:  DB      0       ;SATURATION ALARM LOWER LIMIT
13 70C3      00            SATUL:  DB      0
14 70C4      00            SATULL: DB      0       ;UPPER LIMIT LIMIT
15 70C5      00            RATLLL: DB      0       ;RATE LOWER LIMIT LIMIT
16 70C6      00            RATLL:  DB      0       ;PULSE RATE LOWER LIMIT
17 70C7      00            RATUL:  DB      0       ;DITTO UPPER LIMIT
18 70C8      00            RATULL: DB      0       ;UPPER LIMIT LIMIT
19 70C9      00            ALMFLG: DB      0       ;ALARM FLAG BITS (SALBIT, RALBIT)
20 70CA      00            STATUS: DB      0       ;STATUS REGISTER FOR LEADS OFF BIT
21
22                         ;PULSE PARAMETERS...
23
24 70CB      00            MCHMOD: DB      0
25 70CC      0000          PLSMX1: DW      0       ;CURRENT MAX - CH.1
26 70CE      0000          PLSMN1: DW      0       ;CURRENT CH.1 MIN
27 70D0      0000          PLSSLP: DW      0       ;MAX SLOPE - CH.1
28 70D2      0000          PLSMX2: DW      0       ;CH.2 MAX/MIN
29 70D4      0000          PLSMN2: DW      0
30 70D6      00            MAXIDX: DB      0
31
32 70D7      00            SPLEN:  DB      0       ;SLOPE SPAN (# POINTS, ODD)
33 70D8      00            NOISE:  DB      0       ;NOISE GATE
34 70D9      0000          PLSTHD: DW      0       ;PULSE THRESHHOLD
35 70DB      00            ERRCOD: DB      0       ;ERROR CODE
36 70DC      0000          OLDMAX: DW      0       ;LAST MAX CODE (FOR BLIP)
37 70DE      00            BLPIDX: DB      0       ;DATA BUFFER INDEX FOR BLIP
38
39 70DF      0000          BO1:    DW      0       ;BETA CONSTANTS
40 70E1      0000          BR1:    DW      0
41 70E3      0000          BO2:    DW      0
42 70E5      0000          BR2:    DW      0
43 70E7      00            CALFLG: DB      0       ;COUNT-DOWN FLAG
44 70E8      0000          CALRES: DW      0       ;RESISTOR CODE (CAL/REF)
45
46                         ;BEEPER PARAMETERS...
47
48 70EA      00            BEECNT: DB      0       ;BEEP TIMER (1/60'S SEC, CONTINUOUS IF MINUS)
49 70EB      00            BEEVLL: DB      0       ;LOWER LIMIT FOR BEEP VOL
50 70EC      00            BEEVOL: DB      0       ;NOMINAL VOLUME (NON-ALARM)
51 70ED      00            BEEVUL: DB      0       ;UPPER LIMIT
52 70EE      00            ALMVLL: DB      0       ;ALARM LOWER LIMIT
53 70EF      00            ALMVOL: DB      0       ;ALARM VOLUME
54 70F0      00            ALMVUL: DB      0       ;ALARM UPPER LIMIT
55 70F1      00            ALIFLG: DB      0       ;ALARM INHIBIT FLAG
56 70F2      00            ALICTR: DB      0       ;ALARM INHIBIT TIMER
57
```

```
RESPOX: MICROBENCH 8080/8085 CROSS ASSEMBLER (V2)-436  30-MAR-85 13:30:07 PAGE 119

1  70F3   00              ALILL:  DB      0       ;LOWER PERIOD LIMIT
  2  70F4   00              ALIPER: DB      0       ;ALARM INHIBIT TIMER PERIOD
  3  70F5   00              ALIUL:  DB      0       ;PERIOD UPPER LIMIT
  4
  5  70F6   00              ALMDLY: DB      0       ;DELAYED TIME-OUT ALARM
  6  70F7   00              ALCFLG: DB      0       ;ALARM-CHECKING FLAG
  7
  8                      ;                       EKG STUFF
  9                      ;
 10  70F8   00              EKGTMR: DB      0       ;EKG TIMEOUT COUNTER
 11  70F9   00              POLCGL: DB      0       ;LOWER LIMIT FOR POLARIT
 12  70FA   00              POLEKG: DB      0       ;POLARITY SETTING
 13  70FB   00              POLCGH: DB      0       ;HIGH LIMIT
 14  70FC   00              GNEKGL: DB      0       ;DITTO FOR GAIN
 15  70FD   00              GNEKG:  DB      0
 16  70FE   00              GNEKGH: DB      0
 17  70FF   00              EKGPER: DB      0       ;R WAVE PERIOD COUNTER
 18  7100   00              EKGFLG: DB      0       ;R WAVE FLAG
 19  7101   00              POLSAV: DB      0       ;PRIOR POLARITY SETTING
 20  7102   00              GAINSV: DB      0       ;PRIOR GAIN SETTING
 21  7103   00              DLYEKG: DB      0       ;DELAY FOR CHANGING DATA
 22  7104   00              SN2DLY: DB      0       ;EKG SYNC DELAY
 23  7105   00              HRRFSH: DB      0       ;3 SEC TIMER FOR AGC GAIN REFRESH- ONLY WHEN NO ECG
 24  7106   00              EKGSNC: DB      0       ;EKG SYNC CONDITION FLAG
 25  7107   00              BADEKG: DB      0       ; BAD EKG PULSE REJECT TICKETS
 26  7108   00              DATTRG: DB      0       ;POINTER TO PULSE DATA TO SYNCRONIZE R-WAVE
 27  7109   00              WINTMR: DB      0       ;TIMER FOR R-WAVE TO OPTICAL PULSE DELAY
 28  710A   00              WINFLG: DB      0       ;FLAG TO STOP TIMING WHEN A PULSE IS FOUND
 29  710B   00              RATCLK: DB      0       ;TIMEOUT COUNTER FOR RATE ANALOG OUTPUT
 30  710C   00              SATCLK: DB      0       ;TIMEOUT COUNTER FOR SAT ANALOG OUTPUT
 31  710D   00              LDSFLG: DB      0       ;LEADS OFF DETECTION FLAG
 32
 33
 34                      ;       RESP STUFF
 35                      ;
 36  710E   00              RSPCNT: DB      0       ;PERIOD COUNTER
 37  710F   00              RSPTMR: DB      0       ;TIMEOUT COUNTER
 38  7110   00              RSPFLG: DB      0       ;FLAG
 39  7111   00              RSPSNC: DB      0       ;SYNC CONDITION FLAG
 40  7112   00              SN3DLY: DB      0       ;SYNC DELAY BEFORE DISPLAYING PARAMS
 41  7113   00              RESP:   DB      0       ;UNFILTERED RESP RATE
 42  7114   00              FRSP:   DB      0       ;FILTERED RATE
 43  7115   00              FRSPN:  DB      0       ;FILTER COEFFICIENT
 44  7116   0000            FRSPX:  DW      0       ;OLD FILTERED DATA
 45
 46                      ;DISPLAY PARAMETERS...
 47
 48  7118   00              DIGBNK: DB      0       ;DISPLAY BLINK BITS (1 = BLINK)
 49  7119   00              INDBNK: DB      0       ;BLINK BITS FOR INDICATORS
 50  711A   00              FSTBNK: DB      0       ;FAST BLINK BITS FOR DITTO
 51  711B   00              DIGIDX: DB      0       ;DISPLAY BUFFER INDEX (3 BITS)
 52  711C                   DIGBUF:                 ;BUFFER...FIRST BYTE = DATA, 2ND = MASK BITS
 53  711C   0000            DSPFD1: DW      0       ;UPPER DISPLAY, LSD
 54  711E   0000                    DW      0
 55  7120   0000                    DW      0
 56  7122   0000            DSPFD2: DW      0
 57  7124   0000                    DW      0

RESPOX: MICROBENCH 8080/8085 CROSS ASSEMBLER (V2)-436  30-MAR-85 13:30:07 PAGE 120

1  7126   0000                    DW      0
  2  7128   0000            DSPMTL: DW      0       ;ANALOG METER, LOW BYTE
  3  712A   0000            DSPMTH: DW      0
  4  712C   0000            DSPLMP: DW      0       ;LAMP BITS
  5  712E   00              DSPBKF: DB      0       ;SET NON-ZERO FOR BLANK DISPLAY (BY TIME-OUT)
  6  712F   00              DSPOK:  DB      0       ;FLAG FOR SILENT RUNNING MODE
  7  7130   00              MODESV: DB      0       ;OLD FMODE - USED FOR RETURN FROM SILENT MODE
  8
  9                      ;KNOB & BUTTON PARAMETERS...
 10
 11  7131   00              KNBFLG: DB      0       ;SET TO +/-1 TO SKIP NEXT STEP OF SAME DIRECTION
 12  7132   00              KNBCTR: DB      0       ;KNOB UP/DOWN COUNT REQUEST
 13  7133   00              BUTFIL: DB      0       ;BOUNCE FILTER
 14  7134   00              BUTCOD: DB      0       ;BUTTON CODE (STORED BY INTERRUPT)
 15  7135   00              BUTFLG: DB      0       ;BUTTON STORED FLAG ( " )
 16  7136   00              OLDBUT: DB      0       ;PREVIOUS BUTTON CODE
 17  7137   00              NEWBUT: DB      0
 18
 19  7138   0000            OPNPRM: DW      0       ;POINTER TO OPEN PARAMETER
 20  713A   00              OPNFLG: DB      0       ;SET NON-ZERO TO INHIBIT NORMAL DISPLAY
 21  713B   00              OPNLL:  DB      0       ;LOWER LIMIT FOR ABOVE PARAMETER
 22  713C   00              OPNUL:  DB      0       ;UPPER LIMIT
 23  713D   00              OPNTMR: DB      0       ;TIMER FOR OPEN PARAM.
 24  713E   00              OPNDLY: DB      0       ;NOMINAL TIME FOR ABOVE
 25  713F   0000            ICELL:  DW      0       ;INDIRECT PARAMETER
 26  7141   00              IFLG:   DB      0       ;1 = DIDDLE ADDRESS, 2 = DIDDLE CONTENTS
 27  7142   0000            PRMFLD: DW      0       ;PARAMETER DISPLAY FIELD (DSPFD1 OR DSPFD2)
 28
 29
 30                      ;CLOCK STUFF...
 31
 32  7144   00              MSCTR:  DB      0       ;MILLISECOND COUNTER
 33  7145   00              QSCFLG: DB      0       ;QUARTER-SECOND FLAG
 34  7146   00              QSCCTR: DB      0       ;QUARTER-SECOND COUNTER
 35  7147   00              MINCTR: DB      0       ;MINUTE COUNTER (0 TO 59)
 36  7148   00              HRCTR:  DB      0       ;HOUR COUNTER
 37  7149   00              PLSTMR: DB      0       ;PULSE TIME-OUT
 38  714A   00              SATTMR: DB      0       ;SAT UPDATE TIME-OUT
```

```
39                      ;MISC...
40
41
42 714B   00            ADIDX:  DB      0       ;A/D CONVERSION INDEX
43 714C   0000          V1:     DW      0       ;NON-OFFSET SIGNAL
44 714E   0000          V2:     DW      0
45 7150   0000          OFWSNS: DW      0       ;OVERFLOW SENSE
46 7152   0000          VCAL:   DW      0       ;CAL RESISTOR VOLTAGE
47 7154   0000          VTMP:   DW      0
48 7156   0000          VREF:   DW      0       ;CAL REFERENCE
49 7158   0000          VBAT:   DW      0       ;BATTERY VOLTAGE...
50 715A   0000          IDSP:   DW      0
51
52                      ;SAMPLE-HOLD OUTPUT STUFF...
53
54 715C   00            SHIDX:  DB      0       ;INDEX BIT
55 715D   0000          SHPTR:  DW      0       ;POINTER TO NEXT WORD
56 715F                 SHBUF:
57 715F   0000          VLED1:  DW      0       ;LED CONTROL VOLTAGES
```

RESPOX: MICROBENCH 8080/8085 CROSS ASSEMBLER (V2)-436   30-MAR-85 13:30:07 PAGE 121

```
 1 7161   0000          VLED2:  DW      0
 2 7163   0000          VBEEP:  DW      0       ;BEEPER CONTROL VOLTAGE
 3 7165   0000          VVOL:   DW      0       ;VOLUME
 4 7167   0000          VVOLSV: DW      0       ;SAVED VOLUME (FOR END OF COUNT)
 5 7169   0000          SATOUT: DW      0       ;ANALOG SAT OUT
 6 716B   0000          RATOUT: DW      0       ;RATE OUT
 7 716D   0000          VTH:    DW      0       ;R-WAVE COMPARATOR OUTPUT
 8
 9                      ;FILTER BUFFERS...
10
11 716F   00            FMODLL: DB      0       ;FILTER MODE LIMIT
12 7170   00            FMODE:  DB      0       ;FILTER MODE (1 = NORMAL, 2 = BETA-BEAT, 3 = SAT ONLY)
13 7171   00            FMODUL: DB      0
14
15 7172   0000          RAMIDX: DW      0
16 7174   0000          ROMIDX: DW      0
17 7176   00            ROMSUM: DB      0
18
19                      ;DATA INPUT BUFFER...
20
21        0100                  BUFLEN  EQU     256     ;64 SAMPLES...(APPROX 1 SEC)
22        00FF                  BUFMSK  EQU     BUFLEN-1
23 7177   00            DATCLK: DB      0       ;TIMER
24 7178   00            DATIDX: DB      0       ;BUFFER INDEX, USED BY INTERRUPT ROUTINE
25 7179   00            DTOIDX: DB      0       ;DATA OUT INDEX (USED BY MUNCH ROUTINE)
26 717A                 DATBUF: BLKB    BUFLEN  ;RING BUFFER, 4 BYTES PER 2-VALUE SAMPLE
27
28                      ; COMMUNICATIONS DATA STORAGE...
29
30 727A   00            OCOSTA: DB      0       ;OLD OXIMETER STATUS                    ///
31 727B   00            OCPSTA: DB      0       ;OLD ALARM (PATIENT) STATUS             ///
32 727C   00            COSTA:  DB      0       ;OXIMETER CURRENT STATUS                ///
33 727D   00            CPSTA:  DB      0       ;ALARM (PATIENT) CURRENT STATUS         ///
34
35 727E   00            OSATLL: DB      0       ;OLD SATURATION LIMIT                   ///
36 727F   00            ORATLL: DB      0       ;OLD RATE LOWER LIMIT                   ///
37 7280   00            ORATUL: DB      0       ;OLD RATE UPPER LIMIT                   ///
38
39 7281   00            PLS1:   DB      0       ;PULSE SAMPLE FIRST CHARACTER           ///
40 7282   00            PLS2:   DB      0       ;PULSE SAMPLE SECOND CHARACTER          ///
41
42 7283   0000          LSTOUT: DW      0       ;LAST CHARACTER SENT POINTER            ///
43 7285   0000          BUFPTR: DW      0       ;NEXT CHARACTER INTO BUFFER POINTER     ///
44 7287                 COMBUF: BLKB    32      ;COMMUNICATIONS BUFFER                  ///
45 72A7   00            BUFTOP: DB      0       ;TOP OF COMMUNICATIONS BUFFER           ///
46 72A8   00            CPLSFL: DB      0       ;PULSE IN PROGRESS FLAG                 ///
47 72A9   00            CHAR:   DB      0       ;CHARACTER IN TRANSMISSION              ///
48 72AA   0000          SNDMOD: DW      0       ;MODE OF SERIAL OUTPUT ROUTINE          ///
49 72AC   00            BITCNT: DB      0       ;BIT COUNT FOR SERIAL OUTPUT            ///
50
51 72AD   00            OMINS:  DB      0       ;OLD MINUTES STORAGE                    ///
52 72AE   00            DIGERR: DB      0       ;DIAGNOSTIC CODE STORAGE (BUT NOTHING HAPPENS) ///
53
54 72AF   00            GNMSK:  DB      0       ;GAIN MASK FOR DACH DATA
55                              ;
56                              ;
57                              ;
```

RESPOX: MICROBENCH 8080/8085 CROSS ASSEMBLER (V2)-436   30-MAR-85 13:30:07 PAGE 122

```
 1                      ;STACK...
 2
 3        0040                  STCKLN  EQU     64      ;BYTES
 4
 5        73C0                  ORG     RAMORG+RAMLEN-STCKLN
 6
 7                              BLKB    STCKLN
 8 7400                 STCK:
 9
10
11
12
13                              END
```

RESPOX; MICROBENCH 8080/8085 CROSS ASSEMBLER (V2)-436   30-MAR-85 13:30:07 PAGE 123
SYMBOL TABLE

| A | X0007 | ADCHK | 1976 | ADCHK2 | 19F8 | ADCVT | 1E5E | ADIDX | 714B |
|---|---|---|---|---|---|---|---|---|---|
| ALCFLG | 70F7 | ALICHK | 16C7 | ALICOD= | 0001 | ALICTR | 70F2 | ALIFLG | 70F1 |
| ALILL | 70F3 | ALIPER | 70F4 | ALIUL | 70F5 | ALMCHK | 0C37 | ALHCKD | 0CA0 |
| ALHCKC | 0D49 | ALHCK2 | 0D7E | ALMDLY | 70F6 | ALMFLG | 70C9 | ALHPCH= | 006E |
| ALMULL | 70EE | ALMVOL | 70EF | ALHVUL | 70F0 | AMPAVG | 703C | AMPDIF | 703B |
| AMPHST | 703E | AMPVAR | 703D | ARAT | 70AB | AUDENB= | 0004 | B | X0000 |
| BADEKG | 7107 | BATBIT= | 0008 | BATEL | 1ED3 | BATCHK | 0083 | BATCOD= | 0080 |
| BATLH1= | FBFB | BATLH2= | FB50 | BBTBL | 1EDB | BCGTBL | 10D9 | BEECNT | 70EA |
| BEEP | 14BE | BEEVLL | 70EB | BEEVOL | 70EC | BEEVUL | 70ED | BITCNT | 72AC |
| BLIP | 110D | BLIP2 | 11D0 | BLKOUT | 13F9 | BLPIDX | 70DE | BLPTHI | 11B0 |
| BHPBUF | 1D2D | BNKLIT | 1484 | BNKOFF | 188F | BNKON | 1881 | B01 | 70DF |
| B02 | 70E3 | BPCTR | 70B5 | BRAT | 70AD | BR1 | 70E1 | BR2 | 70E5 |
| BUFCHK | 1CEE | BUFLEN= | 0100 | BUFHSK= | 00FF | BUFFTR | 2285 | BUFTOP | 72A7 |
| BUTCLS | 15B7 | BUTCOD | 7134 | BUTCTO | 15E0 | BUTFIL | 7133 | BUTFLG | 7135 |
| BUTOPN | 1552 | BUTREG= | 0004 | BUTTBL | 175A | BUTTON | 14CE | C | X0001 |
| CALCHK | 0E4E | CALFLG | 70E7 | CALIDX | 7009 | CALOK | 700B | CALRES | 70E8 |
| CALTBL | 1EA5 | CHAR | 72A9 | CHGEKG= | 0006 | CHKEKG | 1AA6 | CHKNCH | 06B6 |
| CHKRSP | 1B04 | CHKWIN | 1AF6 | CKLED1 | 1D48 | CKLED2 | 1D9F | CKRFSH | 1B4D |
| CLKINT | 18B0 | CLOCK | 17A1 | CLRLIT | 1475 | CLRLT2 | 147C | COMBEG | 1BFC |
| COMBUF | 7287 | COMIDL | 1C11 | COMRAT | 06E2 | COMRSP | 070E | COMRT2 | 0708 |
| COMRT3 | 06E5 | COMSAT | 0889 | COM240 | 1CC3 | COSTA | 727C | CPLSFL | 72A8 |
| CPSTA | 727D | CURAMP | 703A | CURDIF | 7016 | CURRAT | 704E | CURVAR | 7015 |
| D | X0002 | DACH | 0001 | DACL | = 0000 | DATBUF | 717A | DATCLK | 7177 |
| DATFLG | 709E | DATIDX | 717B | DATIRG | 7108 | DEC | 12F1 | DECDON | 0414 |
| DECDSP | 1356 | DECTBL | 13F6 | DEKGHX= | 00AF | DIDJFR= | 0001 | DIECHK | 05D3 |
| DIFF | 04F5 | DIFLIH | 701E | DIGBNK | 7118 | DIGBUF | 711C | DIGERR | 72AE |
| DIGIDX | 711B | DIV | 128D | DIVRND | 12C3 | DIV16 | 12F6 | DLOOP | 1292 |
| DLYAVG | 7064 | DLYDIF | 7063 | DLYEKG | 7103 | DLYHST | 7066 | DLYVAR | 7065 |
| DHULT | 12CA | DRTJPR= | 0002 | DSPBKF | 712E | DSPBLK | 1452 | DSPBNK | 1450 |
| DSPCVT | 13A9 | DSPCV2 | 13B5 | DSPDIG= | 0005 | DSPFD1 | 711C | DSPFD2 | 7122 |
| DSPINT | 1913 | DSPLHP | 712C | DSPHIH | 712A | DSPHTL | 7128 | DSPOK | 712F |
| DSPOPN | 161E | DSPRET | 1A1F | DSPSEL= | 0004 | DSPSR | 0A0F | DSPUBK | 1464 |
| DTDIDX | 7179 | E | X0003 | EKGFLG | 7100 | EKGHBF | 7076 | EKGHUP | 06A6 |
| EKGPER | 70FF | EKGPOL= | 0003 | EKGSNC | 7106 | EKGTNO | 0BCC | EKGTHR | 70F8 |
| ENDSHD | 18FC | ERRCOD | 70DB | ERRDSP | 01F0 | EXIT | 12B9 | FD1MSK= | 0007 |
| FD2HSK= | 0038 | FEKGHX= | 00BF | FILMPY | 09BA | FILPLS | 09CA | FILRAT | 0947 |
| FILRSP | 0A1A | FILSAT | 0974 | FILSET | 0A41 | FILTBL | 0AB6 | FMODE | 7170 |
| FMODLL | 716F | FMODUL | 7171 | FRATE | 7004 | FRATIO | 70AF | FRATN | 7006 |
| FRATX | 70BE | FRSP | 7114 | FRSPN | 7115 | FRSPX | 7116 | FSAT | 7002 |
| FSATAC | 70DB | FSATDF | 70BD | FSATN | 7005 | FSATX | 70B9 | FSTBNK | 711A |
| FSTLIT | 1484 | GAINSV | 7102 | GNEKG | 70FD | GNEKGN | 70FE | GNEKGL | 70FC |
| GMHSK | 72AF | GHSEL | 7012 | H | X0004 | HRCTR | 714B | HRESET | 00B3 |
| HRRFSH | 7105 | HRTBIT= | 0001 | HSTAVG | 0530 | HSTBUF | 7026 | HSTCHP | 049E |
| HSTCP1 | 04AD | HSTCP2 | 04B2 | HSTEKG | 04E5 | HSTINC= | 0014 | HSILEN | 7017 |
| HSTMAX= | 000F | HSTRSP | 04ED | HSTUPD | 0668 | HSTUP1 | 0677 | HSTUP2 | 067C |
| HSTVAR | 0567 | ICELL | 713F | IDSP | 715A | IDSPHX= | 009F | IFLG | 7141 |
| ILOOK | 160D | ILOOK2 | 1612 | INBRNK | 7119 | INDRCT | 1600 | INHLED | 7011 |
| INHPER | 7010 | INIDSP | 0242 | INILST | 1F33 | INIT | 022A | INTHE | 132E |
| INTHL | 1334 | ISUM | 10E0 | KNBCTR | 7132 | KNBFLG | 7131 | KNOB | 16FF |
| L | X0005 | LDSCHK | 07F9 | LDSFLG | 710D | LDXSET | 1E14 | LD1SET | 1DF6 |
| LD2SET | 1E05 | LEDTBL | 1E42 | LEDTST | 01A6 | LED1 | 700A | LED1SV | 700B |
| LED2 | 700D | LED2SV | 700E | LEVEL3 | 0266 | LGFLAG | 7013 | LINTRO | 0641 |
| LHCK | 1C45 | LOG | 0505 | LOOP | 0059 | LRTBIT= | 0002 | LSTOUT | 7203 |
| LVL3JR | 072B | L1ITHR | 700C | L2ITHR | 700F | M | X0006 | MARK | = 0040 |
| MAXIDX | 70D6 | MAX1 | 709F | MAX2 | 70A3 | MCHERR | 10AE | MCHER9 | 10D4 |
| MCHHOD | 70CB | MCHRET | 10BD | MCH1 | 0FB3 | MCH2 | 1014 | MCH3 | 102E |
| MINCTR | 7147 | MIN1 | 70A1 | MIN2 | 70A5 | MLOOP | 12E9 | MOUCHG | 1B12 |

RESPOX; MICROBENCH 8080/8085 CROSS ASSEMBLER (V2)-436   30-MAR-85 13:30:07 PAGE 123+
SYMBOL TABLE

| MODESV | 7130 | MPY16 | 1209 | MPY32 | 1232 | MSCTR | 7144 | MULT | 12E4 |
|---|---|---|---|---|---|---|---|---|---|
| MUNCH | 0F38 | MUXSEL= | 0002 | MXSLOP | 70A7 | NCHFLG | 70B6 | NEGCDE | 134E |
| NEGDE | 1340 | NEGHL | 1348 | NEWBHL | 7137 | NOISE | 70D8 | NULHOD | 1B85 |
| OCOSTA | 727A | OCPSTA | 727B | OFFDSP | 16BB | OFWMX | = 004F | OFUSNS | 7150 |
| OLDBUT | 7136 | OLDMAX | 70DC | OMINS | 72AD | OPNDLY | 713E | OPNFLG | 713A |
| OPNLL | 713B | OPNPRH | 7138 | OPNTHR | 713D | OPNUL | 713C | ORATLL | 727F |
| ORATLL | 7280 | OSATLL | 727E | OXIATT= | 0002 | PERAVG | 7028 | PERCTR | 70B3 |
| PERDIF | 7027 | PERHST | 702A | PERIOD | 7026 | PERVAR | 7029 | PLSDLY | 7062 |
| PLSERR | 03CC | PLSHN1 | 70CE | PLSHN2 | 70D4 | PLSMX1 | 70CC | PLSMX2 | 70D2 |
| PLSOK | 031E | PLSRET | 03FF | PLSSLP | 70D0 | PLSTHD | 70D9 | PLSTHO | 0B2C |
| PLSTHR | 7149 | PLS1 | 72B1 | PLS2 | 72B2 | POLCGL | 70FB | POLCGL | 70F9 |
| POLEKG | 70FA | POLSAV | 7101 | PRMFLD | 7142 | PRNTBL | 177A | PSW | X0006 |
| OSCCTR | 7146 | OSCFLG | 7145 | RAHIDL | 0176 | RAHIDX | 7172 | RAHLEN= | 0400 |
| RAHORG= | 7000 | RAHTST | 00FB | RATAVG | 7050 | RATCLK | 710B | RATDIF | 704F |
| RATE | 7003 | RATLL | 70C6 | RATLLL | 70C5 | RATOUT | 716D |
| RATRAT | 70A9 | RATHST | 7052 | RATULL | 70C8 | RATVAR | 7051 | RDYCHK | 1CDE |
| RESP | 7113 | RFSHOP | 15E7 | RHICOD= | 0002 | RLOCOD= | 0002 | RNDOFF | 12BB |
| ROHIDL | 0141 | ROMIDX | 7174 | ROHSUM | 7176 | RONTST | 00DE | RRAVG | 7078 |
| RRDIF | 7077 | RRHST | 707A | RRPER | 7076 | RRVAR | 7079 | RSPAVG | 708C |
| RSPCNT | 710E | RSPCTR | 1A98 | RSPDIF | 708B | RSPFLG | 7110 | RSPHBF | 708A |
| RSPHST | 708E | RSPHUP | 06AE | RSPLV3 | 081A | RSPPER | 708A | RSPSNC | 7111 |
| RSPTHO | 0C0F | RSPTHR | 710F | RSPVAR | 708D | RSTRWV= | 0007 | SAT | 7001 |
| SATBIT= | 0004 | SATCLK | 710C | SATLL | 70C2 | SATLLL | 70C1 | SATOUT | 7169 |
| SATTHO | 0BB9 | SATTHR | 714A | SATUL | 70C3 | SATULL | 70C4 | SAIX | 70B7 |
| SCL100 | 125F | SCL250 | 1276 | SEGE | = 005B | SEGF | = 001B | SEGR | = 001B |
| SEG4 | = 002E | SEG5 | = 006B | SEG6 | = 007B | SEG7 | = 0025 | SEG8 | = 007F |
| SEG9 | = 002F | SENDIT | 1D12 | SHBEEP= | 000B | SHBUF | 715F | SHFTDE | 1A92 |
| SETIRG | 07E3 | SHBCDE | 092D | SHICOD= | 0010 | SHIDX | 715C | SHLED2 | 000D |
| SHFTHL | 1A71 | SETLIT | 146C | SHLED1= | 000E | SHLED2 | 000D | |  |
| SHPTR | 715D | SHVOL | = 0007 | SLOCOD= | 0008 | SNDDEC | 043D | SHDHOD | 72AA |
| SNDMON | 0404 | SNDOUT | 1B66 | SN2DLY | 7104 | SN3DLY | 7112 | SP | X0006 |
| SPACE | = 00C0 | SPINR | 1BD9 | SPLEN | 7D07 | SPLIT | 1D3B | SRCBIT= | 0001 |
| START | 0040 | STARIS | 18B8 | STATUS | 70CA | STCK | 7400 | STCKLN= | 0040 |
| STIK1 | 1133 | STIK2 | 113E | STKCHR | 1D18 | STKSER | 1C23 | STKSR2 | 1C24 |
| STOPBG | 18CB | STSREG= | 0000 | SYNCOD= | 0020 | SYNCOK | 0310 | SYNDLY | 70B4 |

```
SYNFLG  7014    TEST    12A2    TOBUER  1D22    TSTMOD  7007    TWKLED  0E0C
UPDALL  1C65    UPDLIM  1C83    UPDSTA  1C6C    VARCHK  058A    VARLIM  7018
VBAT    7158    VBEEP   7163    VBHX  = 008F    VCAL    7152    VCALHX= 005F
VERCOD  7000    VERSN = 005E    VLED1   715F    VLED2   7161    VREF    7156
VREFHX= 007F    VTH     716D    VTHP    7154    VTHFHX= 006F    VVOL    7165
VVOLSV  7167    V1      714C    V1HX  = 002F    V1PRM = 000F    V2      714E
V2HX  = 003F    V2PRM = 001F    WATMOD  190A    WINFLG  710A    WINTMR  7109
XBLIP2  11F5    XDSPCV  13B4    XFRPLS  044C    XMPY    70C0    XRATIO  70B1
XSAT    08A0
Q_ABSQ  7400    00

MODULE: RESPOX
ERRORS DETECTED: 0

FREE CORE: 118. WORDS
.LP:=RESPOX
```

We claim:

1. An improved method for photoelectrically detecting arterial pulses of a patient comprising:

detecting the blood flow, which may include arterial pulses and artifacts, at the patient's body tissue using a device that calculates blood constituents from the detected blood flow;

detecting the occurrence of a selected portion of the patient's EKG waveform as the occurrence of the heartbeat of the patient;

correlating the occurrence of the heartbeat with the detection of pulses by the blood constituent calculating device by determining a period of time in which an arterial pulse is likely to be detected after the occurrence of a selected portion of the EKG waveform; and determining whether or not a detected pulse is likely to be a detected arterial pulse by determining that a detected pulse is one of either a first pulse acceptable for processing as an arterial pulse when the pulse is detected in the determined period of time after the selected portion of the EKG waveform occurs, or a second pulse not acceptable for processing as an arterial pulse when it is detected other than in the determined period of time after the selected portion of the EKG waveform occurs.

2. The method of claim 1 wherein the selected portion of the patient's EKG waveform is the R wave portion.

3. The method of claim 1 further comprising:
 calculating amounts of blood constituents from the portion of the blood flow detected during the determined period of time.

4. The method of claim 1 wherein the the device that calculates blood constituents is adapted for calculating oxygen saturation of hemoglobin in arterial blood, and the method further comprises measuring oxygen saturation of hemoglobin in arterial blood.

5. Improved apparatus for detecting arterial pulses of a patient comprising:

means for photoelectrically detecting the blood flow, which may include arterial pulses and artifacts, at the body tissue;

means for detecting the electrical heart activity of the patient in the form of an EKG waveform;

circuit means for filtering and processing the EKG waveform to detect a selected component of the EKG waveform, so that the occurrence of that selected component represents the occurrence of a heartbeat;

means for correlating detected arterial pulses with the occurrence of the heartbeat, said correlating means being adapted to establish a time period by which a detected arterial pulse is likely to follow the occurrence of a selected component of the EKG waveform; and means for confirming whether or not a detected pulse is likely to be an arterial pulse, said confirming means being responsive to the detected arterial pulse and a detected heartbeat and adapted to confirm that a detected pulse is acceptable as an arterial pulse by determining that the detected pulse occurs within the established time period.

6. The apparatus of claim 5 wherein the selected component of the EKG waveform is the R wave component.

7. The apparatus of claim 5 further comprising means for determining the amount of blood constituents and heart rate, responsive to the detected blood flow during the established time period.

8. A method for photoelectrically measuring the amount of a blood constituent from the blood flow characteristics in the body tissue of a patient using a device that is transmitting light through the body tissue, detecting and converting the amount of light transmitted from analog blood flow signals having arterial pulses and artifacts to digital signals, comprising:

digitally processing the digital signals to detect arterial pulses and determine an arterial pulse rate and the amount of a blood constituent present in the arterial blood;

detecting the patient's EKG waveform having a selected component corresponding to the onset of a heartbeat;

converting the EKG waveform into a digital EKG waveform having a digital heart pulse corresponding to each occurrence of the selected component of the EKG waveform, determining a digital heart pulse rate, comparing the digital EKG waveform and digital heart pulse rate to the digital signals and the arterial pulse rate to establish a time period by which an arterial pulse follows the occurrence of a digital heart pulse as the period of time after the occurrence of a digital heart pulse when it is likely that an arterial pulse will be detected; and thereafter digitally processing the digital signals detected during the established time period to determine the amount of a blood constituent present in the blood.

9. The method of claim 8 wherein processing of all digital signals re-commences when the digital heart pulse is not detected in a time when a selected number of heartbeats should have occurred based upon the determined heart rate.

10. The method of claim 8 wherein processing of all of the digital signals re-commences when an arterial pulse is not detected during a selected number of time periods.

11. The method of claim 8 wherein the method of measuring amounts of a blood constituent further comprises measuring the oxygen saturation of hemoglobin in arterial blood.

12. An improved non-invasive device for measuring the amount of blood constituents in body tissue of a patient by photoelectrically detecting changes in blood flow characteristics having arterial pulses and artifacts in the form of digital signals, including a microprocessor, comprising:

EKG circuit means for detecting the EKG waveform of the patient and generating a digital waveform having digital heart pulses that correspond to the occurrences of a selected portion of the EKG waveform;

status input means for indicating when a selected portion of the EKG waveform has occurred, said status input means being associated with the microprocessor and responsive to the digital waveform of the EKG circuit means so that each digital heart pulse causes the status input means to indicate a selected portion of the EKG waveform has occurred;

EKG signal processing means for calculating the EKG pulse rate, responsive to the EKG circuit means;

means for analyzing the digital signals and the digital heart pulse waveform over several digital heart pulses, determining the typical time period by which an arterial pulse follows a digital heart pulse, and determining a time period as the period during which it is likely to find a digital signal pulse representative of an arterial pulse after the occurrence of a digital heart pulse, said means being associated with the microprocessor and the EKG signal processing meas; and microprocessor means for analyzing digital signals detected during the determined time period after the occurrence of a digital heart pulse, said microprocessor means being responsive to the determined time period and the digital waveform so that calculations of the amount of the blood constituent will be based on those portions of the changes in the blood flow characteristics detected during the determined time period.

13. The apparatus of claim 12 further comprising a first reset means associated with the microprocessor for causing the microprocessor to analyze all of the digital signals after a selected number of digital heart pulses have occurred and no pulse is detected.

14. The apparatus of claim 12 further comprising a second reset means associated with the microprocessor for causing the microprocessor to analyze all of the digital signals after no digital heart pulse is detected and a selected number of heartbeats should have occurred based on the determined heart rate.

15. The apparatus of claim 12, wherein the EKG circuit means further comprises:

an automatic gain control amplifier having a controllable variable resistor means in the feedback loop for amplifying the EKG waveform and adjusting the gain of the automatic gain control amplifier;

a polarity switch means for noninverting or inverting the electrical heart activity waveform input to said switch to maintain uniform polarity of the signal output from said switch means;

a bandpass filter for selectively passing the frequencies of the electrical heart activity waveform between 15 and 40 Hz, thereby allowing only the related frequencies of the selected component of the EKG waveform to pass; and EKG analog to digital converter means for providing the EKG circuit means with digital signal outputs for processing by the microprocessor means.

16. The apparatus of claim 12 wherein the EKG circuit means further comprises:

a comparator having as its inputs an adjustable reference signal and the EKG waveform, and having as its outputs a digital heart pulse waveform, and a comparator means for comparing the electrical heart activity waveform to a selected reference signal so that when the selected portion of the electrical heart activity waveform corresponds to the reference signal, a digital heart pulse is generated; and a bistable circuit means connected to the comparator means output having a first condition, a second condition, and a reset operation, the first condition occurring on the occurrence of a digital heart pulse causing the status input means to indicate the occurrence of the selected portion of the EKG waveform, the second condition occurring when no selected portion has occurred and the bistable circuit means has been reset, the reset operation being activated by the microprocessor upon detection of the selected portion indication at the status input means to change the bistable circuit means output from the first to the second condition.

17. A method for calculating the amount of blood constituent from the blood flow characteristics of a patient comprising:

detecting an absorption signal corresponding to the absorption of light in the patient's tissue including periodic changes caused by periodic arterial pulses in the blood flow characteristics and changes caused by artifact;

detecting an EKG signal corresponding to the patient's EKG waveform including a selected portion of the EKG waveform corresponding to the periodic electrical heart activity of the patient;

correlating the detected absorption and EKG signals by determining a time relationship between the EKG and absorption signals to determine a time delay by which changes in the absorption signal corresponding to arterial pulses are likely to be detected after an occurrence of the selected portion of the EKG waveform;

processing the absorption signal and the determined correlation to identify the periodic changes in the absorption signal likely to correspond to arterial pulses in the patient's blood flow characteristics by using the determined time relationship and the determined time delay to determine a time window when the probability is high that a detected change in the absorption signal corresponds to an arterial pulse; and calculating the amount of the blood constituent from the identified periodic changes in the absorption signal by using the occurrences of the selected portion of the EKG waveform and the determined time window to identify the periodic changes in the absorption signal likely to correspond to arterial pulses.

18. The method of claim 17 wherein correlating the absorption and EKG signals further comprises:

synchronizing the occurrence of a plurality of changes in the absorption signals;

synchronizing the occurrences of a plurality of selected portions of the EKG signal; and correlating the synchronized portions of the absorption signal with the synchronized portions of the EKG signal.

19. The method of claim 17 wherein calculating the blood constituent further comprises processing the absorption signal that occurs during the time window after each occurrence of the selected portion of the EKG waveform to identify the periodic changes likely to correspond to arterial pulses.

20. The method of claim 17 wherein calculating the blood constituent further comprises rejecting changes in the absorption signal that do not occur during a time window after an occurrence of the selected portion of the EKG waveform so that rejected changes are not used in calculating the blood constituent.

21. The method of claim 17 wherein calculating the amount of a blood constituent further comprises calculating the amount of oxygen saturation of hemoglobin in arterial blood.

22. The method of claim 17 wherein the selected portion of the patient's EKG signal further comprises the R wave component.

23. An apparatus for use in calculating the amount of a blood constituent from the blood flow characteristics of a patient comprising:
  means for photoelectrically detecting an absorption signal corresponding to the absorption of light in the patient's tissue including periodic changes caused by periodic arterial pulses in the blood flow characteristics and changes caused by artifacts;
  means for electrically detecting an EKG signal corresponding to the patient's EKG waveform including a selected portion of the EKG waveform corresponding to the periodic electrical heart activity of the patient;
  first processing means for correlating the detected absorption and EKG signals by processing the absorption and EKG signals and determining a time relationship between the absorption and EKG signals to determine a time delay by which a change in the absorption signal corresponding to an arterial pulse is likely to be detected after the occurrence of a selected portion of the EKG waveform and processing the determined time relationship and the determined time delay to calculate a time window when the probability is high that a detected change in the absorption signal corresponds to an arterial pulse;
  second processing means for processing the absorption signal and the determined correlation by processing the absorption signal using the occurrences of the selected portion of the EKG waveform and the determined time window to identify the periodic changes in the absorption signal likely to correspond to arterial pulses in the patient's blood flow characteristics; and
  means for calculating the blood constituent from the identified periodic changes in the absorption signal.

24. The apparatus of claim 23 wherein the correlating means further comprises:
  first synchronizing means for synchronizing the occurrence of a plurality of changes in the absorption signal;
  second synchronizing means for synchronizing the occurrence of a plurality of selected portions of the EKG signal; and
  means for correlating the synchronized changes in the absorption signal with the synchronized selected portions of the EKG signal.

25. The apparatus of claim 23 wherein the first processing means further comprises processing the absorption signal that occurs during a determined time window after each occurrence of the selected portion of the EKG signal to identify the periodic changes likely to correspond to arterial pulses.

26. The apparatus of claim 23 further comprising means for rejecting changes in the absorption signal that do not occur during a determined time window after the occurrence of the selected portion of the EKG signal so that rejected changes are not used in calculating the blood constituent.

27. The apparatus of claim 23 wherein the calculating means is adapted for calculating the amount of oxygen saturation of hemoglobin in arterial blood.

28. The apparatus of claim 23 wherein means for detecting the selected portion of the patient's EKG signal is adapted for detecting the R wave component.

* * * * *

UNITED STATES PATENT AND TRADEMARK OFFICE
CERTIFICATE OF CORRECTION

PATENT NO. : 4,802,486

DATED : February 7, 1989

INVENTOR(S) : Goodman et al.

It is certified that error appears in the above-identified patent and that said Letters Patent is hereby corrected as shown below:

Column 7, line 49, "material" should be --maternal--

Column 8, line 25, "Oscillation" should be --Oscillator--

Column 11, line 49, delete "LI"

Column 12, line 2, "to" should be --so--

Column 12, line 16, "LEd" should be --LED--

Column 14, line 61, "$V_a$, $V_b$, $V_1$', and $V_b$'," should be --$V_a$' $V_b$' $V_a$'' $V_b$''--

Column 14, line 66, "8AH" should be --8H--

Column 19, line 27, delete "PO"

Column 19, line 33, "lo" should be --log--

Columns 19 and 20, insert line numbers --1 to 18--

Columns 21 and 22, insert line numbers --20 to 49--

Columns 21 and 22, insert line numbers --1 to 57--

Columns 21 and 22, insert line numbers --1 to 9--

UNITED STATES PATENT AND TRADEMARK OFFICE
CERTIFICATE OF CORRECTION

PATENT NO. : 4,802,486

DATED : February 7, 1989

INVENTOR(S) : Goodman et al.

It is certified that error appears in the above-identified patent and that said Letters Patent is hereby corrected as shown below:

```
Columns 23 and 24, insert line numbers   --11 to 23--

Columns 23 and 24, insert line numbers   --1 to 36--

Columns 23 and 24, insert line numbers   --1 to 35--

Columns 25 and 26, insert line numbers   --1 to 24--

Columns 25 and 26, insert line numbers   --1 to 45--

Columns 25 and 26, insert line numbers   --1 to 25--

Columns 27 and 28, insert line numbers   --26 to 43--

Columns 27 and 28, insert line numbers   --1 to 57--

Columns 27 and 28, insert line numbers   --1 to 18--

Columns 29 and 30, insert line numbers   --19 to 42--

Columns 29 and 30, insert line numbers   --1 to 36--

Columns 29 and 30, insert line numbers   --1 to 34--

Columns 31 and 32, insert line numbers   --31 to 32--

Columns 31 and 32, insert line numbers   --1 to 57--

Columns 31 and 32, insert line numbers   --1 to 29--
```

UNITED STATES PATENT AND TRADEMARK OFFICE
CERTIFICATE OF CORRECTION

PATENT NO. : 4,802,486

DATED : February 7, 1989

INVENTOR(S) : Goodman et al.

It is certified that error appears in the above-identified patent and that said Letters Patent is hereby corrected as shown below:

```
Columns 33 and 34, insert line numbers  --30 to 57--

Columns 33 and 34, insert line numbers  --1 to 59--

Columns 33 and 34, insert line numbers  --1 to 6--

Columns 35 and 36, insert line numbers  --6 to 48--

Columns 35 and 36, insert line numbers  --1 to 39--

Columns 35 and 36, insert line numbers  --1 to 14--

Columns 37 and 38, insert line numbers  --15 to 57--

Columns 37 and 38, insert line numbers  --1 to 50--

Columns 39 and 40, insert line numbers  --51 to 57--

Columns 39 and 40, insert line numbers  --1 to 9--

Columns 39 and 40, insert line numbers  --1 to 33--

Columns 39 and 40, insert line numbers  --1 to 25--

Columns 39 and 40, insert line numbers  --1 to 20--

Columns 41 and 42, insert line numbers  --21 to 52--

Columns 41 and 42, insert line numbers  --1 to 51--
```

UNITED STATES PATENT AND TRADEMARK OFFICE
CERTIFICATE OF CORRECTION

PATENT NO. : 4,802,486

DATED : February 7, 1989

INVENTOR(S) : Goodman et al.

It is certified that error appears in the above-identified patent and that said Letters Patent is hereby corrected as shown below:

Columns 41 and 42, insert line numbers --1 to 10--

Columns 43 and 44, insert line numbers --11 to 28--

Columns 49 and 50, insert line numbers --21 to 57--

IN THE CLAIMS

Column 151, line 46, delete "the" (second occurrence)

Column 153, line 34, "meas" should be --means--

Column 153, line 48, after "no" insert --optical--

Column 153, line 59, "EKG" should be

--electrical heart activity--

Column 154, line 7, "EKG" should be

--electrical heart activity--

Signed and Sealed this

Eighteenth Day of April, 1995

*Attest:*

*Attesting Officer*

BRUCE LEHMAN

*Commissioner of Patents and Trademarks*